United States Patent
Carzaniga et al.

(10) Patent No.: US 9,662,323 B2
(45) Date of Patent: May 30, 2017

(54) COMPOUNDS HAVING MUSCARINIC RECEPTOR ANTAGONIST AND BETA2 ADRENERGIC RECEPTOR AGONIST ACTIVITY

(71) Applicant: CHIESI FARMACEUTICI S.p.A., Parma (IT)

(72) Inventors: Laura Carzaniga, Parma (IT); Fabio Rancati, Parma (IT); Andrea Rizzi, Parma (IT); Ian Linney, Saffron Walden (GB); Wolfgang Schmidt, Saffron Walden (GB); Michael Barnes, Saffron Walden (GB); Chris Knight, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/168,466

(22) Filed: May 31, 2016

(65) Prior Publication Data

US 2016/0346271 A1    Dec. 1, 2016

(30) Foreign Application Priority Data

Jun. 1, 2015 (EP) .................... 15170033

(51) Int. Cl.
*A61K 31/4709* (2006.01)
*C07D 453/02* (2006.01)
*A61K 9/00* (2006.01)
*A61M 15/00* (2006.01)
*A61M 16/14* (2006.01)

(52) U.S. Cl.
CPC ........ *A61K 31/4709* (2013.01); *A61K 9/0073* (2013.01); *A61M 15/009* (2013.01); *A61M 16/14* (2013.01); *C07D 453/02* (2013.01); *A61M 2202/064* (2013.01)

(58) Field of Classification Search
None
See application file for complete search history.

(56) References Cited

U.S. PATENT DOCUMENTS

| | | | |
|---|---|---|---|
| 4,534,343 A * | 8/1985 | Nowacki | A61M 15/0086 128/200.23 |
| 2013/0034504 A1 | 2/2013 | Rancati et al. | |
| 2014/0163066 A1 | 6/2014 | Rancati et al. | |

OTHER PUBLICATIONS

Extended European Search Report in Application No. 15170033.3 dated Aug. 6, 2015.

* cited by examiner

*Primary Examiner* — Karl J Puttlitz
(74) *Attorney, Agent, or Firm* — Oblon, McClelland, Maier & Neustadt, L.L.P.

(57) ABSTRACT

Compounds of formula I, defined herein, act both as muscarinic receptor antagonists and beta2 adrenergic receptor agonists and are useful for treating diseases of the respiratory tract.

16 Claims, No Drawings

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application claims priority to European Patent Application No. 15170033.3 filed on Jun. 1, 2015, which is incorporated herein by reference in its entirety.

BACKGROUND OF THE INVENTION

Field of the Invention

The present invention relates to novel compounds which act both as muscarinic receptor antagonists and beta2 adrenergic receptor agonists. The present invention also relates to processes for the preparation of such a compound, compositions which contain such a compound, therapeutic uses of such a compound, and combinations of such a compound with other pharmaceutical active ingredients.

Discussion of the Background

Pulmonary disorders, such as asthma and chronic obstructive pulmonary disease (COPD), are commonly treated with bronchodilators. A well-known class of bronchodilators consists of beta-2 adrenergic receptor agonists, such as salbutamol, fenoterol, formoterol and salmeterol. These compounds are generally administered by inhalation.

Another well-known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive, prompted studies with combinations of the two agents. In 1975, it was shown that that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted to the development of combinations of these agents.

For example, WO 00/69468, which is incorporated herein by reference in its entirety, discloses medicament compositions containing a muscarinic receptor antagonist, such as tiotropium bromide, and beta-2 adrenergic receptor agonists, such as formoterol fumarate or salmeterol, and WO 2005/115467, which is incorporated herein by reference in its entirety, discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both activities of muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds are described in some patent applications, such as WO 2004/074246, WO 2004/074812, WO 2005/051946, WO 2006/023457, WO 2006/023460, WO 2010/123766, and WO 2011/048409 and co-pending patent applications WO 2012/168349, WO 2012/168359, WO2014/086924, and WO 2014/086927, all of which are incorporated herein by reference in their entireties.

However, there remains a need for compounds which possess both beta-2 adrenergic receptor agonist and muscarinic receptor antagonist activity and elevated affinity for the M3 muscarinic receptors and long lasting bronchodilating activity.

SUMMARY OF THE INVENTION

Accordingly, it is one object of the present invention to provide novel compounds which act both as muscarinic receptor antagonists and beta2 adrenergic receptor agonists.

It is another object of the present invention to provide novel processes for the preparation of such a compound.

It is another object of the present invention to provide novel compositions which contain such a compound.

It is another object of the present invention to provided novel therapeutic uses of such a compound.

It is another object of the present invention to provide novel combinations of such a compound with other pharmaceutical active ingredients.

These and other objects, which will become apparent during the following detailed description, have been achieved by the inventors' discovery of compounds of formula I, described below, which act both as muscarinic receptor antagonists and beta2 adrenergic receptor agonists, the processes for the preparation thereof, compositions comprising them, the therapeutic uses and compositions comprising combinations with other pharmaceutical active ingredients among which are, for instance, those currently used in the treatment of respiratory disorders, e.g. corticosteroids, P38 MAP kinase inhibitors, IKK2, HNE inhibitors, PDE4 inhibitors, leukotriene modulators, NSAIDs and mucus regulators.

Thus, it has now been found that some particular aryl or heteroaryl hydroxyacetic ester derivatives, besides possessing both beta-2 adrenergic receptor agonist and muscarinic receptor antagonist activity, possess elevated affinity for the M3 muscarinic receptors and long lasting bronchodilating activity.

DETAILED DESCRIPTION OF THE PREFERRED EMBODIMENTS

In particular, the invention is directed to compounds of formula (I):

I

[Structure I shown with quinolinone, hydroxyl, phenyl ring with $(R_1)_n$, $R_2$, $(CH_2)_s$, $(H_2C)_i$, $(CH_2)_{i'}$, N, L, G, Y, NH groups]

wherein

Y is selected from Y2 and Y1 which are divalent groups of formula

Y2

$$-A_1-B-A_2-C-D-(CH_2)_{n'}-E-(CH_2)_{n''}-$$

or

Y1

$$-A_1-C-B-D-(CH_2)_{n'}-E-$$

wherein

A1 and A2 are independently absent or selected from the group consisting of $(C_1-C_{12})$alkylene, $(C_3-C_8)$cycloalkylene and $(C_3-C_8)$heterocycloalkylene optionally substituted by one or more substituents selected from the group consisting of $(C_1-C_6)$alkyl, aryl$(C_1-C_6)$alkyl and heteroaryl$(C_1-C_6)$alkyl;

B is absent or is selected from the group consisting of $(C_3-C_8)$cycloalkylene, $(C_3-C_8)$heterocycloalkylene, arylene or heteroarylene optionally substituted by one or more groups selected from halogens, nitrile, $(C_1-C_6)$alkyl, $(C_1-C_6)$alkoxy and aryl$(C_1-C_6)$alkyl;

C is absent or is selected from the group consisting of —O—, —C(O)—, —OC(O)—, —(O)CO—, —S—, —S(O)—, —S(O)$_2$— and —N(R$_7$)—, or is one of the following groups C1-C4

C1

$$-(CH_2)_{n'''}-\underset{R_7}{N}-\underset{O}{C}-$$

C2

$$-\underset{O}{C}-\underset{R_7}{N}-(CH_2)_{n'''}-$$

C3

$$-\underset{O}{C}-\underset{R_7}{N}-\underset{R_8}{CH}-$$

C4

[piperidine amide structure]

wherein $R_7$ is in each occurrence independently H or selected from the group consisting of linear or branched $(C_1-C_8)$alkyl, $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl, $(C_1-C_8)$alkylcarbonyl, $(C_3-C_8)$cycloalkylcarbonyl, arylcarbonyl, $(C_1-C_8)$alkoxycarbonyl, $(C_1-C_8)$alkylaminocarbonyl, $(C_1-C_{10})$alkylsulfanyl, $(C_1-C_{10})$alkylsulfinyl, $(C_1-C_{10})$alkylsulfonyl, arylsulfanyl, arylsulfinyl and arylsulfonyl; and wherein $R_7$ may optionally be further substituted by one or more groups selected from halogen, —CN, $(C_1-C_8)$alkyl, halo$(C_1-C_8)$alkyl, aryl, aryl$(C_1-C_6)$alkyl, $(C_1-C_8)$alkoxy, aryl$(C_1-C_8)$alkoxy, $(C_3-C_8)$cycloalkyl, $(C_3-C_8)$heterocycloalkyl, substituted or unsubstituted aryloxy;

$R_8$ is in each occurrence independently H or selected from the group consisting of linear or branched $(C_1-C_8)$alkyl, $(C_3-C_8)$cycloalkyl, $(C_3-C_8)$heterocycloalkyl, aryl, heteroaryl, aryl$(C_1-C_6)$alkyl, $(C_3-C_8)$cycloalkyl$(C_1-C_6)$alkyl, and heteroaryl$(C_1-C_6)$alkyl;

D is absent or is selected from the group consisting of $(C_1-C_{12})$alkylene, arylene, $(C_2-C_{12})$alkenylene, heteroarylene, $(C_3-C_8)$heterocycloalkylene and $(C_2-C_6)$alkynylene;

n, n', n'' and n''' are at each occurrence independently 0 or an integer from 1 to 3;

E is absent or is selected from —O—, —NR$_7$—, —NR$_7$—C(O)—, —C(O)—NR$_7$—, —OC(O)— and —S—;

G is absent or arylene or heteroarylene, optionally substituted by one or more substituents selected from the group consisting of halogen atoms, —OH, oxo (=O), —SH, —NO$_2$, —CN, —CON(R$_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl and $(C_1-C_{10})$alkoxy;

L is absent or a divalent group selected from —C(O)—, —OC(O)—, —S(O)$_2$—, $(C_1-C_8)$alkylene, $(C_1-C_8)$alkylcarbonyl-ene, and $(C_2-C_8)$alkenylcarbonyl-ene; or is one of the following groups L1-L3

L1

$$-(CH_2)_m-\underset{R_7}{N}-\underset{O}{C}-$$

L2

$$-(CH_2)_m-O-\underset{O}{C}-$$

L3

$$-O-(CH_2)_m-\underset{O}{C}-$$

wherein m is 0 or an integer from 1 to 3;
i is 1 or 2;
i' is 1 or 2;

R₁ is at each occurrence selected independently from hydrogen, halogen, $(C_1-C_8)$alkyl and $(C_1-C_{10})$alkoxy;

s is 0 or an integer from 1 to 3;

R₂ is a nitrogen containing group which is selected from:
a group (a) which is $-NR_3R_4$ wherein R₃ and R₄ are independently hydrogen or $(C_1-C_4)$ alkyl or benzyl; and
a group (b) of formula J1, J2, J3, J4 or J5

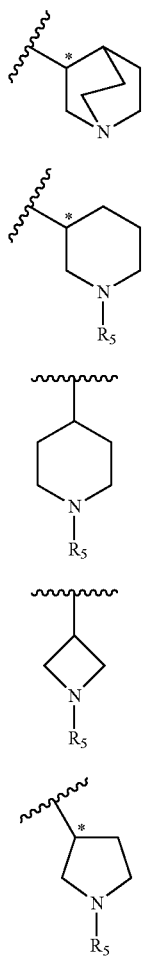

R₅ is a group of formula K

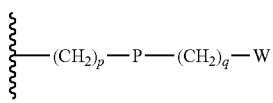

wherein p is 0 or an integer from 1 to 4; q is 0 or an integer from 1 to 4;

P is absent or is selected from the divalent group consisting of O, S, SO, SO₂, CO, NR₆CH=CH, N(R₆)SO₂, N(R₆)COO, N(R₆)C(O), SO₂N(R₆), OC(O)N(R₆) and C(O)N(R₆);

W is selected from the group consisting of H, $(C_1-C_6)$ alkyl, $(C_3-C_8)$cycloalkyl, aryl and heteroaryl, optionally substituted by one or more substituents selected independently from the group consisting of halogen atoms, —OH, oxo (=O), —SH, —NO₂, —CN, —CON(R₆)₂, —NH₂, —NHCOR₆, —CO₂R₆, $(C_1-C_{10})$alkylsulfanyl, $(C_1-C_{10})$alkylsulfinyl, $(C_1-C_{10})$alkylsulfonyl, $(C_1-C_{10})$alkyl, $(C_1-C_{10})$alkoxy and aryl;

R₆ is at each occurrence independently H or selected from the group consisting of $(C_1-C_{10})$alkyl, $(C_1-C_6)$haloalkyl, $(C_2-C_6)$alkynyl, $(C_2-C_6)$alkenyl, $(C_3-C_8)$cycloalkyl, $(C_3-C_8)$cycloalkyl$(C_1-C_6)$alkyl, heteroaryl and aryl optionally substituted by one or more substituents selected from the group consisting of halogen atoms, —OH, oxo (=O), —SH, —NO₂, —CN, —CONH₂, —COOH, $(C_1-C_{10})$alkoxycarbonyl, $(C_1-C_{10})$alkylsulfanyl, $(C_1-C_{10})$alkylsulfinyl, $(C_1-C_{10})$alkylsulfonyl, $(C_1-C_{10})$alkyl and $(C_1-C_{10})$alkoxy;

and pharmaceutically acceptable salts and solvates thereof.

The expression "$(C_1-C_x)$alkyl" refers to straight or branched chain alkyl groups wherein the number of carbon atoms is from 1 to x, preferably from 1 to 6. Examples of groups are methyl, ethyl, n-propyl, isopropyl, t-butyl, pentyl, hexyl, octyl, nonyl, decyl, undecyl, dodecyl and the like.

In an analogous manner, the expression "$(C_1-C_x)$alkylene" herewith refers to divalent groups, such as methylene, ethylene, n-propylene, isopropylene, t-butylene, pentylene, hexylene, octylene, nonylene, decylene, undecylene, dodecylene and the like. With alternative common name, deriving from the name of the corresponding alkanes, the above divalent groups can be referred to also as methanediyl, ethanediyl, n-propanediyl, propan1,2-diyl and the like.

The expression "$(C_1-C_6)$haloalkyl" refers to the above "$(C_1-C_6)$alkyl" group wherein one or more hydrogen atoms are replaced by one or more halogen atoms, which can be the same or different from each other.

Examples of said $(C_1-C_6)$haloalkyl groups include halogenated, poly-halogenated and fully halogenated alkyl groups wherein one or more of the hydrogen atoms are replaced by halogen atoms, e.g. trifluoromethyl group.

The expression "hydroxy$(C_1-C_6)$alkyl" likewise refers to -alkyl-OH groups. The expressions "$(C_1-C_{10})$alkylsulfanyl", "$(C_1-C_{10})$alkylsulfinyl" or "$(C_1-C_{10})$alkylsulfonyl" refer, respectively, to alkyl-S—, alkyl-SO— or alkyl-SO₂— groups.

The expression "$(C_2-C_x)$alkenyl" refers to straight or branched carbon chains with one or more double bonds, wherein the number of carbon atoms is from 1 to x. Examples of said groups comprise ethenyl, propenyl, butenyl, pentenyl, hexenyl, heptenyl, octenyl, nonenyl, decenyl, undecenyl, dodecenyl and the like.

In an analogous manner, the expression "$(C_2-C_x)$alkenylene" refers to divalent groups, such as ethenylene, propenylene, butenylene, pentenylene, hexenylene, heptenylene, octenylene, nonenylene, decenylene, undecenylene, dodecenylene and the like.

The expression "$(C_2-C_x)$alkynyl" refers to straight or branched carbon chains with one or more triple bonds, wherein the number of carbon atoms is from 1 to x. Examples of said groups comprise ethynyl, propynyl, butynyl, pentynyl, hexynyl and the like.

In an analogous manner, the expression "$(C_2-C_6)$alkynylene" refers to divalent groups, such as ethynylene, propynylene, butynylene, pentynylene, hexynylene and the like; otherwise commonly referred to as ethynediyl, propynediyl, butyndiyl and the like.

The expression "$(C_1-C_x)$alkoxy" refers to alkyl-oxy (i.e. alkoxy) groups, being the alkyl portion as above defined, wherein the number of carbon atoms is from 1 to x. Examples of said groups comprise methoxy, ethoxy, n-propoxy, isopropoxy, n-butoxy, isobutoxy, sec-butoxy, tert-butoxy, pentoxy, hexoxy and the like.

The expression "($C_1$-$C_8$)alkylcarbonyl" refers to ($C_1$-$C_8$) alkylC(O)— groups. Non limiting examples of ($C_1$-$C_8$) alkylcarbonyl may thus include acetyl, propionyl, butyryl, pentanoyl, and the like.

The expression "($C_1$-$C_x$)alkylamino" refers to alkylamino (i.e. alkylamino) groups, being the alkyl portion as above defined, wherein the number of carbon atoms is from 1 to x. Examples of said groups comprise methylamino, ethylamino, n-propylamino, isopropylamino, n-butylamino, isobutylamino, sec-butylamino, tert-butylamino, pentylamino, hexylamino, and the like.

The expression "($C_1$-$C_{10}$)alkoxycarbonyl" refers to ($C_1$-$C_{10}$)alkoxyC(O)— groups. Non limiting examples of ($C_1$-$C_{10}$)alkoxycarbonyl may thus include methoxycarbonyl, ethoxycarbonyl, propoxycarbonyl, butoxycarbonyl, isopropoxycarbonyl, and the like.

The expression "($C_1$-$C_8$)alkylaminocarbonyl" refers to ($C_1$-$C_8$)alkylaminoC(O)— groups. Non limiting examples of ($C_1$-$C_8$)alkylaminocarbonyl may thus include methylaminocarbonyl, ethylaminocarbonyl, butylaminocarbonyl, isopropylaminocarbonyl, and the like.

The expression "($C_3$-$C_8$)cycloalkyl" refers to mono or bi-cycloaliphatic hydrocarbon groups with 3 to 8 carbon atoms. Examples include cyclopropyl, cyclobutyl, cyclopentyl, cyclohexyl, cycloheptyl, bicyclo[2.2.1]hept-2-yl and the like.

The expression "($C_3$-$C_8$)heterocycloalkyl" refers to saturated or partially saturated monocyclic ($C_3$-$C_8$)cycloalkyl groups, in which at least one ring carbon atom is replaced by a heteroatom or heteroaromatic group (e.g. N, NH, S or O). Examples include quinuclidinyl, pyrrolidinyl, piperidinyl, morpholinyl, azabicyclo[3.2.1]octan-3-yl and azoniabicyclo[2.2.2]octanyl, [1.2.3.6]tetrahydropyridin-1yl and the like.

In an analogous manner, the expressions "($C_3$-$C_8$)cycloalkylene" and "($C_3$-$C_8$)heterocycloalkylene" herewith refer to divalent groups. The term cycloalkylene refers to saturated cycloalkane-diyl and partially saturated monocyclic groups such as cycloalkene-diyl. Examples of such ($C_3$-$C_8$)cycloalkylene and ($C_3$-$C_8$)heterocycloalkylene are divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene, azoniabicyclo[2.2.2]octanylene, [1.2.3.6]tetrahydropyridin-[1.4]diyl and the like. With alternative common name, deriving from the name of the corresponding alkanes or alkenes, the above divalent groups can be referred to also as cyclopropanediyl, cyclobutanediyl, cyclopentanediyl, cyclohexanediyl, cycloheptanediyl, bicyclo[2.2.1] heptanediyl and quinuclidinediyl, pyrrolidinediyl, piperidinediyl, azabicyclo[3.2.1]octanediyl, azoniabicyclo[2.2.2] octanediyl, [1.2.3.6]tetrahydropyridine-[1.4]diyl and the like.

The expression "($C_3$-$C_8$)cycloalkylcarbonyl" refers to ($C_3$-$C_8$)cycloalkylC(O)— groups. Non limiting examples of ($C_3$-$C_8$)cycloalkylcarbonyl groups include cyclopropylcarbonyl, cyclobutylcarbonyl, cyclopentylcarbonyl, cyclohexylcarbonyl, and the like.

The expression "aryl" refers to mono, bi- or tricyclic ring systems having 5 to 20, preferably from 5 to 15, more preferably from 5 to 8 ring atoms, and wherein at least one ring is aromatic.

The expression "heteroaryl" refers to mono, bi- or tricyclic systems with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthalenyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydro-indene, dihydrobenzo dioxepin, benzo oxazine radicals and the like.

Examples of suitable aryl or heteroaryl tricyclic systems include fluorene radicals as well as benzocondensed derivatives of the aforementioned heteroaryl bicyclic systems. In an analogous manner, the expressions "arylene" and "heteroarylene" refer to divalent groups, such a phenylene, biphenylene and thienylene. Such groups are also commonly named as "arenediyl" or "heteroarenediyl" groups. E.g. o-phenylene is also named benzene-1,2-diyl.

The expressions "aryl($C_1$-$C_6$)alkyl", "heteroaryl($C_1$-$C_6$) alkyl" and "($C_3$-$C_8$)cycloalkyl($C_1$-$C_6$)alkyl" refer to a "($C_1$-$C_6$)alkyl" respectively substituted by one or more aryl, heteroaryl or ($C_3$-$C_8$)cycloalkyl groups, as defined above. Examples of aryl($C_1$-$C_6$)alkyl include triphenylmethyl.

The expression "arylcarbonyl" refers to the above "aryl" group wherein one hydrogen atom is replaced by a carbonyl group. Examples of arylcarbonyl include benzoyl, naphthoyl and fluorenoyl groups.

By way of analogy the expressions "arylsulfanyl", "arylsulfinyl" or "arylsulfonyl" refer, respectively, to aryl-S—, aryl-SO— or aryl-$SO_2$— groups. Preferred aryl groups are Examples are phenyl-S—, phenyl-SO— or phenyl-$SO_2$—.

Likewise the expression "haloaryl" refers to the above "aryl" group wherein one or more hydrogen atoms are replaced by one or more halogen atoms, which can be the same or different from each other.

As used herein an oxo moiety is represented by (O) as an alternative to other common representations, e.g. (=O). Thus, in terms of general formula, the carbonyl group is herein preferably represented as —C(O)— as an alternative to the other common representations such as —CO—, —(CO)— or —C(=O)—. In general the bracketed group is a lateral group, not included into the chain, and brackets are used, when deemed useful, to help distinguish linear chemical formulas; e.g. the sulfonyl group —$SO_2$— might be also represented as —$S(O)_2$— to distinguish from e.g. the sulfinic group —S(O)O—.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as —COOH groups, corresponding physiological cation salts may be present as well, for instance including alkaline or alkaline earth metal ions.

In a first preferred embodiment the invention is directed to group of compounds of general formula I wherein $R_2$ is a group of formula J1:

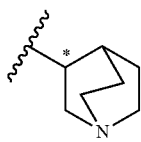

J1 and all the other variables as defined above.

A second preferred group of compounds is that of general formula I wherein $R_2$ is a nitrogen containing group selected from J2, J3, J4 or J5

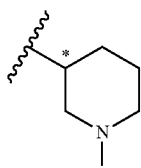

J2

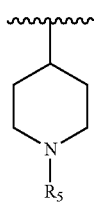

J3

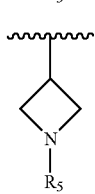

J4

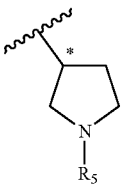

J5 wherein $R_5$ is a group of formula K, wherein p is 0 or 1, P is absent or is CO, q is absent or is 1 and W is H or is selected from $(C_1-C_6)$alkyl, $(C_3-C_8)$cycloalkyl and aryl optionally substituted by hydroxyl, methoxy, phenyl, and all the other variables are as defined above.

In a more preferred embodiment, $R_2$ is a group of formula J3, $R_5$ is methyl or benzyl, and all the other variables are as defined above.

It will be apparent to those skilled in the art that compounds of general formula I wherein $R_2$ is a group selected from J1, J2 or J5 or wherein i is different from i', at least contain two stereogenic centers. Therefore, the invention also includes any of the optical stereoisomers, diastereoisomers and mixtures thereof, in any proportion.

Thus, compounds according to the present invention, having at least two stereogenic centers, may accordingly exist as at least four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In some embodiments each of i and i' is 2 and Y, G, L, $R_1$, $R_2$, n and s are as defined in formula I, and the compounds of the invention are represented by formula IA.

IA

In one embodiment of formula IA, Y is $Y_2$ wherein one of $A_1$, $A_2$, C and D is $(C_1-C_{12})$ alkylene and the others are absent, B is absent, and n' and n" are 0, E is —O—, G is arylene such as phenylene which is substituted by one or more substituents selected from the group of consisting $(C_1-C_{10})$ alkyl such as methyl, $(C_1-C_{10})$ alkoxy such as methoxy, halogen such as F and Cl, aryl such as phenyl and heteroaryl such as thienyl, L is selected in the group consisting of —CO—, —CH$_2$CO—, —CH$_2$CH$_2$CO—, and —CH=CHCO—, n is 0 or 1, $R_1$ is hydrogen or halogen, s is 0, and $R_2$ is J1.

In another embodiment of formula IA, Y is $Y_2$ wherein at least one of $A_1$, $A_2$, C, and D is $(C_1-C_{12})$ alkylene and the others are absent, B is absent or arylene such as phenylene, and n' and n" are 0, E is —N($R_7$)CO— wherein preferably $R_7$ is hydrogen, methyl or ethyl or E is absent, G is arylene such as phenylene or heteroarylene such as thienylene, L is —CO—, n is 0, s is 0, $R_1$ is hydrogen, and $R_2$ is J1.

In another embodiment of formula IA, Y is $Y_2$ wherein $A_1$ is $(C_1-C_{12})$ alkylene, B is arylene such as phenylene, $A_2$ is $(C_1-C_{12})$ alkylene, D is absent and n' and n" are 0, E is —NHCO—, G is arylene such as phenylene, L is —CO—, n is 0, s is 0, $R_1$ is hydrogen, and $R_2$ is J1.

In another embodiment of formula IA, Y is $Y_1$ wherein $A_1$ is $(C_1-C_{12})$ alkylene, B is absent, $A_2$ is absent, C is $C_1$ wherein n''' is 1 and $R_7$ is selected from hydrogen, $(C_1-C_4)$ alkyl such as methyl and ethyl, and aryl $(C_1-C_6)$ alkyl such as benzyl optionally substituted on the phenyl ring by methyl, trifluoromethyl, methoxy, cyano, 3,4-dichlorophenoxy, benzyloxy, fluoro, or 4-morpholino, D is absent, n' is 0, and E is absent, G is heteroarylene such as thienylene, L is —CH$_2$CO— or —CH$_2$CH$_2$CO—, n is 0, s is 0, $R_1$ is hydrogen, and $R_2$ is J1.

In another embodiment of formula IA, Y is $Y_2$ wherein $A_1$ is $(C_1-C_{12})$ alkyklene, B is arylene such as phenylene, $A_2$ is $C_1-C_{12}$ alkylene, C is —N($R_7$)— wherein $R_7$ is selected in the group of $(C_1-C_8)$alkylcarbonyl such as acetyl, $(C_1-C_{10})$ alkylsulphonyl such as methanesulphonyl, arylcarbonyl such as benzoyl, $(C_3-C_8)$cycloalkylcarbonyl such as cyclopropylcarbonyl, arylsulphonyl such as benzenesulphonyl, $(C_1-C_{10})$alkoxycarbonyl such as methoxycarbonyl, and $(C_1-C_8)$alkylaminocarbonyl such as methylaminocarbonyl, D is ($C_1$-$C_{12}$) alkylene and n' and n" are 0, E is absent, G is arylene such as phenylene, L is —CO—, n is 0, s is 0, $R_1$ is hydrogen, and $R_2$ is J1.

In some embodiments each of i and i' is 1 and Y, G, L, $R_1$, $R_2$, n and s are as defined in formula I, and the compounds of the invention are represented by formula IB.

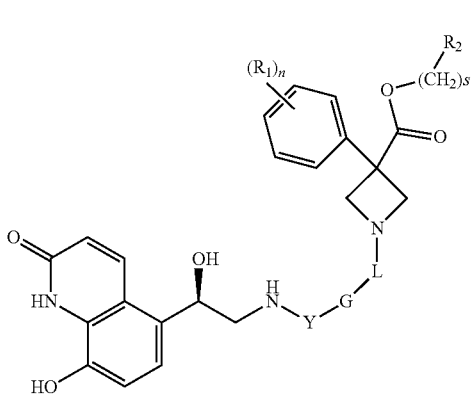

In one embodiment of formula IB, Y is $Y_2$ wherein one of $A_1$, $A_2$, C and D is ($C_1$-$C_{12}$) alkylene and the others are absent, B is absent, and n' and n" are 0, E is —O—, G is phenylene which is substituted by one or more substituents selected from the group of consisting ($C_1$-$C_{10}$) alkyl such as methyl, ($C_1$-$C_{10}$) alkoxy such as methoxy, halogen such as F and Cl, aryl such as phenyl and heteroaryl such as thienyl, L is selected in the group consisting of —CO—, —$CH_2$CO— and —$CH_2CH_2$CO—, n is 0 or 1, s is 0, $R_1$ is hydrogen or halogen, and $R_2$ is J1.

In another embodiment of formula IB, Y is $Y_2$ wherein $A_1$ is ($C_1$-$C_{12}$) alkylene, B is arylene such as phenylene, $A_2$ is ($C_1$-$C_{12}$) alkylene, D is absent, n' and n" are 0, E is —NHCO—, G is arylene such as phenylene, L is —CO—, n is 0, s is 0, $R_1$ is hydrogen, and $R_2$ is J1.

In another embodiment of formula IB, Y is $Y_2$ wherein one of $A_1$, $A_2$, C, and D is ($C_1$-$C_{12}$) alkylene and the others are absent, B is absent or arylene such as phenylene, and n' and n" are 0, E is —N($R_7$)CO— or is absent, G is arylene such as phenylene or heteroarylene such as thienylene, L is —CO—, n is 0, s is 0, $R_1$ is hydrogen, and $R_2$ is J1.

In another embodiment of formula IB, Y is $Y_1$ wherein $A_1$ is ($C_1$-$C_{12}$) alkylene, B is absent, $A_2$ is absent, C is $C_1$ wherein n''' is 1 and $R_7$ is selected from the group of hydrogen, ($C_1$-$C_4$) alkyl such as methyl and ethyl, and aryl ($C_1$-$C_6$) alkyl such as benzyl optionally substituted on the phenyl ring by methyl, trifluoromethyl, methoxy, cyano, 3,4-dichlorophenoxy, benzyloxy, fluoro, or 4-morpholino, D is absent, n' is 0, and E is absent, G is heteroarylene such as thienylene, L is —$CH_2$CO— or —$CH_2CH_2$CO—, n is 0, s is 0, $R_1$ is hydrogen, and $R_2$ is J1.

In another embodiment of formula IB, Y is $Y_2$ wherein $A_1$ is ($C_1$-$C_{12}$) alkylene, B is arylene such as phenylene optionally substituted by ($C_1$-$C_{10}$) alkoxy such as methoxy, C is $C_1$ or $C_2$ wherein n''' is 1 and $R_7$ is hydrogen, D is Absent, E is absent and n' and n" are 0, G is a arylene such as phenylene, L is —CO—, n is 0, s is 0, $R_1$ is hydrogen, and $R_2$ is J1.

In another embodiment of formula IB, Y is $Y_1$ wherein $A_1$ is ($C_1$-$C_{12}$) alkylene, C is $C_1$ wherein n''' is 1 or 2 and $R_7$ is hydrogen, B is arylene such as phenylene, D is absent, n' is 1, and E is —O—, G is arylene such as phenylene, L is —CO—, n is 0, s is 0, $R_1$ is hydrogen, and $R_2$ is J1.

In a preferred embodiment of formula IA or formula IB, Y is $Y_2$ wherein $A_1$ is ($C_1$-$C_{12}$) alkylene, B is arylene optionally substituted, $A_2$ is ($C_1$-$C_{12}$) alkylene, C is absent, D is absent and n' and n" are 0, E is —O—, G is arylene or heteroarylene, both of which are optionally substituted, and L, $R_1$, $R_2$, n and s are as defined in formula I. More preferably, $A_1$ is —$CH_2$— or —$CH_2$—$CH_2$—, B is phenylene, $A_2$ is —$CH_2$—, G is phenylene, L is —CO— or —$CH_2$CO—, $R_1$ is H, $R_2$ is J1, and s is 0.

In another preferred embodiment of formula IA or formula IB, Y is $Y_1$ wherein $A_1$ is ($C_1$-$C_{12}$) alkylene, C is $C_1$, B is absent or arylene, D is absent, n' is 1, and E is —O— or absent, G is arylene or heteroarylene both of them optionally substituted, and L, $R_1$, $R_2$, n and s are as defined in formula I. More preferably, Y is $Y_1$ wherein $A_1$ is —$CH_2$—, C is $C_1$ wherein n''' is 2 and $R_7$ is a benzyl group, said benzyl being optionally substituted by halogen, ($C_1$-$C_8$) alkoxy, —CN or ($C_1$-$C_8$) alkyl, and n is 1, L is —CO— or —$CH_2$CO—, $R_1$ is H, $R_2$ is J1, and s is 0.

In a preferred embodiment of formula IA or formula IB, wherein

A1 is ($C_1$-$C_{12}$)alkylene which is methylene, ethylene, propylene, butylene, pentylene or hexylene and A2 is absent or ($C_1$-$C_{12}$)alkylene which is methylene;

B is absent or is selected from the group consisting of ($C_3$-$C_8$)heterocycloalkylene which is piperidinylene, arylene which is phenylene optionally substituted by one ($C_1$-$C_6$)alkoxy which is methoxy;

C is absent or is —O—, —C(O)—; or —N($R_7$)— wherein $R_7$ is selected from methylcarbonyl, methylaminocarbonyl, methoxycarbonyl, benzylcarbonyl, cyclopropanecarbonyl, methylsulfonyl or phenylsulfonyl; or is C1 with $R_7$ selected from hydrogen, fluoro, methyl, ethyl, benzyl optionally substituted by one methyl, methoxy, tri-fluoromethyl, cyanobenzyl, dichlorophenoxy, benzyloxy or morpholinyl and n''' 0, 1 or 2; C2 with $R_7$ hydrogen and n''' 0 or 1; or C4;

D is absent or is ($C_3$-$C_8$)heterocycloalkylene which is piperidinylene;

n is 0, that is to say $R_1$ is hydrogen, or n is 1 and $R_1$ is chloro, fluoro, or bromo, n' is 0 or 1, n" is 0 or 1;

E is absent or is selected from —O— or —$NR_7$—C(O)— with $R_7$ hydrogen, methyl or ethyl;

G is absent or is arylene such as phenylene which is substituted by one or more substituents selected from methyl, methoxy, F, Cl, phenyl and thyenyl; or is heteroarylene such as thienylene;

L is absent or a divalent group selected from —C(O)—, —$CH_2$CO—, —$CH_2CH_2$CO— and —CH=CHCO—;

s is 0 and;

$R_2$ is J1, or s is 1 and R2 is J3 and $R_5$ is methyl or benzyl optionally substituted by hydroxyl;

and pharmaceutically acceptable salts or solvates thereof. The present invention is also directed to a process for the preparation of the compounds of general formula I.

The present invention also provides pharmaceutical compositions of compounds of formula I alone or in combination with or in admixture with one or more pharmaceutically acceptable carriers and/or excipients.

The present invention also provides the use of compounds of formula I for preparing a medicament.

In a further aspect, the invention provides the use of compounds of formula I for the prevention and/or treatment of any broncho-obstructive or inflammatory disease, preferably asthma or chronic bronchitis or chronic obstructive pulmonary disease (COPD).

In a further aspect, the invention provides the use of compounds of formula I for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula I.

The present invention also provides pharmaceutical compositions suitable for administration by inhalation.

Inhalable preparations include inhalable powders, propellant-containing metering aerosols or propellant-free inhalable formulations.

The invention is also directed to a device which may be a single- or multi-dose dry powder inhaler, a metered dose inhaler and a soft mist nebulizer comprising the compounds of formula I.

The invention is also directed to a kit comprising the pharmaceutical compositions of compounds of formula I alone or in combination with or in admixture with one or more pharmaceutically acceptable carriers and/or excipients and a device which may be a single- or multi-dose dry powder inhaler, a metered dose inhaler and a soft mist nebulizer comprising the said combination or admixture.

According to specific embodiments, the present invention provides the compounds reported below.

| No | CHEMICAL NAME |
|---|---|
| 1 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate |
| 2 | (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate |
| 3 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-methoxybenzoyl)-4-phenylpiperidine-4-carboxylate |
| 4 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-chlorobenzoyl)-4-phenylpiperidine-4-carboxylate |
| 5 | (R)-Quinuclidin-3-yl 1-(3,5-dichloro-4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate |
| 6 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-(thiophen-3-yl)benzoyl)-4-phenylpiperidine-4-carboxylate |
| 7 | (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)phenyl)propanoyl)-4-phenylpiperidine-4-carboxylate |
| 8 | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate |
| 9 | (R)-Quinuclidin-3-yl 1-(3-fluoro-4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate |
| 10 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-methylbenzoyl)-4-phenylpiperidine-4-carboxylate |
| 11 | (R)-Quinuclidin-3-yl 1-(2-(3-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate |
| 12 | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)-3-methylphenyl)acetyl)-4-phenylpiperidine-4-carboxylate |
| 13 | (R)-Quinuclidin-3-yl 1-(2-(3-fluoro-4-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate |
| 14 | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)-3-(thiophen-3-yl)phenyl)acetyl)-4-phenylpiperidine-4-carboxylate |
| 15 | (R)-Quinuclidin-3-yl 1-(2-(6-((5-(((R)-2-hydroxy-2-(8-hydroxy-2-oxo-1,2-dihydroquinolin-5-yl)ethyl)amino)pentyl)oxy)-[1,1'-biphenyl]-3-yl)acetyl)-4-phenylpiperidine-4-carboxylate |
| 16 | (R)-Quinuclidin-3-yl 1-(3-(6-((5-(((R)-2-hydroxy-2-(8-hydroxy-2-oxo-1,2-dihydroquinolin-5-yl)ethyl)amino)pentyl)oxy)-[1,1'-biphenyl]-3-yl)propanoyl)-4-phenylpiperidine-4-carboxylate |
| 17 | (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)-3-methylphenyl)propanoyl)-4-phenylpiperidine-4-carboxylate |
| 18 | (R)-Quinuclidin-3-yl 1-((E)-3-(4-((5-(((R)-2-hydroxy-2-(8-hydroxy-2-oxo-1,2-dihydroquinolin-5-yl)ethyl)amino)pentyl)oxy)-3-methylphenyl)acryloyl)-4-phenylpiperidine-4-carboxylate |
| 19 | (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-4-phenylpiperidine-4-carboxylate |

-continued

| No | CHEMICAL NAME |
|---|---|
| 20 | (R)-Quinuclidin-3-yl 1-(4-(2-(((R)-2-hydroxy-2-(8-hydroxy-2-oxo-1,2-dihydroquinolin-5-yl)ethyl)amino)ethyl)benzoyl)-4-phenylpiperidine-4-carboxylate |
| 21 | (R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-4-phenylpiperidine-4-carboxylate |
| 22 | (R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-4-phenylpiperidine-4-carboxylate |
| 23 | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-4-phenylpiperidine-4-carboxylate |
| 24 | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-4-phenylpiperidine-4-carboxylate |
| 25 | (R)-Quinuclidin-3-yl 1-(4-(ethyl(3-(((R)-2-hydroxy-2-(8-hydroxy-2-oxo-1,2-dihydroquinolin-5-yl)ethyl)amino)propyl)carbamoyl)benzoyl)-4-phenylpiperidine-4-carboxylate |
| 26 | (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)oxy)benzoyl)-4-phenylpiperidine-4-carboxylate |
| 27 | (R)-Quinuclidin-3-yl 1-(5-((3-(((R)-2-hydroxy-2-(8-hydroxy-2-oxo-1,2-dihydroquinolin-5-yl)ethyl)amino)propyl)(methyl)carbamoyl)thiophene-2-carbonyl)-4-phenylpiperidine-4-carboxylate |
| 28 | (R)-Quinuclidin-3-yl 1-(5-(benzyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate |
| 29 | (R)-Quinuclidin-3-yl 1-(5-(ethyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate |
| 30 | (R)-Quinuclidin-3-yl 1-(2-(4-(4-(((R)-2-hydroxy-2-(8-hydroxy-2-oxo-1,2-dihydroquinolin-5-yl)ethyl)amino)butoxy)phenyl)acetyl)-4-phenylpiperidine-4-carboxylate |
| 31 | (R)-Quinuclidin-3-yl 1-(3-(4-((((R)-2-hydroxy-2-(8-hydroxy-2-oxo-1,2-dihydroquinolin-5-yl)ethyl)amino)methyl)benzamido)propanoyl)-4-phenylpiperidine-4-carboxylate |
| 32 | (R)-Quinuclidin-3-yl 1-(3-(4-(4-(((R)-2-hydroxy-2-(8-hydroxy-2-oxo-1,2-dihydroquinolin-5-yl)ethyl)amino)butoxy)phenyl)propanoyl)-4-phenylpiperidine-4-carboxylate |
| 33 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(4-methylbenzyl)amino)-2-oxoethyl)phenyl)acetyl)-4-phenylpiperidine-4-carboxylate |
| 34 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(2-methylbenzyl)amino)-2-oxoethyl)phenyl)acetyl)-4-phenylpiperidine-4-carboxylate |
| 35 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-methylbenzyl)amino)-2-oxoethyl)phenyl)acetyl)-4-phenylpiperidine-4-carboxylate |
| 36 | (R)-Quinuclidin-3-yl 1-(2-(4-(2-(benzyl(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 37 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-(trifluoromethyl)benzyl)amino)-2-oxoethyl)phenyl)acetyl)-4-phenylpiperidine-4-carboxylate |
| 38 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-methoxybenzyl)amino)-2-oxoethyl)phenyl)acetyl)-4-phenylpiperidine-4-carboxylate |
| 39 | (R)-Quinuclidin-3-yl 1-(2-(4-(2-((3-cyanobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 40 | (R)-Quinuclidin-3-yl 1-(2-(4-(2-((3-(3,4-dichlorophenoxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 41 | (R)-Quinuclidin-3-yl 1-(2-(4-(2-((3-(benzyloxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 42 | (R)-Quinuclidin-3-yl 1-(2-(4-(2-((3-fluorobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 43 | (R)-Quinuclidin-3-yl 1-(2-(4-(2-((2-(benzyloxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 44 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(2-morpholinobenzyl)amino)-2-oxoethyl)phenyl)acetyl)-4-phenylpiperidine-4-carboxylate |

| No | CHEMICAL NAME |
|---|---|
| 45 | (R)-Quinuclidin-3-yl 1-(2-(4-(2-((2-fluorobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 46 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate |
| 47 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(methyl)amino)-2-oxoethyl)phenyl)acetyl)-4-phenylpiperidine-4-carboxylate |
| 48 | (R)-Quinuclidin-3-yl 4-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate |
| 49 | (R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-4-phenylpiperidine-4-carboxylate |
| 50 | (R)-Quinuclidin-3-yl 4-(4-bromophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate |
| 51 | (R)-Quinuclidin-3-yl 4-(4-chlorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate |
| 52 | (R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate |
| 53 | (R)-Quinuclidin-3-yl 1-(3-(4-((3-(((R)-2-hydroxy-2-(8-hydroxy-2-oxo-1,2-dihydroquinolin-5-yl)ethyl)amino)propyl)(methyl)carbamoyl)phenyl)propanoyl)-4-phenylpiperidine-4-carboxylate |
| 54 | (R)-Quinuclidin-3-yl 1-(3-(4-(benzyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate |
| 55 | (R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-4-phenylpiperidine-4-carboxylate |
| 56 | (R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-4-phenylpiperidine-4-carboxylate |
| 57 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)acetamido)methyl)benzoyl)-4-phenylpiperidine-4-carboxylate |
| 58 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)methylsulfonamido)-methyl)benzoyl)-4-phenylpiperidine-4-carboxylate |
| 59 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)benzamido)methyl)benzoyl)-4-phenylpiperidine-4-carboxylate |
| 60 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)cyclopropanecarboxamido)-methyl)benzoyl)-4-phenylpiperidine-4-carboxylate |
| 61 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)phenylsulfonamido)-methyl)benzoyl)-4-phenylpiperidine-4-carboxylate |
| 62 | (R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)(methoxycarbonyl)amino)-methyl)benzoyl)-4-phenylpiperidine-4-carboxylate |
| 63 | (R)-Quinuclidin-3-yl 1-(4-((1-(4-((((R)-2-hydroxy-2-(8-hydroxy-2-oxo-1,2-dihydroquinolin-5-yl)ethyl)amino)methyl)benzyl)-3-methylureido)methyl)benzoyl)-4-phenylpiperidine-4-carboxylate |
| 64 | (R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)oxy)methyl)benzoyl)-4-phenylpiperidine-4-carboxylate |
| 1A | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate |
| 2A | (R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-3-phenylazetidine-3-carboxylate |
| 3A | (R)-Quinuclidin-3-yl 3-(4-fluorophenyl)-1-(4-((6-(((R)-2-hydroxy-2-oxo-1,2-dihydroquinolin-5-yl)ethyl)amino)hexyl)oxy)benzoyl)azetidine-3-carboxylate |
| 4A | (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate |
| 5A | (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)phenyl)propanoyl)-3-phenylazetidine-3-carboxylate |

-continued

| No | CHEMICAL NAME |
|---|---|
| 6A | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)phenyl)acetyl)-3-phenylazetidine-3-carboxylate |
| 7A | (R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-3-phenylazetidine-3-carboxylate |
| 8A | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-3-phenylazetidine-3-carboxylate |
| 9A | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-3-phenylazetidine-3-carboxylate |
| 10A | (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-3-phenylazetidine-3-carboxylate |
| 11A | (R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-3-phenylazetidine-3-carboxylate |
| 12A | (R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-3-phenylazetidine-3-carboxylate |
| 13A | (R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-3-phenylazetidine-3 -carboxylate |
| 14A | (R)-Quinuclidin-3-yl 1-(2-(4-(2-(benzyl(3-(((R)-2-hydroxy-2-(8-hydroxy-2-oxo-1,2-dihydroquinolin-5-yl)ethyl)amino)propyl)amino)-2-oxoethyl)phenyl)acetyl)-3-phenylazetidine-3-carboxylate |
| 15A | (R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-3-phenylazetidine-3-carboxylate |
| 16A | (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)carbamoyl)benzoyl)-3-phenylazetidine-3-carboxylate |
| 17A | (R)-Quinuclidin-3-yl 1-(4-((4-((((R)-2-hydroxy-2-(8-hydroxy-2-oxo-1,2-dihydroquinolin-5-yl)ethyl)amino)methyl)benzamido)methyl)benzoyl)-3-phenylazetidine-3-carboxylate |
| 18A | (R)-Quinuclidin-3-yl 1-(4-(4-(((R)-2-hydroxy-2-(8-hydroxy-2-oxo-1,2-dihydroquinolin-5-yl)ethyl)amino)butoxy)benzoyl)-3-phenylazetidine-3-carboxylate |
| 19A | (R)-Quinuclidin-3-yl 1-(4-((4-((3-(((R)-2-hydroxy-2-(8-hydroxy-2-oxo-1,2-dihydroquinolin-5-yl)ethyl)amino)propyl)carbamoyl)benzyl)oxy)benzoyl)-3-phenylazetidine-3-carboxylate |
| 20A | (R)-Quinuclidin-3-yl 1-(4-((4-((((R)-2-hydroxy-2-(8-hydroxy-2-oxo-1,2-dihydroquinolin-5-yl)ethyl)amino)methyl)-3-methoxybenzyl)carbamoyl)benzoyl)-3-phenylazetidine-3-carboxylate |

The compounds of the invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given other process conditions can also be used unless otherwise stated. While the optimum reaction conditions may vary depending on the particular reactants or solvent used, such conditions can be readily determined by one skilled in the art by routine optimization procedures.

Compounds of general formula I may be prepared according to the following synthetic Scheme 1a and Scheme 1b.

Scheme 1a
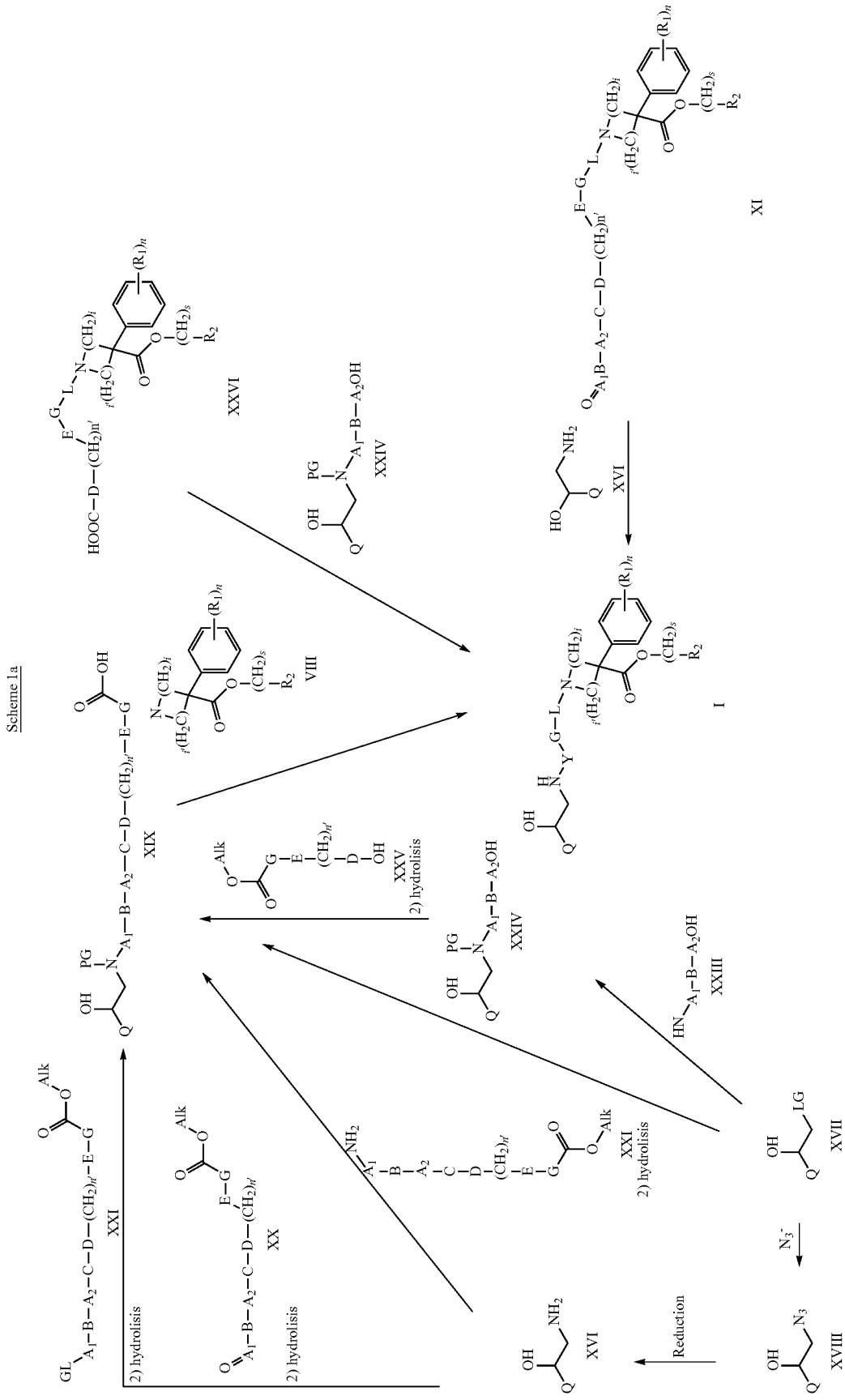

Scheme 1b
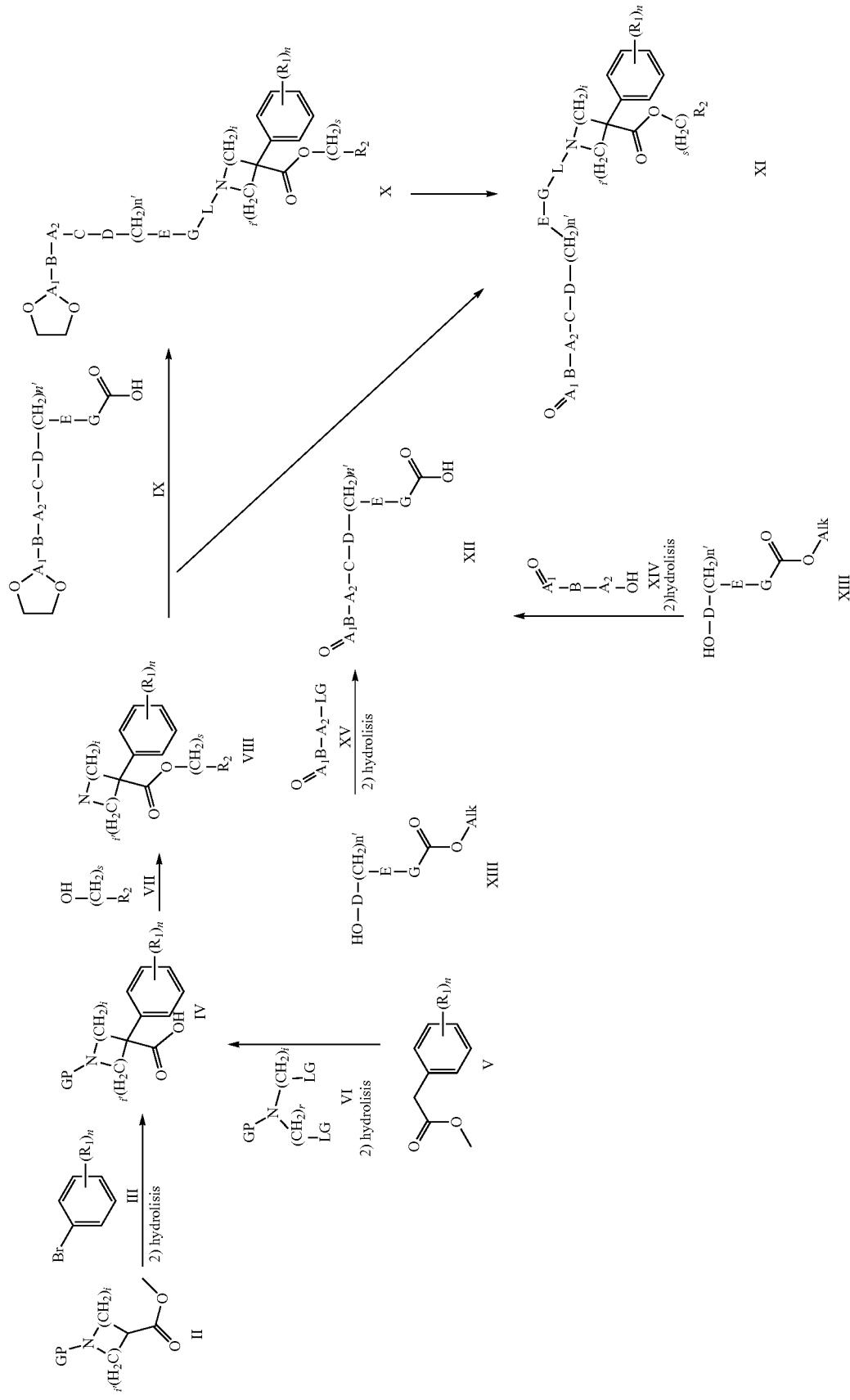

General Procedure for the Preparation of Compounds of Formula I

Compounds of general formula I are compounds in which Y is a divalent group of formula Y1 or Y2. Although groups Y1 and Y2 are different, the approach to be considered for the synthesis of compounds of formula I in which Y is Y1 or Y2 is similar and mainly depends on the functional group present in the linker Y. It is evident for a person skilled in the art that the following synthesis described for Y2 can be extended with minor modification to Y1. In the schemes above Q is

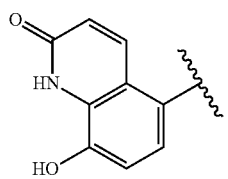 [SMILES: *c1ccc(O)c2[nH]c(=O)ccc12]

Compounds of general formula I can be prepared for example according to scheme 1a, by reaction of a compound of general formula XI with a compound of general formula XVI. This reductive amination reaction can be performed following several different protocols described in the literature and well known for those skilled in the art. For example, it can be performed in solvent such as methanol, ethanol, tetrahydrofuran (THF) or dichloromethane (DCM) using a reducing agent such as $NaBH_4$, $NaCNBH_3$ or $NaB(AcO)_3H$. It could be useful to perform the imine before adding the reducing agent. The reaction proceeds smoothly at room temperature (RT) over 1 to 12 hours.

The compound of general formula XI can be prepared according to scheme 1 b. The intermediate of general formula X represents a compound wherein A1 is alkylene substituted with oxo, leading to an aldehyde or ketone protected as cyclic acetal. The cyclic acetal-protecting group (PG) can be removed leading to the compound of general formula XI.

The intermediate of general formula X can be easily prepared by reaction of a compound of general formula VIII with a compound of formula IX under the well-known condensation conditions for the preparation of amides. The reaction occurs smoothly in an aprotic polar solvent such as ACN, THF or DMF at room or higher temperature in the presence of a condensing agent such as for example EDC, DCC, HATU.

Alternatively, a compound of formula XI can be prepared, using same reaction conditions described above for the preparation of compound of formula X, reacting a compound of formula VIII with an aldehyde of formula XII.

Compound of formula XII and IX can be prepared using similar approach, as IX is XII protected as cyclic acetal. Their preparation can be accomplished using a wide variety of approaches that strongly depend on the nature of functional groups present. An example that allows the preparation of compound of formula XII wherein C is —O-involves the reaction of a compound of formula XIII with a compound of formula XIV. The reaction can be performed for example under the well-known Mitsunobu reaction condition in which an alkylic alcohol is reacted with a phenol derivative in an aprotic solvent such as, but not limited to, THF, in the presence of DIAD (or DEAD) and an organic phosphine, such as for example triphenyl phosphine. The reaction is normally performed at low temperature and completes in time ranging from 1 h to few days at room temperature. Alternatively, the hydroxyl moiety of the alkylic alcohol can be converted into a suitable leaving group such us for example chloride, bromide, mesylate or tosylate, just to mention the most common examples, leading to a compound of general formula XV. This compound can be easily reacted under alkylation of phenols with compound XIII. The reaction is normally performed in polar solvents such as DMF, THF, CAN or DMSO and often requires temperature higher than room temperature to complete over a period of time ranging from 0.5 to 48 hours. Both approaches lead to esters derivatives that are converted into XII under acidic or basic conditions.

A compound of formula VIII cab be obtained by esterification of a compound of formula IV with a compound of formula HO—$(CH_2)_s$—$R_2$ under the well-known condensation conditions for the preparation of esters. The reaction occurs smoothly in an aprotic polar solvent such as DCM, THF or DMF at room or higher temperature in the presence of a condensing agent such as for example EDC, DCC, HATU. Alternatively the acid IV can be converted into the corresponding acyl chloride (e.g. with $COCl_2$ in DMC) or imidazolide (with CDI in DCM or DMF) and then treated with HO—$(CH_2)_s$—$R_2$. The removal of the protecting group present on the nitrogen atom depends on the protecting group used and can be found in the literature as described above.

Compound of formula IV are commercially available or it can be prepared with a method that depends on the dimension of the nitrogen containing ring. For example, the synthesis of compound of formula IV in which i=i'=1 involves the reaction of a compound of formula II with an aryl bromide of formula III. The reaction occurs in an aprotic solvent such as for example toluene, in the presence of a strong base such as for example, but not limited to, LiHMDS and a catalytic amount of palladium catalyst such as $Pd_2(dba)_3$ and an organic phosphine such as $Bu_3P$ stabilized as $HBF_4$ salt. The obtained compound is converted into IV by mean of a hydrolysis of the ester moiety.

The synthesis of compound of formula IV wherein i=i'=2 can be accomplished using the same reaction described above for compound wherein i=i'=1 or reacting a compound of formula V with a bifunctional reactant of formula VI. The reaction requires treating a compound of formula V with a base such as for example NaH in a solvent such as DMF or toluene. The reaction may require temperature higher room temperature up to 100° C. and complete in 1 to 24 hours. A valid alternative is to perform the reaction on a compound of formula V in which the ester moiety is substituted with a cyano group, more stable in the presence of bases. In both cases the product obtained after reaction with compound of formula VI wherein i=i'=2 has to be hydrolysed to convert the ester (or the cyano) into the carboxylic acid moiety present in compound of formula IV.

In another embodiment of the present invention, compound of formula I can be prepared by reaction of compound of formula XIX with a compound of formula VIII (scheme 1a). The reaction is performed under the known reaction condition for the formation of amides as described above for the preparation of a compound of formula X.

Intermediate of formula XIX can be synthesized using different synthetic approaches. For example it can be prepared reacting compound of formula XVII with an intermediate of formula XXII that represents the linker connecting the two heads of the molecule. The leaving group LG in compound XVII, usually chloride or bromine, is easily substituted by the nucleophilic moiety $NH_2$ in XXII. The reaction is performed under condition similar to those described for the reaction of compound XIII with compound XV to give compound XII, and leads to the alkyl ester derivatives of XIX. The ester is easily hydrolyzed under basic or acid aqueous conditions leading to the desired XIX. The protection of the reactive NH (and OH if needed) has to be considered to limit the formation of by-products.

Compound XIX can be also synthesized using a different approach, reacting first a compound of formula XVII with a compound of formula XXIII under the nucleophilic substitution reaction condition leading to a compound of formula XXIV that, by mean of reaction with a compound of formula XXV followed by hydrolysis of the ester, gives compound of formula XIX. Reaction of XXIV with XXV can be performed under the same conditions described for the reaction of compound XIII with XIV.

Compound of formula XIX can also be prepared reacting compound of formula XVI with a compound of formula XXI under nucleophilic substitution reaction conditions described above. Also in this case the first step provides the ester that is hydrolyzed, as previously described, to give the required compound XIX.

Compound of formula XVI can be also converted into XIX by mean of reductive amination condition with compound of formula XX, followed, as clearly understood by a person skilled in the art, by hydrolysis of the ester. The reaction is performed as described for the conversion of compound XI into compound of formula I.

Compounds of general formula XVI can be obtained by simple reduction of the azide of formula XVIII. The reaction can be accomplished by mean of a catalytic hydrogenation in the presence Palladium catalyst. The reaction occurs, in polar solvent such as methanol or ethanol, under hydrogen atmosphere or under hydrogen transfer conditions, using for example 1,4-cyclohexadiene or 1-methyl1,4-cyclohexadiene as source of hydrogen. The reaction proceeds at room temperature. In case it is performed under hydrogen transfer conditions higher temperature can be required. Alternatively, the conversion can be accomplished under Staudinger reaction conditions, reacting the azide for example with triphenyl phosphine, and then with water to hydrolase the formed phosphazene.

The azide XVIII can be easily prepared from XVII, in most of the case featuring the OH protected as silyl ether, by the well-known nucleophilic substitution of alkyl bromide with alkaline azide. The reaction proceeds at a temperature ranging from 50 to 80° C. and in a polar solvent such as for example DMF of NMP and can be accelerated by the presence of alkaline iodide.

Compound of formula XXIV can be also alternatively used for the preparation of compound of formula I by reaction with compound of formula XXVI.

The synthesis of compounds of general formula I may require the protection of potential reactive functionalities in addition to those methods already described (e.g. for intermediate X). In such a case, examples of compatible protecting groups (PG) and their particular methods of protection and deprotection are described in "Protecting groups in organic Synthesis" by T. W. Green and P. Wutz (Wiley-Interscience publication, 1999), which is incorporated herein by reference in its entirety.

It is evident for a person skilled in the art that compounds IX, XII, XX, XXI and XXII represent a linker for the connection of two portions of the molecule. The variety of functional groups that could be present in these linkers is broad. Some possible examples of synthesis have been provided above, but these are just representative of possible approaches and they have not to be considered limiting the scope of the present invention. The synthesis of the linker and the sequence of synthetic steps depend on the functional groups present and on the availability of suitable reagents.

It is apparent for those skilled in the art that compounds of general formula I wherein R2 is J1, J2 or J5 contain two stereogenic centers, as indicated below (wherein e.g. J=J1) with the symbol *. This means that the structure of formula I is characterized by different stereoisomers.

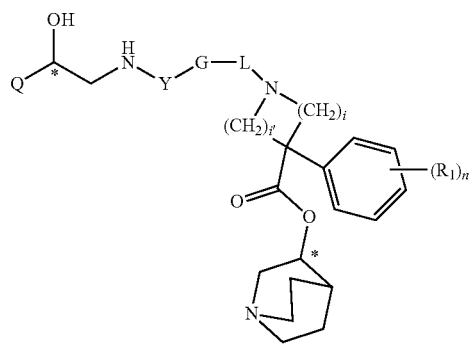

Each diastereoisomer can be obtained theoretically by chromatographic separation of the mixture obtained by reacting racemic mixtures of the required intermediates. It is clear that this approach it is not convenient and that it can be used only for the separation of mixtures containing few diastereoisomers.

In a more convenient approach, the synthesis of each single stereoisomer can be accomplished using, in the reactions described above, only enantiomerically pure intermediates.

The enantiomerically pure alcohol required for the preparation of compounds of general formula I wherein R2 is J1, J2 or J5 are commercially available. The preparation of single enantiomerically pure compounds of general formula XVII wherein LG is bromine is described in WO2005/092861, which is incorporated herein by reference in its entirety (cited in WO2007/107228, which is incorporated herein by reference in its entirety).

Other features of the invention will become apparent in the course of the following descriptions of exemplary embodiments which are given for illustration of the invention and are not intended to be limiting thereof.

EXAMPLES

The intermediate compounds for the synthesis of final compounds of general formula (I) were obtained through the preparations described below.

Preparation of Intermediates and Examples

Chemical Names of the compounds were generated with Structure To Name Enterprise 10.0 Cambridge Software.

Abbreviations

DCC=N,N'-dicyclohexylcarbodiimide;
DIAD=diisopropyl azodicarboxylate;
DIPEA=diisopropylethylamine;
HOBt=hydroxybenzotriazole;
HATU=(dDimethylamino)-N,N-dimethyl(3H-[1,2,3]triazolo[4,5-b]pyridin-3-yloxy)methaniminium hexafluorophosphate;

EDC=1-ethyl-3-(3-dimethylaminopropyl) carbodiimide hydrochloride;
DMAP=4-dimethylaminopyridine;
DMF=dimethylformamide;
EtOAc=Ethyl acetate;
NMP=N-methyl-2-pyrrolidone;
RT=room temperature;
THF=tetrahydrofuran;
DCM=dichloromethane;
LiHMDS=1Lithium bis(trimethylsilyl)amide;
p-TSA-$H_2$O=p-toluenesulphonic acid hydrate;
TFA=trifluoroacetic acid;
LC-MS=liquid chromatography/mass spectrometry;
HPLC=high pressure liquid chromatography;
ESI=electrospray ionization;
APCI=atmospheric pressure chemical ionization;
ESCI=combined ESI-APCI ionization source;
ELS=evaporative light scattering.

General Experimental Details

NMR Characterization $^1$H-NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift. Chemical shifts are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

LC/UV/MS Analytical Methods

LC/MS retention times are estimated to be affected by an experimental error of ±0.5 min.

Method 1
10 cm_Formic_ACE 3 C18 AR_HPLC_CH3CN
HPLC Setup
Solvents:—Acetonitrile (Far UV grade) with 0.1% (V/V) formic acid
Water (High purity via PureLab Ultra unit) with 0.1% formic acid
Column:—Hichrom ACE 3 C18-AR mixed mode column 100×4.6 mm
Flow Rate:—1 ml/min
Gradient:

| Time (min) | % A | % B |
|---|---|---|
| 0.00 | 98 | 2 |
| 3 | 98 | 2 |
| 12 | 0 | 100 |
| 15.4 | 0 | 100 |
| 15.5 | 98 | 2 |
| 17 | 98 | 2 |

Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref. 450 nm, Band Width 100 nm)

Method 2
15 cm_Formic_Ascentic_HPLC_CH3CN
HPLC Setup
Solvents:—Acetonitrile (Far UV grade) with 0.1% (V/V) formic acid
Water (High purity via PureLab Ultra unit) with 0.1% formic acid
Column:—Supelco, Ascentis® Express C18 or Hichrom Halo C18, 2.7 μm C18, 150×4.6 mm.
Flow Rate:—1 ml/min
Gradient:

| Time (min) | % A | % B |
|---|---|---|
| 0.00 | 96 | 4 |
| 3 | 96 | 4 |
| 9 | 0 | 100 |
| 13.6 | 0 | 100 |
| 13.7 | 96 | 4 |
| 15 | 96 | 4 |

Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref. 450 nm, Band Width 100 nm)

Method 3
10 cm_ESCI_Formic_MeCN
HPLC Setup
Solvents:—Acetonitrile (Far UV grade) with 0.1% (V/V) formic acid
Water (High purity via PureLab Option unit) with 0.1% formic acid
Column:—Phenomenex Luna 5μ C18 (2), 100×4.6 mm. (Plus guard cartridge)
Flow Rate:—2 ml/min
Gradient:

| Time (min) | % A | % B |
|---|---|---|
| 0.00 | 95 | 5 |
| 3.5 | 5 | 95 |
| 5.5 | 5 | 95 |
| 5.6 | 95 | 5 |
| 6.5 | 95 | 5 |

Injections 2-7 ul (concentration ~0.2-1 mg/ml).
UV detection via HP or Waters DAD

| Start Range (nm) | 210 | End Range (nm) | 400 | Range interval (nm) | 4.0 |
|---|---|---|---|---|---|

Other wavelength traces are extracted from the DAD data.
Optional ELS detection using Polymer Labs ELS-1000.
MS detection: Micromass ZQ, single quadrupole LC-MS or Quattro Micro LC-MS-MS.
Flow splitter gives approximately 300 ul/min to mass spec
Scan range for MS Data (m/z)

| Start (m/z) | 100 |
|---|---|
| End (m/z) | 650 or 1500 when required |

With +ve/−ve switching
Ionization is routinely ESCI an option which gives both ESI and APCI data from a single run.

Typical ESI voltages and temperatures are:

| Source 120-150 C. | 3.5 KV capillary | 25 V cone |
|---|---|---|

Typical APCI voltages and temperatures are:

| Source 140-160 C. | 17 uA corona | 25 V cone |
|---|---|---|

Method 4
10 cm_Formic_AQ
UPLC Setup
Solvents:—B Acetonitrile (Far UV grade) with 0.1% (V/V) formic acid
A Water (High purity via PureLab Option unit) with 0.1% formic acid
Column:—Acquity UPLC HSS C18 1.8 um 100×2.1 mm. (Plus guard cartridge)
Flow Rate:—0.5 ml/min
Gradient:

| Time (min) | % A | % B |
|---|---|---|
| 0.00 | 95 | 5 |
| 1.2 | 95 | 5 |
| 3.5 | 0 | 100 |
| 4.9 | 0 | 100 |
| 5 | 95 | 5 |
| 6 | 95 | 5 |

Injections 0.5-2 ul
UV detection via Waters DAD

| Start Range (nm) | 210 | End Range (nm) | 400 | Resolution (nm) | 1.2 |
|---|---|---|---|---|---|

MS detection: Waters SQD2, single quadrapole UPLC-MS
Scan range for MS Data (m/z)

| Start (m/z) | 100 |
|---|---|
| End (m/z) | 700 or 1500 when required |

With +ve/−ve switching
Ionisation is ESI.
ESI voltages and temperatures are:

| Source 150 C. | 3.5 KV capillary | 25 V cone |
|---|---|---|

Preparative Reverse-Phase HPLC Conditions

Post-synthesis all compounds were purified using reverse phase HPLC. The column used for the preparative purification of the compounds was a Waters Sunfire OBD, Phenomenex Luna Phenyl Hexyl or Waters Xbridge Phenyl at 10 um 19×150. All compounds were screen analytically prior to the purification step. Each sample was run under both acidic and basic conditions. As it is common practice, the best method and conditions to be used for the purification was chosen depending on where the desired product elutes and the separation achieved.

The modifier used in the purification determined the final salt form obtained (e.g. formate or trifluoroacetate).

Where the preparation of starting materials is not described, these are commercially available, known in the literature, or readily obtainable by those skilled in the art using standard procedures.

Many of the compounds described in the following examples have been prepared from stereochemically pure starting materials, for example 95% ee.

The stereochemistry of the compounds in the Examples, where indicated, has been assigned on the assumption that absolute configuration at resolved stereogenic centers of starting materials is maintained throughout any subsequent reaction conditions.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

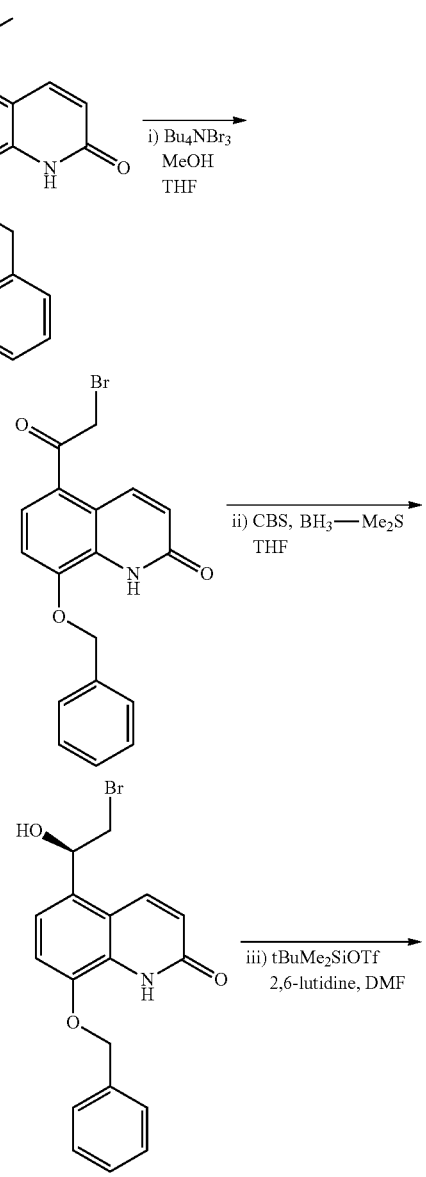

33
-continued

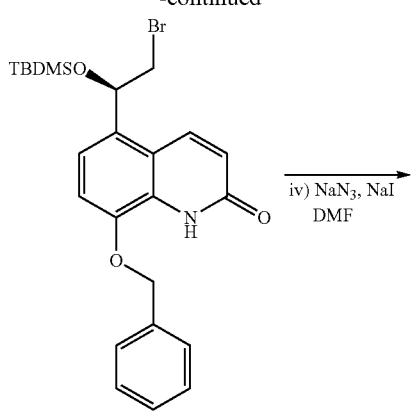

iv) NaN₃, NaI
DMF

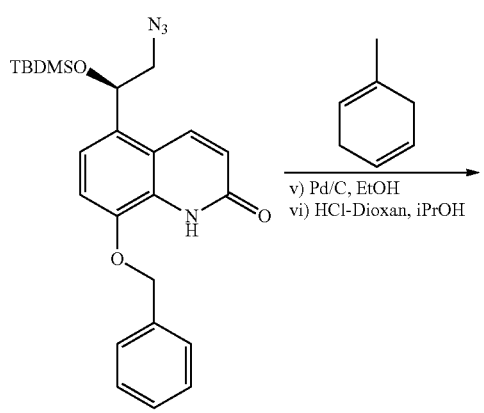

v) Pd/C, EtOH
vi) HCl-Dioxan, iPrOH

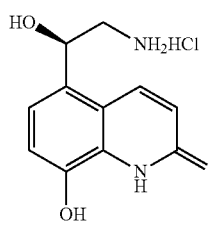

Intermediate 1. (R)-5-(2-Amino-1-hydroxyethyl)-8-hydroxyquinolin-2(1H)-one hydrochloride

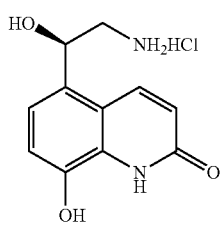

34

Step 1. 8-(Benzyloxy)-5-(2-bromoacetyl)quinolin-2(1H)-one

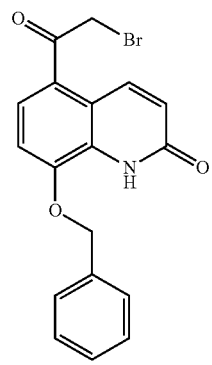 [SMILES: O=C(CBr)c1ccc(OCc2ccccc2)c2[nH]c(=O)ccc12]

To a suspension of 5-acetyl-8-(benzyloxy)quinolin-2(1H)-one (19.4 g, 66.4 mmol) in anhydrous THF (240 mL) and anhydrous methanol (165 mL) was added a solution of tetra-n-butylammonium tribromide (54.5 g, 113.0 mmol) in anhydrous THF (130 mL) drop-wise over 1.5 hours. The resulting solution was stirred at room temperature overnight before concentrating under reduced pressure without heating. The residue was re-dissolved in methanol (200 mL). Saturated aqueous ammonium chloride solution (390 mL) was added with ice-cooling. The resulting suspension was filtered and the solid washed with water and air-dried under vacuum. The solid was suspended in DCM and methanol (1:1 v/v, 100 mL) for 90 minutes. The solid was collected by filtration, washed with DCM and air-dried to afford the title compound (18.0 g, 73%).

$^1$H NMR (400 MHz, DMSO-$d_6$): δ 11.07 (s, 1H), 8.51 (d, J=10.0 Hz, 1H), 7.94-7.83 (m, 1H), 7.60 (d, J=7.5 Hz, 2H), 7.44-7.27 (m, 4H), 6.79-6.65 (m, 1H), 5.53-5.39 (s, 2H), 4.93 (s, 2H)

Step 2. (R)-8-(Benzyloxy)-5-(2-bromo-1-hydroxyethyl)quinolin-2(1H)-one

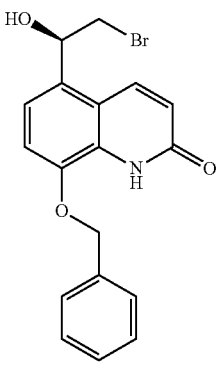 [SMILES: O=c1ccc2c([C@@H](O)CBr)ccc(OCc3ccccc3)c2[nH]1]

8-(Benzyloxy)-5-(2-bromoacetyl)quinolin-2(1H)-one (26.0 g, 69.9 mmol) and (R)-3,3-diphenyl-1-methyltetrahydro-3H-pyrrolo[1,2-c][1,3,2]oxazaborole (21.3 g, 76.8 mmol) were azeotroped with toluene (×3) then suspended in anhydrous THF (400 mL) under an atmosphere of nitrogen. The suspension was cooled to −20° C. (external temperature) and borane dimethyl sulfide complex solution (45.4 mL, 90.8 mmol, 2.0 M solution in THF) was added by syringe pump over 3 hours. After complete addition the reaction mixture was stirred for one hour before quenching with methanol (25 mL). The reaction was warmed to room temperature over 20 minutes. The mixture was concentrated under reduced pressure and the residue was suspended in aqueous hydrochloric acid (500 mL, 1 M solution) and stirred at room temperature for 18 hours. After this time the solid was collected by filtration and washed with water (3×100 mL). The solid was partially dissolved in ethyl acetate and heated at reflux for 2 hours. The remaining solid was removed by hot filtration and the filtrate was evaporated to afford the title compound. The solid collected from the hot ethyl acetate was again partially dissolved in ethyl acetate and heated at reflux for 2 hours then filtered to give filtrate containing pure product. This process was repeated four more times. The combined solid was recrystallised from ethyl acetate and petroleum ether to afford the title compound (20.0 g, 76%).

$^1$H NMR (400 MHz, DMSO-d$_6$): δ 10.68 (s, 1H), 8.19 (d, J=9.9 Hz, 1H), 7.58 (d, J=7.5 Hz, 2H), 7.41-7.36 (m, 2H), 7.34-7.29 (m, 1H), 7.23-7.19 (m, 2H), 6.57 (d, J=9.8 Hz, 1H), 5.94 (d, J=4.7 Hz, 1H), 5.31 (s, 2H); 5.25-5.19 (m, 1H), 3.71-3.58 (m, 2H).

Step 3. (R)-8-(Benzyloxy)-5-(2-bromo-1-((tert-butyldimethylsilyl)oxy)ethyl)quinolin-2(1H)-one

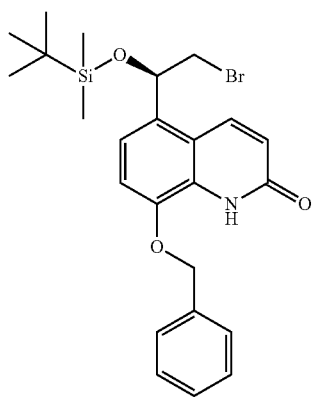 [SMILES: CC(C)(C)[Si](C)(C)O[C@@H](CBr)c1ccc(OCc2ccccc2)c2[nH]c(=O)ccc12]

2,6-Lutidine (6.9 mL, 59.5 mmol) was added to a solution of (R)-8-(benzyloxy)-5-(2-bromo-1-hydroxyethyl)quinolin-2(1H)-one (10.1 g, 27.0 mmol) in DCM (100 mL) at 0° C. The reaction mixture was stirred for 5 minutes then tert-butyldimethylsilyl trifluoromethanesulfonate (13.0 mL, 56.8 mmol) was added dropwise over 15 minutes. The mixture was stirred at 0° C. for 30 minutes, followed by room temperature overnight. After this time the reaction was quenched with saturated aqueous sodium bicarbonate solution and extracted with DCM (×3). The combined organic extracts were dried (magnesium sulfate), filtered and concentrated under reduced pressure. Iso-hexane (500 mL) was added to the crude material and the resulting solid collected by filtration. The solid was recrystallised from ethyl acetate and petroleum ether (40:60) to afford the title compound (11.3 g, 85%).

$^1$H NMR (400 MHz, CDCl$_3$): δ 9.19 (s, 1H), 8.23 (dd, J=9.9, 4.4 Hz, 1H), 7.43 (d, J=4.6 Hz, 5H), 7.17 (dd, J=8.3, 4.5 Hz, 1H), 7.03 (dd, J=8.2, 4.4 Hz, 1H), 6.71 (dd, J=9.9, 3.7 Hz, 1H), 5.18 (d, J=4.5 Hz, 3H), 3.63-3.56 (m, 1H), 3.49 (dd, J=10.4, 4.8 Hz, 1H), 0.88 (t, J=4.4 Hz, 9H), 0.14 (d, J=4.4 Hz, 3H), −0.11 (d, J=4.4 Hz, 3H).

Step 4. R)-5-(2-Azido-1-((tert-butyldimethylsilyl)oxy)ethyl)-8-(benzyloxy)quinolin-2(1H)-one

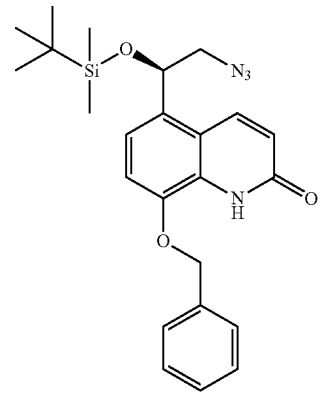 [SMILES: CC(C)(C)[Si](C)(C)O[C@@H](CN=[N+]=[N-])c1ccc(OCc2ccccc2)c2[nH]c(=O)ccc12]

(R)-8-(Benzyloxy)-5-(2-bromo-1-((tert-butyldimethylsilyl)oxy)ethyl)-quinolin-2(1H)-one (10.0 g, 20.5 mmol) was dissolved in DMF (180 mL) and water (20 mL). Sodium iodide (3.39 g, 22.6 mmol) and sodium azide (1.47 g, 22.6 mmol) were added sequentially. The reaction mixture was stirred at RT until all the solid was in solution. The solution was heated at 80° C. for 40 hours then cooled to RT and diluted with ethyl acetate (300 mL). The mixture was washed with water, brine (×2) and the organic extract was dried (magnesium sulfate), filtered and concentrated under reduced pressure. The crude residue was triturated with iso-hexane to afford the desired compound (8.16 g, 88%). Used without further purification in the next step.

$^1$H NMR (400 MHz, CDCl$_3$): δ 9.19 (s, 1H), 8.18 (d, J=9.9 Hz, 1H), 7.45-7.36 (m, 5H), 7.20 (d, J=8.3 Hz, 1H), 7.04 (d, J=8.3 Hz, 1H), 6.70 (dd, J=9.9, 2.2 Hz, 1H), 5.19-5.13 (m, 3H), 3.48 (dd, J=12.7, 8.1 Hz, 1H), 3.26 (dd, J=12.7, 3.8 Hz, 1H), 0.89 (s, 9H), 0.14 (s, 3H), −0.11 (s, 3H).

Step 5. (R)-5-(2-Amino-1-hydroxyethyl)-8-hydroxyquinolin-2(1H)-one hydrochloride

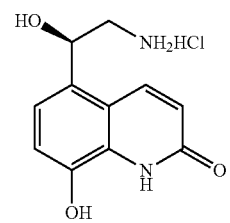

To a solution of (R)-5-(2-azido-1-((tert-butyldimethylsilyl)oxy)ethyl)-8-(benzyloxy)quinolin-2(1H)-one (4.50 g, 10.0 mmol) in ethanol (50 mL) was added 10% palladium on charcoal (4.50 g) followed by 1-methyl-1,4-cyclohexadiene (11.0 mL, 97.9 mmol). The reaction was warmed to 60° C. and then stirred at 60° C. for 2 hours. The reaction mixture was allowed to cool and filtered through a pad of celite. The filtercake was washed with further ethanol and the filtrate was evaporated at reduced pressure. The residue was evaporated from iso-propanol (×2) and dissolved in iso-propanol (30 mL). HCl-dioxane (4M, 50 mL, 200 mmol) was added and the reaction mixture stirred at room temperature for 18 hours. The resultant suspension was filtered, the filtercake washed with ether and the solid dried under vacuum in the presence of $P_2O_5$ to afford the title compound (1.65 g, 62%).

$^1$H NMR (400 MHz, MeOD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

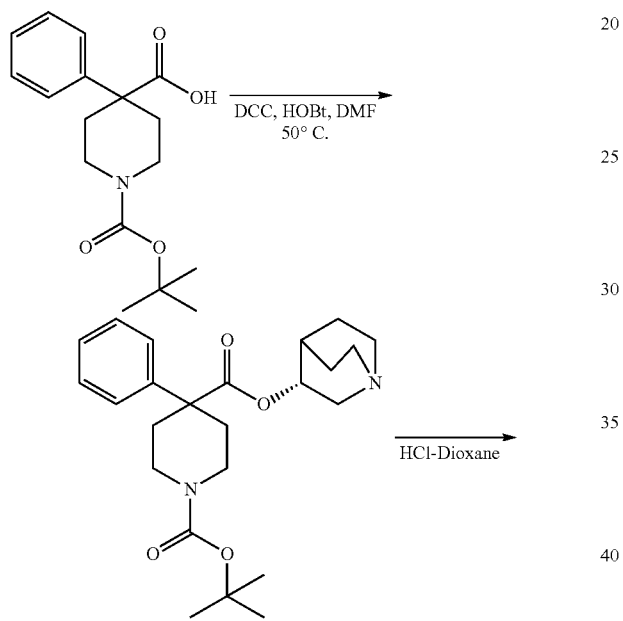

Intermediate 2. (R)-Quinuclidin-3-yl 4-phenylpiperidine-4-carboxylate dihydrochloride

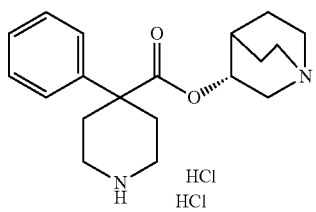 [SMILES: O=C(O[C@H]1CN2CCC1CC2)C1(c2ccccc2)CCNCC1 ; Cl ; Cl]

Step 1. (R)-1-Tert-butyl 4-quinuclidin-3-yl 4-phenylpiperidine-1,4-dicarboxylate

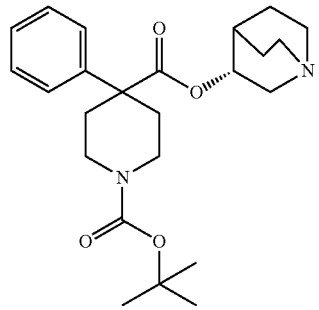 [SMILES: CC(C)(C)OC(=O)N1CCC(C(=O)O[C@H]2CN3CCC2CC3)(c2ccccc2)CC1]

To a solution of 1-(tert-butoxycarbonyl)-4-phenylpiperidine-4-carboxylic acid (10.0 g, 32.8 mmol) in DMF (50 mL) was added N,N-dicyclohexylcarbodiimide (8.1 g, 39.3 mmol), hydroxybenzotriazole (5.31 g, 39.3 mmol) and (R)-3-hydroxyquinuclidine (8.1 g, 39.3 mmol). The reaction mixture was heated at 50° C. for 18 hours. The reaction mixture was filtered through a pad of celite and the filter cake washed with DMF. The filtrate was diluted with ethyl acetate and washed with 2M aqueous sodium carbonate and brine (×3). The organic phase was dried over magnesium sulfate, filtered and the filtrate concentrated under reduced pressure to afford the title compound (18.78 g, >100%). The material was used without further purification.

$^1$H NMR (400 MHz, DMSO-$d_6$); δ 7.42-7.35 (m, 4H), 7.30-7.26 (m, 1H), 4.71-4.66 (m, 1H), 3.84-3.74 (m, 2H), 3.00 (ddd, J=2.0, 8.1, 14.5 Hz, 2H), 2.68-2.53 (m, 3H), 2.49-2.42 (m, 4H), 2.28 (d, J=14.6 Hz, 1H), 1.86-1.75 (m, 4H), 1.57-1.42 (m, 1H), 1.40 (s, 9H), 1.37-1.21 (m, 2H).

Step 2. (R)-Quinuclidin-3-yl 4-phenylpiperidine-4-carboxylate bis-hydrochloride

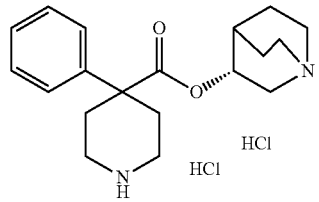 [SMILES: O=C(O[C@H]1CN2CCC1CC2)C1(c2ccccc2)CCNCC1 ; Cl ; Cl]

A solution of HCl-dioxane (4M, 100 mL) was added to (R)-1-tert-butyl 4-quinuclidin-3-yl 4-phenylpiperidine-1,4-dicarboxylate and the resultant mixture stirred at room temperature for 18 hours. The solvent was concentrated under reduced pressure to afford the title compound (14.80 g, >100%).

$^1$H NMR (400 MHz, DMSO-$d_6$); δ 10.83 (s, 1H), 9.30 (d, J=8.0 Hz, 1H), 9.21-9.21 (m, 1H), 7.47-7.40 (m, 4H), 7.36-7.33 (m, 1H), 5.05-5.00 (m, 1H), 3.20-2.91 (m, 7H), 2.73-2.60 (m, 1H), 2.33-2.14 (m, 2H), 2.10-2.09 (m, 1H), 1.87-1.68 (m, 3H), 1.64-1.44 (m, 3H), 1.30-0.99 (m, 2H).

The following intermediates were prepared in the same fashion.

| Intermediate No | Structure | NMR |
|---|---|---|
| 3 | 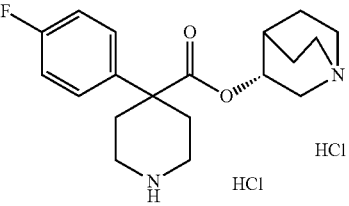 [SMILES: O=C(O[C@H]1CN2CCC1CC2)C1(c2ccc(F)cc2)CCNCC1 ; Cl ; Cl] | (400 MHz, DMSO-d$_6$); δ 10.20 (s, 1H), 8.90 (s, 1H), 7.70 (d, J = 1.1 Hz, 1H), 7.54-7.49 (m, 2H), 7.26 (dd, J = 8.8, 8.8 Hz, 2H), 5.05-5.00 (m, 1H), 3.20-2.91 (m, 7H), 2.73-2.60 (m, 1H), 2.33-2.14 (m, 2H), 2.10-2.09 (m, 1H), 1.87-1.68 (m, 3H), 1.64-1.44 (m, 3H), 1.30-0.99 (m, 2H). |
| 4 | 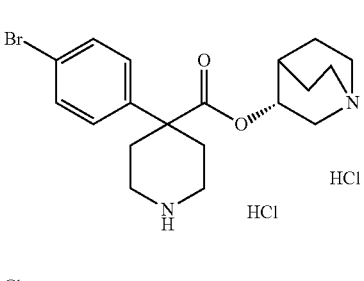 | (400 MHz, DMSO-d$_6$); δ 10.20 (s, 1H), 8.90 (s, 1H), 7.70 (d, J = 1.1 Hz, 1H), 7.68 (2H, d, J = 8.8 Hz), 7.48 (2H, d, J = 8.7 Hz), 5.05-5.00 (m, 1H), 3.20-2.91 (m, 7H), 2.73-2.60 (m, 1H), 2.33-2.14 (m, 2H), 2.10-2.09 (m, 1H), 1.87-1.68 (m, 3H), 1.64-1.44 (m, 3H), 1.30-0.99 (m, 2H). |
| 5 | 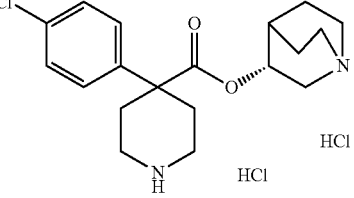 | (400 MHz, DMSO-d$_6$); δ 10.20 (s, 1H), 8.90 (s, 1H), 7.70 (d, J = 1.1 Hz, 1H), 7.49 (s, 4H), 5.05-5.00 (m, 1H), 3.20-2.91 (m, 7H), 2.73-2.60 (m, 1H), 2.33-2.14 (m, 2H), 2.10-2.09 (m, 1H), 1.87-1.68 (m, 3H), 1.64-1.44 (m, 3H), 1.30-0.99 (m, 2H). |
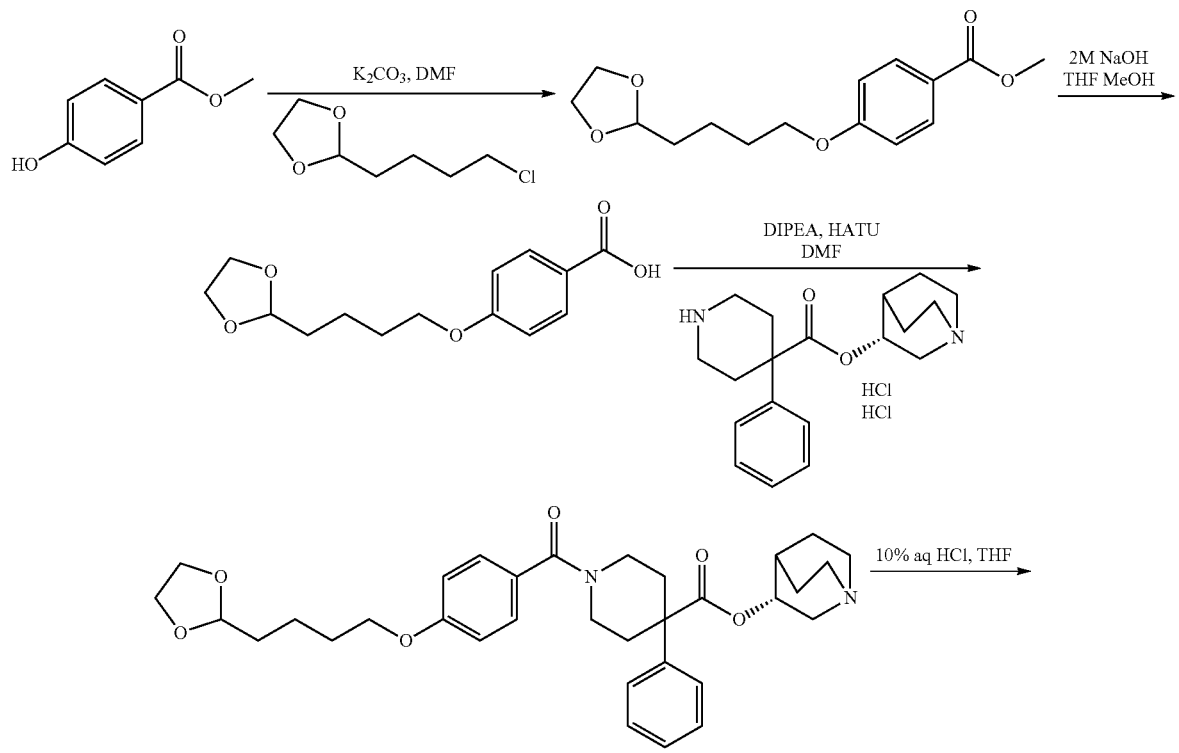

-continued

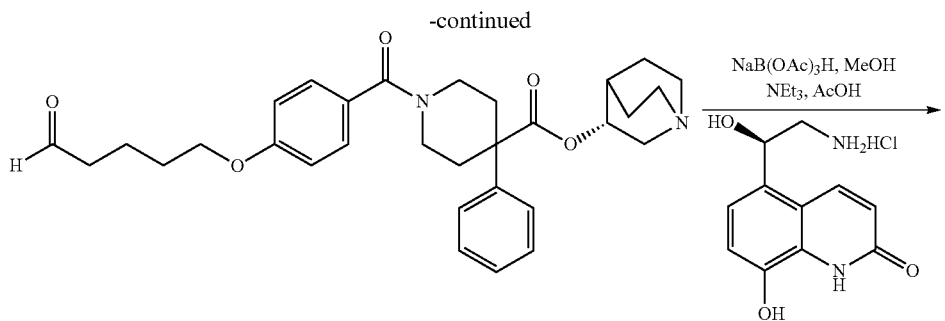

Example 1. (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate (Compound 1)

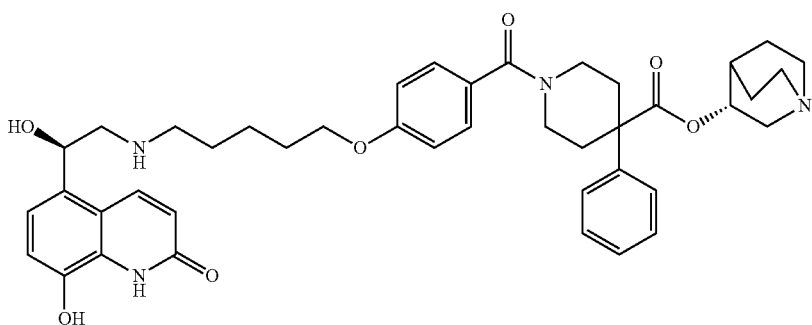

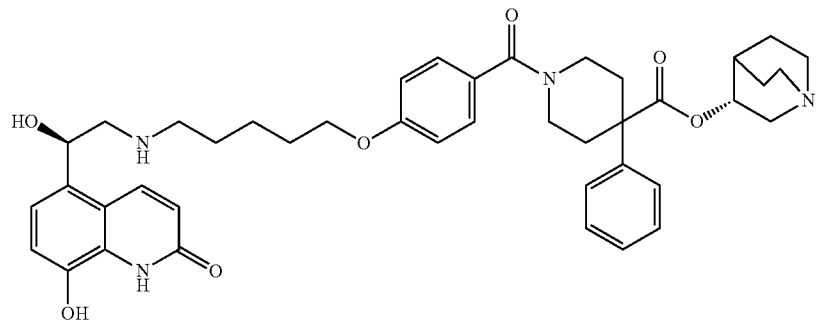 [SMILES: O=C(c1ccc(OCCCCCNC[C@H](O)c2ccc(O)c3[nH]c(=O)ccc23)cc1)N1CCC(C(=O)O[C@H]2CN3CCC2CC3)(c2ccccc2)CC1]

Step 1. Methyl 4-(4-(1,3-dioxolan-2-yl)butoxy)benzoate

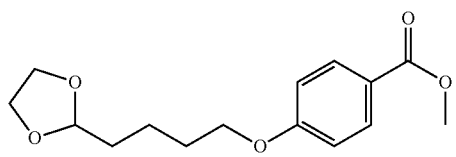 [SMILES: COC(=O)c1ccc(OCCCCC2OCCO2)cc1]

To a stirred solution of methyl 4-hydroxybenzoate (1.0 g, 6.57 mmol) in DMF (10 mL) was added potassium carbonate (2.72 g, 19.71 mmol) followed by 2-(4-chlorobutyl)-1,3-dioxolane (1.22 mL, 8.54 mmol). The reaction mixture was heated at 80° C. for 18 hours. The reaction mixture was diluted with ethyl acetate and washed sequentially with water and brine (×2). The organic phase was dried over anhydrous magnesium sulfate, the suspension filtered and the filtrate concentrated at reduced pressure. The residue triturated with i-hexane to afford the title compound (1.96 g, 100%).

$^1$H NMR (400 MHz, DMSO-$d_6$); δ 7.90 (d, J=8.9 Hz, 2H), 7.03 (d, J=8.9 Hz, 2H), 4.81-4.77 (m, 1H), 4.05 (dd, J=6.4, 6.4 Hz, 2H), 3.88-3.86 (m, 2H), 3.81 (s, 3H), 3.78-3.74 (m, 2H), 1.81-1.46 (m, 6H).

Step 2. 4-(4-(1,3-Dioxolan-2-yl)butoxy)benzoic acid

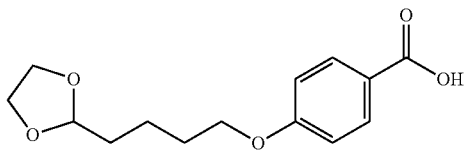 [SMILES: O=C(O)c1ccc(OCCCCC2OCCO2)cc1]

To a stirred solution of methyl 4-(4-(1,3-dioxolan-2-yl)butoxy)benzoate (1.96 g, 7.0 mmol) in methanol/THF (35 mL/35 mL) was added 2M aqueous sodium hydroxide (35mL). The reaction mixture was stirred at room temperature for 18 hours. The reaction mixture was concentrated to ⅓ volume at reduced pressure and the pH adjusted to pH 4. The mixture was extracted with ethyl acetate (×2). The combined organic extracts were washed with brine and dried over anhydrous magnesium sulfate. The suspension was filtered and the filtrate concentrated at reduced pressure to afford the title compound (1.71 g, 92%).

$^1$H NMR (400 MHz, DMSO-$d_6$); δ 7.93 (d, J=9.0 Hz, 2H), 7.06 (d, J=8.9 Hz, 2H), 4.86-4.83 (m, 1H), 4.10 (dd, J=6.3, 6.3 Hz, 2H), 3.95-3.79 (m, 4H), 1.86-1.77 (m, 2H), 1.71-1.65 (m, 2H), 1.59-1.52 (m, 2H).

Step 3. (R)-Quinuclidin-3-yl 1-(4-(4-(1,3-dioxolan-2-yl)butoxy)benzoyl)-4-phenylpiperidine-4-carboxylate

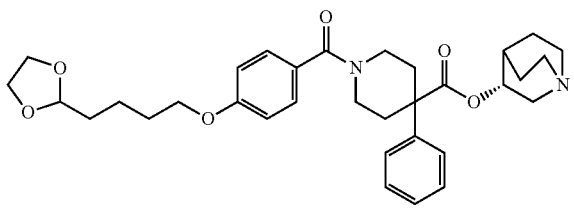 [SMILES: O=C(c1ccc(OCCCCC2OCCO2)cc1)N1CCC(C(=O)O[C@H]2CN3CCC2CC3)(c2ccccc2)CC1]

To a stirred solution of 4-(4-(1,3-dioxolan-2-yl)butoxy)benzoic acid (0.173 g, 0.65 mmol) in DMF (5 mL) was added DIPEA (0.37 mL, 2.15 mmol) and HATU (0.293 g, 0.77 mmol). The reaction mixture was stirred at room temperature for 30 minutes. (R)-Quinuclidin-3-yl 4-phenylpiperidine-4-carboxylate bis-hydrochloride (0.30 g, 0.77 mmol) was added and the reaction mixture stirred at room temperature for 42 hours. The reaction mixture was diluted with ethyl acetate and washed sequentially with water and brine (×2). The organic phase was dried over anhydrous magnesium sulfate, the suspension filtered and the filtrate concentrated at reduced pressure. The residue was purified by reverse phase HPLC to afford the title compound (0.245 g, 67%).

$^1$H NMR (400 MHz, DMSO-$d_6$); δ 7.46-7.30 (m, 7H), 6.99-6.94 (m, 2H), 4.87 (m, 1H), 4.81-4.78 (m, 1H), 4.05-3.98 (m, 2H), 3.90-3.74 (m, 4H), 2.89-2.67 (m, 2H), 2.00-1.91 (m, 6H), 1.78-1.60 (m, 7H), 1.54-1.47 (m, 6H), 1.22-1.18 (m, 1H), 1.11-1.04 (m, 3H).

Step 4. (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate

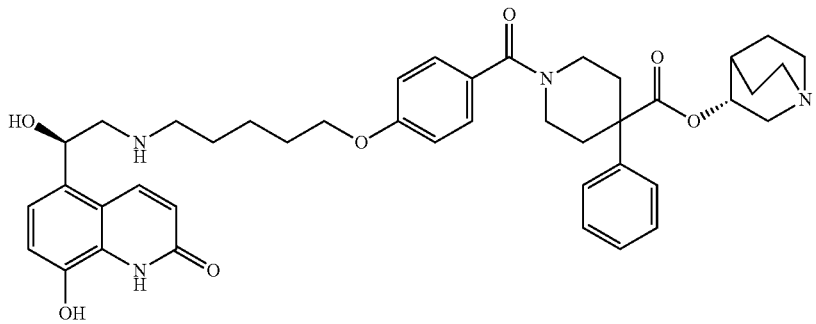 [SMILES: O=C(c1ccc(OCCCCCNC[C@H](O)c2ccc(O)c3[nH]c(=O)ccc23)cc1)N1CCC(C(=O)O[C@H]2CN3CCC2CC3)(c2ccccc2)CC1]

To a stirred solution of (R)-quinuclidin-3-yl 1-(4-(4-(1,3-dioxolan-2-yl)butoxy)benzoyl)-4-phenylpiperidine-4-carboxylate (0.240 g, 0.43 mmol) in THF (2 mL) was added 10% aqueous hydrochloric acid (2 mL). The resultant mixture was stirred at room temperature for 18 hours. To the mixture was added 10% aqueous potassium carbonate and then extracted with ethyl acetate (twice). The combined organic phases were dried and the filtrate was evaporated at reduced pressure. The residue (0.105 g, 0.20 mmol) was dissolved in methanol (1 mL) and added to a pre-stirred (10 minutes) mixture of (R)-5-(2-amino-1-hydroxyethyl)-8-hydroxyquinolin-2(1H)-one hydrochloride (0.062 g, 0.24 mmol, 80% purity) and triethylamine (0.037 mL, 0.26 mmol) in methanol (1 mL). This mixture was stirred at room temperature for 1 hour and then sodium triacetoxyborohydride (0.047 g, 0.22 mmol) followed by acetic acid (0.02 mL) were added. The reaction mixture was stirred for a further 18 hour. The reaction mixture was diluted with iso-butanol and washed with water. The aqueous phase was extracted with further iso-butanol. The combined iso-butanol extracts were evaporated at reduced pressure. The residue was purified by reverse phase preparative HPLC to afford the title compound.

$^1$H NMR (400 MHz, DMSO-$d_6$); δ 8.28 (s, 2H), 8.18 (d, J=20.3 Hz, 1H), 7.44-7.35 (m, 6H), 7.30 (dd, J=7.0, 7.0 Hz, 1H), 7.11 (d, J=8.2 Hz, 1H), 6.98-6.94 (m, 3H), 6.53 (d, J=9.9 Hz, 1H), 5.18 (dd, J=5.1, 7.6 Hz, 1H), 4.72-4.70 (m, 1H), 4.00 (dd, J=6.4, 6.4 Hz, 2H), 3.30-3.10 (brs, 4H), 3.07-3.00 (m, 2H), 2.89-2.74 (m, 4H), 2.68-2.50 (m, 4H), 2.36-2.31 (m, 2H), 1.98-1.91 (m, 2H), 1.84-1.70 (m, 3H), 1.58-1.52 (m, 3H), 1.48-1.41 (m, 4H), 1.24-1.19 (m, 1H).

The following compounds were prepared in an identical fashion with the requisite phenol replacing methyl 4-hydroxybenzoate in Example 1 Step 1.

| Compound number | Requisite phenol | Structure |
|---|---|---|
| Compound 2 | 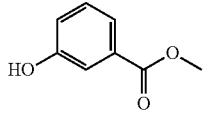 | 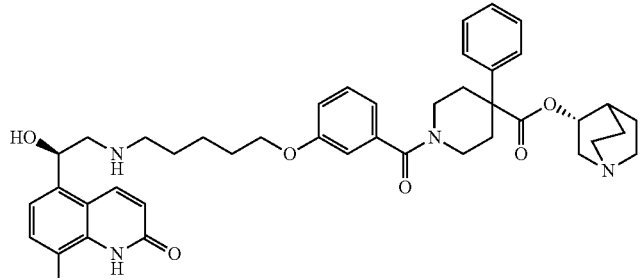 |
| Compound 3 | 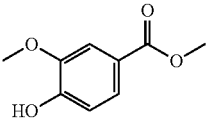 | 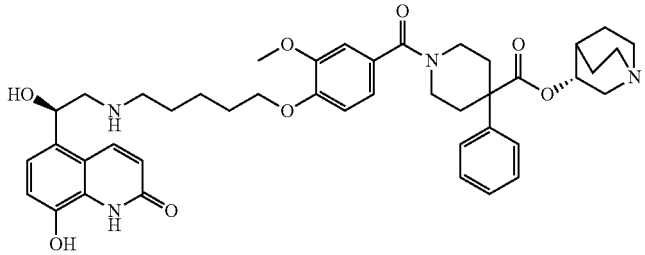 [SMILES: COc1cc(C(=O)N2CCC(C(=O)O[C@H]3CN4CCC3CC4)(c3ccccc3)CC2)ccc1OCCCCCNC[C@H](O)c1ccc(O)c2[nH]c(=O)ccc12] |
| Compound 4 | 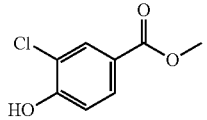 | 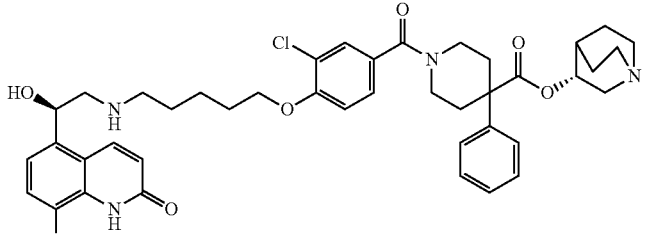 |
| Compound 5 | 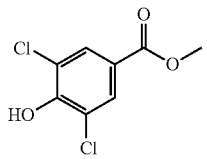 | 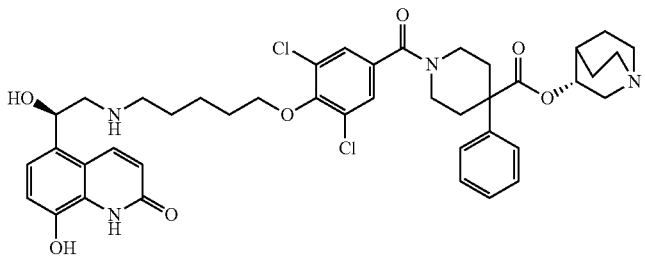 [SMILES: O=C(c1cc(Cl)c(OCCCCCNC[C@H](O)c2ccc(O)c3[nH]c(=O)ccc23)c(Cl)c1)N1CCC(C(=O)O[C@H]2CN3CCC2CC3)(c2ccccc2)CC1] |
| Compound 6 | 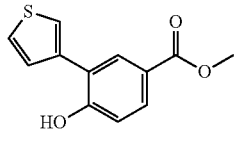 [SMILES: COC(=O)c1ccc(O)c(-c2ccsc2)c1] | 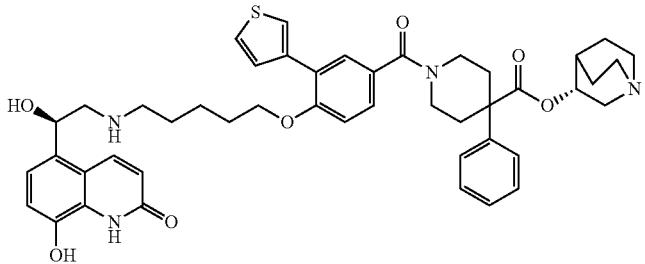 [SMILES: O=C(c1ccc(OCCCCCNC[C@H](O)c2ccc(O)c3[nH]c(=O)ccc23)c(-c2ccsc2)c1)N1CCC(C(=O)O[C@H]2CN3CCC2CC3)(c2ccccc2)CC1] |

| Compound number | Requisite phenol | Structure |
| --- | --- | --- |
| Compound 7 | | 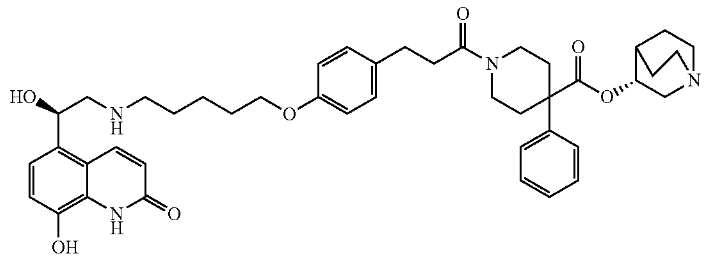 [SMILES: O=C(CCc1ccc(OCCCCCNC[C@H](O)c2ccc(O)c3[nH]c(=O)ccc23)cc1)N1CCC(C(=O)O[C@H]2CN3CCC2CC3)(c2ccccc2)CC1] |
| Compound 8 | | 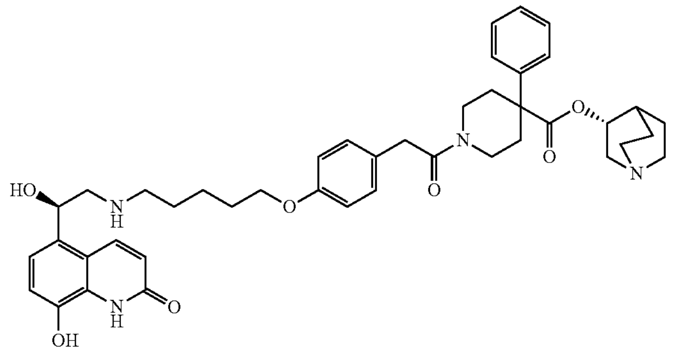 [SMILES: O=C(Cc1ccc(OCCCCCNC[C@H](O)c2ccc(O)c3[nH]c(=O)ccc23)cc1)N1CCC(C(=O)O[C@H]2CN3CCC2CC3)(c2ccccc2)CC1] |
| Compound 9 | | 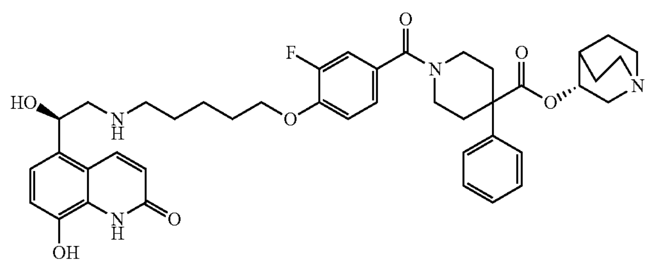 [SMILES: O=C(c1ccc(OCCCCCNC[C@H](O)c2ccc(O)c3[nH]c(=O)ccc23)c(F)c1)N1CCC(C(=O)O[C@H]2CN3CCC2CC3)(c2ccccc2)CC1] |
| Compound 10 | | 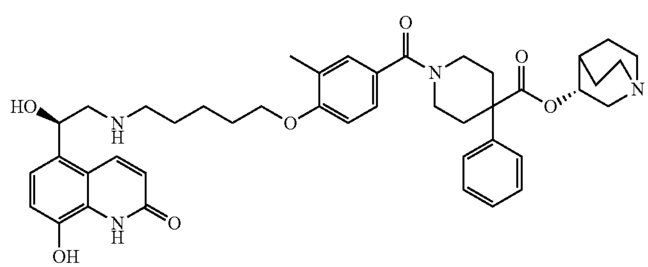 |
| Compound 11 | | 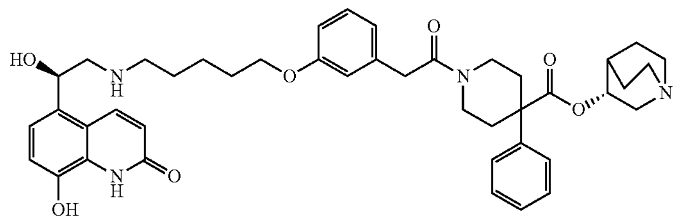 [SMILES: O=C(Cc1cccc(OCCCCCNC[C@H](O)c2ccc(O)c3[nH]c(=O)ccc23)c1)N1CCC(C(=O)O[C@H]2CN3CCC2CC3)(c2ccccc2)CC1] |

-continued
| Compound number | Requisite phenol | Structure |
|---|---|---|
| Compound 12 | 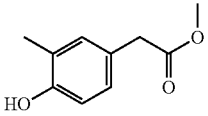 | 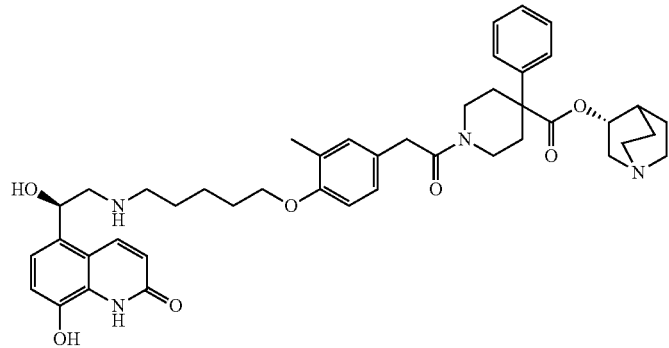 [SMILES: Cc1cc(CC(=O)N2CCC(C(=O)O[C@H]3CN4CCC3CC4)(c3ccccc3)CC2)ccc1OCCCCCNC[C@H](O)c1ccc(O)c2[nH]c(=O)ccc12] |
| Compound 13 | 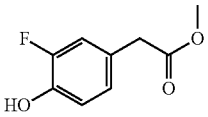 | 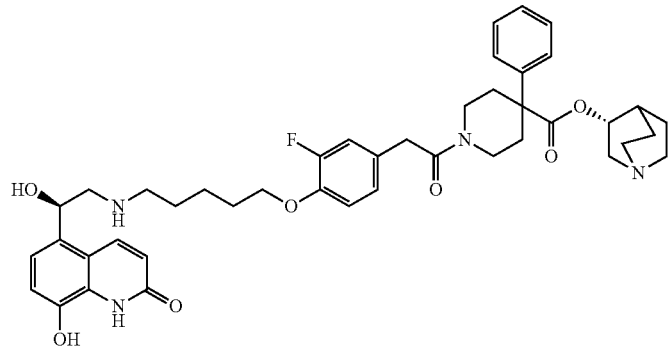 [SMILES: O=C(Cc1ccc(OCCCCCNC[C@H](O)c2ccc(O)c3[nH]c(=O)ccc23)c(F)c1)N1CCC(C(=O)O[C@H]2CN3CCC2CC3)(c2ccccc2)CC1] |
| Compound 14 | 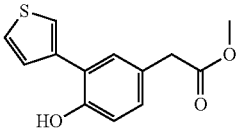 [SMILES: COC(=O)Cc1ccc(O)c(-c2ccsc2)c1] | 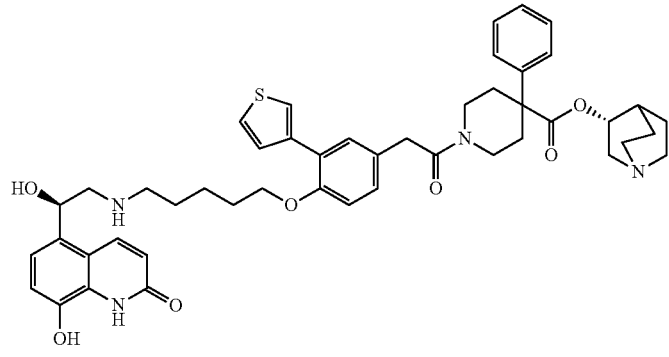 [SMILES: O=C(Cc1ccc(OCCCCCNC[C@H](O)c2ccc(O)c3[nH]c(=O)ccc23)c(-c2ccsc2)c1)N1CCC(C(=O)O[C@H]2CN3CCC2CC3)(c2ccccc2)CC1] |
| Compound 15 | 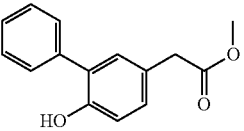 [SMILES: COC(=O)Cc1ccc(O)c(-c2ccccc2)c1] | 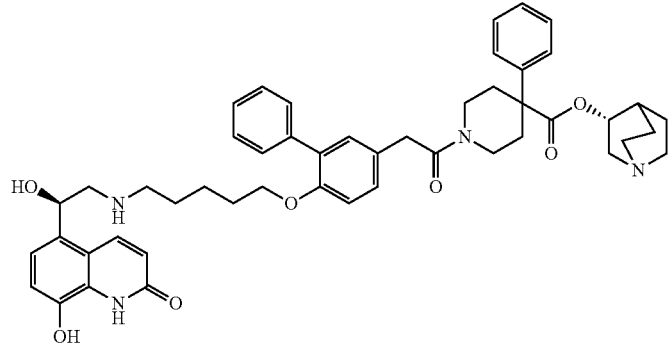 [SMILES: O=C(Cc1ccc(OCCCCCNC[C@H](O)c2ccc(O)c3[nH]c(=O)ccc23)c(-c2ccccc2)c1)N1CCC(C(=O)O[C@H]2CN3CCC2CC3)(c2ccccc2)CC1] |

| Compound number | Requisite phenol | Structure |
|---|---|---|
| Compound 16 | | 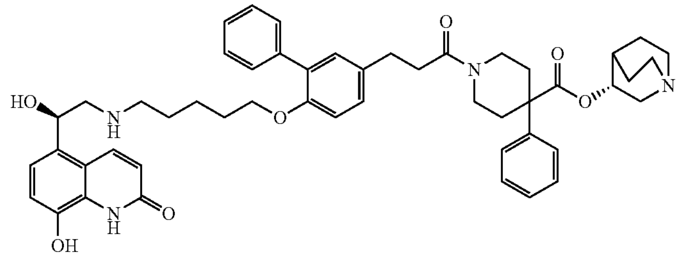 [SMILES: O=C(CCc1ccc(OCCCCCNC[C@H](O)c2ccc(O)c3[nH]c(=O)ccc23)c(-c2ccccc2)c1)N1CCC(C(=O)O[C@H]2CN3CCC2CC3)(c2ccccc2)CC1] |
| Compound 17 | | 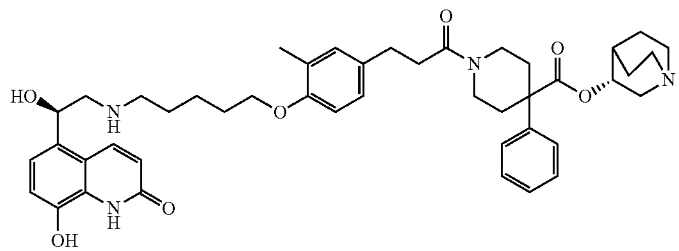 [SMILES: Cc1cc(CCC(=O)N2CCC(C(=O)O[C@H]3CN4CCC3CC4)(c3ccccc3)CC2)ccc1OCCCCCNC[C@H](O)c1ccc(O)c2[nH]c(=O)ccc12] |
| Compound 18 | | 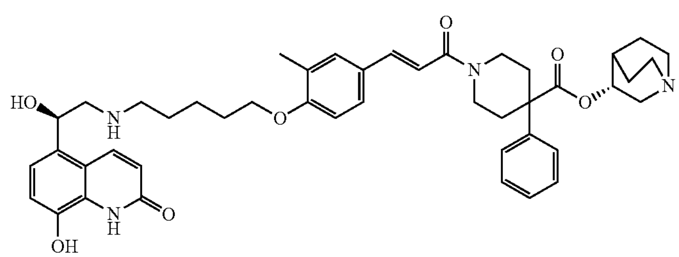 [SMILES: Cc1cc(/C=C/C(=O)N2CCC(C(=O)O[C@H]3CN4CCC3CC4)(c3ccccc3)CC2)ccc1OCCCCCNC[C@H](O)c1ccc(O)c2[nH]c(=O)ccc12] |
Example 2. (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-4-phenylpiperidine-4-carboxylate (Compound 19)
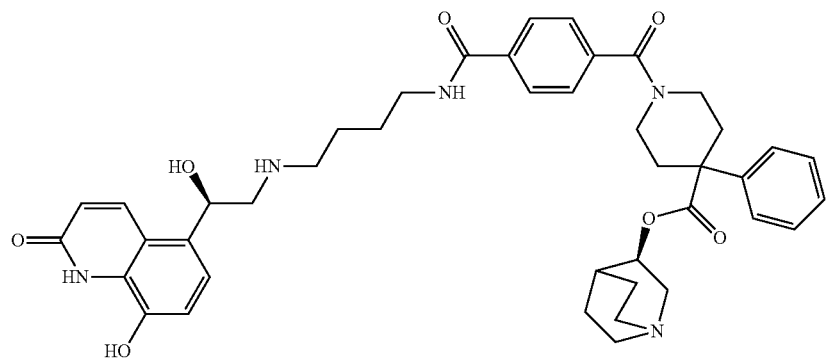 [SMILES: O=C(NCCCCNC[C@H](O)c1ccc(O)c2[nH]c(=O)ccc12)c1ccc(C(=O)N2CCC(C(=O)O[C@H]3CN4CCC3CC4)(c3ccccc3)CC2)cc1]

Step 1. Methyl 4-((4,4-diethoxybutyl)carbamoyl)benzoate

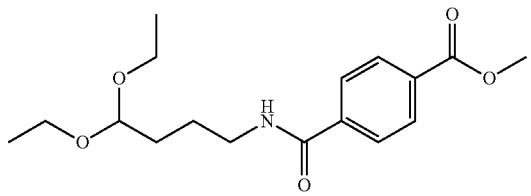 [SMILES: CCOC(CCCNC(=O)c1ccc(C(=O)OC)cc1)OCC]

To a stirred solution of 4-(methoxycarbonyl)benzoic acid (0.50 g, 2.77 mmol) and DIPEA (0.55 mL, 3.0 mmol) in DMF (5 mL) was added HATU (1.15 g, 3.0 mmol). The reaction mixture was stirred at room temperature for 45 minutes. 4,4-Diethoxybutan-1-amine (0.375 g, 2.31 mmol) was added and the reaction mixture stirred at room temperature for 18 hours. The reaction mixture was diluted with ethyl acetate and washed sequentially with saturated aqueous sodium carbonate and brine. The organic phase was dried over anhydrous magnesium sulfate, filtered and the filtrated concentrated at reduced pressure to afford the title compound (1.00 g, >100%).

$^1$H NMR (400 MHz, DMSO-$d_6$); δ 8.66 (dd, J=5.6, 5.6 Hz, 1H), 8.06-8.02 (m, 2H), 7.96 (d, J=8.5 Hz, 2H), 4.51-4.46 (m, 1H), 3.88 (s, 3H), 3.56 (ddd, J=7.0, 9.5, 14.1 Hz, 2H), 3.43 (ddd, J=7.1, 9.6, 14.1 Hz, 2H), 3.30-3.25 (m, 2H), 1.58-1.54 (m, 4H), 1.10 (dd, J=7.0, 7.0 Hz, 6H).

Step 2. 4-((4,4-Diethoxybutyl)carbamoyl)benzoic acid

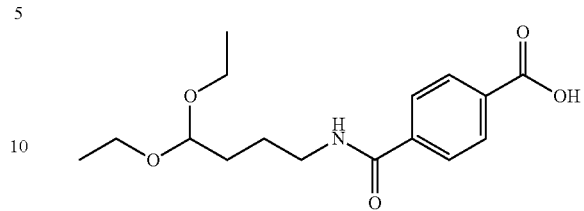

To a solution of methyl 4-((4,4-diethoxybutyl)carbamoyl)benzoate (1.0 g, 3.0 mmol) in THF/methanol (15 mL/15 mL) was added 2M aqueous sodium hydroxide (15 mL) and the reaction mixtures stirred at room temperature. The reaction mixture was concentrated to ⅓ volume at reduced pressure and the pH adjusted to pH 4. The mixture was extracted with ethyl acetate (×2). The combined organic extracts were washed with brine and dried over anhydrous magnesium sulfate. The suspension was filtered and the filtrate concentrated at reduced pressure to afford the title compound (0.750 g, 81%).

$^1$H NMR (400 MHz, DMSO-$d_6$) δ 8.62 (dd, J=5.6, 5.6 Hz, 1H), 8.01 (d, J=8.5 Hz, 2H), 7.93 (d, J=8.5 Hz, 2H), 4.48 (s, 1H), 3.56 (ddd, J=7.1, 9.5, 14.1 Hz, 2H), 3.47-3.40 (m, 2H), 3.31-3.25 (m, 2H), 1.58-1.54 (m, 4H), 1.18-1.08 (m, 6H).

Step 3. (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-4-phenylpiperidine-4-carboxylate (Compound 19)

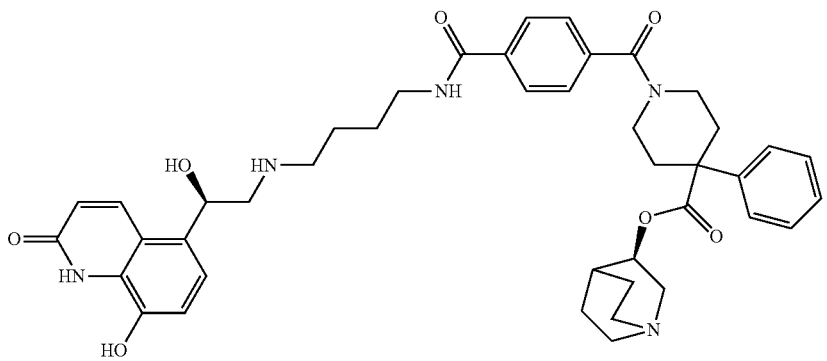 [SMILES: O=C(NCCCCNC[C@H](O)c1ccc(O)c2[nH]c(=O)ccc12)c1ccc(C(=O)N2CCC(C(=O)O[C@H]3CN4CCC3CC4)(c3ccccc3)CC2)cc1]

The title compound was prepared as described in Example 1 with 4-((4,4-diethoxybutyl)carbamoyl)benzoic acid replacing 4-(4-(1,3-dioxolan-2-yl)butoxy)benzoic acid in Step 3 with the subsequent product used in Step 4.

$^1$H NMR (400 MHz, MeOD); δ 8.54 (s, 3H), 8.39 (d, J=9.9 Hz, 1H), 7.92 (d, J=8.3 Hz, 2H), 7.55-7.48 (m, 4H), 7.42 (dd, J=7.7, 7.7 Hz, 2H), 7.35-7.28 (m, 2H), 7.04 (d, J=8.2 Hz, 1H), 6.70 (d, J=9.9 Hz, 1H), 5.40 (dd, J=6.8, 6.8 Hz, 1H), 5.01-4.98 (m, 1H), 3.64-3.61 (m, 1H), 3.48 (dd, J=6.8, 6.8 Hz, 3H), 3.37-3.36 (m, 3H), 3.24 (d, J=6.8 Hz, 2H), 3.15 (dd, J=7.7, 7.7 Hz, 2H), 2.98 (m, 3H), 2.74-2.73 (m, 3H), 2.66-2.66 (m, 1H), 2.09-2.09 (m, 3H), 1.83-1.72 (m, 6H), 1.54-1.51 (m, 2H).

Example 3. (R)-Quinuclidin-3-yl 1-(4-(2-(((R)-2-hydroxy-2-(8-hydroxy-2-oxo-1,2-dihydroquinolin-5-yl)ethyl)amino)ethyl)benzoyl)-4-phenylpiperidine-4-carboxylate (Compound 20)

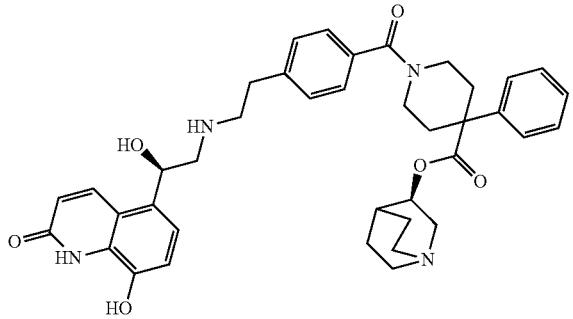 [SMILES: O=C(c1ccc(CCNC[C@H](O)c2ccc(O)c3[nH]c(=O)ccc23)cc1)N1CCC(C(=O)O[C@H]2CN3CCC2CC3)(c2ccccc2)CC1]

The title compound was prepared as described in Example 1 with 4-((1,3-dioxolan-2-yl)methyl)benzoic acid replacing 4-(4-(1,3-dioxolan-2-yl)butoxy)benzoic acid in Step 3.

$^1$H NMR (400 MHz, DMSO-d$_6$); δ 10.49 (d, J=12.2 Hz, 2H), 9.64-9.64 (m, 1H), 8.77 (s, 2H), 8.16 (d, J=44.6 Hz, 1H), 7.47-7.38 (m, 6H), 7.33 (d, J=8.3 Hz, 3H), 7.17 (d, J=8.2 Hz, 1H), 7.00 (d, J=8.2 Hz, 1H), 6.60 (dd, J=1.8, 9.9 Hz, 1H), 6.21 (s, 1H), 5.34 (d, J=8.9 Hz, 1H), 5.04-4.99 (m, 1H), 4.20 (m, 1H), 3.62 (m, 1H), 3.23 (m, 5H), 3.16-2.99 (m, 9H), 2.55-2.35 (m, 2H), 2.09 (s, 1H), 1.88-1.78 (m, 4H), 1.62 (s, 2H).

Example 4. (R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-4-phenylpiperidine-4-carboxylate (Compound 21)

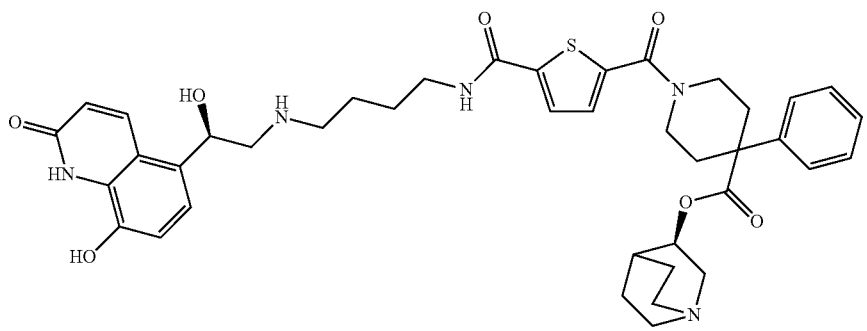 [SMILES: O=C(NCCCCNC[C@H](O)c1ccc(O)c2[nH]c(=O)ccc12)c1ccc(C(=O)N2CCC(C(=O)O[C@H]3CN4CCC3CC4)(c3ccccc3)CC2)s1]

The title compound was prepared as described in Example 2 with 5-(methoxycarbonyl)thiophene-2-carboxylic acid replacing 4-(methoxycarbonyl)benzoic acid in Step 1 and the product used in the subsequent steps described in Example 2.

$^1$H NMR (400 MHz, DMSO-d$_6$); δ 10.49 (d, J=2.9 Hz, 2H), 9.72-9.71 (m, 1H), 8.70 (dd, J=5.6, 5.6 Hz, 1H), 8.60 (s, 2H), 8.15 (d, J=9.9 Hz, 1H), 7.69 (d, J=3.9 Hz, 1H), 7.46 (d, J=7.5 Hz, 2H), 7.44-7.38 (m, 3H), 7.33 (dd, J=7.2, 7.2 Hz, 1H), 7.15 (d, J=8.3 Hz, 1H), 6.99 (d, J=8.2 Hz, 1H), 6.59 (d, J=9.8 Hz, 1H), 6.17 (s, 1H), 5.30 (d, J=9.3 Hz, 1H), 5.04-5.00 (m, 1H), 4.05-4.05 (m, 2H), 3.68-3.61 (m, 1H), 3.30-3.22 (m, 4H), 3.16-3.08 (m, 6H), 3.01 (d, J=5.9 Hz, 4H), 2.58 (m, 1H), 2.15 (d, J=2.4 Hz, 1H), 2.09-1.96 (m, 2H), 1.90-1.79 (m, 2H), 1.71-1.54 (m, 6H).

Example 5. (R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-4-phenylpiperidine-4-carboxylate (Compound 22)

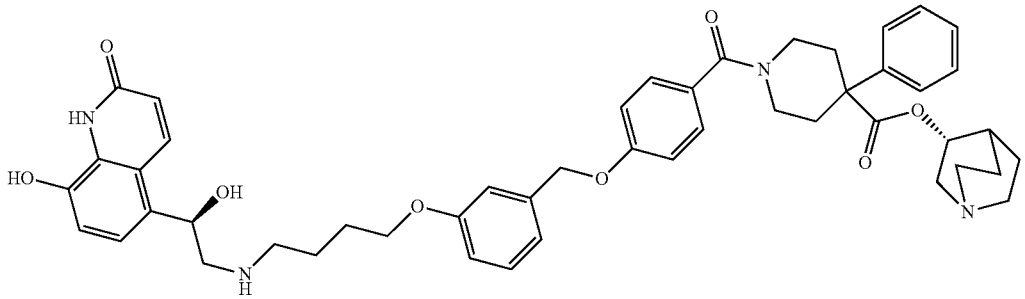 [SMILES: O=C(c1ccc(OCc2cccc(OCCCCNC[C@H](O)c3ccc(O)c4[nH]c(=O)ccc34)c2)cc1)N1CCC(C(=O)O[C@H]2CN3CCC2CC3)(c2ccccc2)CC1]

Step 1. (3-(3-(1,3-Dioxolan-2-yl)propoxy)phenyl) methanol

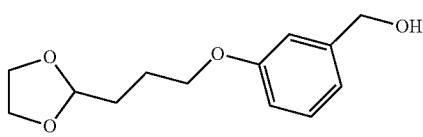 [SMILES: OCc1cccc(OCCCC2OCCO2)c1]

To a stirred solution of 3-(hydroxymethyl)phenol (1.5 g, 12.1 mmol) in DMF (15 mL) was added potassium carbonate (2.0 g, 14.5 mmol). After five minutes 2-(3-chloropropyl)-1,3-dioxolane (2.18 g, 14.52 mmol) was added and the reaction mixture heated at 80° C. for four hours. The reaction mixture was diluted with ethyl acetate and washed with water and brine (×3). The organic phase was dried over anhydrous magnesium sulfate, the suspension filtered and the filtrate was concentrated at reduced pressure. The residue was purified by column chromatography (eluent, 100% i-hexane to 60% ethyl acetate/i-hexane) to afford the title compound (0.97 g, 34%).

$^1$H NMR (400 MHz, DMSO-$d_6$); δ 7.21 (dd, J=7.8, 7.8 Hz, 1H), 6.86 (d, J=7.2 Hz, 2H), 6.77 (dd, J=1.9, 8.9 Hz, 1H), 5.15 (dd, J=5.8, 5.8 Hz, 1H), 4.85 (dd, J=4.5, 4.5 Hz, 1H), 4.46 (d, J=5.8 Hz, 2H), 4.00-3.76 (m, 6H), 1.82-1.68 (m, 4H).

Step 2. 4-((3-(3-(1,3-Dioxolan-2-yl)propoxy)benzyl) oxy)benzoic acid

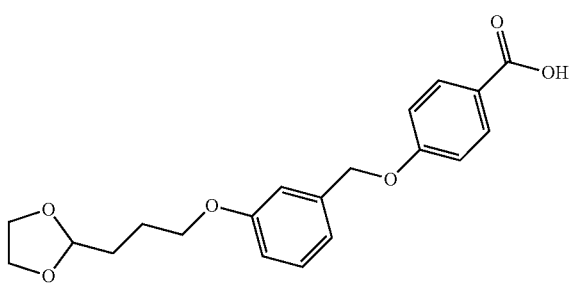 [SMILES: O=C(O)c1ccc(OCc2cccc(OCCCC3OCCO3)c2)cc1]

To a cooled (0° C.) solution of (3-(3-(1,3-dioxolan-2-yl)propoxy)phenyl)methanol (0.97 g, 4.09 mmol) and methyl 4-hydroxybenzoate (0.746 g, 4.91 mmol) in THF (25 mL) was added triphenyl phosphine (1.29 g, 4.91 mmol). DIAD (0.966 mL, 4.91 mmol) was added drop wise and the reaction mixture allowed to warm to room temperature and stirred at this temperature for 72 hours. The reaction mixture was diluted with ethyl acetate and washed with 10% aqueous potassium carbonate, water and brine. The organic phase was dried over anhydrous magnesium sulfate, the suspension filtered and the filtrate was concentrated at reduced pressure. The residue was purified by column chromatography (eluent, 100% i-hexane to 40% ethyl acetate/i-hexane) to afford the title compound (2.14 g, >100%).

The material was dissolved in methanol/THF (20 mL/20 mL) and 2M aqueous sodium hydroxide (20.4 mL) added. The reaction mixture was stirred at room temperature for 5 hours. The organic solvents were removed at reduced pressure and the subsequent aqueous was washed with ethyl acetate. The pH of the aqueous phase was adjusted to pH 5 and extracted with ethyl acetate (×2). The combined ethyl acetate extracts were dried over anhydrous magnesium sulfate, the suspension filtered and the filtrate was concentrated at reduced pressure to afford the title compound (1.17 g, 80%).

$^1$H NMR (400 MHz, DMSO-$d_6$); δ 7.91-7.88 (m, 2H), 7.30 (dd, J=8.0, 8.0 Hz, 1H), 7.09 (d, J=9.0 Hz, 2H), 7.03-7.00 (m, 2H), 6.89 (dd, J=1.8, 8.2 Hz, 1H), 5.15 (s, 2H), 4.85 (dd, J=4.5, 4.5 Hz, 1H), 4.00 (dd, J=6.3, 6.3 Hz, 2H), 3.91-3.75 (m, 4H), 1.81-1.68 (m, 4H).

Step 3. (R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-4-phenylpiperidine-4-carboxylate (Compound 22)

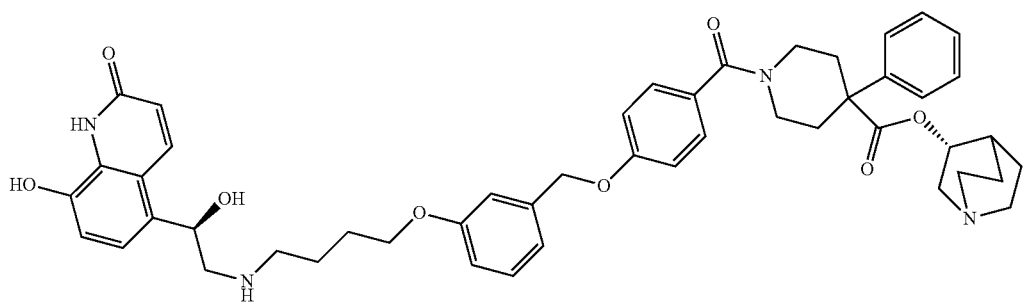 [SMILES: O=C(c1ccc(OCc2cccc(OCCCCNC[C@H](O)c3ccc(O)c4[nH]c(=O)ccc34)c2)cc1)N1CCC(C(=O)O[C@H]2CN3CCC2CC3)(c2ccccc2)CC1]

The title compound was prepared as described in Example 1 with 4-((3-(3-(1,3-dioxolan-2-yl)propoxy)benzyl)oxy)benzoic acid replacing 4-(4-(1,3-dioxolan-2-yl)butoxy)benzoic acid in Step 3.

¹H NMR (400 MHz, DMSO-d₆); δ 10.50 (d, J=7.0 Hz, 2H), 9.67-9.67 (m, 1H), 8.61-8.61 (s, 2H), 8.16 (d, J=9.9 Hz, 1H), 7.45 (d, J=7.4 Hz, 2H), 7.43-7.37 (m, 4H), 7.32 (dd, J=7.8, 7.8 Hz, 2H), 7.16 (d, J=8.2 Hz, 1H), 7.06-6.97 (m, 5H), 6.91 (dd, J=1.9, 8.2 Hz, 1H), 6.59 (d, J=9.9 Hz, 1H), 6.17 (s, 1H), 5.31 (dd, J=1.9, 9.8 Hz, 1H), 5.12 (s, 2H), 5.04-4.99 (m, 1H), 4.01 (dd, J=5.3, 5.3 Hz, 2H), 3.70-3.55 (m, 4H), 3.24-3.19 (m, 3H), 3.16-3.03 (m, 9H), 2.14 (d, J=2.5 Hz, 1H), 2.04-1.90 (m, 2H), 1.87-1.79 (m, 6H), 1.65-1.61 (m, 2H).

Example 6. (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-4-phenylpiperidine-4-carboxylate (Compound 23)

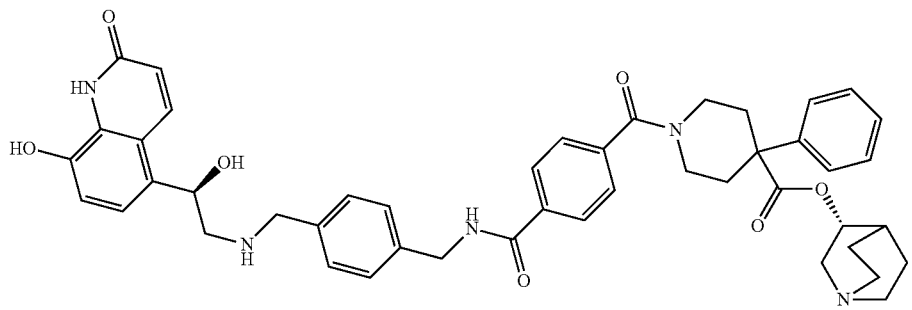 [SMILES: O=C(NCc1ccc(CNC[C@H](O)c2ccc(O)c3[nH]c(=O)ccc23)cc1)c1ccc(C(=O)N2CCC(C(=O)O[C@H]3CN4CCC3CC4)(c3ccccc3)CC2)cc1]

Step 1. 4-(1,3-Dioxolan-2-yl)benzonitrile

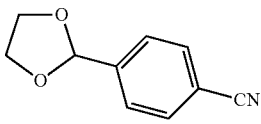 [SMILES: N#Cc1ccc(C2OCCO2)cc1]

A solution of 4-cyanobenzaldehyde (1.5 g, 11.4 mmol), ethylene glycol (2.62 mL, 46.90 mmol) and pTSA-H₂O (0.217 g, 1.14 mmol) in toluene (35 mL) was heated at reflux under Dean and Stark conditions for 1.5 hours. The reaction mixture was diluted with ethyl acetate and washed with water, 10% aqueous potassium carbonate and brine. The organic phase were dried over anhydrous magnesium sulfate, the suspension filtered and the filtrate was concentrated at reduced pressure to afford the title compound (2.02 g, >100%).

¹H NMR (400 MHz, DMSO-d₆); δ 7.88 (d, J=8.4 Hz, 2H), 7.63 (d, J=8.0 Hz, 2H), 5.84 (s, 1H), 4.08-3.96 (m, 4H).

Step 2. (4-(1,3-Dioxolan-2-yl)phenyl)methanamine

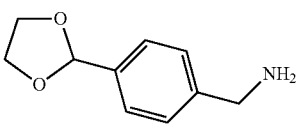 [SMILES: NCc1ccc(C2OCCO2)cc1]

To a cooled (0° C.) solution of 4-(1,3-dioxolan-2-yl)benzonitrile (2.02 g, 11.5 mmol) in THF (13 mL) was added a solution of lithium aluminium hydride (2.0 M in THF, 17 mL, 34.0 mmol). The reaction mixture was allowed to warm to room temperature and the resultant mixture stirred at room temperature for 18 hours. The reaction mixture was then quenched sequentially with water (1.5 mL), 2M aqueous sodium hydroxide (1.5 mL) and water (4.5 mL). Ethyl acetate and anhydrous magnesium sulfate were added to the reaction mixture and the suspension was stirred for 1 hour. The suspension was filtered and the filtrate concentrated at reduced pressure to afford the title compound (1.52 g, 76%).

¹H NMR (400 MHz, CDCl₃); δ 7.45 (d, J=8.1 Hz, 2H), 7.32 (d, J=8.3 Hz, 2H), 5.81 (s, 1H), 4.15-4.01 (m, 4H), 3.87 (s, 2H), 1.50 (s, 2H).

Step 3. Methyl 4-((4-(1,3-dioxolan-2-yl)benzyl)carbamoyl)benzoate

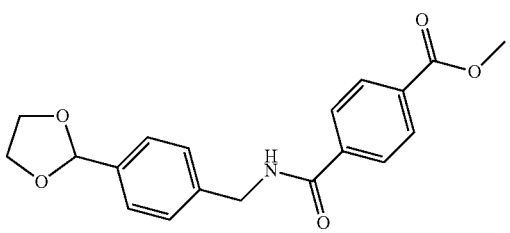 [SMILES: COC(=O)c1ccc(C(=O)NCc2ccc(C3OCCO3)cc2)cc1]

To a solution of 4-(methyoxycarbonyl)benzoic acid (0.419 g, 2.33 mmol) and (4-(1,3-dioxolan-2-yl)phenyl)methanamine (0.500 g, 2.79 mmol) in DMF (5 mL) was added DIPEA (0.526 mL, 3.03 mmol) and HATU (1.06 g, 2.79 mmol). The reaction mixture was stirred at room temperature for 18 hours. The reaction mixture was diluted with ethyl acetate and washed with water and brine (×3). The organic phase were dried over anhydrous magnesium sulfate, the suspension filtered and the filtrate was concentrated at reduced pressure. The residue was purified by column chromatography (eluent, 100% i-hexane to 60% ethyl acetate/i-hexane) to afford the title compound (0.59 g, 74%).

¹H NMR (400 MHz, DMSO-d₆); δ 9.25 (dd, J=6.0, 6.0 Hz, 1H), 8.08-8.01 (m, 4H), 7.40 (d, J=8.2 Hz, 2H), 7.35 (d, J=8.3 Hz, 2H), 5.71 (s, 1H), 4.51 (d, J=6.0 Hz, 2H), 4.05-4.02 (m, 2H), 3.95-3.93 (m, 2H), 3.89 (s, 3H).

Step 4. 4-((4-(1,3-Dioxolan-2-yl)benzyl)carbamoyl)benzoic acid

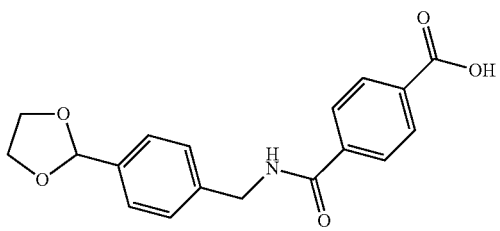 [SMILES: O=C(O)c1ccc(C(=O)NCc2ccc(C3OCCO3)cc2)cc1]

To a stirred solution of methyl 4-((4-(1,3-dioxolan-2-yl)benzyl)carbamoyl)-benzoate (0.59 g, 1.73 mmol) in methanol/THF (8 mL/8 mL) was added 2M aqueous sodium hydroxide (8.7 mL) and the reaction mixture stirred was stirred at room temperature for 5 hours. The organic solvents were removed at reduced pressure and the subsequent aqueous was washed with ethyl acetate. The pH of the aqueous phase was adjusted to pH 5 and extracted with ethyl acetate (×2). The combined ethyl acetate extracts were dried over anhydrous magnesium sulfate, the suspension filtered and the filtrate was concentrated at reduced pressure to afford the title compound (0.348 g, 62%).

$^1$H NMR (400 MHz, DMSO-$d_6$); δ 9.22 (dd, J=5.9, 5.9 Hz, 1H), 8.04-7.97 (m, 4H), 7.40 (d, J=8.2 Hz, 2H), 7.35 (d, J=8.3 Hz, 2H), 5.71 (s, 1H), 4.51 (d, J=5.9 Hz, 2H), 4.06-3.92 (m, 4H).

Step 5. (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-4-phenylpiperidine-4-carboxylate (Compound 23)

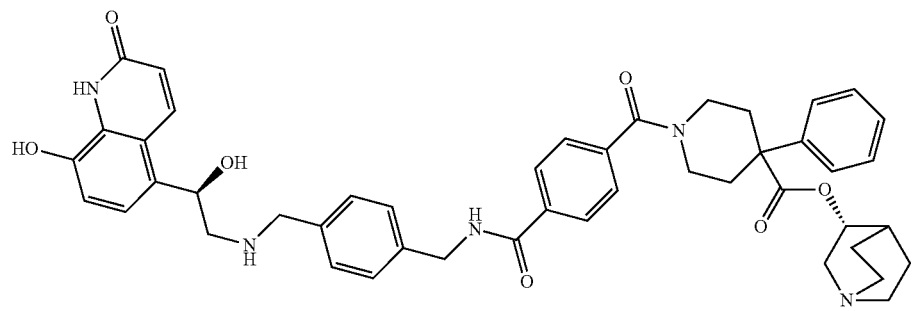 [SMILES: O=C(NCc1ccc(CNC[C@H](O)c2ccc(O)c3[nH]c(=O)ccc23)cc1)c1ccc(C(=O)N2CCC(C(=O)O[C@H]3CN4CCC3CC4)(c3ccccc3)CC2)cc1]

The title compound was prepared as described in Example 1 with 4-((4-(1,3-dioxolan-2-yl)benzyl)carbamoyl)benzoic acid replacing 4-(4-(1,3-dioxolan-2-yl)butoxy)benzoic acid in Step 3.

$^1$H NMR (400 MHz, DMSO-$d_6$); δ 10.50 (s, 2H), 9.70 (s, 1H), 9.19 (dd, J=6.0, 6.0 Hz, 1H), 9.02 (s, 2H), 8.08 (d, J=9.9 Hz, 1H), 7.95 (d, J=8.3 Hz, 2H), 7.54-7.36 (m, 10H), 7.32 (dd, J=7.1, 7.1 Hz, 1H), 7.12 (d, J=8.3 Hz, 1H), 6.97 (d, J=8.2 Hz, 1H), 6.59-6.54 (m, 1H), 6.17 (d, J=3.5 Hz, 1H), 5.33 (d, J=9.9 Hz, 1H), 5.03-5.00 (m, 1H), 4.51 (d, J=5.8 Hz, 2H), 4.21 (m, 3H), 3.66-3.60 (m, 1H), 3.57-3.42 (m, 1H), 3.25-3.25 (m, 2H), 3.16-3.12 (m, 3H), 3.05-2.94 (m, 3H), 2.62 (m, 1H), 2.43 (m, 1H), 2.13 (m, 3H), 1.88-1.78 (m, 2H), 1.70-1.55 (m, 2H).

Example 7. (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-4-phenylpiperidine-4-carboxylate (Compound 24)

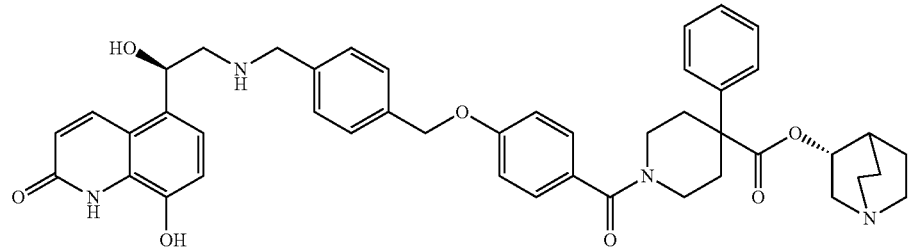 [SMILES: O=C(c1ccc(OCc2ccc(CNC[C@H](O)c3ccc(O)c4[nH]c(=O)ccc34)cc2)cc1)N1CCC(C(=O)O[C@H]2CN3CCC2CC3)(c2ccccc2)CC1]

Step 1. Methyl 4-((4-formylbenzyl)oxy)benzoate

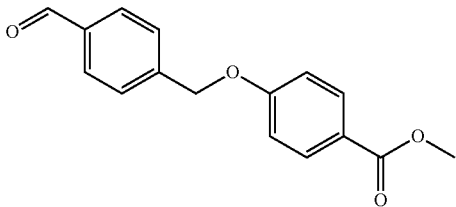 [SMILES: COC(=O)c1ccc(OCc2ccc(C=O)cc2)cc1]

Potassium carbonate (1.66 g, 12 mmol) was added to a solution of methyl 4-hydroxybenzoate (1.67 g, 11 mmol) in DMF (25 mL). After 10 minutes 4-(bromomethyl)benzaldehyde (1.99 g, 10.0 mmol) was added and the mixture stirred at room temperature for 17 hours. The reaction mixture was diluted with ethyl acetate and washed with water, 10% aqueous potassium carbonate and brine (×3). The organic phase was dried over anhydrous magnesium sulfate, the suspension filtered and the filtrate was concentrated at reduced pressure to afford the title compound (2.40 g, 89%).

$^1$H NMR (400 MHz, CDCl$_3$); δ 10.03 (s, 1H), 8.03-7.99 (m, 2H), 7.93-7.91 (m, 2H), 7.61 (d, J=8.0 Hz, 2H), 7.01-6.98 (m, 2H), 5.21 (s, 2H), 3.89 (s, 3H).

Step 2. 4-((4-Formylbenzyl)oxy)benzoic acid

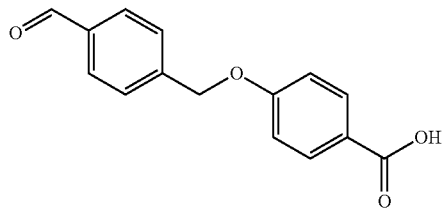 [SMILES: O=Cc1ccc(COc2ccc(C(=O)O)cc2)cc1]

To a stirred solution of methyl 4-((4-formylbenzyl)oxy)benzoate (1.77 g, 6.55 mmol) in methanol/THF (33 mL/33 mL) was added 2M aqueous sodium hydroxide (33 mL). The reaction mixture was stirred at room temperature for 3 hours. The reaction mixture was concentrated at reduced pressure and 2M aqueous hydrochloric acid and ethyl acetate added. The resultant suspension was filtered and the solid dried in vacuo to afford the title compound (1.20 g, 72%).

$^1$H NMR (400 MHz, DMSO-d$_6$); δ 10.02 (s, 1H), 7.94 (d, J=8.3 Hz, 2H), 7.79 (d, J=8.8 Hz, 2H), 7.68 (d, J=8.0 Hz, 2H), 6.89 (d, J=8.9 Hz, 2H), 5.23 (s, 2H).

Step 3. (R)-Quinuclidin-3-yl 1-(4-((4-formylbenzyl)oxy)benzoyl)-4-phenylpiperidine-4-carboxylate

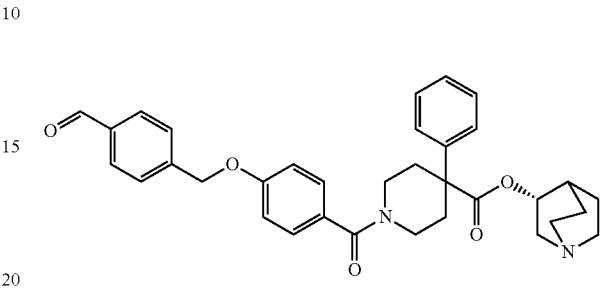

The title compound was prepared as described in Example 1 Step 3 with 4-((4-formylbenzyl)oxy)benzoic acid replacing 4-(4-(1,3-dioxolan-2-yl)butoxy)benzoic acid.

$^1$H NMR (400 MHz, DMSO-d$_6$); δ 10.03 (s, 1H), 7.96 (d, J=8.3 Hz, 2H), 7.69 (d, J=8.0 Hz, 2H), 7.45 (d, J=7.4 Hz, 2H), 7.43-7.37 (m, 4H), 7.31 (dd, J=7.2, 7.2 Hz, 1H), 7.08 (d, J=8.9 Hz, 2H), 5.30 (s, 2H), 5.03-4.97 (m, 1H), 3.62-3.56 (m, 1H), 3.32-3.13 (m, 5H), 3.12-2.98 (m, 4H), 2.12 (d, J=2.8 Hz, 2H), 2.05-1.75 (m, 5H), 1.62 (dd, J=7.8, 7.8 Hz, 2H).

Step 4. (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-4-phenylpiperidine-4-carboxylate (Compound 24)

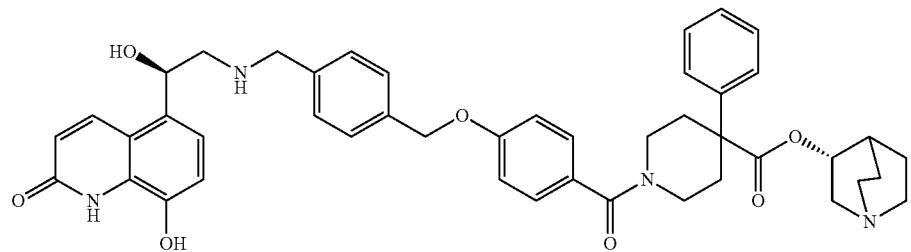 [SMILES: O=C(c1ccc(OCc2ccc(CNC[C@H](O)c3ccc(O)c4[nH]c(=O)ccc34)cc2)cc1)N1CCC(C(=O)O[C@H]2CN3CCC2CC3)(c2ccccc2)CC1]

(R)-Quinuclidin-3-yl 1-(4-((4-formylbenzyl)oxy)benzoyl)-4-phenylpiperidine-4-carboxylate (0.207 g, 0.37 mmol) was dissolved in methanol (2 mL) and added to a pre-stirred (10 minutes) mixture of (R)-5-(2-amino-1-hydroxyethyl)-8-hydroxyquinolin-2(1H)-one hydrochloride (0.120 g, 0.37 mmol, 80% purity) and triethylamine (0.113 mL, 0.81 mmol) in methanol (2 mL). This mixture was stirred at room temperature for 1 hour and then sodium triacetoxyborohydride (0.159 g, 0.75 mmol) followed by acetic acid (0.093 mL) were added. The reaction mixture was stirred for a further 18 hour. The reaction mixture was diluted with iso-butanol and washed with water. The aqueous phase was extracted with further iso-butanol. The combined iso-butanol extracts were evaporated at reduced pressure. The residue was purified by reverse phase preparative HPLC to afford the title compound.

$^1$H NMR (400 MHz, DMSO-$d_6$); δ 10.30 (br s, 1H), 8.23 (2H, s), 8.11 (d, J=9.9 Hz, 1H), 7.44-7.34 (m, 10H), 7.29 (dd, J=7.0, 7.0 Hz, 1H), 7.06 (m, 3H), 6.92 (d, J=8.2 Hz, 1H), 6.48 (d, J=9.9 Hz, 1H), 5.12 (s, 2H), 5.09 (m, 1H), 4.74-4.71 (m, 1H), 3.80 (s, 2H), 3.18-3.02 (m, 4H), 2.76-2.40 (m, 7H), 2.42-2.27 (m, 2H), 1.97-1.82 (m, 3H), 1.59-1.42 (m, 3H), 1.29-1.22 (m, 1H).

Example 8. (R)-Quinuclidin-3-yl 1-(4-(ethyl(3-(((R)-2-hydroxy-2-(8-hydroxy-2-oxo-1,2-dihydroquinolin-5-yl)ethyl)amino)propyl)carbamoyl)benzoyl)-4-phenylpiperidine-4-carboxylate (Compound 25)

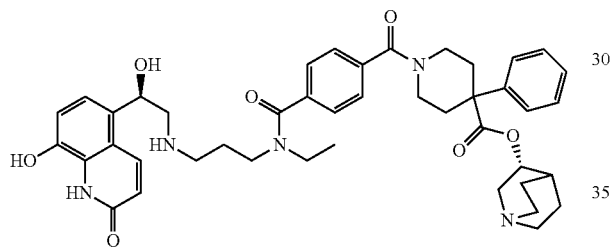

Step 1.
N-Benzyl-2-(1,3-dioxolan-2-yl)-N-ethylethanamine

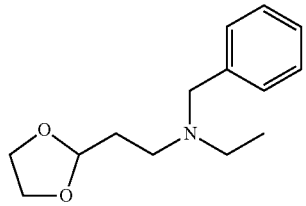 [SMILES: CCN(CCC1OCCO1)Cc1ccccc1]

To a stirred solution of N-benzylethanamine (3 g, 22.22 mmol) and DIPEA (5.8 mL, 33.33 mmol) in acetonitrile (50 mL) was added 2-(2-bromoethyl)-1,3-dioxolane (2.87 mL, 24.44 mmol) and the reaction mixture heated at 50° C. for 18 hours. The reaction mixture was diluted with ethyl acetate and washed with water and brine. The organic phase was dried over anhydrous magnesium sulfate, the suspension filtered and the filtrate was concentrated at reduced pressure. The residue was purified by column chromatography (eluant 0% to 60% ethyl acetate in i-hexanes) to afford the title compound (4.53 g, 87%).

$^1$H NMR (400 MHz, DMSO-$d_6$); δ 7.31-7.29 (m, 4H), 7.25-7.20 (m, 1H), 4.80 (dd, J=4.9, 4.9 Hz, 1H), 3.87-3.70 (m, 6H), 3.52 (s, 2H), 2.47-2.40 (m, 2H), 1.74-1.68 (m, 2H), 0.96 (dd, J=7.1, 7.1 Hz, 3H).

Step 2. 2-(1,3-Dioxolan-2-yl)-N-ethylethanamine

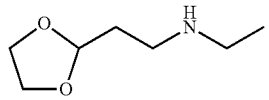

To a stirred solution of N-benzyl-2-(1,3-dioxolan-2-yl)-N-ethylethanamine (4.5 g, 19.15 mmol) in ethanol (100 mL) was added palladium on charcoal (2.2 g) followed by 1-methyl-1,4-cyclohexadiene (10.74 mL). The reaction was heated to reflux and then heated at reflux for 2 hours. The suspension was filtered and the filtrate was concentrated at reduced pressure to afford the title compound (2.32 g, 84%).

$^1$H NMR (400 MHz, DMSO-$d_6$); δ 4.83 (dd, J=5.0, 5.0 Hz, 1H), 3.89-3.72 (m, 4H), 2.58-2.54 (m, 2H), 2.50-2.47 (m, 2H), 1.71-1.66 (m, 2H), 0.98 (dd, J=7.1, 7.1 Hz, 3H).

Step 3. Methyl 4-((2-(1,3-dioxolan-2-yl)ethyl)(ethyl)carbamoyl)benzoate

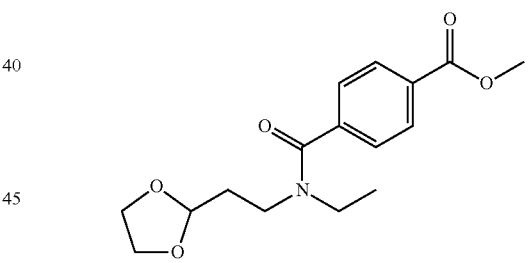

To a solution of 4-(methyoxycarbonyl)benzoic acid (1.0 g, 5.55 mmol) and 2-(1,3-dioxolan-2-yl)-N-ethylethanamine (0.966 g, 6.66 mmol) in DMF (10 mL) was added DIPEA (1.26 mL, 7.22 mmol) and HATU (2.54 g, 6.66 mmol). The reaction mixture was stirred at 40° C. for 3 hours. The reaction mixture was diluted with ethyl acetate and washed with water and brine (×3). The organic phase was dried over anhydrous magnesium sulfate, the suspension filtered and the filtrate was concentrated at reduced pressure. The residue was purified by column chromatography (eluent, 100% i-hexane to 80% ethyl acetate/i-hexane) to afford the title compound (1.55 g, 91%).

$^1$H NMR (400 MHz, DMSO-$d_6$); δ 8.01 (d, J=8.2 Hz, 2H), 7.49 (d, J=8.3 Hz, 2H), 4.90 (dd, J=4.1, 4.1 Hz, 1H), 3.94-3.67 (m, 7H), 3.53-3.12 (m, 4H), 1.96-1.75 (m, 2H), 1.18-1.01 (m, 3H).

Step 4. 4-((2-(1,3-Dioxolan-2-yl)ethyl)(ethyl)carbamoyl)benzoic acid

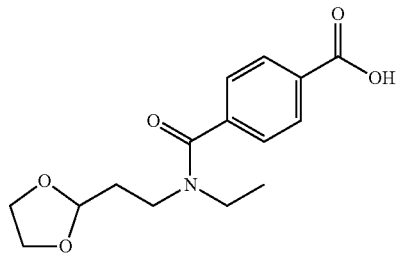 [SMILES: CCN(CCC1OCCO1)C(=O)c1ccc(C(=O)O)cc1]

To a stirred solution of methyl 4-((2-(1,3-dioxolan-2-yl)ethyl)(ethyl)carbamoyl)-benzoate (1.55 g, 5.05 mmol) in methanol/THF (28 mL/28 mL) was added 2M aqueous sodium hydroxide (28 mL) and the reaction mixture stirred was stirred at room temperature for 5 hours. The organic solvents were removed at reduced pressure and the subsequent aqueous was washed with ethyl acetate. The pH of the aqueous phase was adjusted to pH 5 and extracted with ethyl acetate (×2). The combined ethyl acetate extracts were dried over anhydrous magnesium sulfate, the suspension filtered and the filtrate was concentrated at reduced pressure to afford the title compound (1.32 g, 89%).

$^1$H NMR (400 MHz, DMSO-d$_6$); δ 8.01 (d, J=8.2 Hz, 2H), 7.49 (d, J=8.3 Hz, 2H), 4.90 (dd, J=4.1, 4.1 Hz, 1H), 3.94-3.67 (m, 4H), 3.53-3.12 (m, 4H), 1.96-1.75 (m, 2H), 1.18-1.01 (m, 3H).

Step 5. (R)-Quinuclidin-3-yl 1-(4-(ethyl(3-(((R)-2-hydroxy-2-(8-hydroxy-2-oxo-1,2-dihydroquinolin-5-yl)ethyl)amino)propyl)carbamoyl)benzoyl)-4-phenylpiperidine-4-carboxylate (Compound 25)

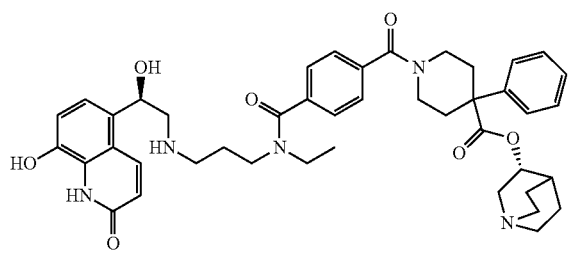 [SMILES: CCN(CCCNC[C@H](O)c1ccc(O)c2[nH]c(=O)ccc12)C(=O)c1ccc(C(=O)N2CCC(C(=O)O[C@H]3CN4CCC3CC4)(c3ccccc3)CC2)cc1]

The title compound was prepared as described in Example 1 with 4-((2-(1,3-dioxolan-2-yl)ethyl)(ethyl)carbamoyl) benzoic acid replacing 4-(4-(1,3-dioxolan-2-yl)butoxy)benzoic acid in Step 3.

$^1$H NMR (400 MHz, DMSO, 90° C.) d 8.18 (d, J=9.9 Hz, 1H), 7.50-7.38 (m, 9H), 7.32 (dd, J=7.1, 7.1 Hz, 1H), 7.16 (d, J=8.2 Hz, 1H), 7.01 (d, J=8.2 Hz, 1H), 6.55 (d, J=9.9 Hz, 1H), 5.35 (dd, J=4.3, 8.5 Hz, 1H), 5.09-5.04 (m, 1H), 3.85 (s, 2H), 3.65 (ddd, J=2.5, 8.6, 14.0 Hz, 1H), 3.53-3.46 (m, 2H), 3.37-2.94 (m, 11H), 2.18-1.99 (m, 6H), 1.95-1.81 (m, 3H), 1.70-1.65 (m, 2H), 1.12 (dd, J=7.1, 7.1 Hz, 3H).

Example 9. (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)oxy)benzoyl)-4-phenylpiperidine-4-carboxylate (Compound 26)

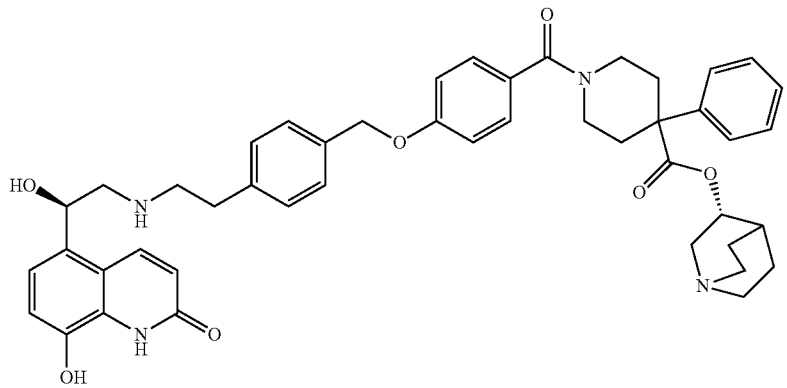 [SMILES: O=C(c1ccc(OCc2ccc(CCNC[C@H](O)c3ccc(O)c4[nH]c(=O)ccc34)cc2)cc1)N1CCC(C(=O)O[C@H]2CN3CCC2CC3)(c2ccccc2)CC1]

Step 1.
(4-((1,3-Dioxolan-2-yl)methyl)phenyl)methanol

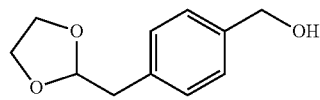 [SMILES: OCc1ccc(CC2OCCO2)cc1]

To a cooled (0° C.) solution of 4-((1,3-dioxolan-2-yl)methyl)benzoic acid (1.27 g, 6.11 mmol) in THF (70 mL) was added drop wise a solution of borane-dimethyl sulfide (2M in THF, 15.26 mL, 30.52 mmol). The reaction mixture was stirred at 0° C. for five minutes and then at room temperature for 36 hours. The reaction cooled (0° C.) and methanol (2 mL) added. Saturated aqueous sodium hydrogen carbonate added and the mixture extracted with ethyl acetate (×2). The combined organic phases were dried over anhydrous magnesium sulfate, the suspension filtered and the filtrate was concentrated at reduced pressure. The residue was purified by column chromatography (eluent, 100% i-hexane to 60% ethyl acetate/i-hexane) to afford the title compound (1.20 g, 100%).

$^1$H NMR (400 MHz, DMSO-d$_6$); δ 7.21 (d, J=4.4 Hz, 4H), 5.11 (dd, J=5.7, 5.7 Hz, 1H), 4.94 (dd, J=5.0, 5.0 Hz, 1H), 4.46 (d, J=5.8 Hz, 2H), 3.90-3.73 (m, 4H), 2.85 (d, J=5.0 Hz, 2H).

Step 2; 4-((4-((1,3-Dioxolan-2-yl)methyl)benzyl)oxy)benzoic acid

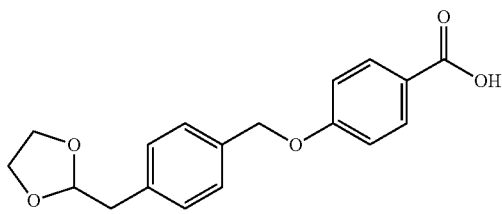 [SMILES: O=C(O)c1ccc(OCc2ccc(CC3OCCO3)cc2)cc1]

The title compound was prepared as described in Example 5 Step 2 with (4-((1,3-dioxolan-2-yl)methyl)phenyl)methanol replacing (3-(3-(1,3-dioxolan-2-yl)propoxy)phenyl)methanol.

$^1$H NMR (400 MHz, DMSO-$d_6$); δ 7.90-7.87 (m, 2H), 7.38 (d, J=8.2 Hz, 2H), 7.28 (d, J=8.3 Hz, 2H), 7.09 (d, J=8.9 Hz, 2H), 5.15 (s, 2H), 4.97 (dd, J=5.0, 5.0 Hz, 1H), 3.90-3.74 (m, 4H), 2.89 (d, J=5.0 Hz, 2H).

Step 3. (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)oxy)benzoyl)-4-phenylpiperidine-4-carboxylate (Compound 26)

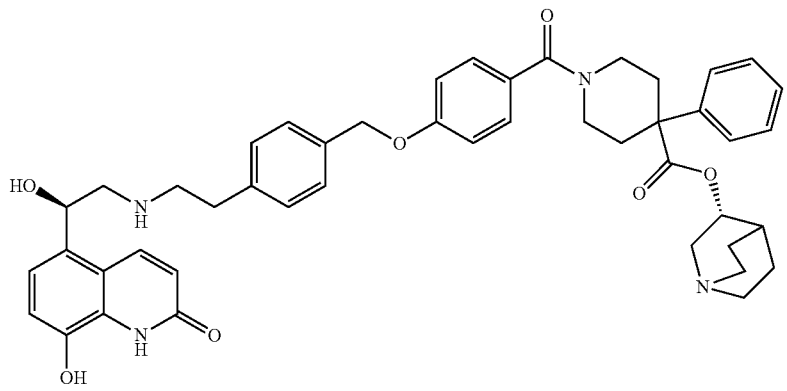 [SMILES: O=C(c1ccc(OCc2ccc(CCNC[C@H](O)c3ccc(O)c4[nH]c(=O)ccc34)cc2)cc1)N1CCC(C(=O)O[C@H]2CN3CCC2CC3)(c2ccccc2)CC1]

The title compound was prepared as described in Example 1 with 4-((4-((1,3-dioxolan-2-yl)methyl)benzyl)oxy)benzoic acid replacing 4-(4-(1,3-dioxolan-2-yl)butoxy)benzoic acid in Step 3.

$^1$H NMR (400 MHz, DMSO-$d_6$); δ 10.49 (s, 2H), 9.72 (s, 1H), 8.77-8.77 (m, 2H), 8.16 (d, J=9.9 Hz, 1H), 7.47-7.36 (m, 8H), 7.34-7.28 (m, 3H), 7.17 (d, J=8.3 Hz, 1H), 7.05 (d, J=8.8 Hz, 2H), 7.00 (d, J=8.2 Hz, 1H), 6.59 (d, J=9.8 Hz, 1H), 6.20 (s, 1H), 5.34 (d, J=7.9 Hz, 1H), 5.13 (s, 2H), 5.04-4.99 (m, 1H), 3.62 (m, 2H), 3.36-3.30 (m, 3H), 3.24-2.95 (m, 12H), 2.16-2.09 (m, 1H), 2.04-1.76 (m, 4H), 1.63 (dd, J=6.8, 6.8 Hz, 2H).

Example 10. (R)-Quinuclidin-3-yl 1-(5-((3-(((R)-2-hydroxy-2-(8-hydroxy-2-oxo-1,2-dihydroquinolin-5-yl)ethyl)amino)propyl)(methyl)carbamoyl)thiophene-2-carbonyl)-4-phenylpiperidine-4-carboxylate (Compound 27)

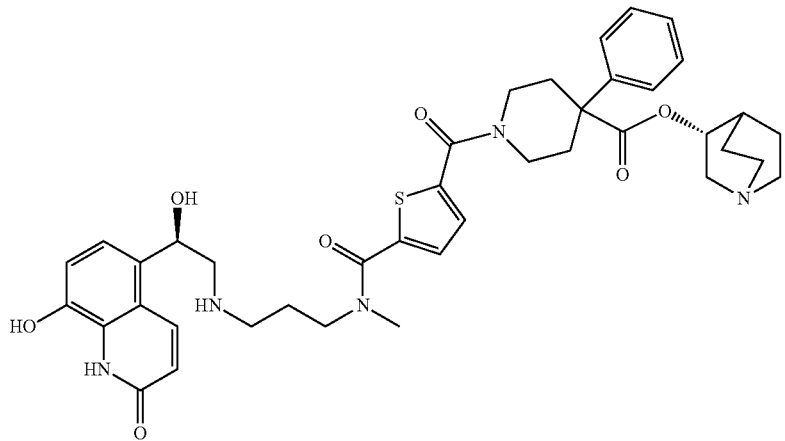 [SMILES: CN(CCCNC[C@H](O)c1ccc(O)c2[nH]c(=O)ccc12)C(=O)c1ccc(C(=O)N2CCC(C(=O)O[C@H]3CN4CCC3CC4)(c3ccccc3)CC2)s1]

Step 1. Methyl 5-((2-(1,3-dioxolan-2-yl)ethyl)(methyl)carbamoyl)thiophene-2-carboxylate

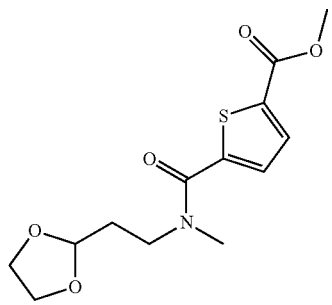 [SMILES: COC(=O)c1ccc(C(=O)N(C)CCC2OCCO2)s1]

To a solution of 5-(methoxycarbonyl)thiophene-2-carboxylic acid (1.03 g, 5.55 mmol) and 2-(1,3-dioxolan-2-yl)-N-methylethanamine (0.872 g, 6.66 mmol) in DMF (10 mL) was added DIPEA (1.26 mL, 7.22 mmol) and HATU (2.54 g, 6.66 mmol). The reaction mixture was stirred at 40° C. for 3 hours. The reaction mixture was diluted with ethyl acetate and washed with water and brine (×3). The organic phase was dried over anhydrous magnesium sulfate, the suspension filtered and the filtrate was concentrated at reduced pressure. The residue was purified by column chromatography (eluent, 100% i-hexane to 80% ethyl acetate/i-hexane) to afford the title compound (1.56 g, 95%).

$^1$H NMR (400 MHz, DMSO-$d_6$); δ 7.76 (d, J=4.0 Hz, 1H), 7.49-7.49 (m, 1H), 4.84-4.84 (m, 1H), 3.88 (s, 2H), 3.85 (s, 3H), 3.77 (s, 2H), 3.55 (dd, J=7.5, 7.5 Hz, 2H), 3.12-3.12 (m, 3H), 1.92-1.92 (m, 2H).

Step 2. 5-((2-(1,3-Dioxolan-2-yl)ethyl)(methyl)carbamoyl)thiophene-2-carboxylic acid

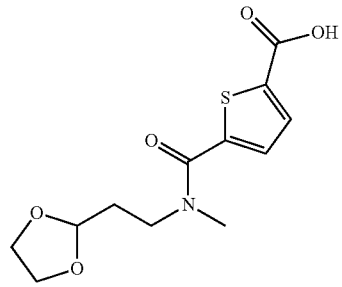 [SMILES: CN(CCC1OCCO1)C(=O)c1ccc(C(=O)O)s1]

To a stirred solution of methyl 5-((2-(1,3-dioxolan-2-yl)ethyl)(methyl)-carbamoyl)thiophene-2-carboxylate (1.56 g, 5.22 mmol) in methanol/THF (25 mL/25 mL) was added 2M aqueous sodium hydroxide (25 mL) and the reaction mixture stirred was stirred at room temperature for 5 hours. The organic solvents were removed at reduced pressure and the subsequent aqueous was washed with ethyl acetate. The pH of the aqueous phase was adjusted to pH 5 and extracted with ethyl acetate (×2). The combined ethyl acetate extracts were dried over anhydrous magnesium sulfate, the suspension filtered and the filtrate was concentrated at reduced pressure to afford the title compound (0.19 g, 13%).

$^1$H NMR (400 MHz, DMSO-$d_6$); δ 7.76 (d, J=4.0 Hz, 1H), 7.49-7.49 (m, 1H), 4.84-4.84 (m, 1H), 3.88 (s, 2H), 3.77 (s, 2H), 3.55 (dd, J=7.5, 7.5 Hz, 2H), 3.12-3.12 (m, 3H), 1.92-1.92 (m, 2H).

Step 3. (R)-Quinuclidin-3-yl 1-(5-((3-(((R)-2-hydroxy-2-(8-hydroxy-2-oxo-1,2-dihydroquinolin-5-yl)ethyl)amino)propyl)(methyl)carbamoyl)thiophene-2-carbonyl)-4-phenylpiperidine-4-carboxylate
(Compound 27)

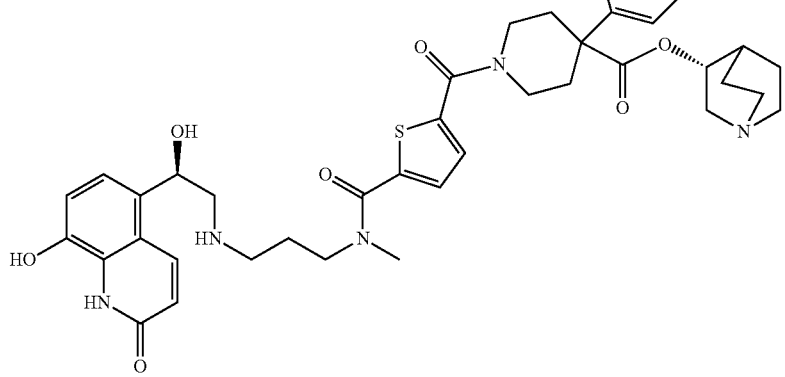

The title compound was prepared as described in Example 1 with 5-((2-(1,3-dioxolan-2-yl)ethyl)(methyl)carbamoyl)thiophene-2-carboxylic acid replacing 4-(4-(1,3-dioxolan-2-yl)butoxy)benzoic acid in Step 3.

$^1$H NMR (400 MHz, DMSO-d$_6$, 90° C.); δ 8.11-8.01 (m, 3H), 7.35-7.25 (m, 7H), 7.24 (d, J=3.8 Hz, 1H), 7.19 (dd, J=7.2, 7.2 Hz, 1H), 6.98 (d, J=8.0 Hz, 1H), 6.85 (d, J=8.2 Hz, 1H), 6.38 (d, J=9.9 Hz, 1H), 4.94 (dd, J=5.0, 7.3 Hz, 1H), 4.67-4.64 (m, 1H), 3.99-3.91 (m, 2H), 3.42 (dd, J=6.5, 7.9 Hz, 2H), 3.31-3.21 (m, 2H), 3.04-2.90 (m, 4H), 2.76-2.63 (m, 1H), 2.60-2.48 (m, 5H), 2.33-2.23 (m, 1H), 1.94 (s, 4H), 1.77-1.61 (m, 3H), 1.53-1.34 (m, 3H), 1.17 (dd, J=11.2, 15.8 Hz, 1H).

Example 11. (R)-Quinuclidin-3-yl 1-(5-(benzyl(3-(((R)-2-hydroxy-2-(8-hydroxy-2-oxo-1,2-dihydro-quinolin-5-yl)ethyl)amino)propyl)carbamoyl)thio-phene-2-carbonyl)-4-phenylpiperidine-4-carboxylate (Compound 28)

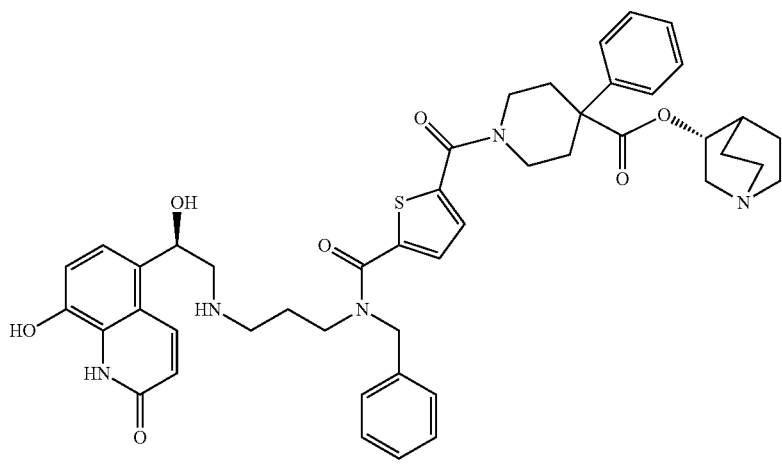 [SMILES: O=C(c1ccc(C(=O)N(CCCNC[C@H](O)c2ccc(O)c3[nH]c(=O)ccc23)Cc2ccccc2)s1)N1CCC(C(=O)O[C@H]2CN3CCC2CC3)(c2ccccc2)CC1]

Step 1. N-Benzyl-2-(1,3-dioxolan-2-yl)ethanamine

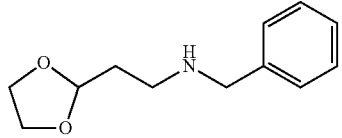 [SMILES: c1ccc(CNCCC2OCCO2)cc1]

To a solution of benzylamine (7.36 g, 68.7 mmol) in acetonitrile (100 mL) was added 2-(2-bromoethyl)-1,3-dioxolane (6.22 g, 34.3 mmol) and DIPEA (9.0 mL, 51.7 mmol) and the resultant mixture heated under reflux for 3 hours. The solvent was concentrated at reduced pressure and the residue dissolved in DCM. The organic phase was washed with water and brine. The organic phase was dried over anhydrous magnesium sulfate, the suspension filtered and the filtrate was concentrated at reduced pressure. The residue was purified by column chromatography (eluent 100% DCM to 5% methanol/DCM) to afford the title compound (4.0 g, 56%).

$^1$H NMR (400 MHz, DMSO-d$_6$); δ 7.32-7.29 (m, 3H), 7.23-7.20 (m, 2H), 4.84 (dd, J=4.9, 4.9 Hz, 1H), 3.87-3.71 (m, 4H), 3.67 (s, 2H), 2.59-2.55 (m, 2H), 1.76-1.71 (m, 2H).

Step 2. (R)-Quinuclidin-3-yl 1-(5-(benzyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate (Compound 28)

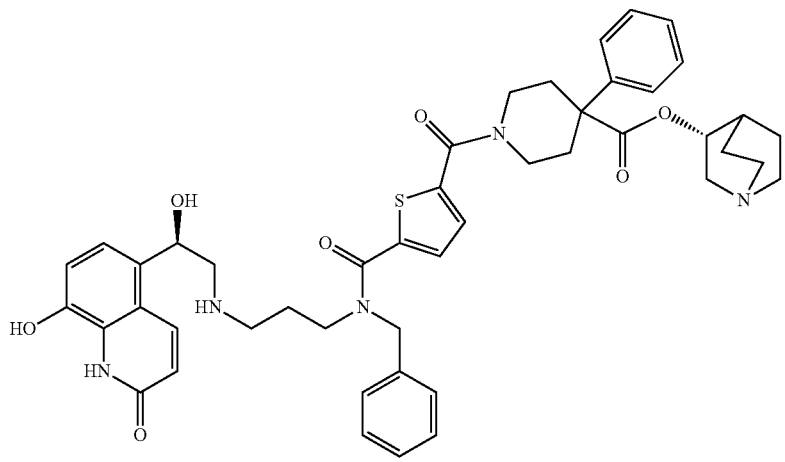 [SMILES: O=C(c1ccc(C(=O)N(CCCNC[C@H](O)c2ccc(O)c3[nH]c(=O)ccc23)Cc2ccccc2)s1)N1CCC(C(=O)O[C@H]2CN3CCC2CC3)(c2ccccc2)CC1]

The title compound was prepared as described in Example 10 using N-benzyl-2-(1,3-dioxolan-2-yl)ethanamine in the place of 2-(1,3-dioxolan-2-yl)-N-methylethanamine.

$^1$H NMR (400 MHz, DMSO-d$_6$, 90° C.); δ 8.17 (d, J=9.9 Hz, 1H), 7.48-7.37 (m, 6H), 7.33-7.27 (m, 6H), 7.15 (d, J=8.2 Hz, 1H), 7.02 (d, J=8.2 Hz, 1H), 6.56 (d, J=9.9 Hz, 1H), 5.33 (dd, J=4.8, 8.3 Hz, 1H), 5.09-5.04 (m, 1H), 4.80 (s, 2H), 4.05-3.95 (m, 2H), 3.66 (ddd, J=2.6, 8.5, 14.0 Hz, 1H), 3.56-3.51 (m, 2H), 3.46-3.36 (m, 2H), 3.25-2.99 (m, 8H), 2.59-2.53 (m, 2H), 2.20-2.00 (m, 6H), 2.00-1.81 (m, 2H), 1.71-1.65 (m, 2H).

Example 12. (R)-Quinuclidin-3-yl 1-(5-(ethyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate (Compound 29)

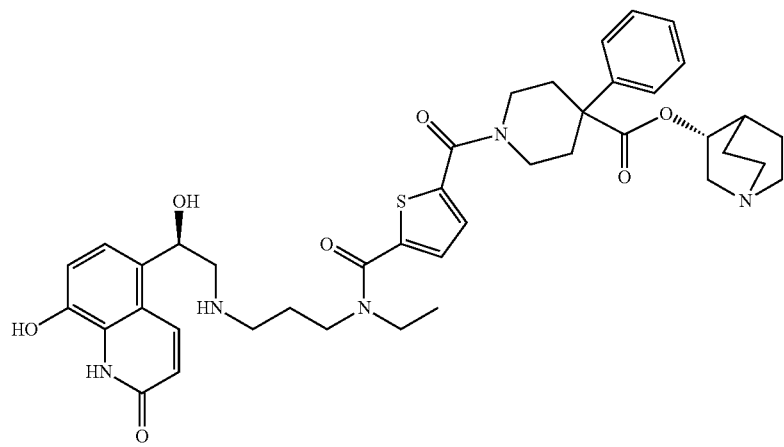 [SMILES: CCN(CCCNC[C@H](O)c1ccc(O)c2[nH]c(=O)ccc12)C(=O)c1ccc(C(=O)N2CCC(C(=O)O[C@H]3CN4CCC3CC4)(c3ccccc3)CC2)s1]

The title compound was prepared as described in Example 10 using N-ethyl-2-(1,3-dioxolan-2-yl)ethanamine in the place of 2-(1,3-dioxolan-2-yl)-N-methylethanamine.

$^1$H NMR (400 MHz, DMSO-d$_6$); δ 10.50 (s, 2H), 9.76 (s, 1H), 8.64 (s, 2H), 8.16 (d, J=9.9 Hz, 1H), 7.46 (d, J=7.5 Hz, 2H), 7.44-7.38 (m, 4H), 7.32 (dd, J=7.1, 7.1 Hz, 1H), 7.16 (d, J=8.3 Hz, 1H), 6.99 (d, J=8.2 Hz, 1H), 6.58 (d, J=9.9 Hz, 1H), 6.20 (s, 1H), 5.31 (dd, J=2.4, 9.5 Hz, 1H), 5.05-5.00 (m, 1H), 4.09-4.07 (m, 2H), 3.67-3.61 (m, 2H), 3.54-3.32 (m, 4H), 3.22-3.00 (m, 9H), 2.60-2.54 (m, 2H), 2.17-1.95 (m, 6H), 1.91-1.77 (m, 2H), 1.64 (dd, J=6.3, 6.3 Hz, 2H), 1.20 (dd, J=6.8, 6.8 Hz, 3H).

Example 13. (R)-Quinuclidin-3-yl 1-(2-(4-(4-(((R)-2-hydroxy-2-(8-hydroxy-2-oxo-1,2-dihydroquinolin-5-yl)ethyl)amino)butoxy)phenyl)acetyl)-4-phenylpiperidine-4-carboxylate (Compound 30)

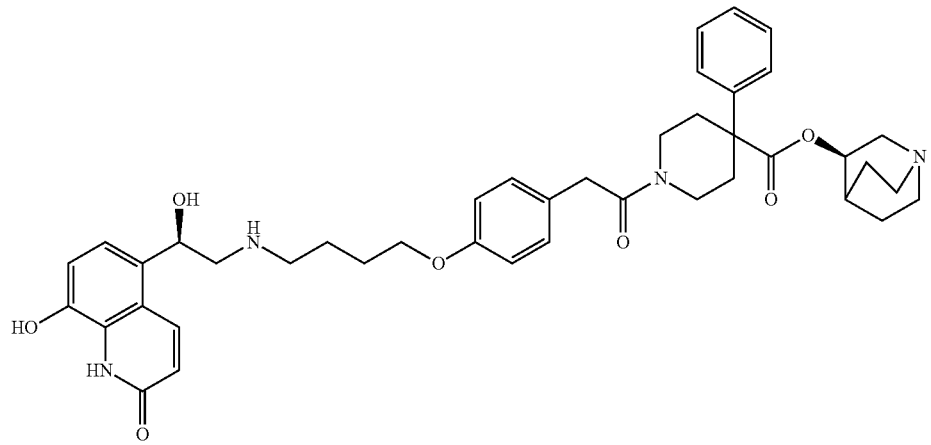 [SMILES: O=C(Cc1ccc(OCCCCNC[C@H](O)c2ccc(O)c3[nH]c(=O)ccc23)cc1)N1CCC(C(=O)O[C@H]2CN3CCC2CC3)(c2ccccc2)CC1]

Step 1. 2-(4-(3-(1,3-Dioxolan-2-yl)propoxy)phenyl)acetic acid

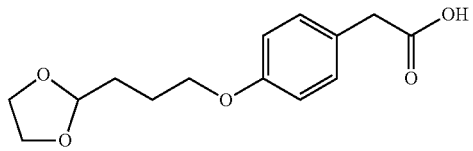 [SMILES: O=C(O)Cc1ccc(OCCCC2OCCO2)cc1]

To a solution of methyl 4-hydroxyphenylacetate (0.500 g, 3.00 mmol) in DMF (10 mL) was added potassium carbonate (0.621 g, 4.5 mmol) and the reaction mixture stirred at room temperature for 20 minutes. 2-(3-Chloropropyl)-1,3-dioxolane (0.435 mL, 3.3 mmol) was added and the reaction mixture heated at 80° C. for 18 hours. The reaction mixture was diluted with ethyl acetate and washed sequentially with water, 10% aqueous potassium carbonate and brine (×2). The organic phase was dried over anhydrous magnesium sulfate, the suspension filtered and the filtrate was concentrated at reduced pressure.

The residue was dissolved in methanol (8 mL) and 2M aqueous sodium hydroxide (8 mL) added. The reaction mixture was stirred at room temperature for 72 hours. The reaction mixture was concentrated at reduced pressure and the residue partitioned between water and ether. The organic phase was discarded and the pH of the aqueous phase was adjusted to 1. The aqueous phase was extracted with DCM (×2) and the combined DCM phases were dried over anhydrous magnesium sulfate, the suspension filtered and the filtrate was concentrated at reduced pressure to afford the title compound (0.219 g, 32%).

$^1$H NMR (400 MHz, CDCl$_3$); δ 7.19-7.17 (m, 2H), 6.87-6.84 (m, 2H), 4.94 (t, J=4.4 Hz, 1H), 4.02-3.94 (m, 4H), 3.87-3.85 (m, 2H), 3.58 (s, 2H), 1.95-1.81 (m, 4H).

Step 2. (R)-Quinuclidin-3-yl 1-(2-(4-(4-(((R)-2-hydroxy-2-(8-hydroxy-2-oxo-1,2-dihydroquinolin-5-yl)ethyl)amino)butoxy)phenyl)acetyl)-4-phenylpiperidine-4-carboxylate (Compound 30)

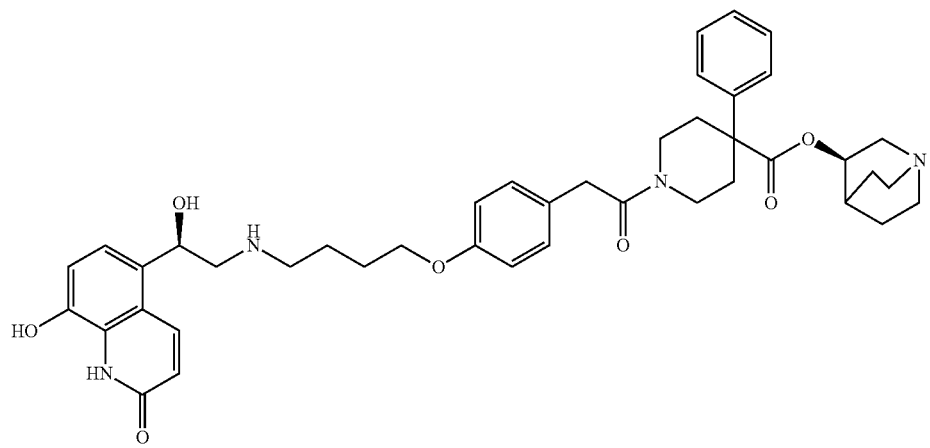 [SMILES: O=C(Cc1ccc(OCCCCNC[C@H](O)c2ccc(O)c3[nH]c(=O)ccc23)cc1)N1CCC(C(=O)O[C@H]2CN3CCC2CC3)(c2ccccc2)CC1]

The title compound was prepared as described in Example 1 with 2-(4-(3-(1,3-dioxolan-2-yl)propoxy)phenyl)acetic acid replacing 4-(4-(1,3-dioxolan-2-yl)butoxy)benzoic acid in Step 3.

$^1$H NMR (400 MHz, MeOD); δ 8.53 (s, 2H), 8.38 (d, J=9.9 Hz, 1H), 7.39 (d, J=7.2 Hz, 4H), 7.32-7.29 (m, 2H), 7.18 (d, J=8.5 Hz, 2H), 7.04 (d, J=8.3 Hz, 1H), 6.90 (d, J=8.4 Hz, 2H), 6.69 (d, J=9.9 Hz, 1H), 5.41 (dd, J=6.8, 6.8 Hz, 1H), 5.01-4.98 (m, 1H), 4.30-4.24 (m, 1H), 4.03 (dd, J=5.5, 5.5 Hz, 2H), 3.89 (dd, J=6.7, 12.9 Hz, 1H), 3.75 (s, 2H), 3.51-3.35 (m, 2H), 3.26-3.01 (m, 7H), 2.86-2.67 (m, 3H), 2.61-2.44 (m, 2H), 2.15-2.07 (m, 1H), 1.97-1.89 (m, 6H), 1.81-1.51 (m, 4H).

Example 14. (R)-Quinuclidin-3-yl 1-(3-(4-((((R)-2-hydroxy-2-(8-hydroxy-2-oxo-1,2-dihydroquinolin-5-yl)ethyl)amino)methyl)benzamido)propanoyl)-4-phenylpiperidine-4-carboxylate (Compound 31)

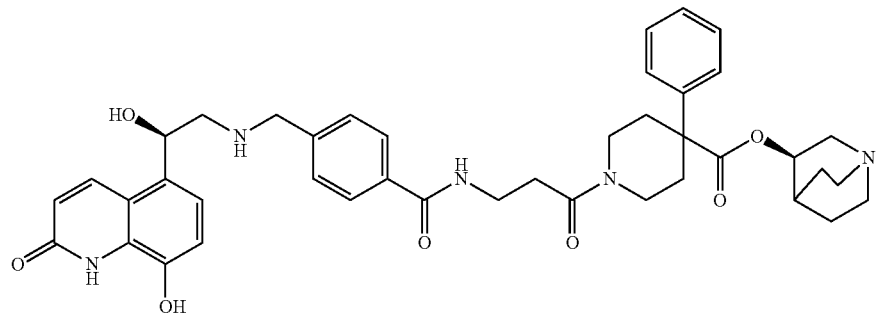 [SMILES: O=C(NCCC(=O)N1CCC(C(=O)O[C@H]2CN3CCC2CC3)(c2ccccc2)CC1)c1ccc(CNC[C@H](O)c2ccc(O)c3[nH]c(=O)ccc23)cc1]

Step 1. tert-Butyl 3-(4-formylbenzamido)propanoate

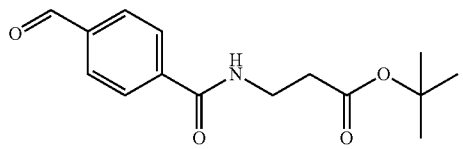 [SMILES: CC(C)(C)OC(=O)CCNC(=O)c1ccc(C=O)cc1]

To a solution of 4-carboxybenzaldehyde (1.13 g, 7.53 mmol) in DMF (30 mL) was added DIPEA (2.60 mL, 14.9 mmol) followed by HATU (2.86 g, 7.52 mmol). The reaction mixture was stirred at room temperature for 40 minutes. tert-Butyl 3-aminopropanoate hydrochloride (0.908 g, 5.0 mmol) was added and the reaction mixture stirred at room temperature for 18 hours. The reaction mixture was diluted with ethyl acetate and washed sequentially with water, 10% aqueous potassium carbonate and brine (×2). The organic phase was dried over anhydrous magnesium sulfate, the suspension filtered and the filtrate was concentrated at reduced pressure. The residue was purified by column chromatography (eluent 100% i-hexane to 3/1 i-hexane/ethyl acetate) to afford the title product (1.23 g, >100%).

$^1$H NMR (400 MHz, CDCl$_3$); δ 10.08 (s, 1H), 7.97-7.91 (m, 4H), 7.00 (br s, 1H), 3.73-3.70 (m, 2H), 2.59-2.56 (m, 2H), 1.47 (s, 9H).

Step 2. 3-(4-Formylbenzamido)propanoic acid

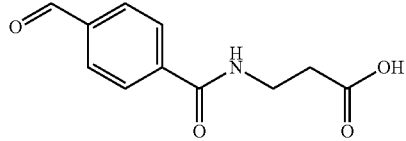 [SMILES: O=Cc1ccc(C(=O)NCCC(=O)O)cc1]

A solution of HCl-dioxane (4M, 10 mL) was added to tert-butyl 3-(4-formylbenzamido)propanoate (1.23 g, 5.0 mmol) and the reaction mixture was stirred at room temperature for 18 hours. The resultant suspension was filtered, the filter cake washed with ether and the solid dried in vacuo to afford the title compound (0.425 g, 38%).

$^1$H NMR (400 MHz, DMSO-d$_6$); δ 10.08 (s, 1H), 8.78-8.75 (m, 1H), 8.03-7.98 (m, 4H), 3.51-3.45 (m, 2H), 2.56-2.53 (m, 2H).

Step 3. (R)-Quinuclidin-3-yl 1-(3-(4-((((R)-2-hydroxy-2-(8-hydroxy-2-oxo-1,2-dihydroquinolin-5-yl)ethyl)amino)methyl)benzamido)propanoyl)-4-phenylpiperidine-4-carboxylate (Compound 31)

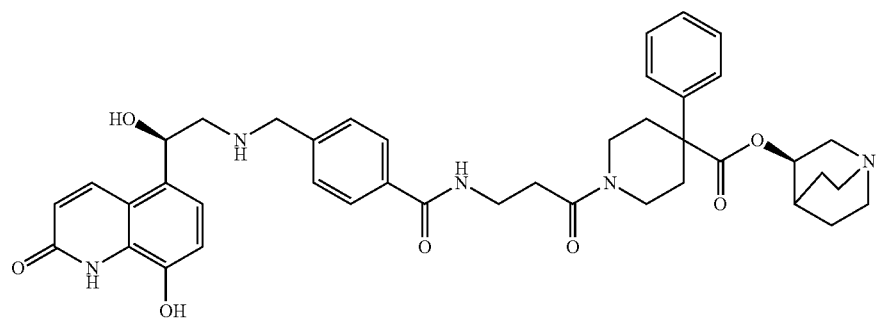 [SMILES: O=C(NCCC(=O)N1CCC(C(=O)O[C@H]2CN3CCC2CC3)(c2ccccc2)CC1)c1ccc(CNC[C@H](O)c2ccc(O)c3[nH]c(=O)ccc23)cc1]

The title compound was prepared as described in Example 7 with 3-(4-formylbenzamido)propanoic acid replacing 4-((4-formylbenzyl)oxy)benzoic acid in Step 3.

¹H NMR (400 MHz, DMSO-d₆); δ 10.52 (s, 1H), 10.49 (s, 1H), 9.62-9.62 (m, 1H), 9.13 (s, 2H), 8.59-8.54 (m, 1H), 8.06 (d, J=9.9 Hz, 1H), 7.87 (d, J=8.2 Hz, 2H), 7.59 (d, J=8.3 Hz, 2H), 7.44-7.36 (m, 4H), 7.33-7.29 (m, 1H), 7.12 (d, J=8.3 Hz, 1H), 6.97 (d, J=8.2 Hz, 1H), 6.57 (d, J=9.8 Hz, 1H), 6.22-6.19 (m, 1H), 5.34 (d, J=8.7 Hz, 1H), 5.04-4.99 (m, 1H), 4.29 (dd, J=5.6, 5.6 Hz, 2H), 4.15-4.08 (m, 1H), 3.76 (dd, J=4.3, 13.7 Hz, 1H), 3.66-3.60 (m, 2H), 3.35-3.22 (m, 2H), 3.15-2.98 (m, 9H), 2.70-2.56 (m, 2H), 2.17-2.12 (m, 1H), 2.00-1.78 (m, 5H), 1.66-1.59 (m, 2H).

Example 15. (R)-Quinuclidin-3-yl 1-(3-(4-(4-(((R)-2-hydroxy-2-(8-hydroxy-2-oxo-1,2-dihydroquinolin-5-yl)ethyl)amino)butoxy)phenyl)propanoyl)-4-phenylpiperidine-4-carboxylate (Compound 32)

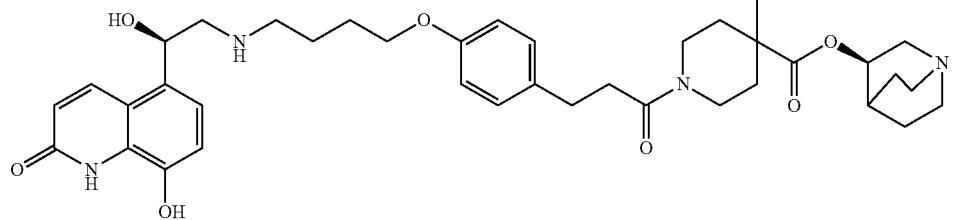

The title compound was prepared as described in Example 13 with methyl 3-(4-hydroxyphenyl)propanoate used in Step 1 in place of methyl 3-(4-hydroxyphenyl)acetate.

¹H NMR (400 MHz, MeOD); δ 8.39 (d, J=9.9 Hz, 1H), 7.40 (d, J=3.3 Hz, 4H), 7.34-7.29 (m, 2H), 7.14 (d, J=8.3 Hz, 2H), 7.05 (d, J=8.1 Hz, 1H), 6.80 (d, J=7.8 Hz, 2H), 6.69 (d, J=9.9 Hz, 1H), 5.41 (dd, J=6.7, 6.7 Hz, 1H), 5.14-5.09 (m, 1H), 4.24-4.24 (m, 1H), 3.95-3.74 (m, 3H), 3.71-3.62 (m, 1H), 3.29-3.16 (m, 7H), 3.08-2.85 (m, 6H), 2.82-2.72 (m, 1H), 2.68-2.53 (m, 2H), 2.48-2.42 (m, 1H), 2.24 (dd, J=2.5, 21.5 Hz, 1H), 2.05-2.05 (m, 8H), 1.75-1.66 (m, 1H), 1.61-1.47 (m, 1H).

Example 16. (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(4-methylbenzyl)amino)-2-oxoethyl)phenyl)acetyl)-4-phenylpiperidine-4-carboxylate (Compound 33)

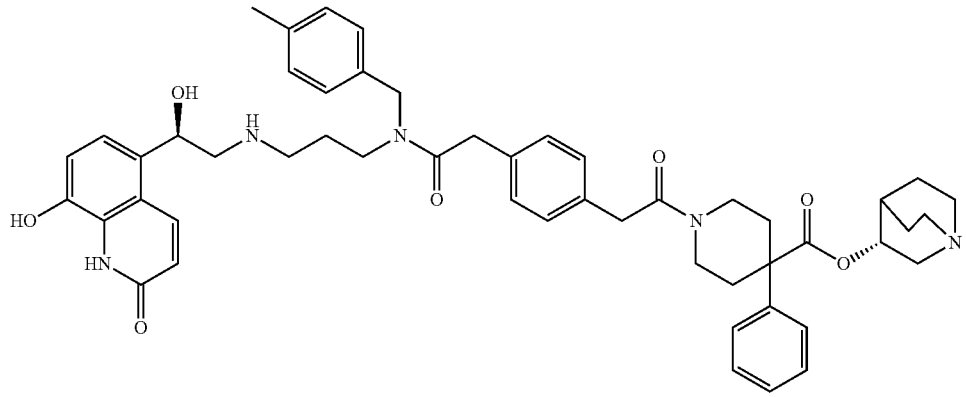 [SMILES: Cc1ccc(CN(CCCNC[C@H](O)c2ccc(O)c3[nH]c(=O)ccc23)C(=O)Cc2ccc(CC(=O)N3CCC(C(=O)O[C@H]4CN5CCC4CC5)(c4ccccc4)CC3)cc2)cc1]

Step 1.
3,3-Diethoxy-N-(4-methylbenzyl)propan-1-amine

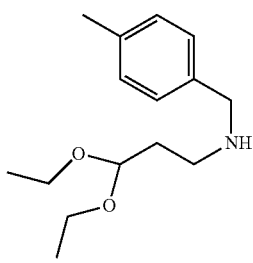 [SMILES: CCOC(CCNCc1ccc(C)cc1)OCC]

To a solution of 1-amino-3,3-diethoxypropane (1.0 mL, 6.18 mmol) and p-tolualdehyde (0.807 mL, 6.84 mmol) in DCM (15 mL) was added anhydrous magnesium sulfate. The reaction mixture was stirred at room temperature for 18 hours. The suspension was filtered and the filtrate was concentrated at reduced pressure. The residue was dissolved in ethanol (15 mL) and sodium borohydride (0.466 g, 12.3 mmol) added in portions. The reaction mixture was stirred at room temperature for 1 hour. The reaction was quenched with 10% aqueous potassium carbonate and then extracted with DCM. The organic phase was dried over anhydrous magnesium sulfate, filtered and the filtrate concentrated at reduced pressure to afford the title compound (1.18 g, 76%).

$^1$H NMR (400 MHz, CDCl$_3$); δ 7.21-7.17 (m, 2H), 7.12 (d, J=7.8 Hz, 2H), 4.59 (dd, J=5.7, 5.7 Hz, 1H), 3.74 (s, 2H), 3.64 (ddd, J=7.1, 9.4, 14.1 Hz, 2H), 3.49 (ddd, J=7.1, 9.4, 14.1 Hz, 2H), 2.70 (dd, J=6.8, 6.8 Hz, 2H), 2.33 (s, 3H), 1.86-1.80 (m, 2H), 1.19 (dd, J=7.1, 7.1 Hz, 6H).

Step 2. Ethyl 2-(4-(2-((3,3-diethoxypropyl)(4-methylbenzyl)amino)-2-oxoethyl)phenyl)acetate

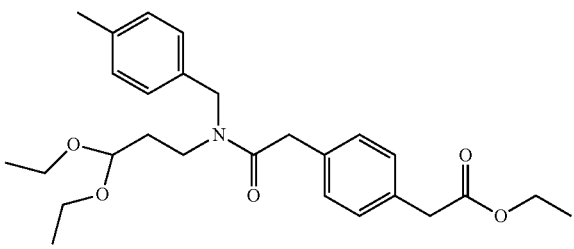 [SMILES: CCOC(=O)Cc1ccc(CC(=O)N(CCC(OCC)OCC)Cc2ccc(C)cc2)cc1]

To a stirred solution of 3,3-diethoxy-N-(4-methylbenzyl)propan-1-amine (0.553 g, 2.2 mmol) and 2-(4-(2-methoxy-2-oxoethyl)phenyl)acetic acid (0.444 g, 2.0 mmol) in DMF (10 mL) was added EDC (0.498 g, 2.6 mmol), HOBt (0.351 g, 2.6 mmol) and DMAP (0.317 g, 2.6 mmol). The reaction mixture was stirred at room temperature for 18 hours. The reaction mixture was diluted with ethyl acetate and washed with water, 10% aqueous potassium carbonate, 10% aqueous potassium hydrogen sulfate and brine (×2). The organic phase was dried over anhydrous magnesium sulfate, filtered and the filtrate concentrated at reduced pressure to afford the title compound (0.908 g, 100%).

$^1$H NMR (400 MHz, CDCl$_3$); δ 7.32-7.20 (m, 4H), 7.19-7.13 (m, 2H), 7.09 (d, J=2.9 Hz, 1H), 7.01 (d, J=7.9 Hz, 1H), 4.56 (s, 1H), 4.49-4.39 (m, 2H), 4.17-4.11 (m, 2H), 3.78 (s, 1H), 3.66 (s, 1H), 3.62-3.26 (m, 8H), 3.46-3.39 (m, 3H), 1.91-1.77 (m, 2H), 1.27-1.13 (m, 9H).

Step 3. 2-(4-(2-((3,3-Diethoxypropyl)(4-methylbenzyl)amino)-2-oxoethyl)phenyl)acetic acid

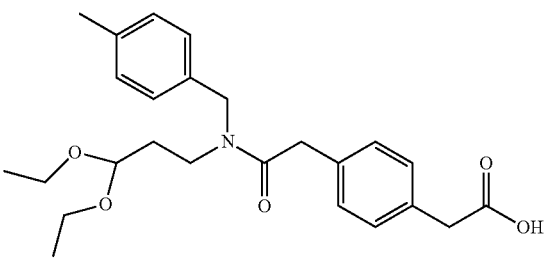 [SMILES: CCOC(CCN(Cc1ccc(C)cc1)C(=O)Cc1ccc(CC(=O)O)cc1)OCC]

To a stirred solution of ethyl 2-(4-(2-((3,3-diethoxypropyl)(4-methylbenzyl)amino)-2-oxoethyl)phenyl)acetate (0.908 g, 2.0 mmol) in methanol (10 mL) was 2M aqueous sodium hydroxide (10 mL). The reaction mixture was stirred at room temperature for 18 hours. 10% aqueous potassium hydrogen sulfate added and the mixture extracted with DCM (×2). The combined organic phases were dried over anhydrous magnesium sulfate, filtered and the filtrate concentrated at reduced pressure to afford the title compound (0.924 g, >100%).

$^1$H NMR (400 MHz, CDCl$_3$); δ 7.32-7.20 (m, 4H), 7.19-7.13 (m, 2H), 7.09 (d, J=2.9 Hz, 1H), 7.01 (d, J=7.9 Hz, 1H), 4.56 (s, 1H), 4.17-4.11 (m, 2H), 3.78 (s, 1H), 3.66 (s, 1H), 3.62-3.26 (m, 8H), 3.46-3.39 (m, 3H), 1.91-1.77 (m, 2H), 1.27-1.13 (m, 6H).

Step 4. (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(4-methylbenzyl)amino)-2-oxoethyl)phenyl)acetyl)-4-phenylpiperidine-4-carboxylate (Compound 33)

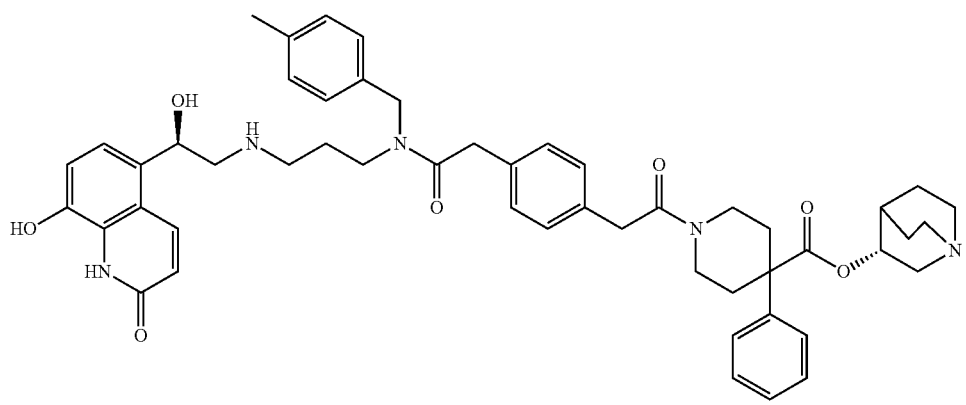 [SMILES: Cc1ccc(CN(CCCNC[C@H](O)c2ccc(O)c3[nH]c(=O)ccc23)C(=O)Cc2ccc(CC(=O)N3CCC(C(=O)O[C@H]4CN5CCC4CC5)(c4ccccc4)CC3)cc2)cc1]

The title compound was prepared as described in Example 1 with 2-(4-(2-((3,3-diethoxypropyl)(4-methylbenzyl)amino)-2-oxoethyl)phenyl)acetic acid replacing 4-(4-(1,3-dioxolan-2-yl)butoxy)benzoic acid in Step 3.

$^1$H NMR (400 MHz, DMSO-$d_6$, 100° C.); δ 8.19 (d, J=9.8 Hz, 1H), 7.37-7.35 (m, 4H), 7.29-7.25 (m, 1H), 7.16 (s, 3H), 7.14-7.09 (m, 2H), 7.08-7.03 (m, 3H), 6.92 (d, J=8.2 Hz, 1H), 6.46 (d, J=9.8 Hz, 1H), 4.99 (dd, J=4.8, 7.5 Hz, 1H), 4.74-4.70 (m, 1H), 4.49 (s, 2H), 3.95-3.95 (m, 3H), 3.30 (dd, J=7.4, 7.4 Hz, 2H), 3.18 (s, 2H), 3.03 (ddd, J=2.2, 8.2, 14.5 Hz, 2H), 2.79-2.52 (m, 6H), 2.46-2.21 (m, 8H), 1.88-1.79 (m, 4H), 1.62-1.43 (m, 6H), 1.29-1.21 (m, 2H).

The following compounds were prepared in an identical fashion with the requisite aldehyde replacing p-tolualdehyde in Example 16 Step 1.

| Compound number | Requisite aldehyde | Structure |
| --- | --- | --- |
| Compound 34 | *2-methylbenzaldehyde* | *structure* |
| Compound 35 | *3-methylbenzaldehyde* | *structure* |
| Compound 36 | *benzaldehyde* | *structure* |
| Compound 37 | *3-(trifluoromethyl)benzaldehyde* | *structure* |

-continued

| Compound number | Requisite aldehyde | Structure |
| --- | --- | --- |
| Compound 38 | | 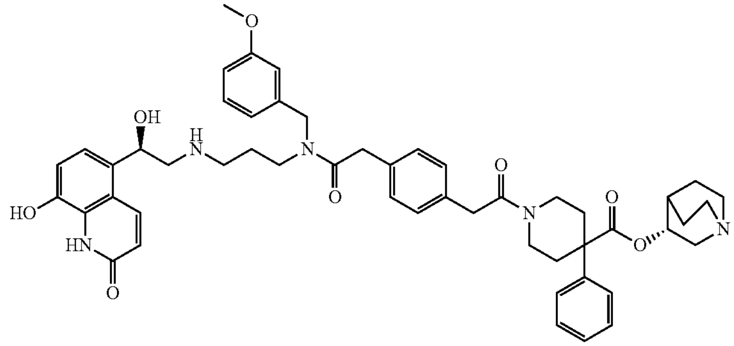 [SMILES: COc1cccc(CN(CCCNC[C@H](O)c2ccc(O)c3[nH]c(=O)ccc23)C(=O)Cc2ccc(CC(=O)N3CCC(C(=O)O[C@H]4CN5CCC4CC5)(c4ccccc4)CC3)cc2)c1] |
| Compound 39 | | 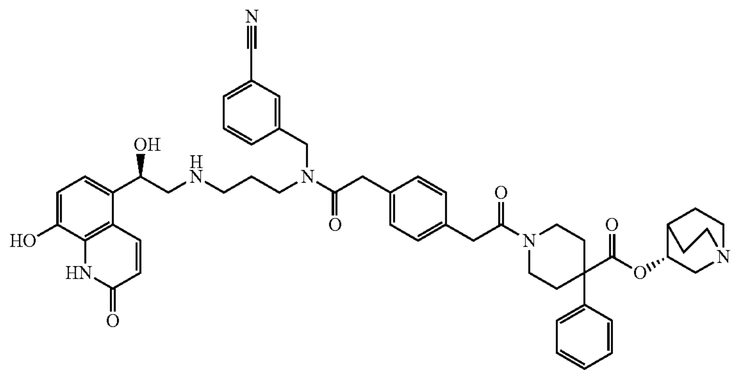 [SMILES: N#Cc1cccc(CN(CCCNC[C@H](O)c2ccc(O)c3[nH]c(=O)ccc23)C(=O)Cc2ccc(CC(=O)N3CCC(C(=O)O[C@H]4CN5CCC4CC5)(c4ccccc4)CC3)cc2)c1] |
| Compound 40 | | 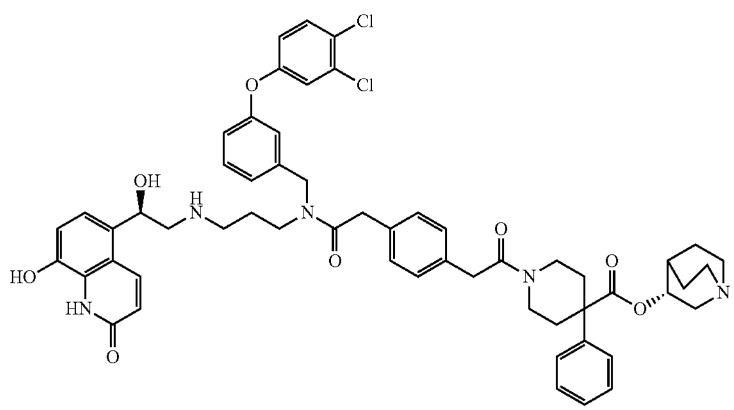 [SMILES: O=C(Cc1ccc(CC(=O)N(CCCNC[C@H](O)c2ccc(O)c3[nH]c(=O)ccc23)Cc2cccc(Oc3ccc(Cl)c(Cl)c3)c2)cc1)N1CCC(C(=O)O[C@H]2CN3CCC2CC3)(c2ccccc2)CC1] |
| Compound 41 | | 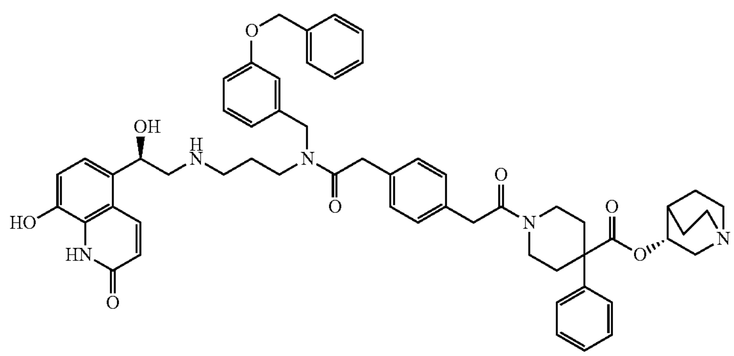 [SMILES: O=C(Cc1ccc(CC(=O)N(CCCNC[C@H](O)c2ccc(O)c3[nH]c(=O)ccc23)Cc2cccc(OCc3ccccc3)c2)cc1)N1CCC(C(=O)O[C@H]2CN3CCC2CC3)(c2ccccc2)CC1] |

| Compound number | Requisite aldehyde | Structure |
|---|---|---|
| Compound 42 | 3-fluorobenzaldehyde | 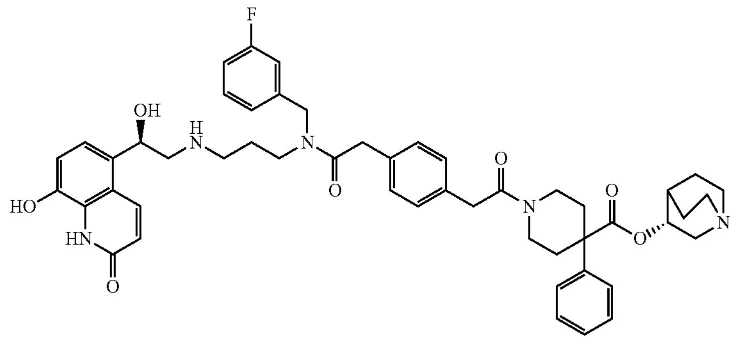 [SMILES: O=C(Cc1ccc(CC(=O)N(CCCNC[C@H](O)c2ccc(O)c3[nH]c(=O)ccc23)Cc2cccc(F)c2)cc1)N1CCC(C(=O)O[C@H]2CN3CCC2CC3)(c2ccccc2)CC1] |
| Compound 43 | 2-(benzyloxy)benzaldehyde | 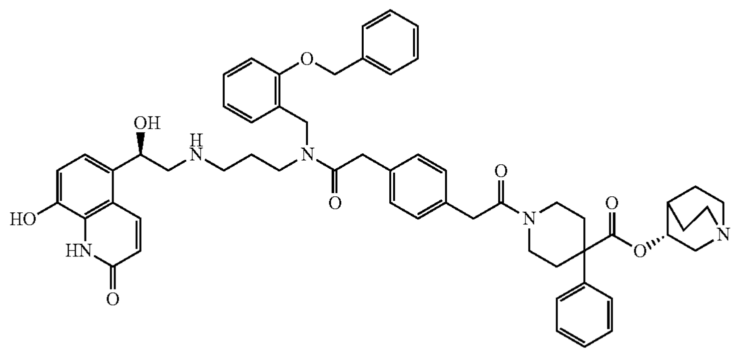 [SMILES: O=C(Cc1ccc(CC(=O)N(CCCNC[C@H](O)c2ccc(O)c3[nH]c(=O)ccc23)Cc2ccccc2OCc2ccccc2)cc1)N1CCC(C(=O)O[C@H]2CN3CCC2CC3)(c2ccccc2)CC1] |
| Compound 44 | 2-morpholinobenzaldehyde | 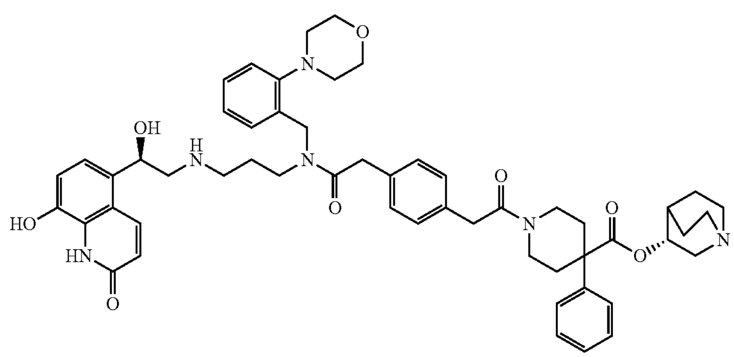 [SMILES: O=C(Cc1ccc(CC(=O)N(CCCNC[C@H](O)c2ccc(O)c3[nH]c(=O)ccc23)Cc2ccccc2N2CCOCC2)cc1)N1CCC(C(=O)O[C@H]2CN3CCC2CC3)(c2ccccc2)CC1] |
| Compound 45 | 2-fluorobenzaldehyde | 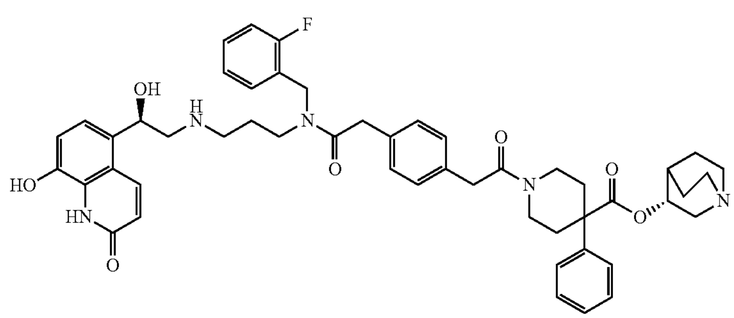 [SMILES: O=C(Cc1ccc(CC(=O)N(CCCNC[C@H](O)c2ccc(O)c3[nH]c(=O)ccc23)Cc2ccccc2F)cc1)N1CCC(C(=O)O[C@H]2CN3CCC2CC3)(c2ccccc2)CC1] |

The following compounds were prepared in an identical fashion with the commercially available amine replacing 3,3-diethoxy-N-(4-methylbenzyl)propan-1-amine in Example 16 Step 2.

| Compound number | Commercially available amine | Structure |
|---|---|---|
| Compound 46 | 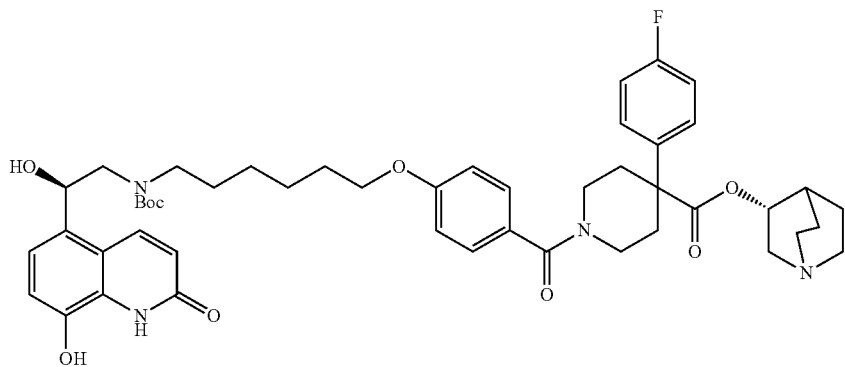 | 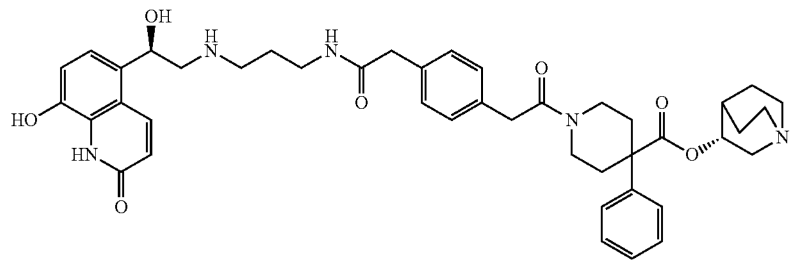 [SMILES: O=C(Cc1ccc(CC(=O)N2CCC(C(=O)O[C@H]3CN4CCC3CC4)(c3ccccc3)CC2)cc1)NCCCNC[C@H](O)c1ccc(O)c2[nH]c(=O)ccc12] |
| Compound 47 | | 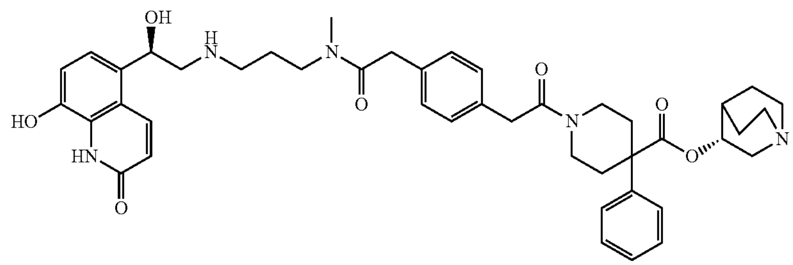 [SMILES: CN(CCCNC[C@H](O)c1ccc(O)c2[nH]c(=O)ccc12)C(=O)Cc1ccc(CC(=O)N2CCC(C(=O)O[C@H]3CN4CCC3CC4)(c3ccccc3)CC2)cc1] |

Example 17. ((R)-Quinuclidin-3-yl 1-(4-((6-((tert-butoxycarbonyl)((R)-2-hydroxy-2-(8-hydroxy-2-oxo-1,2-dihydroquinolin-5-yl)ethyl)amino)hexyl)oxy)benzoyl)-4-(4-fluorophenyl)piperidine-4-carboxylate (Compound 48)

Step 1. (R)-8-(Benzyloxy)-5-(1-((tert-butyldimethylsilyl)oxy)-2-((6-hydroxyhexyl)amino)ethyl)quinolin-2(1H)-one

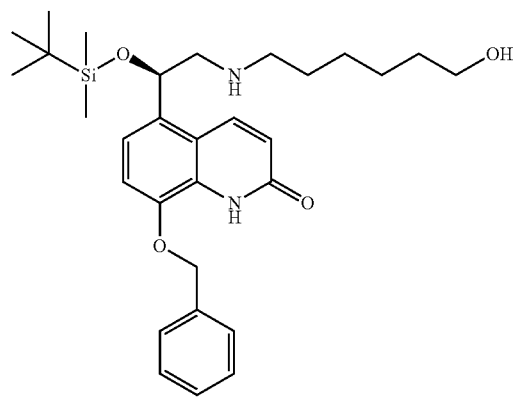 [SMILES: CC(C)(C)[Si](C)(C)O[C@@H](CNCCCCCCO)c1ccc(OCc2ccccc2)c2[nH]c(=O)ccc12]

To a solution of (R)-8-(benzyloxy)-5-(2-bromo-1-((tert-butyldimethylsilyl)-oxy)ethyl)quinolin-2(1H)-one (5.01 g, 10.24 mmol) in NMP (19 mL) was added 6-amino-1-hexanol (5.99 g, 51.22 mmol). The reaction mixture was heated at 80° C. for 18 hours. The reaction mixture was diluted with ethyl acetate and washed with water and brine (×2). The organic phase was dried over anhydrous magnesium sulfate, filtered and the filtrate concentrated at reduced pressure to afford the title compound (5.36 g, 100%).

$^1$H NMR (400 MHz, CDCl$_3$); δ 8.25 (d, J=9.9 Hz, 1H), 7.38-7.33 (m, 5H), 7.07 (d, J=8.2 Hz, 1H), 6.94 (d, J=8.2 Hz, 1H), 6.60-6.58 (m, 1H), 5.09 (s, 2H), 5.08-5.06 (m, 1H), 4.08-4.01 (m, 2H), 3.60-3.52 (m, 3H), 3.34-3.27 (m, 1H), 2.90-2.81 (m, 1H), 2.70-2.49 (m, 3H), 1.55-1.39 (m, 2H), 1.30 (d, J=2.5 Hz, 2H), 0.81 (s, 9H), 0.00 (s, 3H), −0.26 (s, 3H).

Step 2. (R)-tert-Butyl (2-(8-(benzyloxy)-2-oxo-1,2-dihydroquinolin-5-yl)-2-((tert-butyldimethylsilyl)oxy)ethyl)(6-hydroxyhexyl)carbamate

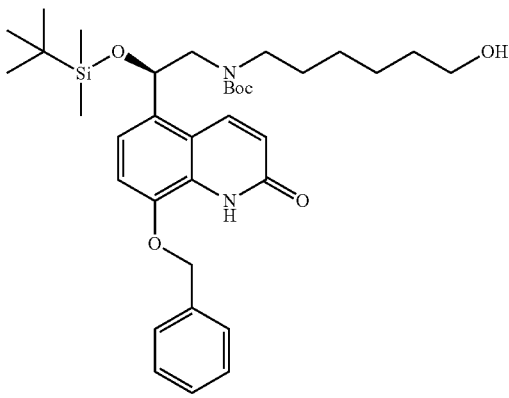 [SMILES: CC(C)(C)OC(=O)N(CCCCCCO)C[C@H](O[Si](C)(C)C(C)(C)C)c1ccc(OCc2ccccc2)c2[nH]c(=O)ccc12]

To a stirred solution of (R)-8-(benzyloxy)-5-(1-((tert-butyldimethylsilyl)oxy)-2-((6-hydroxyhexyl)amino)ethyl)quinolin-2(1H)-one (5.36 g, 10.24 mmol) in DCM (50 mL) was added di-tert-butyldicarbonate (4.47 g, 20.48 mmol). The reaction mixture was stirred at room temperature for 18 hours. The solvent was concentrated at reduced pressure and the residue purified by flash column chromatography (eluent 100% i-hexane to 100% ethyl acetate) to afford the title compound (4.05 g, 63%).

$^1$H NMR (400 MHz, CDCl$_3$); δ 9.17 (s, 1H), 8.54-8.45 (m, 1H), 7.46-7.26 (m, 5H), 7.12-6.99 (m, 1H), 6.79-6.62 (m, 1H), 5.49 (s, 1H), 5.23-5.15 (m, 2H), 3.66-2.91 (m, 6H), 1.64-1.16 (m, 17H), 0.91-0.85 (s, 9H), 0.06 (s, 3H), −0.13 (s, 3H).

Step 3. (R)-Methyl 4-((6-((2-(8-(benzyloxy)-2-oxo-1,2-dihydroquinolin-5-yl)-2-((tert-butyldimethylsilyl)oxy)ethyl)(tert-butoxycarbonyl)amino)hexyl)oxy)benzoate

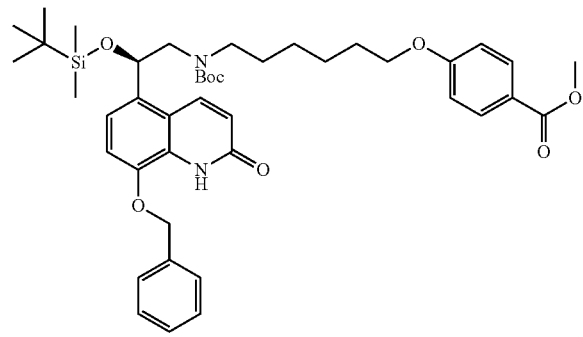 [SMILES: COC(=O)c1ccc(OCCCCCCN(C[C@H](O[Si](C)(C)C(C)(C)C)c2ccc(OCc3ccccc3)c3[nH]c(=O)ccc23)C(=O)OC(C)(C)C)cc1]

To a stirred solution of (R)-tert-butyl (2-(8-(benzyloxy)-2-oxo-1,2-dihydroquinolin-5-yl)-2-((tert-butyldimethylsilyl)oxy)ethyl)(6-hydroxyhexyl)carbamate (4.05 g, 6.47 mmol), methyl 4-hydroxybenzoate (1.08 g, 7.12 mmol) and triphenylphosphine (2.03 g, 7.77 mmol) in DCM was added DIAD (1.53 mL, 7.77 mmol). The reaction mixture was stirred at room temperature for 36 hours. The solvent was concentrated at reduced pressure and the residue purified by column chromatography (eluent 100% i-hexane to 30% ethyl acetate/i-hexane) to afford the title compound (3.49 g, 71%).

$^1$H NMR (400 MHz, CDCl$_3$); δ 9.17 (s, 1H), 8.54-8.45 (m, 1H), 8.00-7.96 (m, 2H), 7.46-7.26 (m, 5H), 7.12-6.99 (m, 1H), 6.90-6.86 (m, 2H), 6.79-6.62 (m, 1H), 5.49 (s, 1H), 5.23-5.15 (m, 2H), 3.88 (s, 3H), 3.66-2.91 (m, 6H), 1.64-1.16 (m, 17H), 0.91-0.85 (s, 9H), 0.06 (s, 3H), −0.13 (s, 3H).

Step 4. (R)-4-((6-((2-(8-(Benzyloxy)-2-oxo-1,2-dihydroquinolin-5-yl)-2-((tert-butyldimethylsilyl)oxy)ethyl)(tert-butoxycarbonyl)amino)hexyl)oxy)benzoic acid

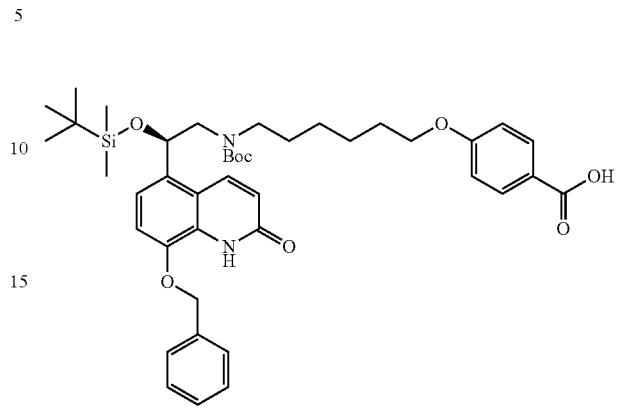

To a stirred solution of (R)-methyl 4-((6-((2-(8-(benzyloxy)-2-oxo-1,2-dihydroquinolin-5-yl)-2-((tert-butyldimethylsilyl)oxy)ethyl)(tert-butoxycarbonyl)amino)-hexyl)oxy)benzoate (3.49 g, 4.59 mmol) in methanol/THF/water (15 mL/75 mL/15 mL) was added lithium hydroxide monohydrate (0.772 g, 18.3 mmol). The reaction mixture was stirred at room temperature for 18 hours. The reaction mixture was quenched with 1M aqueous hydrochloric acid and extracted with ethyl acetate. The organic phase was dried over anhydrous magnesium sulfate, filtered and the filtrate concentrated at reduced pressure to afford the title compound (3.06 g, 89%).

$^1$H NMR (400 MHz, CDCl$_3$); δ 9.17 (s, 1H), 8.54-8.45 (m, 1H), 8.00-7.96 (m, 2H), 7.46-7.26 (m, 5H), 7.12-6.99 (m, 1H), 6.90-6.86 (m, 2H), 6.79-6.62 (m, 1H), 5.49 (s, 1H), 5.23-5.15 (m, 2H), 3.66-2.91 (m, 6H), 1.64-1.16 (m, 17H), 0.91-0.85 (s, 9H), 0.06 (s, 3H), −0.13 (s, 3H).

Step 5. (R)-4-((6-((tert-Butoxycarbonyl)(2-((tert-butyldimethylsilyl)oxy)-2-(8-hydroxy-2-oxo-1,2-dihydroquinolin-5-yl)ethyl)amino)hexyl)oxy)benzoic acid

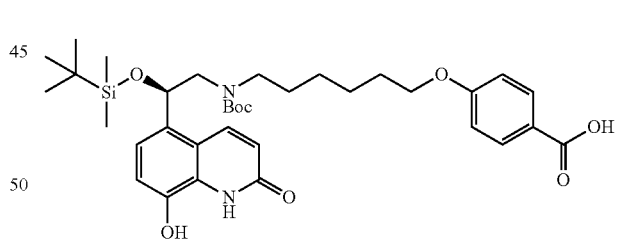

To a solution of (R)-4-((6-((2-(8-(benzyloxy)-2-oxo-1,2-dihydroquinolin-5-yl)-2-((tert-butyldimethylsilyl)oxy)ethyl)(tert-butoxycarbonyl)amino)hexyl)oxy)benzoic acid (0.401 g, 0.54 mmol) in ethanol (6 mL) was added palladium on carbon (0.055 g) and 1-methyl-1,4-cyclohexadiene (0.302 mL, 2.7 mmol). The reaction mixture was heated to reflux and heated under reflux for 3 hours. The suspension was filtered and the filtrate concentrated at reduced pressure to afford the title compound (0.374 g, >100%).

$^1$H NMR (400 MHz, CDCl$_3$); δ 9.17 (s, 1H), 8.54-8.45 (m, 1H), 8.00-7.96 (m, 2H), 7.12-6.99 (m, 1H), 6.90-6.86 (m, 2H), 6.79-6.62 (m, 1H), 5.49 (s, 1H), 3.66-2.91 (m, 6H), 1.64-1.16 (m, 17H), 0.91-0.85 (s, 9H), 0.06 (s, 3H), −0.13 (s, 3H).

Step 6. (R)-Quinuclidin-3-yl 4-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate (Compound 48)

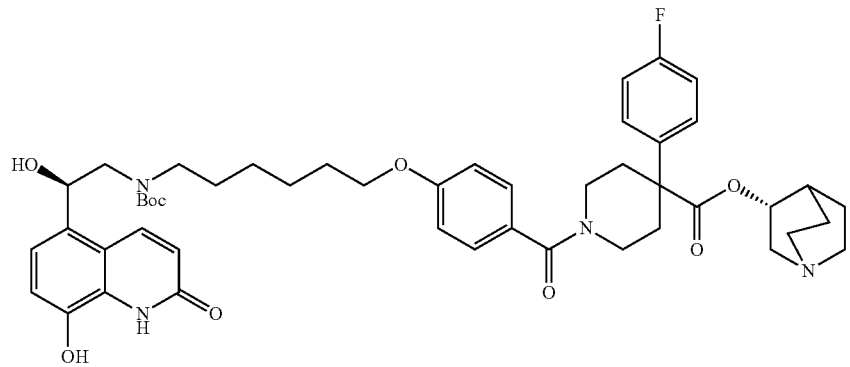 [SMILES: CC(C)(C)OC(=O)N(CCCCCCOc1ccc(C(=O)N2CCC(C(=O)O[C@H]3CN4CCC3CC4)(c3ccc(F)cc3)CC2)cc1)C[C@H](O)c1ccc(O)c2[nH]c(=O)ccc12]

To a stirred solution of (R)-4-((6-(((tert-butoxycarbonyl)(2-(((tert-butyldimethylsilyl)oxy)-2-(8-hydroxy-2-oxo-1,2-dihydroquinolin-5-yl)ethyl)amino)hexyl)oxy)benzoic acid (0.216 g, 0.33 mmol) in DMF (3 mL) was added DIPEA (0.153 mL, 0.90 mmol), HATU (0.137 g, 0.36 mmol) and a solution of (R)-quinuclidin-3-yl 4-(4-fluorophenyl)piperidine-4-carboxylate dihydrochloride (Intermediate 3, 0.111 g, 0.30 mmol) in DMF (3 mL). The reaction mixture was stirred at room temperature for 18 hours. The reaction mixture was diluted with ethyl acetate and washed with 1M aqueous sodium hydroxide and brine (×2). The organic phase was dried over anhydrous magnesium sulfate, filtered and the filtrate concentrated at reduced pressure. The residue treated with a solution of HCl in dioxane (4M, 1 mL) and the reaction mixture stirred at room temperature for 2 hours. The reaction mixture was concentrated at reduced pressure and the residue was purified by reverse phase preparative HPLC to afford the title compound.

$^1$H NMR (400 MHz, MeOD); δ 8.53 (s, 2H), 8.38 (d, J=9.9 Hz, 1H), 7.54-7.49 (m, 2H), 7.40 (d, J=8.8 Hz, 2H), 7.30 (d, J=8.4 Hz, 1H), 7.15 (dd, J=8.8, 8.8 Hz, 2H), 7.04 (d, J=8.2 Hz, 1H), 6.99 (d, J=8.9 Hz, 2H), 6.71 (d, J=9.9 Hz, 1H), 5.39 (dd, J=5.5, 7.8 Hz, 1H), 5.00-4.92 (m, 1H), 4.47-4.14 (m, 1H), 4.06 (dd, J=6.3, 6.3 Hz, 2H), 3.93-3.68 (m, 1H), 3.45-3.36 (m, 2H), 3.26-3.22 (m, 2H), 3.16-3.06 (m, 2H), 3.00-2.95 (m, 4H), 2.82-2.54 (m, 4H), 2.08-1.95 (m, 3H), 1.88-1.74 (m, 6H), 1.63-1.49 (m, 6H).

The following compounds were prepared in the same fashion with the requisite amine used in Step 6.

| Compound | Requisite amine | Structure |
|---|---|---|
| Compound 49 | | 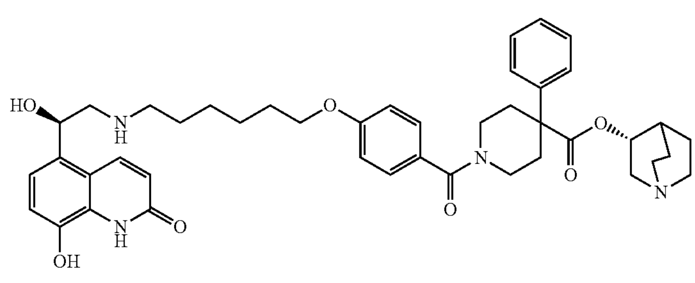 [SMILES: O=C(c1ccc(OCCCCCCNC[C@H](O)c2ccc(O)c3[nH]c(=O)ccc23)cc1)N1CCC(C(=O)O[C@H]2CN3CCC2CC3)(c2ccccc2)CC1] |
| Compound 50 | | 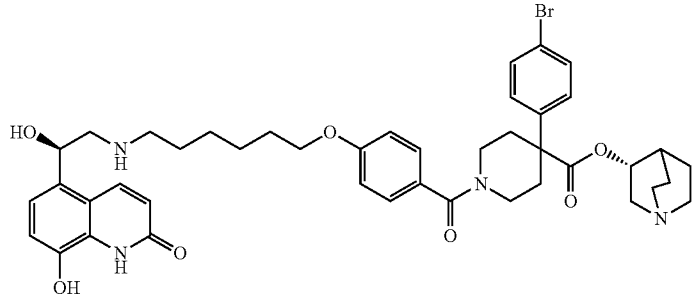 [SMILES: O=C(c1ccc(OCCCCCCNC[C@H](O)c2ccc(O)c3[nH]c(=O)ccc23)cc1)N1CCC(C(=O)O[C@H]2CN3CCC2CC3)(c2ccc(Br)cc2)CC1] |

| Compound | Requisite amine | Structure |
|---|---|---|
| Compound 51 | 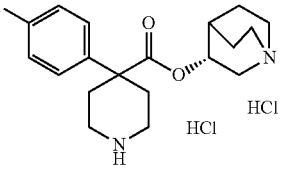 | 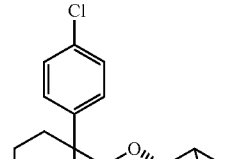 |

Example 18. (R)-Quinuclidin-3-yl 1-(3-(4-(ethyl(3-(((R)-2-hydroxy-2-(8-hydroxy-2-oxo-1,2-dihydro-quinolin-5-yl)ethyl)amino)propyl)carbamoyl)phenyl)propanoyl)-4-phenylpiperidine-4-carboxylate (Compound 52)

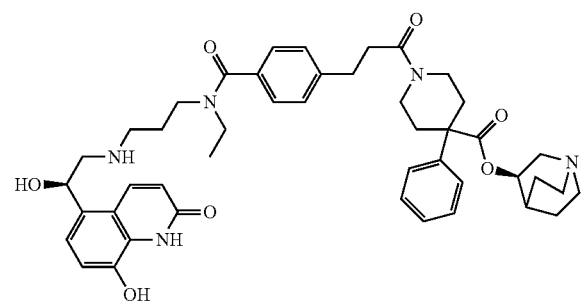 [SMILES: CCN(CCCNC[C@H](O)c1ccc(O)c2[nH]c(=O)ccc12)C(=O)c1ccc(CCC(=O)N2CCC(C(=O)O[C@H]3CN4CCC3CC4)(c3ccccc3)CC2)cc1]

Step 1. N-(2-(1,3-Dioxolan-2-yl)ethyl)-4-bromo-N-ethylbenzamide

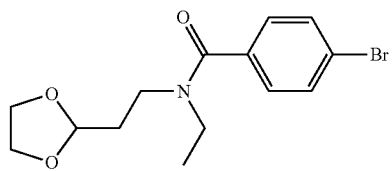 [SMILES: CCN(CCC1OCCO1)C(=O)c1ccc(Br)cc1]

To a stirred solution of N-ethyl-2-(1,3-dioxolan-2-yl)ethanamine (2.33 g, 16.05 mmol), 4-bromobenzoic acid (2.58 g, 12.85 mmol) in DMF (20 mL) was added DIPEA (2.9 mL, 16.71 mmol) and HATU (5.86 g, 15.42 mmol). The reaction mixture was stirred at room temperature for 48 hours. The reaction mixture was diluted with ethyl acetate and washed with saturated aqueous sodium hydrogen carbonate and brine (×2). The organic phase was dried over anhydrous magnesium sulfate, filtered and the filtrate concentrated at reduced pressure. The residue was purified by column chromatography (100% i-hexane to 60% ethyl acetate/i-hexane) to afford the title compound (4.3 g, 100%).

$^1$H NMR (400 MHz, DMSO-$d_6$); δ 7.63 (d, J=8.3 Hz, 2H), 7.31 (d, J=8.4 Hz, 2H), 4.89 and 4.65 (m, 1H), 3.91-3.64 (m, 4H), 3.52-3.41 (m, 2H), 3.28-3.11 (m, 2H), 1.91-1.77 (m, 2H), 1.20-0.98 (m, 3H).

Step 2. (E)-Ethyl 3-(4-((2-(1,3-dioxolan-2-yl)ethyl)(ethyl)carbamoyl)phenyl)acrylate

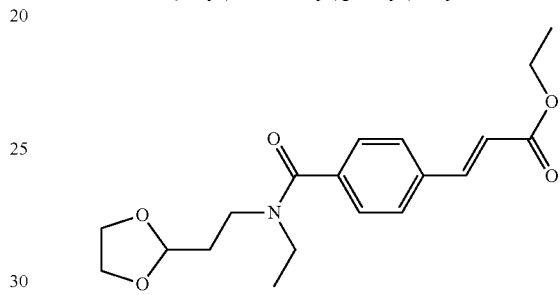

A solution of N-(2-(1,3-dioxolan-2-yl)ethyl)-4-bromo-N-ethylbenzamide (1.0 g, 3.04 mmol), ethyl acrylate (3.32 mL, 30.4 mmol) and triethylamine (1.69 mL, 12.16 mL) in DMF (10 mL) was de-gassed with nitrogen for five minutes. Triphenylphosphine (0.48 g, 1.82 mmol) and palladium (II) acetate (0.02 g, 0.09 mmol) were added and the mixture further de-gassed for five minutes. The reaction mixture was heated for 18 hours. The reaction mixture was diluted with ethyl acetate and washed with saturated aqueous sodium hydrogen carbonate and brine (×2). The organic phase was dried over anhydrous magnesium sulfate, filtered and the filtrate concentrated at reduced pressure. The residue was purified by column chromatography (100% i-hexane to 60% ethyl acetate/i-hexane) to afford the title compound (0.659 g, 63%).

$^1$H NMR (400 MHz, DMSO-$d_6$); δ 7.78 (d, J=8.2 Hz, 2H), 7.70 (d, J=16.6 Hz, 1H), 7.38 (d, J=8.2 Hz, 2H), 6.69 (d, J=16.6 Hz, 1H), 4.90 and 4.65 (s, 1H), 4.21 (q, J=7.1 Hz, 2H), 3.91-3.64 (m, 4H), 3.52-3.41 (m, 2H), 3.28-3.11 (m, 2H), 1.91-1.77 (m, 2H), 1.27 (t, J=7.1 Hz, 3H) 1.20-0.98 (m, 3H)

Step 3. Ethyl 3-(4-((2-(1,3-dioxolan-2-yl)ethyl)(ethyl)carbamoyl)phenyl)propanoate

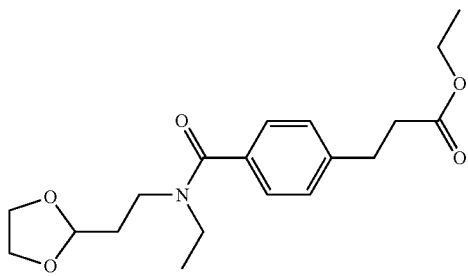 [SMILES: CCOC(=O)CCc1ccc(C(=O)N(CC)CCC2OCCO2)cc1]

To a stirred solution of (E)-ethyl 3-(4-((2-(1,3-dioxolan-2-yl)ethyl)(ethyl)-carbamoyl)phenyl)acrylate (0.78 g, 2.25 mmol) in ethanol was added palladium on carbon (0.39 g) and 1-methyl-1,4-cyclohexadiene (1.26 mL, 11.25 mmol). The reaction mixture was heated at reflux for two hours. The reaction mixture was filtered and the filtrate evaporated at reduced pressure to afford the title compound (0.815 g, >100%).

$^1$H NMR (400 MHz, DMSO-d$_6$); δ 7.29-7.23 (m, 4H), 4.90 and 4.65 (s, 1H), 4.21 (q, J=7.1 Hz, 2H), 3.91-3.64 (m, 6H), 3.52-3.41 (m, 2H), 3.28-3.11 (m, 4H), 1.91-1.77 (m, 2H), 1.27 (t, J=7.1 Hz, 3H) 1.20-0.98 (m, 3H)

Step 4. 3-(4-((2-(1,3-Dioxolan-2-yl)ethyl)(ethyl)carbamoyl)phenyl)propanoic acid

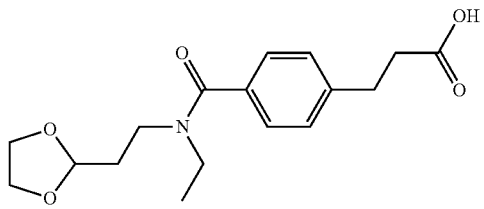 [SMILES: CCN(CCC1OCCO1)C(=O)c1ccc(CCC(=O)O)cc1]

To a stirred solution of ethyl 3-(4-((2-(1,3-dioxolan-2-yl)ethyl)(ethyl)carbamoyl)-phenyl)propanoate (0.815 g, 2.34 mmol) in THF/methanol (12 mL/12 mL) was added 2M aqueous sodium hydroxide (12 mL). The reaction mixture was stirred at room temperature for two hours. The organic solvents were concentrated at reduced pressure and the pH adjusted to pH 4. The mixture extracted with ethyl acetate (×3). The combined organic extracts were dried over anhydrous magnesium sulfate, filtered and the filtrate concentrated at reduced pressure to afford the title compound (0.650 g, 86%).

$^1$H NMR (400 MHz, DMSO-d$_6$); δ 7.29-7.23 (m, 4H), 4.90 and 4.65 (s, 1H), 3.91-3.64 (m, 6H), 3.52-3.41 (m, 2H), 3.28-3.11 (m, 4H), 1.91-1.77 (m, 2H), 1.20-0.98 (m, 3H)

Step 4. (R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate (Compound 52)

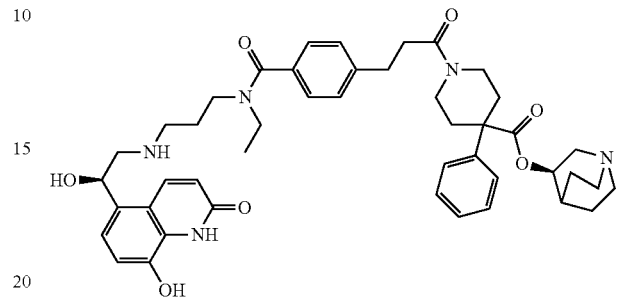

The title compound was prepared as described in Example 1 with 3-(4-((2-(1,3-dioxolan-2-yl)ethyl)(ethyl)carbamoyl)phenyl)propanoic acid replacing 4-(4-(1,3-dioxolan-2-yl)butoxy)benzoic acid in Step 3.

$^1$H NMR (400 MHz, DMSO, 90° C.); δ 8.19 (d, J=9.9 Hz, 1H), 8.15 (s, 2H), 7.38 (d, J=6.5 Hz, 4H), 7.28 (d, J=8.4 Hz, 3H), 7.22 (d, J=8.2 Hz, 2H), 7.08 (d, J=8.0 Hz, 1H), 6.95 (d, J=8.2 Hz, 1H), 6.48 (d, J=9.9 Hz, 1H), 5.02 (dd, J=5.1, 7.4 Hz, 1H), 4.76-4.72 (m, 1H), 3.90 (s, 2H), 3.36-3.27 (m, 4H) 3.10-3.02 (m, 1H), 2.92-2.53 (m, 12H), 2.48-2.32 (m, 4H), 1.92-1.81 (m, 4H), 1.73-1.43 (m, 4H), 1.28-1.23 (m, 1H), 1.07 (dd, J=7.0, 7.0 Hz, 3H).

The following compounds were prepared in the same fashion with the requisite amine used in Step 1.

| Compound | Requisite amine | Structure |
|---|---|---|
| Compound 53 | ![amine with N-methyl dioxolane] | ![structure 53] |
| Compound 54 | ![amine with N-benzyl dioxolane] | ![structure 54] |

Example 19. (R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-4-phenylpiperidine-4-carboxylate
(Compound 55)

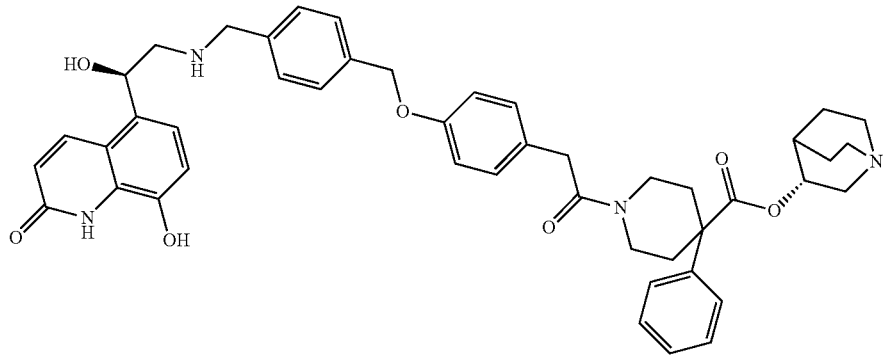 [SMILES: O=C(Cc1ccc(OCc2ccc(CNC[C@H](O)c3ccc(O)c4[nH]c(=O)ccc34)cc2)cc1)N1CCC(C(=O)O[C@H]2CN3CCC2CC3)(c2ccccc2)CC1]

The title compound was prepared as described in Example 7 with methyl 4-hydroxyphenylacetate replacing methyl 4-hydroxybenzoate in Step 1.

$^1$H NMR (400 MHz, DMSO, 100° C.); δ 8.10 (d, J=11.4 Hz, 1H), 7.57-7.49 (m, 4H), 7.40 (dd, J=7.8, 13.5 Hz, 4H), 7.34-7.29 (m, 1H), 7.16-7.12 (m, 3H), 6.98 (ddd, J=10.7, 10.7, 10.7 Hz, 3H), 6.55 (d, J=8.6 Hz, 1H), 5.39-5.35 (m, 1H), 5.11 (s, 2H), 5.08-5.02 (m, 1H), 4.27 (d, J=5.7 Hz, 2H), 3.67-3.61 (m, 2H), 3.29-2.95 (m, 11H), 2.46-2.43 (m, 1H), 2.16 (t, J=4.3 Hz, 1H), 1.96-1.77 (m, 5H), 1.70-1.62 (m, 2H).

Example 20. (R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-4-phenylpiperidine-4-carboxylate
(Compound 56)

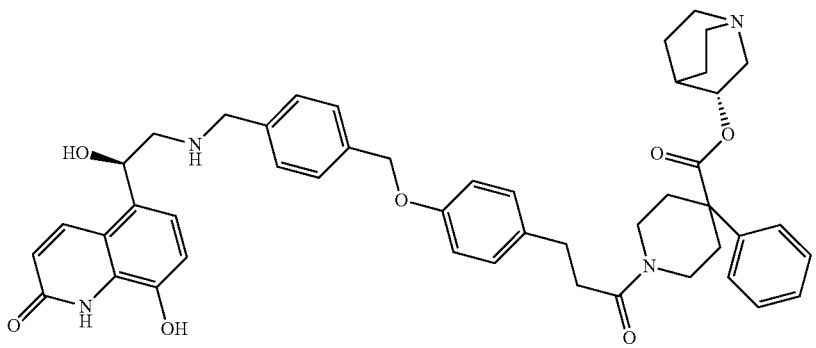 [SMILES: O=C(CCc1ccc(OCc2ccc(CNC[C@H](O)c3ccc(O)c4[nH]c(=O)ccc34)cc2)cc1)N1CCC(C(=O)O[C@H]2CN3CCC2CC3)(c2ccccc2)CC1]

The title compound was prepared as described in Example 7 with methyl 3-(4-hydroxyphenyl)propionate replacing methyl 4-hydroxybenzoate in Step 1.

$^1$H NMR (400 MHz, DMSO-$d_6$); δ 10.51 (s, 2H), 9.64 (s, 1H), 9.06 (s, 2H), 8.06 (d, J=12.0 Hz, 1H), 7.54 (d, J=9.9 Hz, 2H), 7.49 (d, J=8.4 Hz, 2H), 7.42-7.35 (m, 4H), 7.29 (tt, J=3.6, 4.1 Hz, 1H), 7.13 (t, J=9.1 Hz, 3H), 6.97 (d, J=8.4 Hz, 1H), 6.90 (d, J=7.4 Hz, 2H), 6.57 (d, J=10.2 Hz, 1H), 6.20 (s, 1H), 5.34 (d, J=9.9 Hz, 1H), 5.07 (s, 2H), 5.03-4.98 (m, 2H), 4.24 (t, J=10.5 Hz, 2H), 4.13 (dd, J=14.7, 24.8 Hz, 2H), 3.78-3.58 (m, 2H), 3.28-2.89 (m, 8H), 2.74 (ddd, J=7.1, 7.1, 7.1 Hz, 2H), 2.62 (td, J=7.6, 41.8 Hz, 2H), 2.40 (dd, J=22.5, 29.8 Hz, 3H), 2.13 (d, J=23.9 Hz, 1H), 1.75 (dt, J=22.6, 44.5 Hz, 4H).

Example 21. (R)-Quinuclidin-3-yl 1-(4-((N-(4-((((R)-2-hydroxy-2-(8-hydroxy-2-oxo-1,2-dihydro-quinolin-5-yl)ethyl)amino)methyl)benzyl)acetamido)methyl)benzoyl)-4-phenylpiperidine-4-carboxylate (Compound 57)

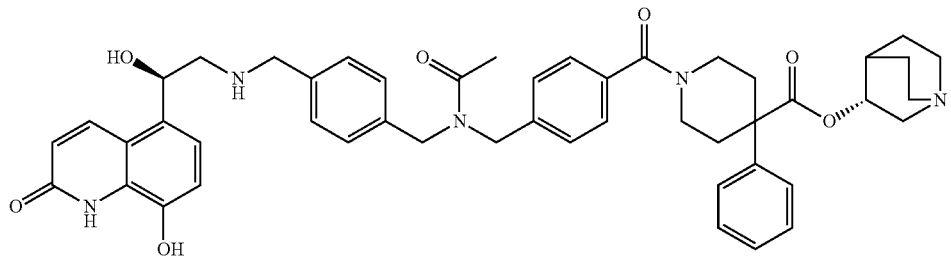 [SMILES: CC(=O)N(Cc1ccc(CNC[C@H](O)c2ccc(O)c3[nH]c(=O)ccc23)cc1)Cc1ccc(C(=O)N2CCC(C(=O)O[C@H]3CN4CCC3CC4)(c3ccccc3)CC2)cc1]

Step 1. Methyl 4-(((4-(1,3-dioxolan-2-yl)benzyl)amino)methyl)benzoate

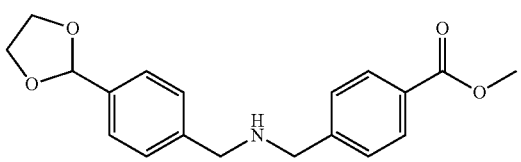 [SMILES: COC(=O)c1ccc(CNCc2ccc(C3OCCO3)cc2)cc1]

A stirred solution of (4-(1,3-dioxolan-2-yl)phenyl)methanamine (1.34 g, 7.49 mmol) and methyl 4-formylbenzoate (1.02 g, 6.24 mmol) in DCM (21 mL) was heated at reflux for 18 hours. The solvent was concentrated at reduced pressure. The residue was dissolved in methanol (21 mL) and the reaction mixture was cooled (0° C.). Sodium borohydride (0.472 g, 12.48 mmol) was added and the reaction mixture stirred at this temperature for 30 minutes and at room temperature for five hours. The reaction mixture was quenched with saturated aqueous sodium hydrogen carbonate and then extracted with DCM (×3) and ethyl acetate. The combined organic extracts were dried over anhydrous magnesium sulfate, filtered and the filtrate concentrated at reduced pressure. The residue was purified by column chromatography (eluent 100% DCM to 10% methanol/DCM) to afford the title compound (1.82 g, 89%).

$^1$H NMR (400 MHz, CDCl$_3$); δ 8.00 (d, J=8.4 Hz, 2H), 7.43 (dd, J=8.2, 18.1 Hz, 4H), 7.37-7.33 (m, 2H), 5.81 (s, 1H), 4.16-4.01 (m, 4H), 3.91 (s, 3H), 3.83 (d, J=9.7 Hz, 4H).

Step 2. Methyl 4-((N-(4-(1,3-dioxolan-2-yl)benzyl)acetamido)methyl)benzoate

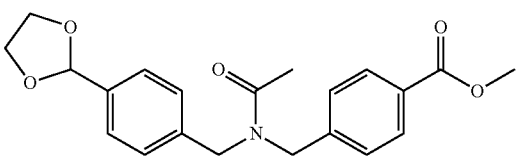 [SMILES: COC(=O)c1ccc(CN(Cc2ccc(C3OCCO3)cc2)C(C)=O)cc1]

To a cooled (0° C.) stirred solution of methyl 4-(((4-(1,3-dioxolan-2-yl)benzyl)amino)methyl)benzoate (0.616 g, 1.88 mmol) in DCM (18 mL) was added triethylamine (0.524 mL, 3.76 mmol) and acetyl chloride (0.161 mL, 2.26 mmol). The reaction mixture allowed to warm to room temperature and then stirred at room temperature for five hours. The reaction mixture was washed with saturated aqueous sodium hydrogen carbonate, water and brine. The organic phase was dried over anhydrous magnesium sulfate, filtered and the filtrate concentrated at reduced pressure to afford the title compound (0.682 g, 98%).

$^1$H NMR (400 MHz, CDCl$_3$); δ 8.04 (d, J=8.3 Hz, 1H), 7.98 (d, J=8.4 Hz, 1H), 7.49 (d, J=8.2 Hz, 1H), 7.44 (d, J=8.0 Hz, 1H), 7.28-7.26 (m, 1H), 7.23 (dd, J=5.6, 8.0 Hz, 2H), 7.17 (d, J=8.2 Hz, 1H), 5.82-5.81 (m, 1H), 4.62 (d, J=8.3 Hz, 2H), 4.45 (s, 3H), 4.17-4.03 (m, 4H), 3.93-3.91 (m, 2H), 2.23-2.20 (m, 3H).

Step 3. (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)acetamido)methyl)benzoyl)-4-phenylpiperidine-4-carboxylate (Compound 57)

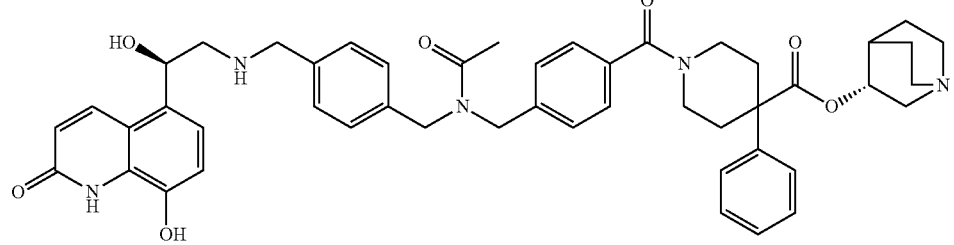

The title compound was prepared as described in Example 1 with methyl 4-((N-(4-(1,3-dioxolan-2-yl)benzyl)acetamido)methyl)benzoate replacing methyl 4-(4-(1,3-dioxolan-2-yl)butoxy)benzoate in Step 2.

$^1$H NMR (400 MHz, DMSO-d$_6$); δ 8.12 (dd, J=5.6, 10.0 Hz, 1H), 7.45-7.34 (m, 5H), 7.31-7.23 (m, 6H), 7.14 (dd, J=8.7, 8.7 Hz, 2H), 7.06 (d, J=8.2 Hz, 1H), 6.90 (d, J=8.0 Hz, 1H), 6.46 (d, J=9.9 Hz, 1H), 5.34 (s, 1H), 5.05 (dd, J=4.4, 7.3 Hz, 1H), 4.72-4.68 (m, 1H), 4.54-4.46 (m, 4H), 4.25 (s, 1H), 3.72 (d, J=5.3 Hz, 2H), 3.18-3.15 (m, 3H), 3.06-2.97 (m, 1H), 2.73-2.63 (m, 1H), 2.61-2.60 (m, 5H), 2.59-2.54 (m, 1H), 2.30 (d, J=14.7 Hz, 1H), 2.11 (d, J=3.0 Hz, 3H), 1.95-1.87 (m, 2H), 1.81 (d, J=2.9 Hz, 1H), 1.57-1.39 (m, 3H), 1.26-1.18 (m, 1H).

The following compounds were prepared in the same fashion with the requisite electrophile used in place of acetyl chloride used in Step 2.

| Compound | Requisite electrophile | Structure |
| --- | --- | --- |
| Compound 58 | Methanesulfonyl chloride | 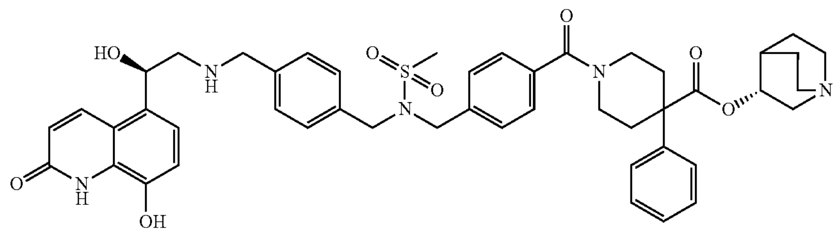 [SMILES: CS(=O)(=O)N(Cc1ccc(CNC[C@H](O)c2ccc(O)c3[nH]c(=O)ccc23)cc1)Cc1ccc(C(=O)N2CCC(C(=O)O[C@H]3CN4CCC3CC4)(c3ccccc3)CC2)cc1] |
| Compound 59 | Benzoyl chloride | 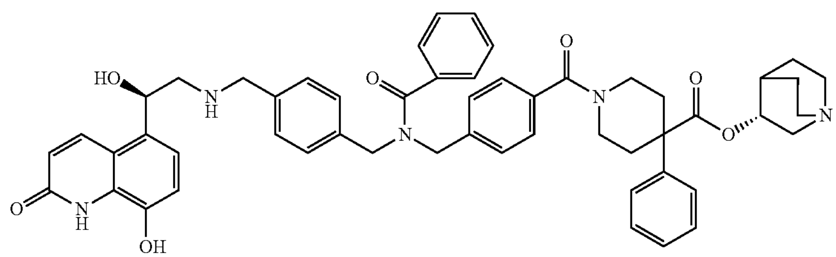 [SMILES: O=C(c1ccc(CN(Cc2ccc(CNC[C@H](O)c3ccc(O)c4[nH]c(=O)ccc34)cc2)C(=O)c2ccccc2)cc1)N1CCC(C(=O)O[C@H]2CN3CCC2CC3)(c2ccccc2)CC1] |
| Compound 60 | | 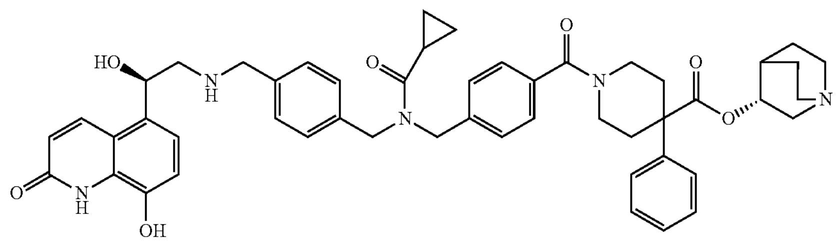 [SMILES: O=C(c1ccc(CN(Cc2ccc(CNC[C@H](O)c3ccc(O)c4[nH]c(=O)ccc34)cc2)C(=O)C2CC2)cc1)N1CCC(C(=O)O[C@H]2CN3CCC2CC3)(c2ccccc2)CC1] |
| Compound 61 | Phenylsulfonyl chloride | 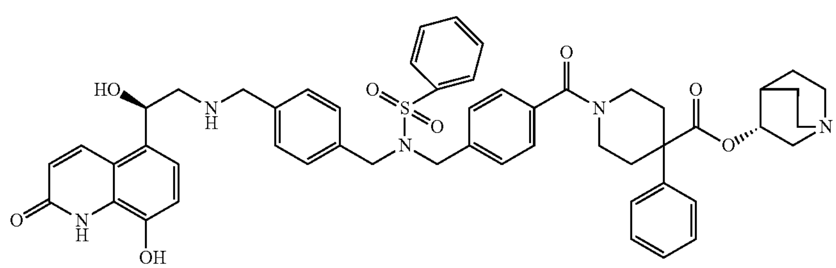 [SMILES: O=C(c1ccc(CN(Cc2ccc(CNC[C@H](O)c3ccc(O)c4[nH]c(=O)ccc34)cc2)S(=O)(=O)c2ccccc2)cc1)N1CCC(C(=O)O[C@H]2CN3CCC2CC3)(c2ccccc2)CC1] |
| Compound 62 | Methyl chloroformate | 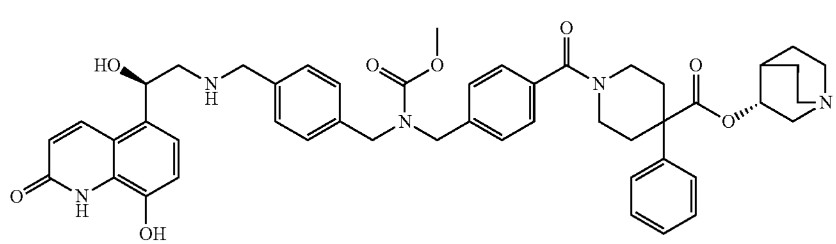 [SMILES: COC(=O)N(Cc1ccc(CNC[C@H](O)c2ccc(O)c3[nH]c(=O)ccc23)cc1)Cc1ccc(C(=O)N2CCC(C(=O)O[C@H]3CN4CCC3CC4)(c3ccccc3)CC2)cc1] |

| Compound | Requisite electrophile | Structure |
|---|---|---|
| Compound 63 | Methyl isocyanate | 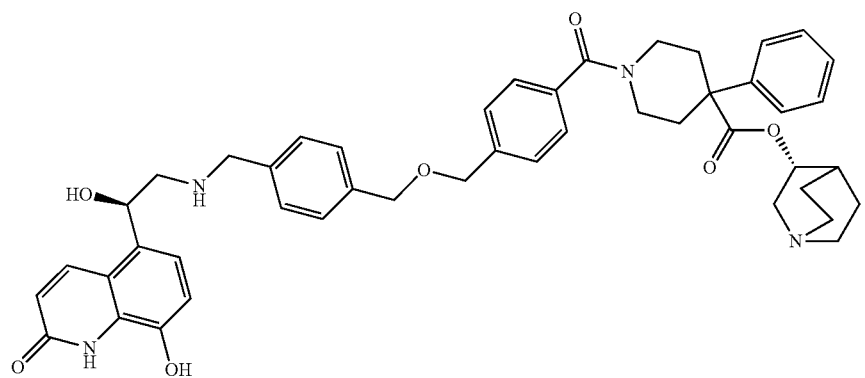 [SMILES: O=C(c1ccc(COCc2ccc(CNC[C@H](O)c3ccc(O)c4[nH]c(=O)ccc34)cc2)cc1)N1CCC(C(=O)O[C@H]2CN3CCC2CC3)(c2ccccc2)CC1] |

Example 22. (R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)oxy)methyl)benzoyl)-4-phenylpiperidine-4-carboxylate (Compound 64)

Step 1. Methyl 4-(((4-(dimethoxymethyl)benzyl)oxy)methyl)benzoate

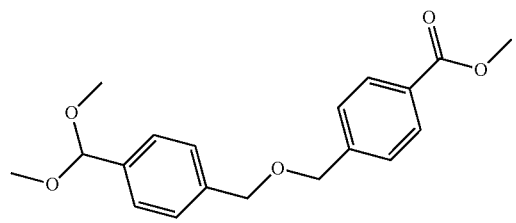

A solution of 4-hydroxymethylbenzaldehyde dimethylacetal (0.50 g, 2.75 mmol) in THF (10 mL) was added to sodium hydride (60% dispersion in mineral oil, 0.11 g, 2.75 mmol). The mixture was stirred at room temperature for ten minutes. A solution of methyl 4-(bromomethyl)benzoate (0.755 g, 3.3 mmol) in THF (8 mL) was added and the mixture stirred at room temperature for 72 hours. The reaction mixture was quenched with saturated aqueous sodium hydrogen carbonate and extracted with ethyl acetate. The organic phase was washed with brine, dried over anhydrous magnesium sulfate, filtered and the filtrate concentrated at reduced pressure. The crude material was used directly in the next step with no further purification.

Step 2. (R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)oxy)methyl)benzoyl)-4-phenylpiperidine-4-carboxylate (Compound 64)

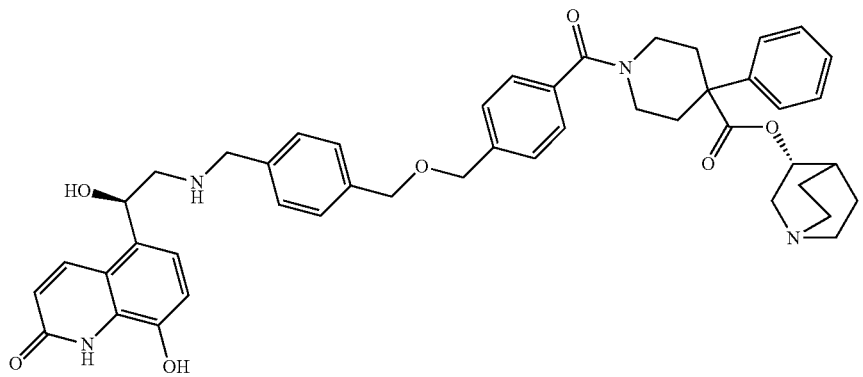 [SMILES: O=C(c1ccc(COCc2ccc(CNC[C@H](O)c3ccc(O)c4[nH]c(=O)ccc34)cc2)cc1)N1CCC(C(=O)O[C@H]2CN3CCC2CC3)(c2ccccc2)CC1]

The title compound was prepared as described in Example 1 with methyl 4-(((4-(dimethoxymethyl)benzyl)oxy)methyl)benzoate replacing methyl 4-(4-(1,3-dioxolan-2-yl)butoxy)benzoate in Step 2.

$^1$H NMR (400 MHz, DMSO-d$_6$); δ 10.50 (s, 2H), 9.73-9.72 (m, 1H), 9.07 (s, 2H), 8.07 (d, J=9.0 Hz, 1H), 7.53 (d, J=8.3 Hz, 2H), 7.46-7.40 (m, 10H), 7.32 (dd, J=7.1, 7.1 Hz, 1H), 7.12 (d, J=8.3 Hz, 1H), 6.97 (d, J=8.2 Hz, 1H), 6.57 (d, J=9.9 Hz, 1H), 6.19-6.19 (m, 1H), 5.34 (d, J=9.3 Hz, 1H), 5.04-5.00 (m, 1H), 4.59 (s, 4H), 4.24 (s, 2H), 3.68-3.60 (m, 2H), 3.25-3.06 (m, 10H), 3.00 (s, 1H), 2.10 (d, J=20.6 Hz, 2H), 1.95 (s, 2H), 1.92-1.73 (m, 2H), 1.63 (s, 2H).

Intermediate 6. (R)-Quinuclidin-3-yl 3-phenylazetidine-3-carboxylate

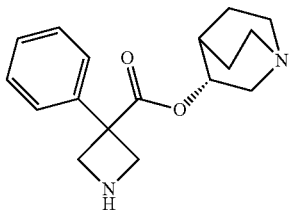 [SMILES: O=C(O[C@H]1CN2CCC1CC2)C1(c2ccccc2)CNC1]

Step 1. 1-Benzyl 3-tert-butyl azetidine-1,3-dicarboxylate

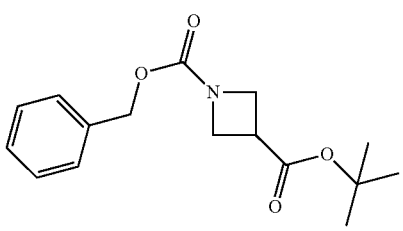 [SMILES: CC(C)(C)OC(=O)C1CN(C(=O)OCc2ccccc2)C1]

A solution of 1-((benzyloxy)carbonyl)azetidine-3-carboxylic acid (5.0 g, 21.2 mmol) and tert-butanol (3.94 g, 53.2 mmol) in anhydrous DCM was treated with DMAP (1.30 g, 10.6 mmol) followed by EDC (8.15 g, 42.6 mmol). The reaction was stirred at room temperature for 18 hours. The reaction mixture was concentrated at reduced pressure and the residue was partitioned between ethyl acetate and 10% aqueous citric acid. The organic phase was washed with sat. aqueous sodium hydrogen carbonate and brine. The organic phase was dried over magnesium sulfate, filtered and the filtrate concentrated under reduced pressure to afford the title compound (5.44 g, 88%).

$^1$H NMR (400 MHz, CDCl$_3$); δ 7.36-7.30 (m, 5H), 5.10 (s, 2H), 4.13 (d, J=7.6 Hz, 4H), 3.32-3.24 (m, 1H), 1.46 (s, 9H).

Step 2. 1-Benzyl 3-tert-butyl 3-phenylazetidine-1,3-dicarboxylate

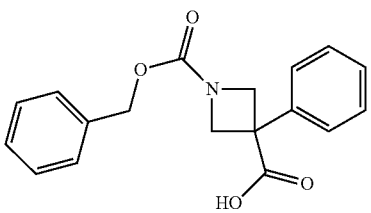 [SMILES: O=C(OCc1ccccc1)N1CC(C(=O)O)(c2ccccc2)C1]

To a vessel containing Pd$_2$(dba)$_3$ (1.34 g, 1.46 mmol) and BE$_4$H.$^t$Bu$_3$P (0.69 g, 2.37 mmol), under N$_2$, was added a solution of LHMDS (1M in toluene, 54.8 mL, 54.8 mmol). The reaction was stirred for 30 min. before being treated with bromobenzene (5.74 g, 36.6 mmol) followed immediately by a solution of 1-benzyl 3-tert-butyl azetidine-1,3-dicarboxylate (5.32 g, 18.2 mmol) in anhydrous, degassed toluene (50 mL) over 15 min. The reaction was stirred for 1 hr before being quenched with aqueous 1M citric acid solution. The mixture was extracted with ethyl acetate (×2) and the combined organics washed with brine, dried over magnesium sulfate, filtered and the filtrate concentrated at reduced pressure. The residue was purified by column chromatography (100 g SNAP Si, 0% to 30% ethyl acetate in $^i$hexanes, 12 column volumes) to afford the title compound (4.83 g, >95% purity, dba remained).

$^1$H NMR (400 MHz, CDCl$_3$); δ 7.38-7.24 (m, 10H), 5.10 (s, 2H), 4.63 (d, J=8.8 Hz, 2H), 4.33 (d, J=8.6 Hz, 2H), 1.38 (s, 9H).

Step 3. 1-((Benzyloxy)carbonyl)-3-phenylazetidine-3-carboxylic acid

To a stirred solution of 1-benzyl 3-tert-butyl 3-phenylazetidine-1,3-dicarboxylate (1.41 g, 3.8 mmol) in DCM (10 mL) was added trifluoroacetic acid (5 mL). The reaction mixture was stirred at room temperature for 3 hours. The reaction mixture was concentrated at reduced pressure to afford the title compound (1.15 $^1$H NMR (400 MHz, CDCl$_3$); δ 7.43-7.22 (m, 10H), 5.09 (s, 2H), 4.70 (d, J=8.8 Hz, 2H), 4.41 (d, J=8.9 Hz, 2H).

Step 4. (R)-1-Benzyl 3-quinuclidin-3-yl 3-phenylazetidine-1,3-dicarboxylate

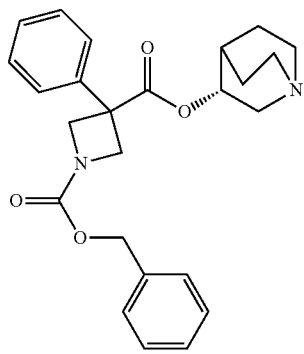 [SMILES: O=C(OCc1ccccc1)N1CC(C(=O)O[C@H]2CN3CCC2CC3)(c2ccccc2)C1]

To a stirred solution of 1-((benzyloxy)carbonyl)-3-phenylazetidine-3-carboxylic acid (1.15 g, 3.70 mmol), 1-hydroxybenzotriazole (0.75 g, 5.55 mmol) and (R)-3-hydroxyquinuclidine (0.71 g, 5.55 mmol) in DMF (20 mL) was added N,N-dicyclohexylcarbodiimide (1.14 g, 5.55 mmol). The reaction mixture was stirred at room temperature for 18 hours. The reaction mixture was filtered through a pad of celite and the filter cake washed with DMF. The filtrate was diluted with ethyl acetate and washed with 2M aqueous sodium carbonate and brine (×3). The organic phase was dried over magnesium sulfate, filtered and the filtrate concentrated under reduced pressure. The crude residue to afford the title compound (18.78 g, >100%). The residue was purified by column chromatography (eluent, 100% EtOAc to 10% ammonia in methanol/ethyl acetate) to afford the title compound (1.34 g, 86%).

$^1$H NMR (400 MHz, CDCl$_3$); δ 7.38-7.27 (m, 10H), 5.10 (s, 2H), 4.81-4.77 (m, 1H), 4.69 (dd, J=2.8, 8.7 Hz, 2H), 4.41 (dd, J=4.3, 8.5 Hz, 2H), 3.13 (ddd, J=2.1, 8.2, 14.8 Hz, 1H), 2.77-2.63 (m, 3H), 1.96-1.90 (m, 3H), 1.54-1.24 (m, 3H), 1.21-1.04 (m, 1H).

Step 5. (R)-Quinuclidin-3-yl 3-phenylazetidine-3-carboxylate

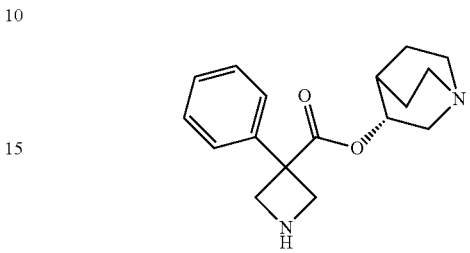

To a stirred solution of (R)-1-benzyl 3-quinuclidin-3-yl 3-phenylazetidine-1,3-dicarboxylate (1.34 g, 3.2 mmol) in ethanol (20 mL) was added 10% Pd—C (0.338 g) and 1-methyl-1,4-cyclohexadiene (1.5 g, 15.9 mmol). The reaction mixture was heated to reflux and then heated under reflux for 3 hours. The suspension was filtered, the filtercake washed with further ethanol and the filtrate concentrated at reduced pressure to afford the title compound (0.97 g, >100%).

$^1$H NMR (400 MHz, CDCl$_3$); δ 7.37-7.32 (m, 5H), 4.82-4.78 (m, 1H), 4.29 (d, J=8.0 Hz, 2H), 4.08 (dd, J=6.3, 8.2 Hz, 2H), 3.14 (ddd, J=2.2, 8.3, 14.8 Hz, 1H), 2.77-2.62 (m, 3H), 2.55-2.46 (m, 1H), 1.97-1.05 (m, 7H).

The following compound was prepared as described in Intermediate 6 with 4-fluorobromobenzene used in Step 2.

| Intermediate No | Structure | NMR |
|---|---|---|
| 7 | 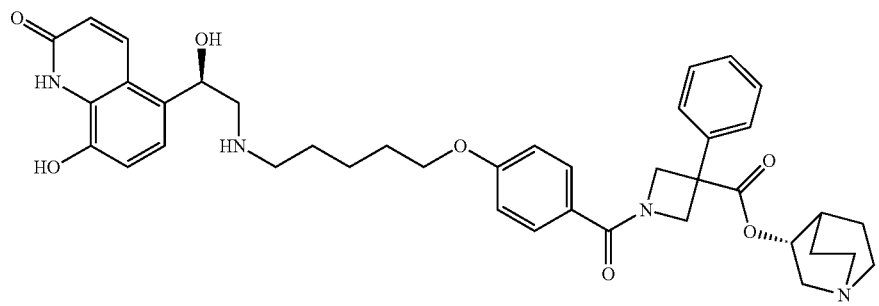 [SMILES: O=C(c1ccc(OCCCCCNC[C@H](O)c2ccc(O)c3[nH]c(=O)ccc23)cc1)N1CC(C(=O)O[C@H]2CN3CCC2CC3)(c2ccccc2)C1] | $^1$H NMR (400 MHz, CDCl$_3$); δ 7.26-7.20 (m, 2H), 7.06-7.00 (m, 2H), 4.82-4.78 (m, 1H), 4.29 (d, J = 8.0 Hz, 2H), 4.08 (dd, J = 6.3, 8.2 Hz, 2H), 3.14 (ddd, J = 2.2, 8.3, 14.8 Hz, 1H), 2.77-2.62 (m, 3H), 2.55-2.46 (m, 1H), 1.97-1.05 (m, 7H). |

Example 1A. (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate (Compound 1A)

The title material was prepared as described in Example 1 with (R)-quinuclidin-3-yl 3-phenylazetidine-3-carboxylate replacing (R)-quinuclidin-3-yl 4-phenylpiperidine-4-carboxylate bis-hydrochloride in Step 3.

$^1$H NMR (400 MHz, DMSO-$d_6$); δ 10.54 (s, 2H), 9.82 (d, J=1.3 Hz, 1H), 8.65 (s, 2H), 8.21 (d, J=9.9 Hz, 1H), 7.70 (d, J=8.8 Hz, 2H), 7.48 (d, J=4.3 Hz, 4H), 7.44-7.38 (m, 1H), 7.20 (d, J=8.1 Hz, 1H), 7.06-7.01 (m, 3H), 6.63 (dd, J=1.9, 10.0 Hz, 1H), 6.24-6.22 (m, 1H), 5.37 (d, J=9.6 Hz, 1H), 5.09-5.00 (m, 2H), 4.87-4.80 (m, 3H), 4.09 (dd, J=6.2, 6.2 Hz, 2H), 3.71-3.63 (m, 2H), 3.29-3.04 (m, 8H), 2.15 (d, J=1.8 Hz, 1H), 1.91-1.62 (m, 8H), 1.57-1.48 (m, 2H,).

Example 2A. (R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-3-phenylazetidine-3-carboxylate (Compound 2A)

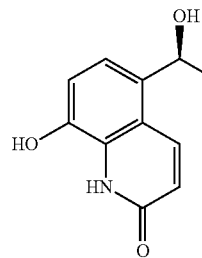
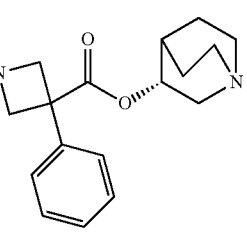

The title compound was prepared as described in Example 17 with (R)-quinuclidin-3-yl 3-phenylazetidine-3-carboxylate replacing (R)-quinuclidin-3-yl 4-phenylpiperidine-4-carboxylate bis-hydrochloride in Step 6.

$^1$H NMR (400 MHz, DMSO-$d_6$); δ 8.34 (s, 2H), 8.24 (d, J=10.1 Hz, 1H), 7.69 (d, J=8.8 Hz, 2H), 7.50-7.43 (m, 3H), 7.42-7.37 (m, 2H), 7.16 (d, J=8.3 Hz, 1H), 7.02 (dd, J=8.7, 8.7 Hz, 3H), 6.58 (d, J=9.9 Hz, 1H), 5.27 (dd, J=3.9, 8.5 Hz, 1H), 4.96-4.94 (m, 1H), 4.80-4.74 (m, 3H), 4.48-4.48 (m, 1H), 4.07 (dd, J=6.4, 6.4 Hz, 3H), 3.09 (ddd, J=2.0, 8.1, 14.6 Hz, 1H), 2.98-2.80 (m, 4H), 2.73-2.62 (m, 2H), 2.45-2.37 (m, 2H), 1.88 (d, J=2.8 Hz, 1H), 1.81-1.73 (m, 2H), 1.65-1.39 (m, 8H), 1.30-1.22 (m, 2H).

Example 3A. (R)-Quinuclidin-3-yl 3-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)azetidine-3-carboxylate (Compound 3A)

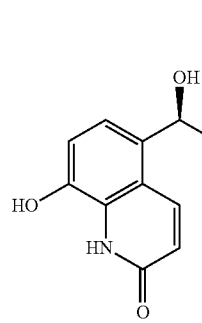

The title compound was prepared as described in Example 17 with (R)-quinuclidin-3-yl 3-(4-fluoro-phenyl)azetidine-3-carboxylate replacing (R)-quinuclidin-3-yl 4-phenylpiperidine-4-carboxylate bis-hydrochloride in Step 6.

$^1$H NMR (400 MHz, MeOD); δ 8.39 (d, J=9.8 Hz, 1H), 7.67 (d, J=8.9 Hz, 2H), 7.48-7.43 (m, 2H), 7.30 (d, J=8.3 Hz, 1H), 7.19 (dd, J=8.8, 8.8 Hz, 2H), 7.03 (dd, J=8.5, 15.4 Hz, 3H), 6.71 (d, J=9.9 Hz, 1H), 5.41 (dd, J=6.8, 6.8 Hz, 1H), 5.17 (ddd, J=2.5, 4.2, 8.4 Hz, 1H), 5.09 (s, 1H), 4.08 (dd, J=6.3, 6.3 Hz, 2H), 3.74-3.68 (m, 1H), 3.38-3.35 (m, 1H), 3.31-3.24 (m, 7H), 3.15-3.09 (m, 3H), 2.33-2.32 (m, 1H), 2.05-1.76 (m, 9H), 1.64-1.50 (m, 4H).

Example 4A. (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate (Compound 4A)

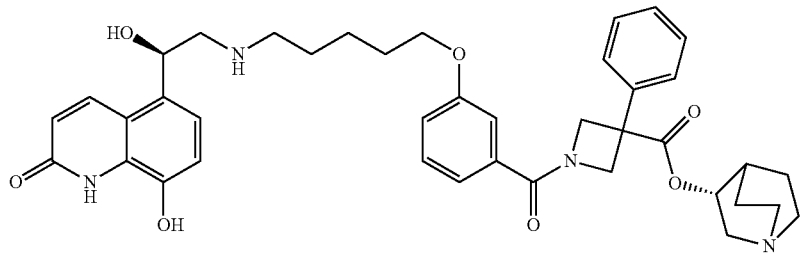 [SMILES: O=C(c1cccc(OCCCCCNC[C@H](O)c2ccc(O)c3[nH]c(=O)ccc23)c1)N1CC(C(=O)O[C@H]2CN3CCC2CC3)(c2ccccc2)C1]

Step 1. Methyl 3-(4-(1,3-dioxolan-2-yl)butoxy)benzoate

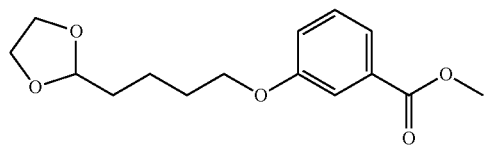 [SMILES: COC(=O)c1cccc(OCCCCC2OCCO2)c1]

To a stirred solution of methyl 3-hydroxybenzoate (3.08 g, 20.3 mmol) in DMF (60 mL) was added potassium carbonate (6.6 g, 40.5 mmol) followed by 2-(4-chlorobutyl)-1,3-dioxolane (5.0 g, 30.4 mmol). The reaction mixture was heated at 90° C. for 18 hours. The reaction mixture was diluted with ethyl acetate and washed sequentially with water and brine (×2). The organic phase was dried over anhydrous magnesium sulfate, the suspension filtered and the filtrate concentrated at reduced pressure. The residue triturated with i-hexane to afford the title compound (7.5 g, >100%).

$^1$H NMR (400 MHz, CDCl$_3$); δ 7.61 (d, J=7.7 Hz, 1H), 7.55-7.53 (m, 1H), 7.32 (dd, J=8.0, 8.0 Hz, 1H), 7.08 (dd, J=2.3, 8.2 Hz, 1H), 4.90-4.86 (m, 1H), 4.02-3.91 (m, 9H), 1.89-1.59 (m, 6H).

Step 2. 3-(4-(1,3-Dioxolan-2-yl)butoxy)benzoic acid

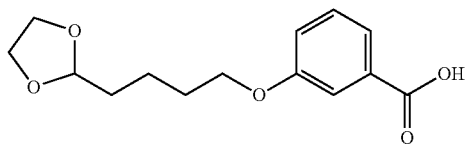 [SMILES: O=C(O)c1cccc(OCCCCC2OCCO2)c1]

To a stirred solution of methyl 3-(4-(1,3-dioxolan-2-yl)butoxy)benzoate (7.5 g, 26.8 mmol) in THF (50 mL) was added a solution of lithium hydroxide—monohydrate (2.55 g, 60.8 mmol) in water (50 mL). The reaction mixture stirred at room temperature for 18 hours. The organic solvent was concentrated at reduced pressure and the resultant aqueous solution was washed with ether. The pH of the aqueous phase was adjusted to pH 4.5 and then extracted with DCM (×3). The combined organic phases were passed through a hydrophobic frit and the filtrate concentrated at reduced pressure to afford the title compound (5.04 g, 71%).

$^1$H NMR (400 MHz, CDCl$_3$); δ 7.70 (d, J=7.9 Hz, 1H), 7.62-7.60 (m, 1H), 7.36 (dd, J=8.0, 8.0 Hz, 1H), 7.14 (dd, J=2.3, 8.2 Hz, 1H), 4.90 (dd, J=4.6, 4.6 Hz, 1H), 4.05-3.84 (m, 6H), 1.90-1.83 (m, 2H), 1.79-1.73 (m, 2H), 1.67-1.60 (m, 2H).

Step 3. (R)-Quinuclidin-3-yl 1-(3-(4-(1,3-dioxolan-2-yl)butoxy)benzoyl)-3-phenylazetidine-3-carboxylate

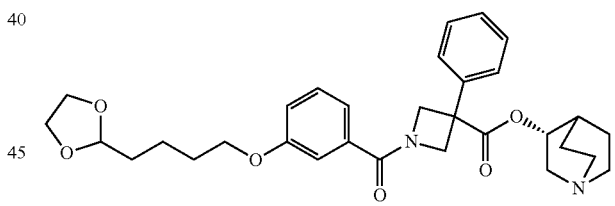

To a solution of 3-(4-(1,3-dioxolan-2-yl)butoxy)benzoic acid (0.19 g, 0.71 mmol) and HATU (0.294 g, 0.77 mmol) in DMF (2 mL) was added triethylamine (0.15 g, 1.48 mmol). The reaction mixture was stirred at room temperature for 15 minutes. A solution of (R)-quinuclidin-3-yl 3-phenylazetidine-3-carboxylate (0.17 g, 0.59 mmol) in DMF (2 mL) was added and the reaction mixture was stirred at room temperature for 18 hours. The reaction mixture was dissolved in ethyl acetate and washed with water and brine (×2). The organic phase was dried over anhydrous magnesium sulfate, the suspension filtered and the filtrate concentrated at reduced pressure. The residue was purified by SCX-2 cartridge eluting first with acetonitrile followed by 15% triethylamine/acetonitrile to afford the title compound (0.283 g, 89%).

$^1$H NMR (400 MHz, CDCl3) δ 7.42-7.36 (m, 2H), 7.34-7.28 (m, 4H), 7.19-7.15 (m, 2H), 7.02-6.98 (m, 1H), 5.02-4.56 (m, 2H), 4.01-3.85 (m, 4H), 3.23-3.06 (m, 1H), 2.78-2.52 (m, 4H), 1.90-1.17 (m, 18H).

Step 4. (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate (Compound 4A)

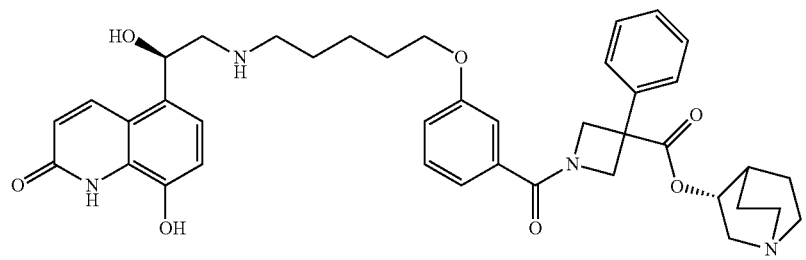 [SMILES: O=C(c1cccc(OCCCCCNC[C@H](O)c2ccc(O)c3[nH]c(=O)ccc23)c1)N1CC(C(=O)O[C@H]2CN3CCC2CC3)(c2ccccc2)C1]

The title compound was prepared as described in Example 1 with (R)-quinuclidin-3-yl 1-(3-(4-(1,3-dioxolan-2-yl)butoxy)benzoyl)-3-phenylazetidine-3-carboxylate replacing (R)-quinuclidin-3-yl 1-(4-(4-(1,3-dioxolan-2-yl)butoxy)benzoyl)-4-phenylpiperidine-4-carboxylate in Step 4.

$^1$H NMR (400 MHz, DMSO-$d_6$); δ 10.54 (s, 2H), 9.84 (d, J=12.1 Hz, 1H), 8.65 (s, 2H), 8.21 (d, J=10.1 Hz, 1H), 7.49-7.46 (m, 4H), 7.46-7.39 (m, 2H), 7.31-7.25 (m, 1H), 7.22-7.12 (m, 3H), 7.04 (d, J=8.1 Hz, 1H), 6.63 (dd, J=1.8, 9.9 Hz, 1H), 6.21 (d, J=1.0 Hz, 1H), 5.36 (d, J=9.3 Hz, 1H), 5.09-5.04 (m, 1H), 4.98 (d, J=3.5 Hz, 1H), 4.87-4.74 (m, 2H), 4.49 (dd, J=10.6, 25.0 Hz, 1H), 4.09-4.03 (m, 2H), 3.70-3.63 (m, 1H), 3.31-3.14 (m, 6H), 3.04 (d, J=7.6 Hz, 4H), 2.16 (d, J=1.8 Hz, 1H), 1.93-1.84 (m, 1H), 1.83-1.63 (m, 6H), 1.57-1.49 (m, 2H).

The following compounds were prepared in an identical fashion with the requisite phenol replacing methyl 3-hydroxybenzoate in Example 4A Step 1.

| Compound number | Requisite phenol | Structure |
|---|---|---|
| Compound 5A | methyl 3-(4-hydroxyphenyl)propanoate | (structure shown) |
| Compound 6A | methyl 2-(4-hydroxyphenyl)acetate | (structure shown) |

The following compounds were prepared in an identical fashion with the requisite acid replacing 3-(4-(1,3-dioxolan-2-yl)butoxy)benzoic acid in Example 4A Step 2.

| Compound number | Requisite acid | Structure |
|---|---|---|
| Compound 7A | 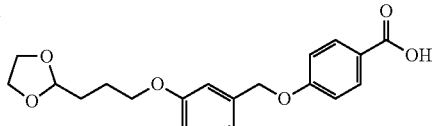<br>see Example 5 | 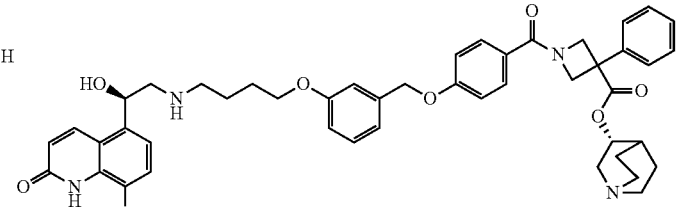 |
| Compound 8A | 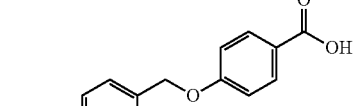<br>see Example 7 | 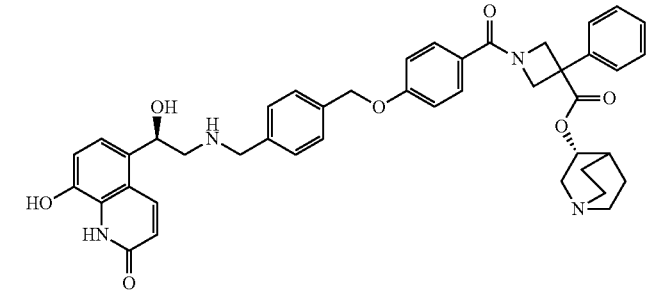 [SMILES: O=C(c1ccc(OCc2ccc(CNC[C@H](O)c3ccc(O)c4[nH]c(=O)ccc34)cc2)cc1)N1CC(C(=O)O[C@H]2CN3CCC2CC3)(c2ccccc2)C1] |
| Compound 9A | 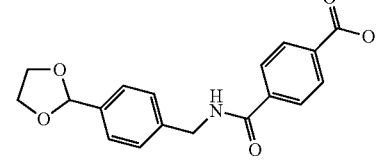<br>see Example 6 | 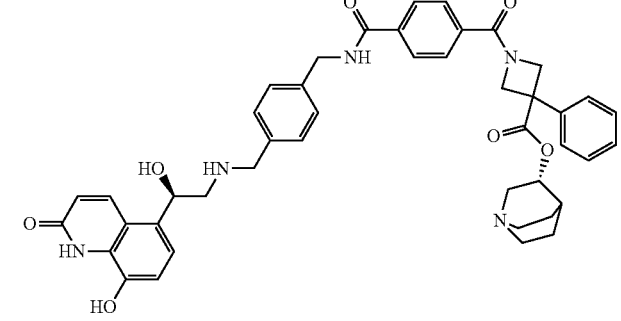 |
| Compound 10A | 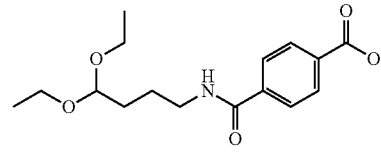<br>see Example 2 | 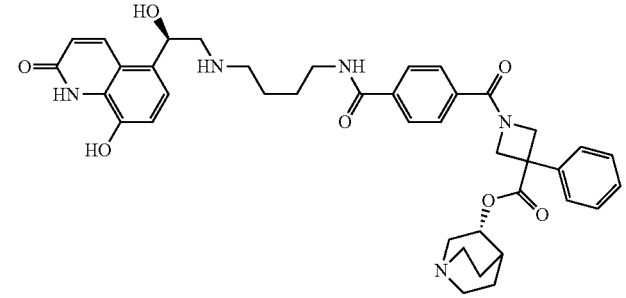 [SMILES: O=C(NCCCCNC[C@H](O)c1ccc(O)c2[nH]c(=O)ccc12)c1ccc(C(=O)N2CC(C(=O)O[C@H]3CN4CCC3CC4)(c3ccccc3)C2)cc1] |
| Compound 11A | 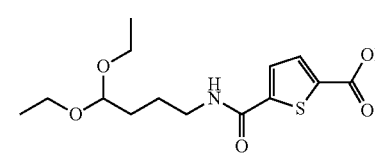<br>see Example 4 | 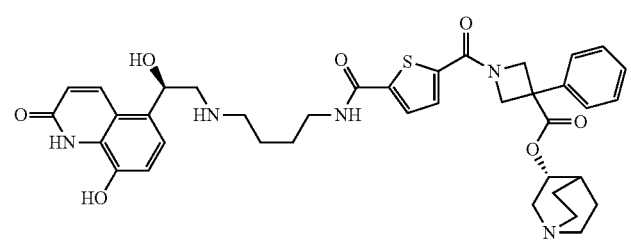 [SMILES: O=C(NCCCCNC[C@H](O)c1ccc(O)c2[nH]c(=O)ccc12)c1ccc(C(=O)N2CC(C(=O)O[C@H]3CN4CCC3CC4)(c3ccccc3)C2)s1] |

| Compound number | Requisite acid | Structure |
| --- | --- | --- |
| Compound 12A | see Compound 52 | 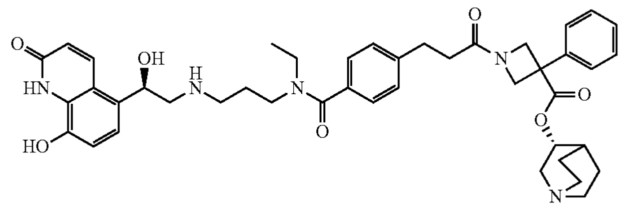 [SMILES: CCN(CCCNC[C@H](O)c1ccc(O)c2[nH]c(=O)ccc12)C(=O)c1ccc(CCC(=O)N2CC(C(=O)O[C@H]3CN4CCC3CC4)(c3ccccc3)C2)cc1] |
| Compound 13A | see Compound 56 | 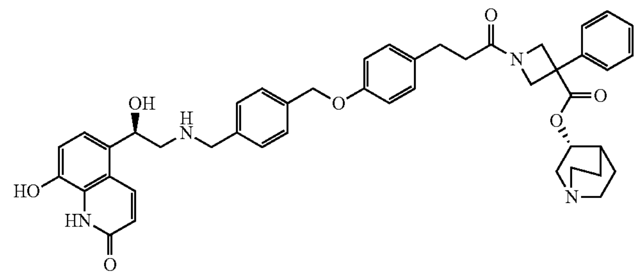 [SMILES: O=C(CCc1ccc(OCc2ccc(CNC[C@H](O)c3ccc(O)c4[nH]c(=O)ccc34)cc2)cc1)N1CC(C(=O)O[C@H]2CN3CCC2CC3)(c2ccccc2)C1] |
| Compound 14A | see Compound 36 | 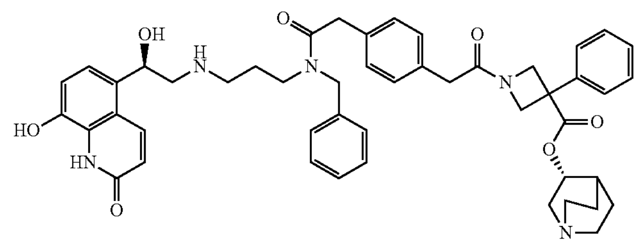 [SMILES: O=C(Cc1ccc(CC(=O)N2CC(C(=O)O[C@H]3CN4CCC3CC4)(c3ccccc3)C2)cc1)N(CCCNC[C@H](O)c1ccc(O)c2[nH]c(=O)ccc12)Cc1ccccc1] |
| Compound 15A | see Compound 55 | 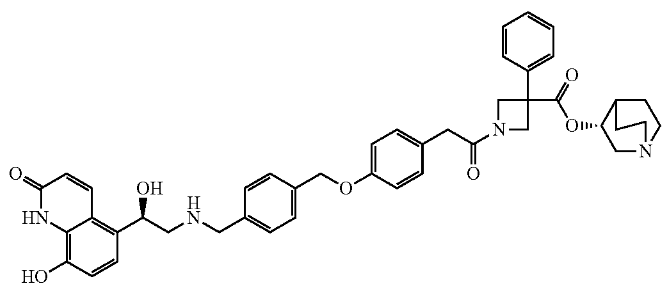 [SMILES: O=C(Cc1ccc(OCc2ccc(CNC[C@H](O)c3ccc(O)c4[nH]c(=O)ccc34)cc2)cc1)N1CC(C(=O)O[C@H]2CN3CCC2CC3)(c2ccccc2)C1] |
Example 5A. (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)carbamoyl)benzoyl)-3-phenylazetidine-3-carboxylate (Compound 16A)
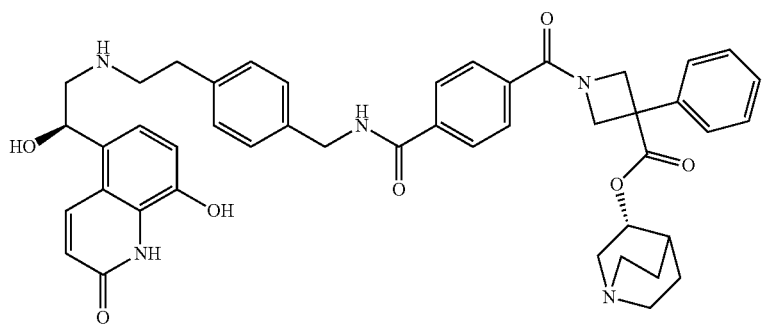 [SMILES: O=C(NCc1ccc(CCNC[C@H](O)c2ccc(O)c3[nH]c(=O)ccc23)cc1)c1ccc(C(=O)N2CC(C(=O)O[C@H]3CN4CCC3CC4)(c3ccccc3)C2)cc1]

Step 1. Methyl 4-((4-bromobenzyl)carbamoyl)benzoate

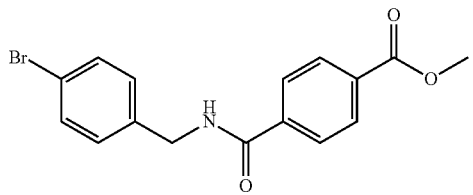 [SMILES: COC(=O)c1ccc(C(=O)NCc2ccc(Br)cc2)cc1]

To a stirred solution of 4-(methoxycarbonyl)benzoic acid (1.0 g, 5.56 mmol) and HATU (2.30 g, 6.06 mmol) in DMF (24 mL) was added triethylamine (1.75 mL, 12.6 mmol) and the reaction mixture stirred at room temperature for five minutes. 4-Bromobenzylamine hydrochloride (1.12 g, 5.05 mmol) was added and the resultant reaction mixture stirred at room temperature for 18 hours. The reaction mixture was diluted with ethyl acetate and washed sequentially with saturated aqueous sodium hydrogen carbonate, 1M aqueous hydrochloric acid and brine (×2). The organic phase was dried over anhydrous magnesium sulfate, filtered and the filtrate concentrated at reduced pressure to afford the title compound (1.80 g, >100%).

$^1$H NMR (400 MHz, CDCl$_3$); δ 8.10 (d, J=8.5 Hz, 2H), 7.84 (d, J=8.5 Hz, 2H), 7.50-7.47 (m, 2H), 7.24 (d, J=8.5 Hz, 2H), 6.47-6.46 (m, 1H), 4.61 (d, J=5.9 Hz, 2H), 3.94 (s, 3H).

Step 2. (E)-Methyl 4-((4-(2-ethoxyvinyl)benzyl)carbamoyl)benzoate

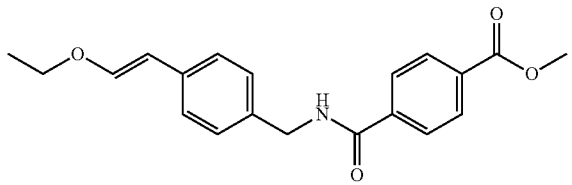 [SMILES: CCO/C=C/c1ccc(CNC(=O)c2ccc(C(=O)OC)cc2)cc1]

To a stirred solution of methyl 4-((4-bromobenzyl)carbamoyl)benzoate (1.0 g, 2.87 mmol) in 1,4-dioxane (30 mL) was added (E)-2-(2-ethoxyvinyl)-4,4,5,5-tetramethyl-1,3,2-dioxaborolane (0.68 g, 3.45 mmol), potassium carbonate (0.79 g, 5.75 mmol) and bis-(triphenylphosphine) palladium (II) dichloride (0.202 g, 0.29 mmol). The reaction mixture was heated at 100° C. for 18 hours. The reaction mixture was diluted with ethyl acetate and washed sequentially with water and brine (×2).). The organic phase was dried over anhydrous magnesium sulfate, filtered and the filtrate concentrated at reduced pressure. The residue was purified by column chromatography (eluent 100% i-hexane to 50% ethyl acetate/i-hexane) to afford the title compound (0.499 g, 57%).

$^1$H NMR (400 MHz, DMSO-d$_6$); δ 9.18 (dd, J=6.0, 6.0 Hz, 1H), 8.05 (d, J=8.5 Hz, 2H), 8.00 (d, J=8.5 Hz, 2H), 7.26-7.18 (m, 5H), 5.81 (d, J=12.9 Hz, 1H), 4.43 (d, J=5.9 Hz, 2H), 3.93-3.84 (m, 5H), 1.28-1.25 (m, 6H).

Step 3. (E)-4-((4-(2-Ethoxyvinyl)benzyl)carbamoyl) benzoic acid

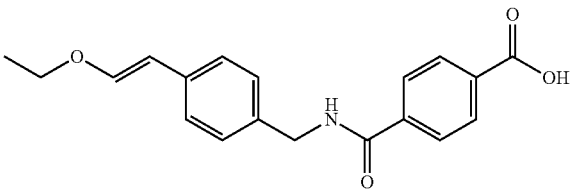 [SMILES: CCO/C=C/c1ccc(CNC(=O)c2ccc(C(=O)O)cc2)cc1]

To a stirred solution of (E)-methyl 4-((4-(2-ethoxyvinyl)benzyl)carbamoyl)-benzoate (0.5 g, 1.48 mmol) in THF (5 mL) was added a solution of lithium hydroxide-monohydrate (0.177 g, 4.42 mmol) in water (5 mL). The reaction mixture stirred at room temperature for 18 hours. The organic solvent was concentrated at reduced pressure and the resultant aqueous solution was washed with ether. The pH of the aqueous phase was adjusted to pH 4.5 and then extracted with DCM (×3). The combined organic phases were passed through a hydrophobic fit and the filtrate concentrated at reduced pressure to afford the title compound (0.433 g, 90%).

$^1$H NMR (400 MHz, DMSO-d$_6$); δ 9.18 (dd, J=6.0, 6.0 Hz, 1H), 8.05 (d, J=8.5 Hz, 2H), 8.00 (d, J=8.5 Hz, 2H), 7.26-7.18 (m, 5H), 5.81 (d, J=12.9 Hz, 1H), 4.43 (d, J=5.9 Hz, 2H), 3.93-3.84 (m, 2H), 1.28-1.25 (m, 6H).

Step 4. (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)carbamoyl)benzoyl)-3-phenylazetidine-3-carboxylate (Compound 16A)

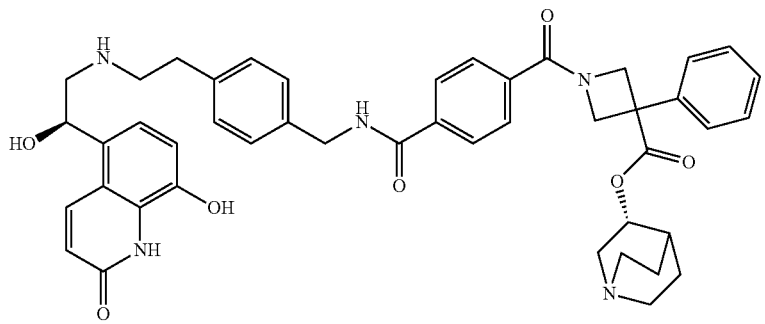 [SMILES: O=C(NCc1ccc(CCNC[C@H](O)c2ccc(O)c3[nH]c(=O)ccc23)cc1)c1ccc(C(=O)N2CC(C(=O)O[C@H]3CN4CCC3CC4)(c3ccccc3)C2)cc1]

The title compound was prepared as described in Example 4A with (E)-4-((4-(2-ethoxyvinyl)benzyl)carbamoyl)benzoic acid replacing 3-(4-(1,3-dioxolan-2-yl)butoxy)benzoic acid in Step 3.

$^1$H NMR (400 MHz, DMSO-d$_6$); δ 10.52-10.48 (m, 2H), 9.81 (s, 1H), 9.20 (dd, J=5.9, 5.9 Hz, 1H), 8.85-8.70 (m, 2H), 8.17 (d, J=10.9 Hz, 1H), 7.96 (d, J=8.4 Hz, 2H), 7.76 (d, J=6.5 Hz, 2H), 7.45-7.41 (m, 4H), 7.40-7.34 (m, 1H), 7.30 (d, J=8.2 Hz, 2H), 7.22 (d, J=8.2 Hz, 2H), 7.16 (d, J=8.3 Hz, 1H), 6.99 (d, J=8.2 Hz, 1H), 6.58 (dd, J=2.1, 9.9 Hz, 1H), 6.20 (d, J=3.5 Hz, 1H), 5.36-5.32 (m, 1H), 5.02-4.95 (m, 2H), 4.84-4.75 (m, 2H), 4.51-4.45 (m, 3H), 3.65-3.58 (m, 1H), 3.24-3.09 (m, 8H), 3.05-2.92 (m, 3H), 2.11-2.11 (m, 1H), 1.87-1.76 (m, 2H), 1.59 (d, J=7.2 Hz, 2H)

Example 6A. (R)-Quinuclidin-3-yl 1-(4-((4-((((R)-2-hydroxy-2-(8-hydroxy-2-oxo-1,2-dihydroquinolin-5-yl)ethyl)amino)methyl)benzamido)methyl)benzoyl)-3-phenylazetidine-3-carboxylate (Compound 17A)

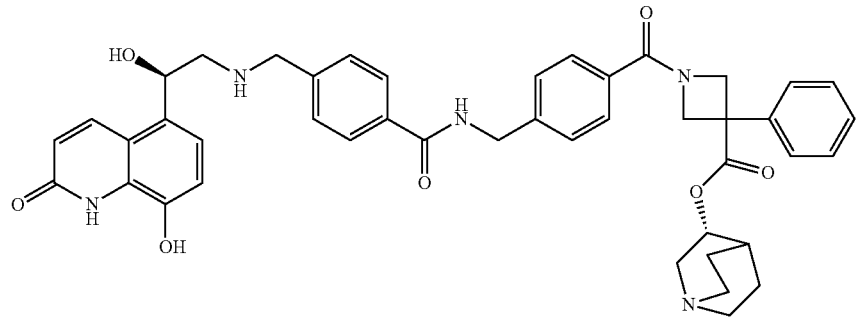 [SMILES: O=C(NCc1ccc(C(=O)N2CC(C(=O)O[C@H]3CN4CCC3CC4)(c3ccccc3)C2)cc1)c1ccc(CNC[C@H](O)c2ccc(O)c3[nH]c(=O)ccc23)cc1]

Step 1. (R)-Quinuclidin-3-yl 1-(4-(aminomethyl)benzoyl)-3-phenylazetidine-3-carboxylate dihydrochloride

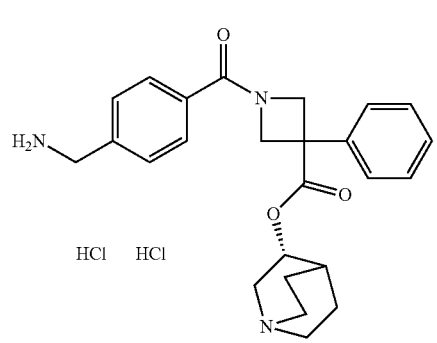 [SMILES: NCc1ccc(C(=O)N2CC(C(=O)O[C@H]3CN4CCC3CC4)(c3ccccc3)C2)cc1 ; Cl ; Cl]

To a stirred solution of 4-(((tert-butoxycarbonyl)amino)methyl)benzoic acid (0.330 g, 1.05 mmol) and HATU (0.429 g, 1.13 mmol) in DMF (5 mL) was added triethylamine (0.30 mL, 2.18 mmol). The reaction mixture was stirred at room temperature for 15 minutes and a solution of (R)-quinuclidin-3-yl 3-phenylazetidine-3-carboxylate (0.25 g, 0.87 mmol) in DMF (2 mL) was added. The reaction mixture was stirred at room temperature for 18 hours. The reaction mixture was dissolved in ethyl acetate and washed with water and brine (×2). The organic phase was dried over anhydrous magnesium sulfate, the suspension filtered and the filtrate concentrated at reduced pressure. The residue was purified by column chromatography (eluent 100% ethyl acetate to 10% ammonia methanol/ethyl acetate). The residue was dissolved in a solution of HCl in dioxane (1.6 mL) and the mixture stirred at room temperature for 18 hours. The solvent was concentrated at reduced pressure to afford the title compound (0.391 g, 91%).

$^1$H NMR (400 MHz, DMSO-d$_6$); δ 10.86-10.80 (m, 1H), 8.56-8.55 (m, 3H), 7.73 (d, J=7.2 Hz, 2H), 7.60 (d, J=8.3 Hz, 2H), 7.43 (d, J=5.3 Hz, 4H), 7.41-7.33 (m, 1H), 5.01-4.93 (m, 2H), 4.85-4.73 (m, 2H), 4.49-4.37 (m, 1H), 4.09 (q, J=5.8 Hz, 2H), 3.21-3.16 (m, 3H), 3.10 (d, J=7.8 Hz, 2H), 3.02-2.89 (m, 1H), 2.15-2.09 (m, 1H), 1.88-1.69 (s, 3H), 1.60 (s, 1H).

Step 2. (R)-Quinuclidin-3-yl 1-(4-((4-formylbenzamido)methyl)benzoyl)-3-phenylazetidine-3-carboxylate

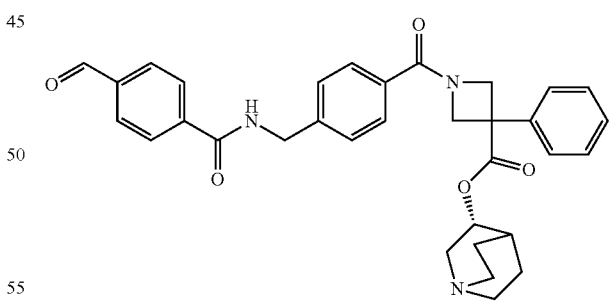

To a stirred solution of 4-formylbenzoic acid (0.116 g, 0.77 mmol) and HATU (0.315 g, 0.83 mmol) in DMF (8 mL) was added triethylamine (0.36 mL, 2.56 mmol). The reaction mixture was stirred at room temperature for 15 minutes and a solution of (R)-quinuclidin-3-yl 1-(4-(aminomethyl)benzoyl)-3-phenylazetidine-3-carboxylate dihydrochloride (0.391 g, 0.64 mmol) in DMF (8 mL) was added. The reaction mixture was stirred at room temperature for 18 hours. The reaction mixture was dissolved in ethyl acetate and washed with water, saturated aqueous sodium hydrogen carbonate water and brine (×2). The organic phase was dried over anhydrous magnesium sulfate, the suspension filtered and the filtrate concentrated at reduced pressure to afford the title compound (0.346 g, 98%).

¹H NMR (400 MHz, DMSO-d₆); δ 10.10 (s, 1H), 9.34 (dd, J=6.0, 6.0 Hz, 1H), 8.10 (d, J=8.3 Hz, 2H), 8.03 (d, J=8.4 Hz, 2H), 7.96 (s, 2H), 7.65 (d, J=8.2 Hz, 2H), 7.44-7.39 (m, 4H), 7.39-7.32 (m, 1H), 4.92-4.88 (m, 1H), 4.77-4.72 (m, 3H), 4.56 (d, J=5.9 Hz, 2H), 4.46-4.38 (m, 1H), 3.08 (dd, J=7.8, 14.5 Hz, 2H), 2.69-2.39 (m, 3H), 1.84-1.84 (m, 1H), 1.61-1.41 (m, 3H), 1.24-1.14 (m, 2H).

Step 4. (R)-Quinuclidin-3-yl 1-(4-((4-((((R)-2-hydroxy-2-(8-hydroxy-2-oxo-1,2-dihydroquinolin-5-yl)ethyl)amino)methyl)benzamido)methyl)benzoyl)-3-phenylazetidine-3-carboxylate (Compound 17A)

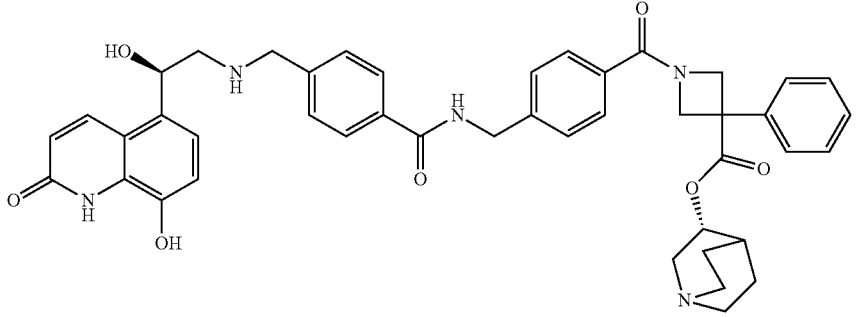 [SMILES: O=C(NCc1ccc(C(=O)N2CC(C(=O)O[C@H]3CN4CCC3CC4)(c3ccccc3)C2)cc1)c1ccc(CNC[C@H](O)c2ccc(O)c3[nH]c(=O)ccc23)cc1]

The title compound was prepared as described in Example 7 with (R)-quinuclidin-3-yl 1-(4-((4-formylbenzamido)methyl)benzoyl)-3-phenylazetidine-3-carboxylate replacing (R)-quinuclidin-3-yl 1-(4-((4-formylbenzyl)oxy)benzoyl)-4-phenylpiperidine-4-carboxylate in Step 4.

Example 7A. (R)-Quinuclidin-3-yl 1-(4-(4-(((R)-2-hydroxy-2-(8-hydroxy-2-oxo-1,2-dihydroquinolin-5-yl)ethyl)amino)butoxy)benzoyl)-3-phenylazetidine-3-carboxylate (Compound 18A)

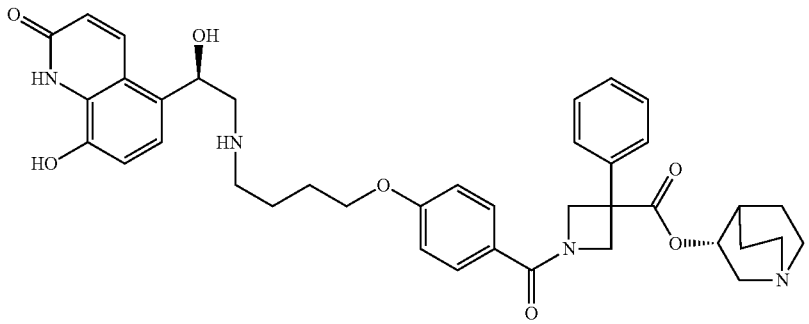 [SMILES: O=C(c1ccc(OCCCCNC[C@H](O)c2ccc(O)c3[nH]c(=O)ccc23)cc1)N1CC(C(=O)O[C@H]2CN3CCC2CC3)(c2ccccc2)C1]

Step 1. Methyl 4-(3-(1,3-dioxolan-2-yl)propoxy)benzoate

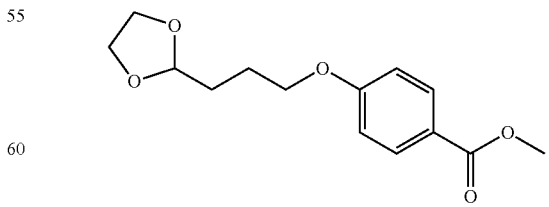

The title compound was prepared as described in Example 1A Step 1 with methyl 4-hydroxybenzoate and 2-(3-chloropropyl)-1,3-dioxolane replacing methyl 3-hydroxybenzoate and 2-(4-chlorobutyl)-1,3-dioxolane respectively.

¹H NMR (400 MHz, CDCl₃); δ 7.99-7.96 (m, 2H), 6.92-6.89 (m, 2H), 4.96-4.90 (m, 1H), 3.88-3.88 (m, 9H), 1.96-1.81 (m, 4H).

Step 2. 4-(3-(1,3-Dioxolan-2-yl)propoxy)benzoic acid

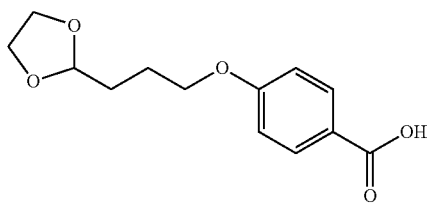 [SMILES: O=C(O)c1ccc(OCCCC2OCCO2)cc1]

The title compound was prepared as described in Example 1A Step 2.

¹H NMR (400 MHz, CDCl₃); δ 8.05 (d, J=8.9 Hz, 2H), 6.93 (d, J=8.9 Hz, 2H), 4.95 (dd, J=4.5, 4.5 Hz, 1H), 4.10-3.86 (m, 6H), 1.96-1.81 (m, 4H).

Step 3. (R)-Quinuclidin-3-yl 1-(4-(4-(((R)-2-hydroxy-2-(8-hydroxy-2-oxo-1,2-dihydroquinolin-5-yl)ethyl)amino)butoxy)benzoyl)-3-phenylazetidine-3-carboxylate (Compound 18A)

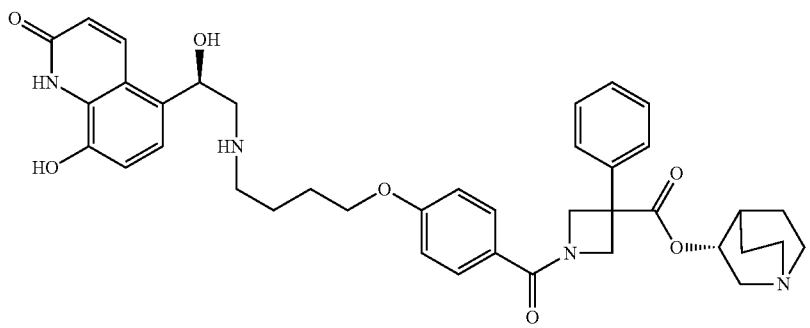 [SMILES: O=C(c1ccc(OCCCCNC[C@H](O)c2ccc(O)c3[nH]c(=O)ccc23)cc1)N1CC(C(=O)O[C@H]2CN3CCC2CC3)(c2ccccc2)C1]

The title compounds was as described in Example 4A with 4-(3-(1,3-dioxolan-2-yl)propoxy)benzoic acid replacing 3-(4-(1,3-dioxolan-2-yl)butoxy)benzoic acid in Step 3.

Example 8A. (R)-Quinuclidin-3-yl 1-(4-((4-((3-(((R)-2-hydroxy-2-(8-hydroxy-2-oxo-1,2-dihydroquinolin-5-yl)ethyl)amino)propyl)carbamoyl)benzyl)oxy)benzoyl)-3-phenylazetidine-3-carboxylate (Example 19A)

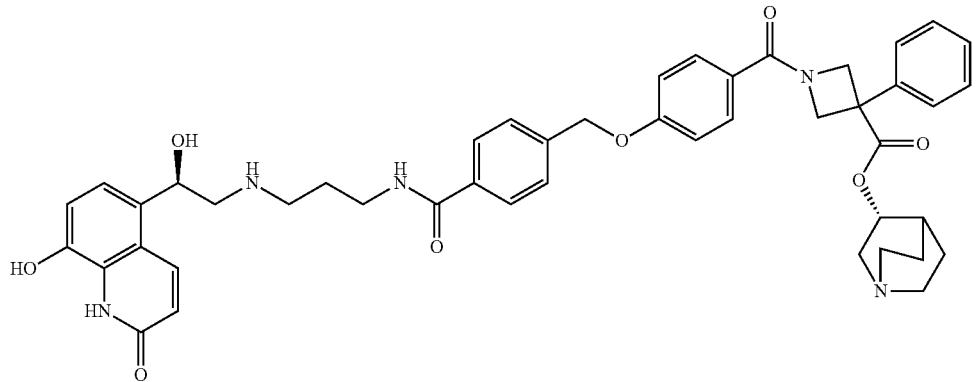 [SMILES: O=C(NCCCNC[C@H](O)c1ccc(O)c2[nH]c(=O)ccc12)c1ccc(COc2ccc(C(=O)N3CC(C(=O)O[C@H]4CN5CCC4CC5)(c4ccccc4)C3)cc2)cc1]

Step 1. (R)-Quinuclidin-3-yl 1-(4-((4-(tert-butoxycarbonyl)benzyl)oxy)benzoyl)-3-phenylazetidine-3-carboxylate

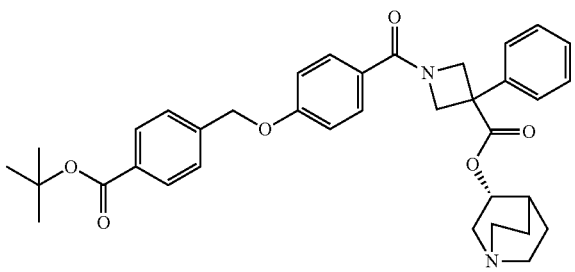 [SMILES: CC(C)(C)OC(=O)c1ccc(COc2ccc(C(=O)N3CC(C(=O)O[C@H]4CN5CCC4CC5)(c4ccccc4)C3)cc2)cc1]

To a stirred solution of 4-((4-(tert-butoxycarbonyl)benzyl)oxy)benzoic acid (0.291 g, 0.88 mmol) and HATU (0.368 g, 0.98 mmol) in DMF (10 mL) was added triethylamine (0.28 mL, 2.02 mmol). The reaction mixture was stirred at room temperature for 15 minutes and (R)-quinuclidin-3-yl 3-phenylazetidine-3-carboxylate dihydrochloride (0.231 g, 0.81 mmol) in DMF (8 mL) was added. The reaction mixture was stirred at room temperature for 18 hours. The reaction mixture was dissolved in ethyl acetate and washed with water, saturated aqueous sodium hydrogen carbonate water and brine (×2). The organic phase was dried over anhydrous magnesium sulfate, the suspension filtered and the filtrate concentrated at reduced pressure. The residue was purified by column chromatography (eluent 100% ethyl acetate to 10% ammonia methanol/ethyl acetate) to afford the title compound (0.273 g, 57%).

$^1$H NMR (400 MHz, CDCl$_3$); δ 8.01 (d, J=8.4 Hz, 2H), 7.64-7.61 (m, 2H), 7.46 (d, J=8.4 Hz, 2H), 7.38 (dd, J=7.3, 7.3 Hz, 2H), 7.33-7.28 (m, 4H), 6.97 (d, J=8.9 Hz, 1H), 5.16 (s, 2H), 5.01 (m, 1H), 4.82-4.79 (m, 1H), 4.63-4.63 (m, 1H), 3.12 (m, 1H), 2.84-2.35 (m, 5H), 2.04-1.39 (s, 14H), 1.53-1.50 (m, 1H), 1.36-1.30 (m, 1H).

Step 2. (R)-Quinuclidin-3-yl 1-(4-((4-((3,3-diethoxypropyl)carbamoyl)benzyl)oxy)-benzoyl)-3-phenylazetidine-3-carboxylate

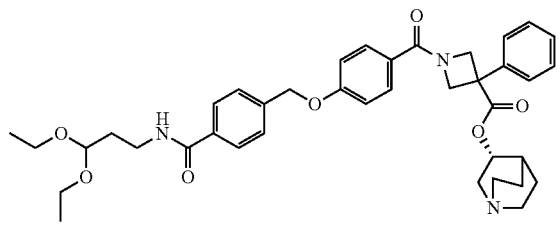 [SMILES: CCOC(CCNC(=O)c1ccc(COc2ccc(C(=O)N3CC(C(=O)O[C@H]4CN5CCC4CC5)(c4ccccc4)C3)cc2)cc1)OCC]

A solution of HCl in dioxane (4M, 2 mL) added to (R)-quinuclidin-3-yl 1-(4-((4-(tert-butoxycarbonyl)benzyl)oxy)benzoyl)-3-phenylazetidine-3-carboxylate (0.273 g, 0.46 mmol) and the reaction mixture stirred at room temperature for 72 hours. The solvent was concentrated at reduced pressure to afford the title compound. The residue was dissolved in DMF (10 mL) and triethylamine (0.190 mL, 1.37 mmol) and HATU (0.208 g, 0.55 mmol) added. The reaction mixture was stirred at room temperature for 15 minutes. 3,3-Diethoxypropan-1-amine (0.080 g, 0.55 mmol) was added and the reaction mixture stirred at room temperature for 18 hours. Further HATU (0.104 g) and triethylamine (0.095 mL) was added and the reaction stirred for a further 3 hours. The reaction mixture was dissolved in ethyl acetate and washed with water, saturated aqueous sodium hydrogen carbonate water and brine (×2). The organic phase was dried over anhydrous magnesium sulfate, the suspension filtered and the filtrate concentrated at reduced pressure. The residue was purified by column chromatography (eluent 100% ethyl acetate to 10% ammonia methanol/ethyl acetate) to afford the title compound (0.283 g, 92%).

$^1$H NMR (400 MHz, CDCl3) δ 7.79 (d, J=8.4 Hz, 2H), 7.65-7.62 (m, 2H), 7.50-7.45 (m, 2H), 7.38 (q, J=7.6 Hz, 2H), 7.34-7.28 (m, 3H), 7.05 (dd, J=4.9, 4.9 Hz, 1H), 6.99-6.96 (m, 2H), 5.15 (s, 2H), 5.00 (s, 1H), 4.83-4.81 (m, 2H), 4.67-4.59 (m, 3H), 4.12 (q, J=7.1 Hz, 1H), 3.77-3.48 (m, 6H), 3.14 (s, 1H), 2.83-2.70 (m, 4H), 2.05-1.93 (m, 3H), 1.85-1.45 (m, 4H), 1.24 (dd, J=7.1, 7.1 Hz, 6H).

Step 3. (R)-Quinuclidin-3-yl 1-(4-((4-((3-(((R)-2-hydroxy-2-(8-hydroxy-2-oxo-1,2-dihydroquinolin-5-yl)ethyl)amino)propyl)carbamoyl)benzyl)oxy)benzoyl)-3-phenylazetidine-3-carboxylate (Example 19A)

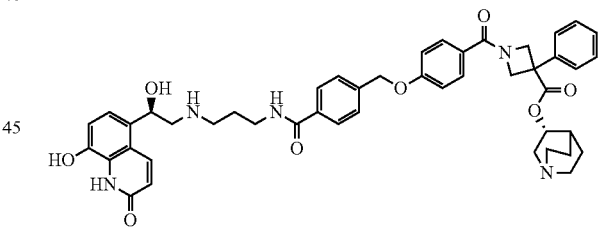

The title compound was prepared as described in Example 1 with (R)-quinuclidin-3-yl 1-(4-((4-((3,3-diethoxypropyl)carbamoyl)benzyl)oxy)benzoyl)-3-phenylazetidine-3-carboxylate replacing (R)-quinuclidin-3-yl 1-(4-(4-(1,3-dioxolan-2-yl)butoxy)benzoyl)-4-phenylpiperidine-4-carboxylate in Step 4.

$^1$H NMR (400 MHz, MeOD); δ 8.41 (d, J=9.8 Hz, 1H), 7.90 (d, J=8.4 Hz, 2H), 7.70 (d, J=8.9 Hz, 2H), 7.60 (d, J=8.4 Hz, 2H), 7.46-7.31 (m, 6H), 7.12 (d, J=8.9 Hz, 2H), 7.05 (d, J=8.2 Hz, 1H), 6.69 (d, J=9.8 Hz, 1H), 5.46 (dd, J=5.5, 7.7 Hz, 1H), 5.26 (s, 2H), 5.17 (ddd, J=2.5, 4.3, 8.3 Hz, 1H), 5.13-5.05 (m, 1H), 4.70-4.55 (m, 1H), 3.73-3.67 (m, 1H), 3.61-3.52 (m, 2H), 3.36-3.30 (m, 3H), 3.31-3.24 (m, 3H), 3.20-3.14 (m, 2H), 3.09-3.01 (m, 1H), 2.35-2.26 (m, 1H), 2.10-1.92 (m, 4H), 1.74-1.69 (m, 2H).

Example 9A. (R)-Quinuclidin-3-yl 1-(4-((4-((((R)-2-hydroxy-2-(8-hydroxy-2-oxo-1,2-dihydroquinolin-5-yl)ethyl)amino)methyl)-3-methoxybenzyl)carbamoyl)benzoyl)-3-phenylazetidine-3-carboxylate (Compound 20A)

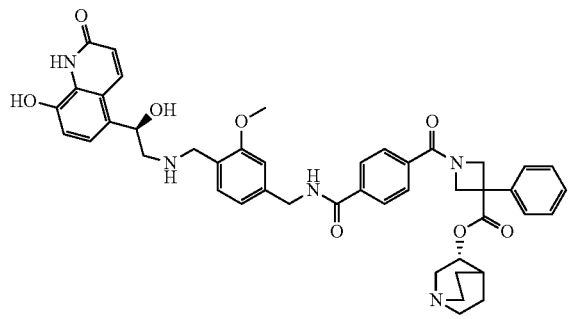 [SMILES: COc1cc(CNC(=O)c2ccc(C(=O)N3CC(C(=O)O[C@H]4CN5CCC4CC5)(c4ccccc4)C3)cc2)ccc1CNC[C@H](O)c1ccc(O)c2[nH]c(=O)ccc12]

Step 1. (4-(1,3-Dioxolan-2-yl)-3-methoxyphenyl)methanamine

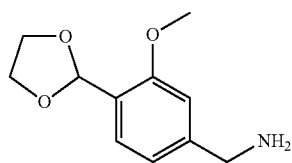

The title compound was prepared as described in Example 6 Step 1 and Step 2 with 2-methoxy-4-cyanobenzaldehyde replacing 4-cyanobenzaldehyde in Step 1.

$^1$H NMR (400 MHz, CDCl$_3$); δ 7.49 (d, J=7.8 Hz, 1H), 6.92-6.88 (m, 2H), 6.14 (s, 1H), 4.15-4.00 (m, 4H), 3.88 (s, 3H), 3.86 (s, 2H), 1.50 (s, 2H).

Step 2. (R)-Quinuclidin-3-yl 1-(4-((4-((((R)-2-hydroxy-2-(8-hydroxy-2-oxo-1,2-dihydroquinolin-5-yl)ethyl)amino)methyl)-3-methoxybenzyl)carbamoyl)benzoyl)-3-phenylazetidine-3-carboxylate (Compound 20A)

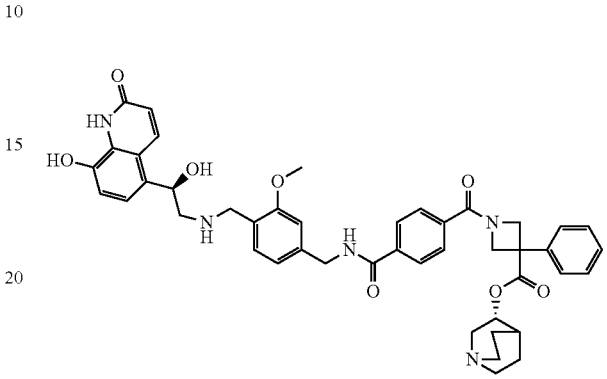

The title compound was prepared as described for Example 9A.

$^1$H NMR (400 MHz, MeOD); δ 8.48 (s, 2H), 8.22 (d, J=9.9 Hz, 1H), 7.98 (d, J=8.5 Hz, 2H), 7.80 (d, J=8.3 Hz, 2H), 7.47-7.34 (m, 6H), 7.26 (d, J=8.4 Hz, 1H), 7.12 (s, 1H), 7.05-7.02 (m, 2H), 6.64 (d, J=9.8 Hz, 1H), 5.41-5.36 (m, 1H), 5.12-5.06 (m, 2H), 4.98-4.80 (m, 1H), 4.67-4.62 (m, 3H), 4.29 (s, 2H), 3.92 (s, 3H), 3.56-3.49 (m, 1H), 3.20-3.10 (m, 7H), 3.01-2.98 (m, 1H), 2.23-2.17 (m, 1H), 1.99-1.91 (m, 1H), 1.86-1.81 (m, 1H), 1.63-1.63 (m, 2H).

The compounds prepared in the above described Examples 1-20 and 1A-9A are reported in the following table along with their analytical and NMR data.

| No. | LCMS/HPLC R$_t$ (min) | purity (%) | Method | NMR data |
|---|---|---|---|---|
| 1 | 8.52 | 95.2 | 2 | (400 MHz, DMSO-d$_6$); δ 8.28 (s, 2H), 8.18 (d, J = 20.3 Hz, 1H), 7.44-7.35 (m, 6H), 7.30 (dd, J = 7.0, 7.0 Hz, 1H), 7.11 (d, J = 8.2 Hz, 1H), 6.98-6.94 (m, 3H), 6.53 (d, J = 9.9 Hz, 1H), 5.18 (dd, J = 5.1, 7.6 Hz, 1H), 4.72-4.70 (m, 1H), 4.00 (dd, J = 6.4, 6.4 Hz, 2H), 3.30-3.10 (brs, 4H), 3.07-3.00 (m, 2H), 2.89-2.74 (m, 4H), 2.68-2.50 (m, 4H), 2.36-2.31 (m, 2H), 1.98-1.91 (m, 2H), 1.84-1.70 (m, 3H), 1.58-1.52 (m, 3H), 1.48-1.41 (m, 4H), 1.24-1.19 (m, 1H) |
| 2 | 8.37 | 95.1 | 1 | (400 MHz, DMSO-d$_6$, 90° C.); δ 8.22-8.18 (m, 3H), 7.45-7.28 (m, 6H), 7.08 (d, J = 8.2 Hz, 1H), 7.00-6.92 (m, 4H), 6.49 (d, J = 9.9 Hz, 1H), 5.04 (dd, J = 5.0, 7.5 Hz, 1H), 4.77-4.71 (m, 1H), 4.02 (t, J = 6.5 Hz, 2H), 3.93-3.81 (m, 2H), 3.30-3.20 (m, 2H), 3.05 (ddd, J = 2.2, 8.1, 14.5 Hz, 2H), 2.84-2.74 (m, 2H), 2.72-2.45 (m, 7H), 2.40-2.32 (m, 2H), 2.03-1.94 (m, 2H), 1.86-1.80 (m, 1H), 1.77-1.69 (m, 2H), 1.63-1.41 (m, 6H), 1.30-1.21 (m, 1H). |
| 3 | 8.61 | 95.3 | 2 | $^1$H NMR (400 MHz, MeOD); δ 8.38 (d, J = 9.9 Hz, 1H), 7.51 (d, J = 7.5 Hz, 2H), 7.43 (dd, J = 7.7, 7.7 Hz, 2H), 7.36-7.29 (m, 2H), 7.06-7.01 (m, 4H), 6.70 (d, J = 9.8 Hz, 1H), 5.41 (dd, J = 6.7, 6.7 Hz, 1H), 5.18-5.13 (m, 1H), 4.09 (t, J = 6.0 Hz, 2H), 3.83 (s, 3H), 3.71-3.65 (m, 1H), 3.43-3.42 (m, 2H), 3.29-3.23 (m, 6H), 3.15 (t, J = 7.9 Hz, 2H), 2.98-2.98 (m, 4H), 2.68-2.64 (m, 2H), 2.28 (s, 2H), 2.06-1.82 (m, 6H), 1.70-1.63 (m, 4H). |

| | | | |
|---|---|---|---|
| | | -continued | |
| 4 | 9.06 | 91 | 2 | ¹H NMR (400 MHz, MeOD); δ 8.53 (s, 2H), 8.39 (d, J = 9.9 Hz, 1H), 7.52-7.48 (m, 3H), 7.45-7.28 (m, 5H), 7.15 (d, J = 8.5 Hz, 1H), 7.04 (d, J = 8.2 Hz, 1H), 6.70 (d, J = 9.8 Hz, 1H), 5.41 (dd, J = 6.8, 6.8 Hz, 1H), 5.07-5.01 (m, 1H), 4.31 (br s, 1H), 4.17 (dd, J = 6.0, 6.0 Hz, 2H), 3.79-3.74 (m, 1H), 3.47-3.45 (m, 3H), 3.25 (d, J = 6.8 Hz, 2H), 3.17-3.01 (m, 6H), 2.81-2.80 (m, 2H), 2.68 (s, 1H), 2.65-2.61 (m, 1H), 2.15-2.09 (m, 3H), 1.99-1.80 (m, 5H), 1.73-1.64 (m, 3H), 1.58 (s, 1H). |
| 5 | 2.37 | 98.7 | 3 | ¹H NMR (400 MHz, MeOD); δ 8.39 (d, J = 9.9 Hz, 1H), 7.52 (s, 1H), 7.50 (s, 3H), 7.43 (dd, J = 7.7, 7.7 Hz, 2H), 7.36-7.29 (m, 2H), 7.05 (d, J = 8.2 Hz, 1H), 6.70 (d, J = 9.8 Hz, 1H), 5.42 (dd, J = 6.7, 6.7 Hz, 1H), 5.16-5.13 (m, 1H), 4.29 (br s, 1H), 4.12 (dd, J = 6.0, 6.0 Hz, 2H), 3.69 (dd, J = 8.7, 12.4 Hz, 2H), 3.51-3.36 (m, 4H), 3.30-3.13 (m, 6H), 3.11-2.88 (m, 2H), 2.78-2.50 (m, 2H), 2.32-1.83 (m, 8H), 1.78-1.69 (m, 4H). |
| 6 | 7.31 | 98 | 2 | ¹H NMR (400 MHz, DMSO-d₆); δ 10.53-10.46 (m, 2H), 9.60 (s, 1H), 8.66-8.46 (m, 2H), 8.15 (d, J = 49.7 Hz, 1H), 7.84 (dd, J = 1.1, 2.9 Hz, 1H), 7.60-7.57 (m, 2H), 7.52 (dd, J = 1.1, 5.0 Hz, 1H), 7.46 (d, J = 7.5 Hz 2H), 7.43-7.32 (m, 4H), 7.17-7.13 (m, 2H), 6.99 (d, J = 8.2 Hz, 1H), 6.59 (dd, J = 1.9, 9.8 Hz, 1H), 6.17 (s, 1H), 5.30 (d, J = 9.8 Hz, 1H), 5.04-4.99 (m, 1H), 4.10 (dd, J = 6.3, 6.3 Hz, 1H), 3.66-3.63 (m, 1H), 3.13-2.96 (m, 14H), 2.13 (d, J = 2.3 Hz, 1H), 1.97 (s, 2H), 1.86-1.61 (m, 9H), 1.51-1.45 (m, 2H); |
| 7 | 7.12 | 95.5 | 2 | ¹H NMR (400 MHz, DMSO-d₆); δ 8.30 (s, 2H), 8.18 (d, J = 9.9 Hz, 1H), 7.37 (d, J = 4.5 Hz, 4H), 7.31-7.25 (m, 1H), 7.14-7.08 (m, 3H), 6.95 (d, J = 8.2 Hz, 1H), 6.79 (d, J = 8.7 Hz, 2H), 6.52 (d, J = 9.9 Hz, 1H), 5.15 (dd, J = 6.3, 6.3 Hz, 1H), 4.71-4.67 (m, 1H), 4.20-4.15 (m, 1H), 3.88-3.83 (m, 3H), 3.18-3.12 (m, 1H), 3.05-2.99 (m, 1H), 2.87-2.81 (m, 3H), 2.76-2.54 (m, 8H), 2.35 (m, 5H), 1.81 (s, 1H), 1.72-1.64 (m, 4H), 1.57-1.40 (m, 7H), 1.22 (s, 1H); |
| 8 | 7.09 | 92.6 | 2 | ¹H NMR (400 MHz, DMSO-d₆); δ 8.30 (s, 2H), 8.18 (d, J = 39.3 Hz, 1H), 7.36 (d, J = 4.4 Hz, 4H), 7.30-7.25 (m, 1H), 7.11 (m, 3H), 6.95 (d, J = 8.2 Hz, 1H), 6.84 (d, J = 8.7 Hz, 2H), 6.52 (d, J = 9.9 Hz, 1H), 5.18 (dd, J = 4.8, 7.7 Hz, 1H), 4.70-4.67 (m, 1H), 4.13 (dd, J = 3.1, 13.2 Hz, 1H), 3.91 (dd, J = 6.4, 6.4 Hz, 2H), 3.85-3.81 (m, 1H), 3.17 (m, 1H), 3.05-2.56 (m, 9H), 2.34-2.25 (m, 6H), 1.80-1.66 (m, 5H), 1.59-1.38 (m, 7H), 1.24-1.24 (m, 1H); |
| 9 | 7.12 | 96.2 | 2 | ¹H NMR (400 MHz, DMSO-d₆); δ 10.51 (d, J = 5.0 Hz, 2H), 9.82 (m, 1H), 8.63 (m, 2H), 8.17 (d, J = 9.9 Hz, 1H), 7.47-7.38 (m, 4H), 7.34-7.28 (m, 2H), 7.21 (d, J = 4.6 Hz, 2H), 7.15 (d, J = 8.3 Hz, 1H), 6.99 (d, J = 8.2 Hz, 1H), 6.58 (d, J = 9.9 Hz, 1H), 6.19 (d, J = 3.4 Hz, 1H), 5.34-5.29 (m, 1H), 5.03-4.99 (m, 1H), 4.10 (dd, J = 6.3, 6.3 Hz, 2H), 3.68-3.60 (m, 1H), 3.24-3.01 (m, 14H), 2.14-2.08 (m, 1H), 2.06-1.75 (m, 3H), 1.75 (m, 6H), 1.63-1.61 (m, 1H), 1.51-1.44 (m, 2H); |
| 10 | 7.18 | 97.6 | 2 | ¹H NMR (400 MHz, DMSO-d₆); δ 8.36 (s, 2H), 8.20 (d, J = 9.9 Hz, 1H), 7.44-7.36 (m, 4H), 7.29 (m, 1H), 7.23 (d, J = 7.4 Hz, 2H), 7.09 (d, J = 8.2 Hz, 1H), 6.95 (dd, J = 8.2, 8.2 Hz, 2H), 6.51 (d, J = 9.8 Hz, 1H), 5.19 (dd, J = 4.9, 7.5 Hz, 1H), 4.72-4.70 (m, 1H), 4.01 (dd, J = 6.2, 6.2 Hz, 2H), 3.18-3.14 (m, 2H), 3.09-2.97 (m, 1H), 2.90-2.54 (m, 7H), 2.38-2.27 (m, 2H), 2.16 (s, 3H), 1.95-1.87 (m, 2H), 1.84-1.71 (m, 3H), 1.61-1.50 (m, 5H), 1.48-1.43 (m, 5H), 1.27-1.22 (m, 2H); |
| 11 | 7.93 | 96.7 | 2 | ¹H NMR (400 MHz, DMSO-d₆); δ d 10.6 (s, 1H), 10.5 (s, 1H), 9.70 (s, 1H), 8.61-8.60 (m, 2H), 8.16 (d, J = 9.9 Hz, 1H), 7.38 (d, J = 4.5 Hz, 4H), 7.37-7.27 (m, 1H), 7.22-7.14 (m, 2H), 6.99 (d, J = 8.2 Hz, 1H), 6.78 (dd, J = 7.0, 7.0 Hz, 3H), 6.59 (d, J = 9.9 Hz, 1H), 6.18 (s, 1H), 5.31 (dd, J = 2.2, 9.7 Hz, 1H), 5.01-4.99 (m, 1H), 4.12 (dd, J = 5.0, 13.6 Hz, 1H), 3.92 (dd, J = 6.3, 6.3 Hz, 2H), 3.85-3.56 (m, |

| | | | | |
|---|---|---|---|---|
| | | | | 4H), 3.31-3.05 (m, 6H), 2.99 (dd, J = 13.8, 13.8 Hz, 6H), 2.14-2.08 (m, 1H), 1.85-1.56 (m, 10H), 1.47-1.39 (m, 2H). |
| 12 | 7.16 | 98.2 | 2 | $^1$H NMR (400 MHz, DMSO-d$_6$); δ 10.57-10.52 (2H, m), 9.69 (1H, s), 8.62-8.61 (2H, m), 8.20 (1H, d, J = 9.9 Hz), 7.45-7.42 (4H, m), 7.39-7.32 (1H, m), 7.20 (1H, d, J = 8.1 Hz), 7.05-7.01 (3H, m), 6.88 (1H, d, J = 9.1 Hz), 6.64 (1H, d, J = 9.4 Hz), 6.26-6.23 (1H, m), 5.35 (1H, dd, J = 2.3, 9.9 Hz), 5.08-5.04 (1H, m), 4.19-4.12 (3H, m), 3.98 (3H, dd, J = 6.1, 6.1 Hz), 3.87-3.81 (2H, m), 3.71-3.62 (4H, m), 3.36-3.00 (9H, m), 2.16 (4H, s), 1.92-1.50 (10H, m) |
| 13 | 7.19 | 98.1 | 2 | $^1$H NMR (400 MHz, DMSO-d$_6$); δ 10.54 (2H, s), 9.77 (1H, s), 8.61 (2H, d, J = 4.3 Hz), 8.21 (1H, d, J = 10.2 Hz), 7.45 (4H, d, J = 6.6 Hz), 7.39-7.33 (1H, m), 7.32 (1H, d, J = 1.8 Hz), 7.21-7.15 (2H, m), 7.11 (1H, d, J = 8.6 Hz), 7.04 (1H, d, J = 8.1 Hz), 6.63 (1H, d, J = 9.9 Hz), 6.22-6.15 (1H, m), 5.36 (1H, dd, J = 2.4, 10.0 Hz), 5.06 (1H, dd, J = 4.0, 4.0 Hz), 4.19-4.11 (2H, m), 4.07 (2H, t, J = 6.3 Hz), 3.89-3.83 (2H, m), 3.79-3.72 (1H, m), 3.66 (1H, t, J = 6.8 Hz), 3.39-3.12 (5H, m), 3.06-3.04 (7H, m), 2.52-2.46 (1H, m), 2.18 (1H, d, J = 18.9 Hz), 1.94-1.64 (9H, m), 1.58-1.49 (2H, m) |
| 14 | 7.27 | 96.5 | 2 | $^1$H NMR (400 MHz, DMSO-d$_6$); δ 10.57-10.53 (2H, m), 9.70-9.69 (1H, m), 8.61 (2H, d, J = 1.0 Hz), 8.20 (1H, d, J = 9.4 Hz), 7.76 (1H, dd, J = 1.1, 2.9 Hz), 7.60 (1H, dd, J = 2.9, 4.9 Hz), 7.49 (1H, dd, J = 1.3, 5.1 Hz), 7.46-7.41 (5H, m), 7.38-7.32 (1H, m), 7.21-7.15 (2H, m), 7.05 (2H, dd, J = 8.5, 12.8 Hz), 6.63 (1H, d, J = 9.9 Hz), 6.22-6.16 (1H, m), 5.35 (1H, dd, J = 2.0, 9.9 Hz), 5.06-5.02 (1H, m), 4.20-4.13 (2H, m), 4.05 (2H, dd, J = 6.2, 6.2 Hz), 3.94-3.88 (2H, m), 3.81-3.70 (6H, m), 3.39-2.99 (10H, m), 1.92-1.65 (9H, m), 1.60 (1H, d, J = 12.1 Hz), 1.54-1.45 (2H, m) |
| 15 | 7.32 | 97.9 | 2 | $^1$H NMR (400 MHz, MeOD); δ 8.35 (d, J = 10.3 Hz, 1H), 7.44-7.36 (m, 6H), 7.35-7.17 (m, 7H), 7.06-7.01 (m, 2H), 6.69 (d, J = 9.9 Hz, 1H), 5.36 (dd, J = 4.6, 8.8 Hz, 1H), 5.14-5.09 (m, 1H), 4.33-4.27 (m, 1H), 4.00 (t, J = 6.5 Hz, 2H), 3.96-3.90 (m, 1H), 3.87-3.76 (m, 2H), 3.71-3.62 (m, 1H), 3.50-3.41 (m, 1H), 3.28-2.84 (m, 10H), 2.63-2.47 (m, 2H), 2.28-2.21 (m, 1H), 2.06-1.81 (m, 3H), 1.80-1.67 (m, 6H), 1.56-1.45 (m, 3H). |
| 16 | 7.29 | 99 | 2 | $^1$H NMR (400 MHz, MeOD); δ 8.35 (d, J = 9.9 Hz, 1H), 7.40 (d, J = 5.9 Hz, 4H), 7.36-7.23 (m, 7H), 7.18-7.13 (m, 2H), 7.05 (d, J = 8.2 Hz, 1H), 6.93 (dd, J = 2.1, 8.3 Hz, 1H), 6.68 (d, J = 9.9 Hz, 1H), 5.36 (dd, J = 4.8, 8.7 Hz, 1H), 5.11-5.07 (m, 1H), 4.32-4.27 (m, 1H), 3.91-3.77 (m, 3H), 3.70-3.60 (m, 1H), 3.29-3.10 (m, 4H), 3.07-2.83 (m, 9H), 2.68-2.39 (m, 3H), 2.26-2.18 (m, 1H), 2.02-1.38 (m, 12H). |
| 17 | 2.30 | 99 | 3 | $^1$H NMR (400 MHz, MeOD); δ 8.38 (d, J = 9.9 Hz, 1H), 7.42-7.39 (m, 4H), 7.35-7.29 (m, 2H), 7.05 (d, J = 8.2 Hz, 1H), 6.98 (d, J = 5.9 Hz, 2H), 6.74-6.68 (m, 2H), 5.43-5.38 (m, 1H), 5.13-5.08 (m, 1H), 3.91-3.62 (m, 4H), 3.29-3.20 (m, 7H), 3.16-2.76 (m, 9H), 2.61-2.53 (m, 2H), 2.42-2.38 (m, 1H), 2.27-2.21 (m, 1H), 2.10 (s, 3H), 2.06-1.78 (m, 6H), 1.77-1.56 (m, 4H), 1.47-1.35 (m, 1H). |
| 18 | 2.51 | 95 | 4 | $^1$H NMR (400 MHz, MeOD); δ 8.38 (d, J = 9.9 Hz, 1H), 7.55-7.47 (m, 4H), 7.41 (dd, J = 7.7, 7.7 Hz, 3H), 7.33-7.27 (m, 2H), 7.05-7.00 (m, 2H), 6.92 (d, J = 8.4 Hz, 1H), 6.70 (d, J = 9.9 Hz, 1H), 5.38 (dd, J = 4.8, 8.7 Hz, 1H), 4.95-4.92 (m, 2H), 4.41-4.34 (m, 1H), 4.21-4.15 (m, 1H), 4.13-4.06 (m, 2H), 3.59-3.49 (m, 1H), 3.35-3.30 (m, 4H), 3.28-3.24 (m, 1H), 3.23-3.18 (m, 2H), 3.09 (t, J = 7.7 Hz, 2H), 2.89-2.85 (m, 2H), 2.74-2.52 (m, 3H), 2.23 (s, 3H), 2.09-1.99 (m, 3H), 1.95-1.88 (m, 2H), 1.86-1.75 (m, 2H), 1.69-1.53 (m, 3H), 1.51-1.40 (m, 1H) |
| 19 | 6.88 | 91.8 | 2 | $^1$H NMR (400 MHz, MeOD); δ 8.54 (s, 3H), 8.39 (d, J = 9.9 Hz, 1H), 7.92 (d, J = 8.3 Hz, 2H), 7.55-7.48 (m, 4H), 7.42 (dd, J = 7.7, 7.7 Hz, 2H), |

| | | | | |
|---|---|---|---|---|
| | | | | 7.35-7.28 (m, 2H), 7.04 (d, J = 8.2 Hz, 1H), 6.70 (d, J = 9.9 Hz, 1H), 5.40 (dd, J = 6.8, 6.8 Hz, 1H), 5.01-4.98 (m, 1H), 3.64-3.61 (m, 1H), 3.48 (dd, J = 6.8, 6.8 Hz, 3H), 3.37-3.36 (m, 3H), 3.24 (d, J = 6.8 Hz, 2H), 3.15 (dd, J = 7.7, 7.7 Hz, 2H), 2.98 (m, 3H), 2.74-2.73 (m, 3H), 2.66-2.66 (m, 1H), 2.09-2.09 (m, 3H), 1.83-1.72 (m, 6H), 1.54-1.51 (m, 2H). |
| 20 | 6.87 | 98.6 | 2 | $^1$H NMR (400 MHz, DMSO-$d_6$); δ 10.49 (d, J = 12.2 Hz, 2H), 9.64-9.64 (m, 1H), 8.77 (s, 2H), 8.16 (d, J = 44.6 Hz, 1H), 7.47-7.38 (m, 6H), 7.33 (d, J = 8.3 Hz, 3H), 7.17 (d, J = 8.2 Hz, 1H), 7.00 (d, J = 8.2 Hz, 1H), 6.60 (dd, J = 1.8, 9.9 Hz, 1H), 6.21 (s, 1H), 5.34 (d, J = 8.9 Hz, 1H), 5.04-4.99 (m, 1H), 4.20 (m, 1H), 3.62 (m, 1H), 3.23 (m, 5H), 3.16-2.99 (m, 9H), 2.55-2.35 (m, 2H), 2.09 (s, 1H), 1.88-1.78 (m, 4H), 1.62 (s, 2H). |
| 21 | 6.91 | 96.6 | 2 | $^1$H NMR (400 MHz, DMSO-$d_6$); δ 10.49 (d, J = 2.9 Hz, 2H), 9.72-9.71 (m, 1H), 8.70 (dd, J = 5.6, 5.6 Hz, 1H), 8.60 (s, 2H), 8.15 (d, J = 9.9 Hz, 1H), 7.69 (d, J = 3.9 Hz, 1H), 7.46 (d, J = 7.5 Hz, 2H), 7.44-7.38 (m, 3H), 7.33 (dd, J = 7.2, 7.2 Hz, 1H), 7.15 (d, J = 8.3 Hz, 1H), 6.99 (d, J = 8.2 Hz, 1H), 6.59 (d, J = 9.8 Hz, 1H), 6.17 (s, 1H), 5.30 (d, J = 9.3 Hz, 1H), 5.04-5.00 (m, 1H), 4.05-4.05 (m, 2H), 3.68-3.61 (m, 1H), 3.30-3.22 (m, 4H), 3.16-3.08 (m, 6H), 3.01 (d, J = 5.9 Hz, 4H), 2.58 (m, 2H), 2.15 (d, J = 2.4 Hz, 1H), 2.09-1.96 (m, 2H), 1.90-1.79 (m, 2H), 1.71-1.54 (m, 6H). |
| 22 | 7.37 | 97.4 | 2 | $^1$H NMR (400 MHz, DMSO-$d_6$); δ 10.50 (d, J = 7.0 Hz, 2H), 9.67-9.67 (m, 1H), 8.61-8.61 (s, 2H), 8.16 (d, J = 9.9 Hz, 1H), 7.45 (d, J = 7.4 Hz, 2H), 7.43-7.37 (m, 4H), 7.32 (dd, J = 7.8, 7.8 Hz, 2H), 7.16 (d, J = 8.2 Hz, 1H), 7.06-6.97 (m, 5H), 6.91 (dd, J = 1.9, 8.2 Hz, 1H), 6.59 (d, J = 9.9 Hz, 1H), 6.17 (s, 1H), 5.31 (dd, J = 1.9, 9.8 Hz, 1H), 5.12 (s, 2H), 5.04-4.99 (m, 1H), 4.01 (dd, J = 5.3, 5.3 Hz, 2H), 3.70-3.55 (m, 4H), 3.24-3.19 (m, 3H), 3.16-3.03 (m, 9H), 2.14 (d, J = 2.5 Hz, 1H), 2.04-1.90 (m, 2H), 1.87-1.79 (m, 6H), 1.65-1.61 (m, 2H). |
| 23 | 6.96 | 96.5 | 2 | $^1$H NMR (400 MHz, DMSO-$d_6$); δ 10.50 (s, 2H), 9.70 (s, 1H), 9.19 (dd, J = 6.0, 6.0 Hz, 1H), 9.02 (s, 2H), 8.08 (d, J = 9.9 Hz, 1H), 7.95 (d, J = 8.3 Hz, 2H), 7.54-7.36 (m, 10H), 7.32 (dd, J = 7.1, 7.1 Hz, 1H), 7.12 (d, J = 8.3 Hz, 1H), 6.97 (d, J = 8.2 Hz, 1H), 6.59-6.54 (m, 1H), 6.17 (d, J = 3.5 Hz, 1H), 5.33 (d, J = 9.9 Hz, 1H), 5.03-5.00 (m, 1H), 4.51 (d, J = 5.8 Hz, 2H), 4.21 (m, 3H), 3.66-3.60 (m, 1H), 3.57-3.42 (m, 1H), 3.25-3.25 (m, 2H), 3.16-3.12 (m, 3H), 3.05-2.94 (m, 3H), 2.62 (m, 1H), 2.43 (m, 1H), 2.13 (m, 3H), 1.88-1.78 (m, 2H), 1.70-1.55 (m, 2H). |
| 24 | 7.15 | 96.1 | 2 | $^1$H NMR (400 MHz, DMSO-$d_6$); δ 10.30 (br s, 1H), 8.23 (2H, s), 8.11 (d, J = 9.9 Hz, 1H), 7.44-7.34 (m, 10H), 7.29 (dd, J = 7.0, 7.0 Hz, 1H), 7.06 (m, 3H), 6.92 (d, J = 8.2 Hz, 1H), 6.48 (d, J = 9.9 Hz, 1H), 5.12 (s, 2H), 5.09 (m, 1H), 4.74-4.71 (m, 1H), 3.80 (s, 2H), 3.18-3.02 (m, 4H), 2.76-2.40 (m, 7H), 2.42-2.27 (m, 2H), 1.97-1.82 (m, 3H), 1.59-1.42 (m, 3H), 1.29-1.22 (m, 1H). |
| 25 | 6.91 | 93.7 | 2 | $^1$H NMR (400 MHz, DMSO-$d_6$, 90° C.); δ 8.18 (d, J = 9.9 Hz, 1H), 7.50-7.38 (m, 9H), 7.32 (dd, J = 7.1, 7.1 Hz, 1H), 7.16 (d, J = 8.2 Hz, 1H), 7.01 (d, J = 8.2 Hz, 1H), 6.55 (d, J = 9.9 Hz, 1H), 5.35 (dd, J = 4.3, 8.5 Hz, 1H), 5.09-5.04 (m, 1H), 3.85 (s, 2H), 3.65 (ddd, J = 2.5, 8.6, 14.0 Hz, 1H), 3.53-3.46 (m, 2H), 3.37-2.94 (m, 11H), 2.18-1.99 (m, 6H), 1.95-1.81 (m, 3H), 1.70-1.65 (m, 2H), 1.12 (dd, J = 7.1, 7.1 Hz, 3H). |
| 26 | 7.13 | 96.3 | 2 | $^1$H NMR (400 MHz, DMSO-$d_6$); δ 10.49 (s, 2H), 9.72 (s, 1H), 8.77-8.77 (m, 2H), 8.16 (d, J = 9.9 Hz, 1H), 7.47-7.36 (m, 8H), 7.34-7.28 (m, 3H), 7.17 (d, J = 8.3 Hz, 1H), 7.05 (d, J = 8.8 Hz, 2H), 7.00 (d, J = 8.2 Hz, 1H), 6.59 (d, J = 9.8 Hz, 1H), 6.20 (s, 1H), 5.34 (d, J = 7.9 Hz, 1H), 5.13 (s, 2H), 5.04-4.99 (m, 1H), 3.62 (m, 2H), 3.36-3.30 (m, 3H), 3.24-2.95 (m, 12H), 2.16-2.09 (m, 1H), 2.04-1.76 (m, 4H), 1.63 (dd, J = 6.8, 6.8 Hz, 2H). |
| 27 | 6.90 | 93.9 | 2 | $^1$H NMR (400 MHz, DMSO-$d_6$, 90° C.); δ 8.01 (m, 3H), 7.35-7.25 (m, 7H), 7.24 (d, J = 3.8 Hz, |

| | | | | |
|---|---|---|---|---|
| | | | | 1H), 7.19 (dd, J = 7.2, 7.2 Hz, 1H), 6.98 (d, J = 8.0 Hz, 1H), 6.85 (d, J = 8.2 Hz, 1H), 6.38 (d, J = 9.9 Hz, 1H), 4.94 (dd, J = 5.0, 7.3 Hz, 1H), 4.67-4.64 (m, 1H), 3.99-3.91 (m, 2H), 3.42 (dd, J = 6.5, 7.9 Hz, 2H), 3.31-3.21 (m, 2H), 3.04-2.90 (m, 4H), 2.76-2.63 (m, 1H), 2.60-2.48 (m, 5H), 2.33-2.23 (m, 1H), 1.94 (s, 4H), 1.77-1.61 (m, 3H), 1.53-1.34 (m, 3H), 1.17 (dd, J = 11.2, 15.8 Hz, 1H). |
| 28 | 7.20 | 96.5 | 2 | $^1$H NMR (400 MHz, DMSO-d$_6$, 90° C.); δ 8.17 (d, J = 9.9 Hz, 1H), 7.48-7.37 (m, 6H), 7.33-7.27 (m, 6H), 7.15 (d, J = 8.2 Hz, 1H), 7.02 (d, J = 8.2 Hz, 1H), 6.56 (d, J = 9.9 Hz, 1H), 5.33 (dd, J = 4.8, 8.3 Hz, 1H), 5.09-5.04 (m, 1H), 4.80 (s, 2H), 4.05-3.95 (m, 2H), 3.66 (ddd, J = 2.6, 8.5, 14.0 Hz, 1H), 3.56-3.51 (m, 2H), 3.46-3.36 (m, 2H), 3.25-2.99 (m, 8H), 2.59-2.53 (m, 2H), 2.20-2.00 (m, 6H), 2.00-1.81 (m, 2H), 1.71-1.65 (m, 2H). |
| 29 | 6.98 | 95.38 | 2 | $^1$H NMR (400 MHz, DMSO-d$_6$); δ 10.50 (s, 2H), 9.76 (s, 1H), 8.64 (s, 2H), 8.16 (d, J = 9.9 Hz, 1H), 7.46 (d, J = 7.5 Hz, 2H), 7.44-7.38 (m, 4H), 7.32 (dd, J = 7.1, 7.1 Hz, 1H), 7.16 (d, J = 8.3 Hz, 1H), 6.99 (d, J = 8.2 Hz, 1H), 6.58 (d, J = 9.9 Hz, 1H), 6.20 (s, 1H), 5.31 (dd, J = 2.4, 9.5 Hz, 1H), 5.05-5.00 (m, 1H), 4.09-4.07 (m, 2H), 3.67-3.61 (m, 2H), 3.54-3.32 (m, 4H), 3.22-3.00 (m, 9H), 2.60-2.54 (m, 2H), 2.17-1.95 (m, 6H), 1.91-1.77 (m, 2H), 1.64 (dd, J = 6.3, 6.3 Hz, 2H), 1.20 (dd, J = 6.8, 6.8 Hz, 3H). |
| 30 | 7.04 | 95.0 | 2 | $^1$H NMR (400 MHz, MeOD); δ 8.53 (s, 2H), 8.38 (d, J = 9.9 Hz, 1H), 7.39 (d, J = 7.2 Hz, 4H), 7.32-7.29 (m, 2H), 7.18 (d, J = 8.5 Hz, 2H), 7.04 (d, J = 8.3 Hz, 1H), 6.90 (d, J = 8.4 Hz, 2H), 6.69 (d, J = 9.9 Hz, 1H), 5.41 (dd, J = 6.8, 6.8 Hz, 1H), 5.01-4.98 (m, 1H), 4.30-4.24 (m, 1H), 4.03 (dd, J = 5.5, 5.5 Hz, 2H), 3.89 (dd, J = 6.7, 12.9 Hz, 1H), 3.75 (s, 2H), 3.51-3.35 (m, 2H), 3.26-3.01 (m, 7H), 2.86-2.67 (m, 3H), 2.61-2.44 (m, 2H), 2.15-2.07 (m, 1H), 1.97-1.89 (m, 6H), 1.81-1.51 (m, 4H). |
| 31 | 6.77 | 98.8 | 2 | $^1$H NMR (400 MHz, DMSO-d$_6$); δ 10.52 (s, 1H), 10.49 (s, 1 H), 9.62-9.62 (m, 1H), 9.13 (s, 2H), 8.59-8.54 (m, 1H), 8.06 (d, J = 9.9 Hz, 1H), 7.87 (d, J = 8.2 Hz, 2H), 7.59 (d, J = 8.3 Hz, 2H), 7.44-7.36 (m, 4H), 7.33-7.29 (m, 1H), 7.12 (d, J = 8.3 Hz, 1H), 6.97 (d, J = 8.2 Hz, 1H), 6.57 (d, J = 9.8 Hz, 1H), 6.22-6.19 (m, 1H), 5.34 (d, J = 8.7 Hz, 1H), 5.04-4.99 (m, 1H), 4.29 (dd, J = 5.6, 5.6 Hz, 2H), 4.15-4.08 (m, 1H), 3.76 (dd, J = 4.3, 13.7 Hz, 1H), 3.66-3.60 (m, 2H), 3.35-3.22 (m, 2H), 3.15-2.98 (m, 9H), 2.70-2.56 (m, 2H), 2.17-2.12 (m, 1H), 2.00-1.78 (m, 5H), 1.66-1.59 (m, 2H). |
| 32 | 7.03 | 97.5 | 2 | $^1$H NMR (400 MHz, MeOD); δ 8.39 (d, J = 9.9 Hz, 1H), 7.40 (d, J = 3.3 Hz, 4H), 7.34-7.29 (m, 2H), 7.14 (d, J = 8.3 Hz, 2H), 7.05 (d, J = 8.1 Hz, 1H), 6.80 (d, J = 7.8 Hz, 2H), 6.69 (d, J = 9.9 Hz, 1H), 5.41 (dd, J = 6.7, 6.7 Hz, 1H), 5.14-5.09 (m, 1H), 4.24-4.24 (m, 1H), 3.95-3.74 (m, 3H), 3.71-3.62 (m, 1H), 3.29-3.16 (m, 7H), 3.08-2.85 (m, 6H), 2.82-2.72 (m, 1H), 2.68-2.53 (m, 2H), 2.48-2.42 (m, 1H), 2.24 (dd, J = 2.5, 21.5 Hz, 1H), 2.05-2.05 (m, 8H), 1.75-1.66 (m, 1H), 1.61-1.47 (m, 1H). |
| 33 | 2.52 | 95.01 | 4 | $^1$H NMR (400 MHz, DMSO-d$_6$, 100° C.); δ 8.19 (d, J = 9.8 Hz, 1H), 7.37-7.35 (m, 4H), 7.29-7.25 (m, 1H), 7.16 (s, 3H), 7.14-7.09 (m, 2H), 7.08-7.03 (m, 3H), 6.92 (d, J = 8.2 Hz, 1H), 6.46 (d, J = 9.8 Hz, 1H), 4.99 (dd, J = 4.8, 7.5 Hz, 1H), 4.74-4.70 (m, 1H), 4.49 (s, 2H), 3.95-3.95 (m, 3H), 3.30 (dd, J = 7.4, 7.4 Hz, 2H), 3.18 (s, 2H), 3.03 (ddd, J = 2.2, 8.2, 14.5 Hz, 1H), 2.79-2.52 (m, 6H), 2.46-2.21 (m, 8H), 1.88-1.79 (m, 4H), 1.62-1.43 (m, 6H), 1.29-1.21 (m, 2H). |
| 34 | 2.54 | 98.7 | 4 | $^1$H NMR (400 MHz, DMSO-d$_6$, 100° C.); δ 8.17 (d, J = 9.9 Hz, 1H), 7.37-7.35 (m, 4H), 7.29-7.24 (m, 1H), 7.18-7.13 (m, 7H), 7.06-7.01 (m, 2H), 6.91 (d, J = 8.2 Hz, 1H), 6.45 (d, J = 9.9 Hz, 1H), 4.98 (dd, J = 4.8, 7.6 Hz, 1H), 4.74-4.70 (m, 1H), 4.54 (s, 2H), 3.95-3.95 (m, 2H), 3.69 (s, 4H), 3.31 (dd, J = 7.4, 7.4 Hz, 2H), 3.18 (s, 2H), 3.03 (ddd, J = 2.2, 8.2, 14.6 Hz, 1H), 2.80-2.53 (m, 8H), 2.48-2.24 (m, 3H), 2.23 (s, 3H), 1.88-1.80 (m, 3H), |

| | | | | |
|---|---|---|---|---|
| | | | | 1.63-1.53 (m, 3H), 1.48-1.41 (m, 2H), 1.28-1.21 (m, 1H). |
| 35 | 2.52 | 96.65 | 4 | $^1$H NMR (400 MHz, DMSO-d$_6$, 100° C.); δ 8.15 (d, J = 9.9 Hz, 1H), 7.41-7.37 (m, 4H), 7.32-7.29 (m, 1H), 7.21 (d, J = 7.7 Hz, 1H), 7.18-7.11 (m, 5H), 7.08 (d, J = 6.7 Hz, 1H), 7.03-6.99 (m, 3H), 6.56 (d, J = 9.8 Hz, 1H), 5.33-5.28 (m, 1H), 5.08-5.04 (m, 1H), 4.58 (s, 2H), 3.90 (s, 1H), 3.74-3.61 (m, 6H), 3.56-3.30 (m, 2H), 3.24-3.15 (m, 6H), 3.09 (d, J = 7.4 Hz, 2H), 2.97 (d, J = 7.7 Hz, 4H), 2.54 (s, 1H), 2.28 (s, 3H), 2.16 (s, 1H), 1.93-1.85 (m, 6H), 1.67 (dd, J = 8.4, 8.4 Hz, 2H). |
| 36 | 7.24 | 97.77 | 2 | $^1$H NMR (400 MHz, DMSO-d$_6$, 90° C.); δ 8.16 (d, J = 9.9 Hz, 1H), 7.38 (d, J = 3.9 Hz, 4H), 7.36-7.24 (m, 5H), 7.20-7.12 (m, 6H), 7.02 (d, J = 8.2 Hz, 1H), 6.57 (d, J = 9.9 Hz, 1H), 5.28 (dd, J = 6.5, 6.5 Hz, 1H), 5.06-5.02 (m, 1H), 4.59 (s, 2H), 3.90 (s, 2H), 3.71 (s, 2H), 3.67 (s, 2H), 3.61 (ddd, J = 2.6, 8.5, 14.0 Hz, 1H), 3.40-3.35 (m, 2H), 3.24-3.12 (m, 4H), 3.15-3.07 (m, 3H), 2.96 (dd, J = 7.6, 7.6 Hz, 4H), 2.47-2.41 (m, 2H), 2.15 (d, J = 3.0 Hz, 1H), 1.93-1.79 (m, 6H), 1.67-1.63 (m, 2H). |
| 37 | 2.55 | 96 | 4 | $^1$H NMR (400 MHz, DMSO-d$_6$); δ 8.15 (m, 1H), 7.58 (d, J = 7.9 Hz, 1H), 7.55-7.42 (m, 3H), 7.37-7.31 (m, 4H), 7.29-7.23 (m, 1H), 7.17 (s, 3H), 7.11 (s, 1H), 7.03 (d, J = 8.2 Hz, 1H), 6.88 (d, J = 8.2 Hz, 1H), 6.48-6.44 (m, 1H), 5.01-4.93 (m, 1H), 4.71-4.62 (m, 2H), 4.57 (d, J = 8.0 Hz, 1H), 4.20-4.14 (m, 1H), 3.85-3.81 (m, 1H), 3.77 (s, 2H), 3.72-3.62 (m, 3H), 3.30-3.15 (m, 3H), 3.02-2.86 (m, 2H), 2.71-2.45 (m, 7H), 2.37-2.33 (m, 1H), 2.24 (d, J = 14.2 Hz, 1H), 1.78-1.65 (m, 3H), 1.54 (d, J = 6.8 Hz, 3H), 1.40-1.40 (m, 3H), 1.25-1.15 (m, 1H). |
| 38 | 2.49 | 92.88 | 4 | $^1$H NMR (400 MHz, DMSO-d$_6$); δ 8.15 (d, J = 8.8 Hz, 1H), 7.39-7.30 (m, 4H), 7.30-7.22 (m, 2H), 7.21-7.08 (m, 4H), 7.04 (d, J = 8.4 Hz, 1H), 6.90 (d, J = 7.9 Hz, 1H), 6.86-6.67 (m, 3H), 6.47 (dd, J = 3.2, 9.9 Hz, 1H), 5.03-4.94 (m, 1H), 4.71-4.64 (m, 1H), 4.53-4.41 (m, 2H), 4.21-4.11 (m, 1H), 3.89-3.80 (m, 1H), 3.76-3.62 (m, 8H), 3.27-3.15 (m, 3H), 3.02-2.85 (m, 3H), 2.63 (tt, J = 13.2, 14.4 Hz, 5H), 2.35 (ddt, J = 15.6, 27.6, 26.6 Hz, 9H), 1.82-1.36 (m, 3H), 1.25-1.16 (m, 1H). |
| 39 | 2.43 | 96.75 | 4 | $^1$H NMR (400 MHz, DMSO-d$_6$, 100° C.); δ 8.16 (d, J = 9.9 Hz, 1H), 7.69 (d, J = 7.0 Hz, 1H), 7.57-7.52 (m, 3H), 7.41-7.39 (m, 4H), 7.33-7.28 (m, 1H), 7.17 (s, 4H), 7.14 (d, J = 8.3 Hz, 1H), 7.02 (d, J = 8.2 Hz, 1H), 6.57 (d, J = 9.9 Hz, 1H), 5.31 (dd, J = 5.1, 7.8 Hz, 1H), 5.08-5.03 (m, 1H), 4.65 (s, 2H), 3.74 (s, 2H), 3.69 (s, 4H), 3.64 (ddd, J = 2.6, 8.5, 14.0 Hz, 1H), 3.42 (dd, J = 7.2, 7.2 Hz, 2H), 3.27-3.09 (m, 7H), 3.03-2.95 (m, 4H), 2.48-2.43 (m, 2H), 2.17-2.14 (m, 1H), 1.97-1.83 (m, 6H), 1.69-1.65 (m, 2H). |
| 40 | 2.74 | 96.8 | 4 | $^1$H NMR (400 MHz, DMSO-d$_6$); δ 8.15-8.12 (m, 1H), 7.64-7.60 (m, 1H), 7.42-7.31 (m, 5H), 7.29-7.24 (m, 2H), 7.11 (s, 3H), 7.09-6.87 (m, 7H), 6.48-6.44 (m, 1H), 5.35 (s, 1H), 5.02-4.94 (m, 1H), 4.69-4.64 (m, 1H), 4.60-4.44 (m, 2H), 4.20-4.15 (m, 1H), 3.85-3.81 (m, 1H), 3.74-3.59 (m, 4H), 3.29-3.17 (m, 3H), 3.04-2.85 (m, 2H), 2.69-2.53 (m, 4H), 2.49-2.43 (m, 4H), 2.36 (s, 1H), 2.26 (dd, J = 7.0, 14.4 Hz, 1H), 1.81-1.61 (m, 3H), 1.54 (dd, J = 6.7, 6.7 Hz, 3H), 1.42 (d, J = 6.4 Hz, 2H), 1.21-1.20 (m, 1H). |
| 41 | 2.65 | 98.53 | 4 | $^1$H NMR (400 MHz, DMSO-d$_6$, 90° C.); δ 8.15 (d, J = 9.9 Hz, 1H), 7.44-7.26 (m, 12H), 7.22-7.11 (m, 4H), 7.11-7.05 (m, 1H), 6.95-6.90 (m, 1H), 6.79-6.71 (m, 2H), 6.49 (dd, J = 7.9, 9.8 Hz, 1H), 5.07-5.03 (m, 2H), 5.00 (s, 1H), 4.68 (dd, J = 3.5, 7.5 Hz, 1H), 4.55-4.46 (m, 2H), 4.16-4.13 (m, 1H), 3.83-3.79 (m, 1H), 3.74 (s, 1H), 3.69-3.60 (m, 3H), 3.28-3.14 (m, 3H), 3.00 (dd, J = 8.3, 14.4 Hz, 1H), 2.91-2.85 (m, 1H), 2.76-2.54 (m, 6H), 2.48-2.34 (m, 4H), 2.28-2.25 (m, 1H), 1.82-1.68 (m, 4H), 1.66-1.49 (m, 4H), 1.43-1.41 (m, 2H), 1.26-1.17 (m, 1H). |

| | | | | |
|---|---|---|---|---|
| 42 | 2.49 | 91.39 | 4 | ¹H NMR (400 MHz, DMSO-d₆, 90° C.); δ 8.16 (1H, d, J = 9.8 Hz), 7.37-7.35 (6H, m), 7.28-7.24 (1H, m), 7.16 (3H, s), 7.04-6.98 (3H, m), 6.98-6.93 (1H, m), 6.82 (1H, d, J = 8.0 Hz), 6.43 (1H, d, J = 9.8 Hz), 4.96 (1H, dd, J = 4.8, 7.7 Hz), 4.73-4.69 (1H, m), 4.55 (2H, s), 3.85 (1H, s), 3.33 (3H, dd, J = 7.4, 7.4 Hz), 3.22 (1H, s), 3.14 (1H, s), 3.02 (2H, ddd, J = 2.3, 8.2, 14.6 Hz), 2.79-2.54 (8H, m), 2.44-2.30 (4H, m), 1.85-1.77 (3H, m), 1.63-1.42 (7H, m), 1.28-1.20 (1H, m); |
| 43 | 2.75 | 95.7 | 4 | ¹H NMR (400 MHz, DMSO-d₆, 90° C.); δ 8.15 (d, J = 9.7 Hz, 1H), 7.45 (d, J = 7.3 Hz, 2H), 7.40-7.35 (m, 6H), 7.33-7.26 (m, 3H), 7.13 (d, J = 8.0 Hz, 5H), 7.08 (d, J = 7.4 Hz, 2H), 7.01 (d, J = 8.2 Hz, 1H), 6.97-6.90 (m, 1H), 6.56 (d, J = 9.9 Hz, 1H), 5.31-5.27 (m, 1H), 5.17 (s, 2H), 5.07-5.02 (m, 1H), 4.59 (s, 2H), 3.92-3.92 (m, 2H), 3.66-3.59 (m, 4H), 3.39 (dd, J = 7.2, 7.2 Hz, 2H), 3.26-3.15 (m, 5H), 3.08-2.90 (m, 6H), 2.48-2.42 (m, 3H), 2.15 (d, J = 2.9 Hz, 1H), 1.95-1.79 (m, 6H), 1.66 (dd, J = 6.0, 9.1 Hz, 2H). |
| 44 | 2.63 | 95.19 | 4 | ¹H NMR (400 MHz, DMSO-d₆, 90° C.); δ 8.16 (d, J = 9.9 Hz, 1H), 7.41-7.37 (m, 4H), 7.30 (dd, J = 6.3, 6.3 Hz, 2H), 7.24-7.10 (m, 5H), 7.09 (s, 3H), 7.02 (d, J = 8.0 Hz, 1H), 6.56 (d, J = 9.9 Hz, 1H), 5.31 (dd, J = 5.1, 7.7 Hz, 1H), 5.06 (dd, J = 3.2, 11.7 Hz, 1H), 4.66 (s, 2H), 4.00 (t, J = 8.1 Hz, 1H), 3.75-3.60 (m, 11H), 3.24-3.16 (m, 8H), 3.09 (d, J = 6.7 Hz, 2H), 2.99-2.97 (m, 4H), 2.84 (dd, J = 4.2, 4.2 Hz, 4H), 2.16 (s, 1H), 1.94-1.83 (m, 6H), 1.66 (s, 2H) |
| 45 | 96.64 | 2.47 | 4 | ¹H NMR (400 MHz, DMSO-d₆); δ 10.51-10.51 (m, 2H), 9.64 (s, 1H), 8.56-8.56 (m, 2H), 8.13 (d, J = 11.1 Hz, 1H), 7.39 (dd, J = 2.6, 6.0 Hz, 7H), 7.33-7.27 (m, 1H), 7.19-7.11 (m, 6H), 6.99 (dd, J = 2.8, 8.0 Hz, 1H), 6.58 (dd, J = 4.5, 9.5 Hz, 1H), 6.17 (s, 1H), 5.28 (dd, J = 7.1, 7.1 Hz, 1H), 5.00 (t, J = 3.2 Hz, 1H), 4.69 (s, 1H), 4.56 (s, 1H), 4.13 (s, 1H), 3.75-3.59 (m, 2H), 3.41-3.21 (m, 7H), 3.16-3.05 (m, 6H), 3.01-2.89 (m, 6H), 2.12 (d, J = 20.6 Hz, 1H), 1.87-1.74 (m, 6H), 1.60-1.60 (m, 2H). |
| 46 | 6.87 | 96.67 | 2 | ¹H NMR (400 MHz, DMSO-d₆, 90° C.); δ 8.16 (d, J = 9.9 Hz, 1H), 7.41-7.39 (m, 4H), 7.33-7.28 (m, 1H), 7.20 (d, J = 8.3 Hz, 2H), 7.17-7.13 (m, 3H), 7.01 (d, J = 8.2 Hz, 1H), 6.57 (d, J = 9.9 Hz, 1H), 5.31 (dd, J = 5.1, 7.7 Hz, 1H), 5.08-5.03 (m, 1H), 3.90 (s, 2H), 3.68 (s, 2H), 3.64 (ddd, J = 2.6, 8.6, 14.1 Hz, 1H), 3.42 (s, 2H), 3.26-3.09 (m, 7H), 3.03-2.95 (m, 5H), 2.55 (s, 1H), 2.48-2.43 (m, 3H), 2.16 (d, J = 3.0 Hz, 1H), 1.95-1.80 (m, 5H), 1.68-1.64 (m, 2H). |
| 47 | 6.94 | 96.67 | 2 | ¹H NMR (400 MHz, DMSO-d₆, 90° C.); δ 8.16 (d, J = 9.9 Hz, 1H), 7.41-7.37 (m, 4H), 7.33-7.29 (m, 1H), 7.17 (s, 3H), 7.13 (s, 2H), 7.01 (d, J = 8.0 Hz, 1H), 6.57 (d, J = 9.9 Hz, 1H), 5.32 (dd, J = 4.8, 7.8 Hz, 1H), 5.08-5.03 (m, 1H), 3.92 (s, 2H), 3.70-3.63 (m, 6H), 3.24-3.11 (m, 7H), 3.00-2.91 (m, 9H), 2.55 (s, 1H), 2.15 (s, 1H), 1.92-1.86 (m, 6H), 1.66 (s, 2H). |
| 48 | 7.21 | 96.81 | 2 | ¹H NMR (400 MHz, MeOD); δ 8.53 (s, 2H), 8.38 (d, J = 9.9 Hz, 1H), 7.54-7.49 (m, 2H), 7.40 (d, J = 8.8 Hz, 2H), 7.30 (d, J = 8.4 Hz, 1H), 7.15 (dd, J = 8.8, 8.8 Hz, 2H), 7.04 (d, J = 8.2 Hz, 1H), 6.99 (d, J = 8.9 Hz, 2H), 6.71 (d, J = 9.9 Hz, 1H), 5.39 (dd, J = 5.5, 7.8 Hz, 1H), 5.00-4.92 (m, 1H), 4.47-4.14 (m, 1H), 4.06 (dd, J = 6.3, 6.3 Hz, 2H), 3.93-3.68 (m, 1H), 3.45-3.36 (m, 2H), 3.26-3.22 (m, 2H), 3.16-3.06 (m, 2H), 3.00-2.95 (m, 4H), 2.82-2.54 (m, 4H), 2.08-1.95 (m, 3H), 1.88-1.74 (m, 6H), 1.63-1.49 (m, 6H). |
| 49 | 7.17 | 98.45 | 2 | ¹H NMR (400 MHz, DMSO-d₆); δ 10.48 (d, J = 18.9 Hz, 2H), 9.57 (s, 1H), 8.54 (s, 2H), 8.16 (d, J = 9.9 Hz, 1H), 7.47-7.32 (m, 6H), 7.15 (d, J = 8.2 Hz, 1H), 6.97 (dd, J = 8.5, 8.5 Hz, 3H), 6.59 (dd, J = 2.0, 9.9 Hz, 1H), 6.17 (s, 1H), 5.31 (d, J = 9.5 Hz, 1H), 5.04-4.99 (m, 1H), 4.01 (dd, J = 6.4, 6.4 Hz, 2H), 3.70-3.40 (m, 7H), 3.31-2.93 (m, 10H), 2.15-2.08 (m, 1H), 2.04-1.63 (m, 9H), 1.47-1.36 (m, 4H). |

| | | | | |
|---|---|---|---|---|
| 50 | 7.30 | 98.2 | 2 | ¹H NMR (400 MHz, DMSO-d₆); δ 10.49 (d, J = 16.8 Hz, 2H), 9.60-9.60 (m, 1H), 8.55-8.54 (m, 2H), 8.16 (d, J = 13.1 Hz, 1H), 7.60 (d, J = 8.8 Hz, 2H), 7.41 (d, J = 8.8 Hz, 2H), 7.37 (d, J = 8.7 Hz, 2H), 7.15 (d, J = 8.3 Hz, 1H), 6.97 (dd, J = 8.8, 8.8 Hz, 3H), 6.59 (dd, J = 1.7, 10.0 Hz, 1H), 6.17-6.16 (m, 1H), 5.32-5.29 (m, 1H), 5.04-4.99 (m, 1H), 4.01 (dd, J = 6.3, 6.3 Hz, 3H), 3.26-2.95 (m, 11H), 2.16 (d, J = 2.4 Hz, 1H), 2.00-1.61 (m, 12H), 1.47-1.36 (m, 4H). |
| 51 | 7.29 | 98.09 | 2 | ¹H NMR (400 MHz, DMSO-d₆); δ 10.49 (d, J = 19.6 Hz, 2H), 9.58-9.57 (m, 1H), 8.55 (s, 2H), 8.15 (d, J = 11.5 Hz, 1H), 7.47 (d, J = 1.8 Hz, 4H), 7.37 (d, J = 8.7 Hz, 2H), 7.15 (d, J = 8.3 Hz, 1H), 6.97 (dd, J = 8.7, 8.7 Hz, 3H), 6.60 (dd, J = 1.9, 9.9 Hz, 1H), 6.17-6.16 (m, 1H), 5.31 (d, J = 8.8 Hz, 1H), 5.04-4.99 (m, 1H), 4.01 (dd, J = 6.3, 6.3 Hz, 3H), 3.25-2.94 (m, 11H), 2.15 (d, J = 2.5 Hz, 1H), 2.00-1.61 (m, 12H), 1.47-1.36 (m, 4H). |
| 52 | 7.01 | 97.50 | 2 | ¹H NMR (400 MHz, DMSO-d₆, 90° C.); δ 8.19 (d, J = 9.9 Hz, 1H), 8.15 (s, 2H), 7.38 (d, J = 6.5 Hz, 4H), 7.28 (d, J = 8.4 Hz, 3H), 7.22 (d, J = 8.2 Hz, 2H), 7.08 (d, J = 8.0 Hz, 1H), 6.95 (d, J = 8.2 Hz, 1H), 6.48 (d, J = 9.9 Hz, 1H), 5.02 (dd, J = 5.1, 7.4 Hz, 1H), 4.76-4.72 (m, 1H), 3.90 (s, 2H), 3.36-3.27 (m, 4H) 3.10-3.02 (m, 1H), 2.92-2.53 (m, 12H), 2.48-2.32 (m, 4H), 1.92-1.81 (m, 4H), 1.73-1.43 (m, 4H), 1.28-1.23 (m, 1H), 1.07 (dd, J = 7.0, 7.0 Hz, 3H). |
| 53 | 6.93 | 95.04 | 2 | ¹H NMR (400 MHz, DMSO-d₆, 90° C.); δ 8.18 (d, J = 9.8 Hz, 1H), 8.13 (s, 2H), 7.42-7.34 (m, 4H), 7.31-7.21 (m, 5H), 7.09 (d, J = 8.2 Hz, 1H), 6.96 (d, J = 8.2 Hz, 1H), 6.50 (d, J = 9.8 Hz, 1H), 5.08-5.05 (m, 1H), 4.77-4.72 (m, 1H), 3.90 (s, 2H), 3.39 (dd, J = 7.1, 7.1 Hz, 2H), 3.22-2.74 (m, 14H), 2.70-2.62 (m, 6H), 1.86-1.84 (m, 3H), 1.74 (dd, J = 6.7, 6.7 Hz, 2H), 1.63-1.41 (m, 3H), 1.28 (s, 1H). |
| 54 | 7.21 | 95.83 | 2 | ¹H NMR (400 MHz, DMSO-d₆, 90° C.); δ 8.19 (d, J = 9.9 Hz, 1H), 7.44-7.23 (m, 12H), 7.16 (d, J = 8.3 Hz, 1H), 7.04 (d, J = 8.0 Hz, 1H), 6.57 (d, J = 9.9 Hz, 1H), 5.35 (dd, J = 5.3, 7.7 Hz, 1H), 5.10-5.05 (m, 1H), 4.59 (s, 2H), 3.89-3.88 (m, 2H), 3.67 (ddd, J = 2.6, 8.5, 14.1 Hz, 1H), 3.45-3.40 (m, 2H), 3.30-3.12 (m, 9H), 3.06-2.97 (m, 4H), 2.94-2.89 (m, 2H), 2.69 (dd, J = 7.5, 7.5 Hz, 2H), 2.50-2.45 (m, 1H), 2.19 (dd, J = 3.3, 6.4 Hz, 1H), 2.03-1.84 (m, 6H), 1.73-1.67 (m, 2H). |
| 55 | 2.42 | 97.06 | 4 | ¹H NMR (400 MHz, DMSO-d₆, 100° C.); δ 8.10 (d, J = 11.4 Hz, 1H), 7.57-7.49 (m, 4H), 7.40 (dd, J = 7.8, 13.5 Hz, 4H), 7.34-7.29 (m, 1H), 7.16-7.12 (m, 3H), 6.98 (ddd, J = 10.7, 10.7, 10.7, 3H), 6.55 (d, J = 8.6 Hz, 1H), 5.39-5.35 (m, 1H), 5.11 (s, 2H), 5.08-5.02 (m, 1H), 4.27 (d, J = 5.7 Hz, 2H), 3.67-3.61 (m, 2H), 3.29-2.95 (m, 11H), 2.46-2.43 (m, 1H), 2.16 (t, J = 4.3 Hz, 1H), 1.96-1.77 (m, 5H), 1.70-1.62 (m, 2H). |
| 56 | 2.45 | 97.34 | 4 | ¹H NMR (400 MHz, DMSO-d₆); δ 10.51 (s, 2H), 9.64 (s, 1H), 9.06 (s, 2H), 8.06 (d, J = 12.0 Hz, 1H), 7.54 (d, J = 9.9 Hz, 2H), 7.49 (d, J = 8.4 Hz, 2H), 7.42-7.35 (m, 4H), 7.29 (tt, J = 3.6, 4.1 Hz, 1H), 7.13 (t, J = 9.1 Hz, 3H), 6.97 (d, J = 8.4 Hz, 1H), 6.90 (d, J = 7.4 Hz, 2H), 6.57 (d, J = 10.2 Hz, 1H), 6.20 (s, 1H), 5.34 (d, J = 9.9 Hz, 1H), 5.07 (s, 2H), 5.03-4.98 (m, 2H), 4.24 (t, J = 10.5 Hz, 2H), 4.13 (dd, J = 14.7, 24.8 Hz, 2H), 3.78-3.58 (m, 2H), 3.28-2.89 (m, 8H), 2.74 (ddd, J = 7.1, 7.1, 7.1 Hz, 2H), 2.62 (td, J = 7.6, 41.8 Hz, 2H), 2.40 (dd, J = 22.5, 29.8 Hz, 3H), 2.13 (d, J = 23.9 Hz, 1H), 1.75 (dt, J = 22.6, 44.5 Hz, 4H). |
| 57 | 2.35 | 97.23 | 4 | ¹H NMR (400 MHz, DMSO-d₆); δ 8.12 (dd, J = 5.6, 10.0 Hz, 1H), 7.45-7.34 (m, 5H), 7.31-7.23 (m, 6H), 7.14 (dd, J = 8.7, 8.7 Hz, 2H), 7.06 (d, J = 8.2 Hz, 1H), 6.90 (d, J = 8.0 Hz, 1H), 6.46 (d, J = 9.9 Hz, 1H), 5.34 (s, 1H), 5.05 (dd, J = 4.4, 7.3 Hz, 1H), 4.72-4.68 (m, 1H), 4.54-4.46 (m, 4H), 4.25 (s, 1H), 3.72 (d, J = 5.3 Hz, 2H), 3.18-3.15 (m, 3H), 3.06-2.97 (m, 1H), 2.73-2.63 (m, 1H), 2.61-2.60 (m, 5H), 2.59-2.54 (m, 1H), 2.30 (d, J = 14.7 Hz, 1H), 2.11 (d, J = 3.0 Hz, 3H), 1.95-1.87 (m, 2H), 1.81 (d, |

| | | | | |
|---|---|---|---|---|
| | | | | J = 2.9 Hz, 1H), 1.57-1.39 (m, 3H), 1.26-1.18 (m, 1H). |
| 58 | 2.39 | 98.91 | 4 | ¹H NMR (400 MHz, DMSO-d₆); δ 10.51 (s, 2H), 9.66 (s, 1H), 9.01 (s, 2H), 8.08 (d, J = 10.9 Hz, 1H), 7.45 (d, J = 8.4 Hz, 4H), 7.39 (dd, J = 7.6, 7.6 Hz, 2H), 7.33 (d, J = 7.5 Hz, 6H), 7.29 (s, 1H), 7.12 (d, J = 8.2 Hz, 1H), 6.97 (d, J = 8.2 Hz, 1H), 6.56 (d, J = 9.9 Hz, 1H), 6.17-6.16 (m, 1H), 5.34 (dd, J = 2.2, 9.6 Hz, 2H), 5.04-4.98 (m, 3H), 4.37 (s, 5H), 4.22 (s, 4H), 3.66-3.60 (m, 2H), 3.22-3.11 (m, 5H), 3.05 (s, 2H), 2.13 (s, 2H), 2.09-2.08 (m, 2H), 1.92-1.77 (m, 3H), 1.62-1.61 (m, 2H). |
| 59 | 2.48 | 95.31 | 4 | ¹H NMR (400 MHz, DMSO d₆); δ 10.52 (s, 1H), 10.49 (s, 1H), 9.63 (s, 1H), 9.05-9.05 (m, 2H), 8.09 (d, J = 10.2 Hz, 1H), 7.53 (d, J = 6.1 Hz, 2H), 7.50-7.43 (m, 6H), 7.40 (dd, J = 7.7, 7.7 Hz, 7H), 7.32 (dd, J = 7.1, 7.1 Hz, 1H), 7.24 (s, 2H), 7.13 (d, J = 8.2 Hz, 1H), 6.98 (d, J = 8.2 Hz, 1H), 6.58 (d, J = 9.8 Hz, 1H), 6.21-6.19 (m, 1H), 5.35 (d, J = 8.4 Hz, 1H), 5.05-4.99 (m, 1H), 4.63 (s, 2H), 4.48 (s, 2H), 4.24 (s, 4H), 3.67-3.61 (m, 1H),, 3.29-3.01 (m, 10H), 2.13 (s, 2H), 2.06-1.91 (m, 2H), 1.92-1.73 (m, 3H), 1.63 (s, 1H). |
| 60 | 2.40 | 97.35 | 4 | ¹H NMR (400 MHz, DMSO d₆); δ 10.53-10.46 (m, 2H), 9.66-9.66 (m, 1H), 9.06 (s, 2H), 8.08 (d, J = 9.9 Hz, 1H), 7.54 (d, J = 8.2 Hz, 1H), 7.51-7.44 (m, 3H), 7.44-7.36 (m, 4H), 7.35-7.25 (m, 5H), 7.12 (d, J = 8.2 Hz, 1H), 6.97 (d, J = 8.2 Hz, 1H), 6.57 (d, J = 9.9 Hz, 1H), 6.18 (s, 1H), 5.34 (d, J = 9.5 Hz, 1H), 5.05-4.99 (m, 1H), 4.77 (d, J = 4.0 Hz, 2H), 4.55 (s, 2H), 4.21 (d, J = 4.6 Hz, 3H), 3.62 (d, J = 12.5 Hz, 4H), 3.23-3.00 (m, 9H), 2.14-2.08 (m, 1H), 1.99-1.75 (m, 5H), 1.61 (s, 2H), 0.83 (d, J = 2.9 Hz, 2H), 0.77-0.68 (m, 2H). |
| 61 | 2.57 | 95.58 | 4 | ¹H NMR (400 MHz, DMSO d₆); δ 10.52-10.47 (m, 2H), 9.64 (s, 1H), 9.00 (s, 2H), 8.10-8.07 (m, 1H), 7.89 (d, J = 7.2 Hz, 2H), 7.73-7.68 (m, 1H), 7.62 (dd, J = 7.5, 7.5 Hz, 2H), 7.45 (d, J = 7.5 Hz, 2H), 7.39 (dd, J = 7.8, 15.7 Hz, 4H), 7.31 (dd, J = 7.2, 7.2 Hz, 1H), 7.24 (d, J = 7.9 Hz, 2H), 7.18-7.10 (m, 5H), 6.97 (d, J = 8.2 Hz, 1H), 6.56 (dd, J = 2.0, 9.9 Hz, 1H), 6.17-6.17 (m, 1H), 5.32 (d, J = 9.4 Hz, 1H), 5.03-4.98 (m, 1H), 4.37 (d, J = 9.8 Hz, 4H), 4.16 (s, 3H), 3.66-3.58 (m, 3H), 3.21-3.10 (m, 4H), 3.03-2.97 (m, 3H), 2.62-2.34 (m, 3H), 2.13 (s, 1H), 2.05-1.75 (m, 5H), 1.62 (s, 1H). |
| 62 | 2.52 | 95.83 | 4 | ¹H NMR (400 MHz, DMSO d₆); δ 10.50 (s, 2H), 9.66 (s, 1H), 9.05-9.05 (m, 2H), 8.08 (d, J = 11.8 Hz, 1H), 7.50 (d, J = 8.2 Hz, 2H), 7.45 (d, J = 7.5 Hz, 2H), 7.40 (dd, J = 7.6, 7.6 Hz, 4H), 7.34-7.30 (m, 5H), 7.13 (d, J = 8.3 Hz, 1H), 6.97 (d, J = 8.2 Hz, 1H), 6.57 (d, J = 9.9 Hz, 1H), 6.19 (s, 1H), 5.34 (dd, J = 2.4, 9.8 Hz, 1H), 5.04-4.99 (m, 1H), 4.44 (s, 4H), 4.23 (dd, J = 5.6, 5.6 Hz, 3H), 3.64-3.61 (m, 1H), 3.60 (s, 3H), 3.23-2.99 (m, 9H), 2.47-2.34 (m, 1H), 2.13-2.13 (m, 1H), 2.10-1.76 (m, 6H), 1.63 (s, 2H). |
| 63 | 2.32 | 94.37 | 4 | ¹H NMR (400 MHz, DMSO d₆); δ 10.53 (s, 2H), 9.66 (s, 1H), 9.05-9.05 (m, 1H), 8.09 (d, J = 9.9 Hz, 1H), 7.55-7.36 (m, 9H), 7.32 (dd, J = 7.1, 7.1 Hz, 1H), 7.26 (dd, J = 7.8, 7.8 Hz, 4H), 7.12 (d, J = 8.2 Hz, 1H), 6.97 (d, J = 8.2 Hz, 1H), 6.60-6.55 (m, 2H), 6.18 (s, 1H), 5.36-5.33 (m, 1H), 5.03-4.99 (m, 1H), 4.42 (d, J = 5.3 Hz, 4H), 4.22 (dd, J = 5.5, 5.5 Hz, 3H), 3.66-3.59 (m, 2H), 3.15-3.00 (m, 10H), 2.62 (d, J = 4.0 Hz, 4H), 2.48-2.34 (m, 1H), 2.13 (s, 1H), 2.08-1.73 (m, 3H), 1.63 (s, 2H). |
| 64 | 2.55 | 97.82 | 4 | ¹H NMR (400 MHz, DMSO d₆); δ 10.50 (s, 2H), 9.73-9.72 (m, 1H), 9.07 (s, 2H), 8.07 (d, J = 9.0 Hz, 1H), 7.53 (d, J = 8.3 Hz, 2H), 7.46-7.40 (m, 10H), 7.32 (dd, J = 7.1, 7.1 Hz, 1H), 7.12 (d, J = 8.3 Hz, 1H), 6.97 (d, J = 8.2 Hz, 1H), 6.57 (d, J = 9.9 Hz, 1H), 6.19-6.19 (m, 1H), 5.34 (d, J = 9.3 Hz, 1H), 5.04-5.00 (m, 1H), 4.59 (s, 4H), 4.24 (s, 2H), 3.68-3.60 (m, 2H), 3.25-3.06 (m, 10H), 3.00 (s, 1H), 2.10 (d, J = 20.6 Hz, 2H), 1.95 (s, 2H), 1.92-1.73 (m, 2H), 1.63 (s, 2H). |
| 1A | 7.03 | 97.38 | 2 | ¹H NMR (400 MHz, DMSO-d6); δ 10.54 (s, 2H), 9.82 (d, J = 1.3 Hz, 1H), 8.65 (s, 2H), 8.21 (d, J = 9.9 Hz, |

| | | | | |
|---|---|---|---|---|
| | | | | 1H), 7.70 (d, J = 8.8 Hz, 2H), 7.48 (d, J = 4.3 Hz, 4H), 7.44-7.38 (m, 1H), 7.20 (d, J = 8.1 Hz, 1H), 7.06-7.01 (m, 3H), 6.63 (dd, J = 1.9, 10.0 Hz, 1H), 6.24-6.22 (m, 1H), 5.37 (d, J = 9.6 Hz, 1H), 5.09-5.00 (m, 2H), 4.87-4.80 (m, 3H), 4.09 (dd, J = 6.2, 6.2 Hz, 2H), 3.71-3.63 (m, 2H), 3.29-3.04 (m, 8H), 2.15 (d, J = 1.8 Hz, 1H), 1.91-1.62 (m, 8H), 1.57-1.48 (m, 2H,). |
| 2A | 7.11 | 96.52 | 2 | $^1$H NMR (400 MHz, DMSO-d6); δ 8.34 (s, 2H), 8.24 (d, J = 10.1 Hz, 1H), 7.69 (d, J = 8.8 Hz, 2H), 7.50-7.43 (m, 3H), 7.42-7.37 (m, 2H), 7.16 (d, J = 8.3 Hz, 1H), 7.02 (dd, J = 8.7, 8.7 Hz, 3H), 6.58 (d, J = 9.9 Hz, 1H), 5.27 (dd, J = 3.9, 8.5 Hz, 1H), 4.96-4.94 (m, 1H), 4.80-4.74 (m, 3H), 4.48-4.48 (m, 1H), 4.07 (dd, J = 6.4, 6.4 Hz, 3H), 3.09 (ddd, J = 2.0, 8.1, 14.6 Hz, 1H), 2.98-2.80 (m, 4H), 2.73-2.62 (m, 2H), 2.45-2.37 (m, 2H), 1.88 (d, J = 2.8 Hz, 1H), 1.81-1.73 (m, 2H), 1.65-1.39 (m, 8H), 1.30-1.22 (m, 2H,). |
| 3A | 7.14 | 95.02 | 2 | $^1$H NMR (400 MHz, MeOD); δ 8.39 (d, J = 9.8 Hz, 1H), 7.67 (d, J = 8.9 Hz, 2H), 7.48-7.43 (m, 2H), 7.30 (d, J = 8.3 Hz, 1H), 7.19 (dd, J = 8.8, 8.8 Hz, 2H), 7.03 (dd, J = 8.5, 15.4 Hz, 3H), 6.71 (d, J = 9.9 Hz, 1H), 5.41 (dd, J = 6.8, 6.8 Hz, 1H), 5.17 (ddd, J = 2.5, 4.2, 8.4 Hz, 1H), 5.09 (s, 1H), 4.08 (dd, J = 6.3, 6.3 Hz, 2H), 3.74-3.68 (m, 1H), 3.38-3.35 (m, 1H), 3.31-3.24 (m, 7H), 3.15-3.09 (m, 3H), 2.33-2.32 (m, 1H), 2.05-1.76 (m, 9H), 1.64-1.50 (m, 4H). |
| 4A | 7.04 | 96.64 | 2 | $^1$H NMR (400 MHz, DMSO-d6); δ 10.54 (s, 2H), 9.84 (d, J = 12.1 Hz, 1H), 8.65 (s, 2H), 8.21 (d, J = 10.1 Hz, 1H), 7.49-7.46 (m, 4H), 7.46-7.39 (m, 2H), 7.31-7.25 (m, 1H), 7.22-7.12 (m, 3H), 7.04 (d, J = 8.1 Hz, 1H), 6.63 (dd, J = 1.8, 9.9 Hz, 1H), 6.21 (d, J = 1.0 Hz, 1H), 5.36 (d, J = 9.3 Hz, 1H), 5.09-5.04 (m, 1H), 4.98 (d, J = 3.5 Hz, 1H), 4.87-4.74 (m, 2H), 4.49 (dd, J = 10.6, 25.0 Hz, 1H), 4.09-4.03 (m, 2H), 3.70-3.63 (m, 1H), 3.31-3.14 (m, 6H), 3.04 (d, J = 7.6 Hz, 4H), 2.16 (d, J = 1.8 Hz, 1H), 1.93-1.84 (m, 1H), 1.83-1.63 (m, 6H), 1.57-1.49 (m, 2H). |
| 5A | 7.03 | 96.67 | 2 | $^1$H NMR (400 MHz, MeOD) d 8.38 (d, J = 9.9 Hz, 1H), 7.42 (dd, J = 7.3, 7.3 Hz, 2H), 7.38-7.26 (m, 4H), 7.10 (d, J = 8.3 Hz, 2H), 7.05 (d, J = 8.2 Hz, 1H), 6.75 (d, J = 8.3 Hz, 2H), 6.70 (d, J = 9.8 Hz, 1H), 5.41 (dd, J = 6.8, 6.8 Hz, 1H), 5.14-5.11 (m, 1H), 4.63 (dd, J = 3.9, 10.0 Hz, 1H), 4.37-4.17 (m, 2H), 3.95-3.88 (m, 2H), 3.73-3.64 (m, 1H), 3.29-3.11 (m, 10H), 2.84 (dd, J = 7.2, 7.2 Hz, 2H), 2.47-2.41 (m, 2H), 2.27 (dd, J = 1.9, 21.1 Hz, 1H), 2.06-1.97 (m, 1H), 1.92-1.59 (m, 9H). |
| 6A | 7.03 | 96.61 | 2 | "$^1$H NMR (400 MHz, MeOD); δ 8.38 (d, J = 9.9 Hz, 1H), 7.47-7.42 (m, 2H), 7.40-7.37 (m, 3H), 7.30 (d, J = 8.4 Hz, 1H), 7.17 (d, J = 8.5 Hz, 2H), 7.05 (d, J = 8.2 Hz, 1H), 6.87 (d, J = 8.7 Hz, 2H), 6.70 (d, J = 9.9 Hz, 1H), 5.40 (dd, J = 5.8, 7.7 Hz, 1H), 5.18-5.13 (m, 1H), 4.98 (d, J = 9.4 Hz, 1H), 4.72-4.60 (m, 2H), 4.45 (dd, J = 10.2, 21.3 Hz, 1H), 4.01 (t, J = 6.1 Hz, 2H), 3.74-3.66 (m, 1H), 3.51 (s, 2H), 3.35-3.31 (m, 4H), 3.31-3.10 (m, 6H), 3.03-3.00 (m, 1H), 2.31-2.25 (m, 1H), 2.06-1.99 (m, 1H), 1.90-1.73 (m, 5H), 1.66-1.60 (m, 2H). |
| 7A | 7.29 | 96.50 | 2 | "$^1$H NMR (400 MHz, MeOD); δ 8.38 (d, J = 10.1 Hz, 1H), 7.68 (d, J = 8.8 Hz, 2H), 7.47-7.37 (m, 5H), 7.33-7.28 (m, 2H), 7.10-7.02 (m, 5H), 6.93-6.89 (m, 1H), 6.69 (d, J = 9.9 Hz, 1H), 5.41 (dd, J = 6.7, 6.7 Hz, 1H), 5.19-5.16 (m, 1H), 5.15 (s, 2H), 4.97-4.91 (m, 4H), 4.71-4.54 (m, 1H), 4.08 (dd, J = 5.6, 5.6 Hz, 2H), 3.73-3.67 (m, 1H), 3.36-3.30 (m, 4H), 3.29-3.15 (m, 4H), 3.08-3.01 (m, 1H), 2.30-2.27 (m, 1H), 2.04-1.89 (m, 5H), 1.76-1.70 (m, 2H) |
| 8A | 7.04 | 98.55 | 2 | $^1$H NMR (400 MHz, MeOD); δ 8.25 (d, J = 9.9 Hz, 1H), 7.69 (d, J = 8.9 Hz, 2H), 7.62-7.55 (m, 4H), 7.47-7.38 (m, 5H), 7.28 (d, J = 8.5 Hz, 1H), 7.12 (d, J = 9.0 Hz, 2H), 7.04 (d, J = 8.2 Hz, 1H), 6.66 (d, J = 9.9 Hz, 1H), 5.41 (dd, J = 6.8, 6.8 Hz, 1H), 5.23 (s, 2H), 5.19-5.05 (m, 2H), 4.70-4.58 (m, 1H), 4.34 (s, 2H), 3.77-3.67 (m, 1H), 3.34-3.31 (m, |

| | | | | |
|---|---|---|---|---|
| | | | | 4H), 3.30-3.22 (m, 3H), 3.23-3.14 (m, 1H), 3.09-3.02 (m, 1H), 2.34-2.26 (m, 1H), 2.07-1.99 (m, 1H), 1.96-1.87 (m, 1H), 1.82-1.61 (m, 2H) |
| 9A | 2.30 | 95.69 | 4 | $^1$H NMR (400 MHz, MeOD); δ 9.21 (t, J = 5.8 Hz, 1H), 8.26 (d, J = 9.9 Hz, 1H), 7.97 (d, J = 8.5 Hz, 2H), 7.80 (d, J = 8.2 Hz, 2H), 7.50-7.43 (m, 9H), 7.27 (d, J = 8.4 Hz, 1H), 7.03 (d, J = 8.2 Hz, 1H), 6.66 (d, J = 9.8 Hz, 1H), 5.42-5.37 (m, 1H), 5.20-5.15 (m, 1H), 5.12-5.07 (m, 1H), 4.97-4.91 (m, 1H), 4.84-4.89 (m, 1H), 4.70-4.63 (m, 3H), 4.31 (s, 2H), 3.68-3.68 (m, 1H), 3.36-3.15 (m, 6H), 3.07-3.01 (m, 1H), 2.35-2.25 (m, 1H), 2.06-1.87 (m, 2H), 1.79-1.65 (m, 2H). |
| 10A | 2.24 | 97.43 | 4 | $^1$H NMR (400 MHz, DMSO-d6); δ 10.49 (d, J = 11.2 Hz, 2H), 9.70 (s, 1H), 8.66 (t, J = 5.6 Hz, 1H), 8.62-8.54 (m, 2H), 8.15 (d, J = 9.6 Hz, 1H), 7.91 (d, J = 8.4 Hz, 2H), 7.76 (d, J = 7.5 Hz, 2H), 7.45-7.42 (m, 4H), 7.40-7.34 (m, 1H), 7.15 (d, J = 8.3 Hz, 1H), 6.99 (d, J = 8.2 Hz, 1H), 6.58 (dd, J = 1.9, 9.9 Hz, 1H), 6.17 (s, 1H), 5.31 (d, J = 9.4 Hz, 1H), 5.04-4.93 (m, 2H), 4.85-4.75 (m, 2H), 4.47 (dd, J = 10.2, 25.3 Hz, 1H), 3.65-3.59 (m, 2H), 3.34-3.28 (m, 3H), 3.23-3.13 (m, 5H), 3.03-3.00 (m, 4H), 2.11-2.11 (m, 1H), 1.86-1.56 (m, 6H). |
| 11A | 2.26 | 98.24 | 4 | $^1$H NMR (400 MHz, DMSO-d6); δ 10.54 (d, J = 7.3 Hz, 2H), 9.96-9.95 (m, 1H), 8.81 (dd, J = 5.8, 5.8 Hz, 1H), 8.73-8.66 (m, 2H), 8.21 (d, J = 9.9 Hz, 1H), 7.81 (d, J = 4.0 Hz, 1H), 7.65 (d, J = 3.8 Hz, 1H), 7.52-7.48 (m, 4H), 7.48-7.39 (m, 1H), 7.20 (d, J = 8.3 Hz, 1H), 7.04 (d, J = 8.1 Hz, 1H), 6.63 (d, J = 9.9 Hz, 1H), 6.21 (s, 1H), 5.37 (d, J = 8.8 Hz, 1H), 5.24-5.18 (m, 1H), 5.09-4.95 (m, 2H), 4.89-4.81 (m, 1H), 4.55-4.44 (m, 1H), 3.70-3.63 (m, 2H), 3.34-3.28 (m, 4H), 3.23-3.01 (m, 6H), 2.18 (s, 1H), 1.94-1.80 (m, 2H), 1.78-1.58 (m, 6H). |
| 12A | 2.30 | 92.78 | 4 | $^1$H NMR (400 MHz, MeOD); δ 8.39 (d, J = 9.9 Hz, 1H), 7.40 (m, J = 8.4, 36.2 Hz, 10H), 7.05 (d, J = 8.2 Hz, 1H), 6.60 (d, J = 10.2 Hz, 1H), 5.46 (dd, J = 5.1, 7.0 Hz, 1H), 5.16-5.14 (m, 1H), 4.67 (t, J = 9.7 Hz, 1H), 4.57-4.35 (m, 2H), 3.76-3.67 (m, 3H), 3.33-3.31 (m, 2H), 3.30-3.13 (m, 8H), 3.00-2.95 (m, 3H), 2.57 (t, J = 7.0 Hz, 2H), 2.30-2.24 (m, 1H), 2.13 (dd, J = 6.0, 6.0 Hz, 2H), 2.06-1.88 (m, 3H), 1.75-1.64 (m, 2H), 1.16 (t, J = 6.1 Hz, 3H). |
| 13A | 2.40 | 94.79 | 4 | $^1$H NMR (400 MHz, MeOD); δ 8.26 (d, J = 9.9 Hz, 1H), 7.56 (s, 4H), 7.40 (dd, J = 7.5, 7.5 Hz, 2H), 7.32-7.26 (m, 4H), 7.12 (d, J = 7.5 Hz, 2H), 7.04 (d, J = 8.2 Hz, 1H), 6.85 (d, J = 7.3 Hz, 2H), 6.65 (d, J = 9.8 Hz, 1H), 5.41 (dd, J = 6.7, 6.7 Hz, 1H), 5.15-5.09 (m, 1H), 5.05-5.02 (m, 2H), 4.70-4.60 (m, 2H), 4.37-4.28 (m, 3H), 4.20 (dd, J = 9.0, 18.7 Hz, 1H), 3.36-3.31 (2H, m), 3.29-3.09 (m, 5H), 3.06-2.97 (m, 1H), 2.85 (dd, J = 7.2, 7.2 Hz, 2H), 2.48-2.41 (m, 2H), 2.30-2.23 (m, 1H), 2.06-1.94 (m, 1H), 1.90-1.81 (m, 1H), 1.74-1.63 (m, 2H). |
| 14A | 2.45 | 93.16 | 4 | $^1$H NMR (400 MHz, MeOD); δ 8.34 (d, J = 9.9 Hz, 1H), 7.47-7.16 (m, 15H), 7.05 (d, J = 8.2 Hz, 1H), 6.67 (d, J = 9.8 Hz, 1H), 5.41-5.35 (m, 1H), 5.17-5.12 (m, 1H), 5.02-4.96 (m, 1H), 4.75-4.63 (m, 3H), 4.48-4.37 (m, 1H), 3.84 (s, 2H), 3.70 (ddd, J = 2.5, 8.5, 14.2 Hz, 1H), 3.57-3.35 (m, 5H), 3.29-3.09 (m, 5H), 3.04-2.97 (m, 3H), 2.31-2.23 (m, 1H), 2.06-2.00 (m, 1H), 1.95-1.87 (m, 3H), 1.78-1.63 (m, 3H). |
| 15A | 2.38 | 97.27 | 4 | $^1$H NMR (400 MHz, MeOD); δ 8.24 (dd, J = 1.4, 9.9 Hz, 1H), 7.59-7.52 (m, 4H), 7.48-7.43 (m, 2H), 7.39 (d, J = 7.3 Hz, 3H), 7.28 (d, J = 8.2 Hz, 1H), 7.19 (d, J = 8.8 Hz, 2H), 7.04 (d, J = 8.2 Hz, 1H), 6.97 (d, J = 8.8 Hz, 2H), 6.66 (d, J = 9.8 Hz, 1H), 5.42-5.37 (m, 1H), 5.14 (m, 3H), 5.01-4.97 (m, 1H), 4.72-4.61 (m, 2H), 4.45 (dd, J = 10.2, 21.1 Hz, 1H), 4.30 (s, 2H), 3.70 (dd, J = 8.5, 14.2 Hz, 1H), 3.37-3.31 (m, 3H), 3.30-3.22 (m, 4H), 3.21-2.98 (m, 2H), 2.28 (dd, J = 3.5, 21.1 Hz, 1H), 2.08-1.98 (m, 1H), 1.96-1.88 (m, 1H), 1.79-1.63 (m, 2H). |
| 16A | 2.33 | 97.46 | 4 | $^1$H NMR (400 MHz, DMSO-d6); δ 10.52-10.48 (m, 2H), 9.81 (s, 1H), 9.20 (dd, J = 5.9, 5.9 Hz, 1H), 8.85-8.70 (m, 2H), 8.17 (d, J = 10.9 Hz, 1H), 7.96 (d, J = 8.4 Hz, 2H), 7.76 (d, J = 6.5 Hz, 2H), |

| | | | | |
|---|---|---|---|---|
| 17A | 2.29 | 96.31 | 4 | ¹H NMR (400 MHz, MeOD); δ 8.29 (d, J = 9.9 Hz, 1H), 7.98 (d, J = 8.4 Hz, 2H), 7.67 (dd, J = 8.3, 12.2 Hz, 4H), 7.52-7.38 (m, 7H), 7.29 (d, J = 8.4 Hz, 1H), 7.04 (d, J = 8.2 Hz, 1H), 6.67 (d, J = 9.9 Hz, 1H), 5.43 (dd, J = 5.6, 7.9 Hz, 1H), 5.19-5.13 (m, 1H), 5.07 (t, J = 8.2 Hz, 1H), 4.69-4.59 (m, 3H), 4.40 (s, 2H), 3.73-3.68 (m, 1H), 3.31-3.24 (m, 8H), 3.05-3.01 (m, 1H), 2.29 (d, J = 20.3 Hz, 1H), 2.05-2.00 (m, 1H), 1.94-1.92 (m, 1H), 1.76-1.66 (m, 2H). |
| | | | | 7.45-7.41 (m, 4H), 7.40-7.34 (m, 1H), 7.30 (d, J = 8.2 Hz, 2H), 7.22 (d, J = 8.2 Hz, 2H), 7.16 (d, J = 8.3 Hz, 1H), 6.99 (d, J = 8.2 Hz, 1H), 6.58 (dd, J = 2.1, 9.9 Hz, 1H), 6.20 (d, J = 3.5 Hz, 1H), 5.36-5.32 (m, 1H), 5.02-4.95 (m, 2H), 4.84-4.75 (m, 2H), 4.51-4.45 (m, 3H), 3.65-3.58 (m, 1H), 3.24-3.09 (m, 8H), 3.05-2.92 (m, 3H), 2.11-2.11 (m, 1H), 1.87-1.76 (m, 2H), 1.59 (d, J = 7.2 Hz, 2H) |
| 18A | 2.31 | 96.82 | 4 | ¹H NMR (400 MHz, MeOD); δ 8.38 (d, J = 9.9 Hz, 1H), 7.68 (d, J = 8.9 Hz, 2H), 7.47-7.38 (m, 5H), 7.31 (d, J = 8.4 Hz, 1H), 7.04 (dd, J = 6.4, 8.5 Hz, 3H), 6.70 (d, J = 9.8 Hz, 1H), 5.41 (dd, J = 6.7, 6.7 Hz, 1H), 5.19-5.04 (m, 2H), 4.16-4.10 (m, 2H), 3.70 (d, J = 2.8 Hz, 1H), 3.31-3.17 (m, 10H), 2.34-2.33 (m, 1H), 2.04-1.92 (m, 6H), 1.75-1.75 (m, 3H). |
| 19A | 2.97 | 97.25 | 4 | ¹H NMR (400 MHz, MeOD); δ 8.41 (d, J = 9.8 Hz, 1H), 7.90 (d, J = 8.4 Hz, 2H), 7.70 (d, J = 8.9 Hz, 2H), 7.60 (d, J = 8.4 Hz, 2H), 7.46-7.31 (m, 6H), 7.12 (d, J = 8.9 Hz, 2H), 7.05 (d, J = 8.2 Hz, 1H), 6.69 (d, J = 9.8 Hz, 1H), 5.46 (dd, J = 5.5, 7.7 Hz, 1H), 5.26 (s, 2H), 5.17 (ddd, J = 2.5, 4.3, 8.3 Hz, 1H), 5.13-5.05 (m, 1H), 4.70-4.55 (m, 1H), 3.73-3.67 (m, 1H), 3.61-3.52 (m, 2H), 3.36-3.30 (m, 3H), 3.31-3.24 (m, 3H), 3.20-3.14 (m, 2H), 3.09-3.01 (m, 1H), 2.35-2.26 (m, 1H), 2.10-1.92 (m, 4H), 1.74-1.69 (m, 2H). |
| 20A | 2.31 | 92.02 | 4 | ¹H NMR (400 MHz, MeOD); δ 8.48 (s, 2H), 8.22 (d, J = 9.9 Hz, 1H), 7.98 (d, J = 8.5 Hz, 2H), 7.80 (d, J = 8.3 Hz, 2H), 7.47-7.34 (m, 6H), 7.26 (d, J = 8.4 Hz, 1H), 7.12 (s, 1H), 7.05-7.02 (m, 2H), 6.64 (d, J = 9.8 Hz, 1H), 5.41-5.36 (m, 1H), 5.12-5.06 (m, 2H), 4.98-4.80 (m, 1H), 4.67-4.62 (m, 3H), 4.29 (s, 2H), 3.92 (s, 3H), 3.56-3.49 (m, 1H), 3.20-3.10 (m, 7H), 3.01-2.98 (m, 1H), 2.23-2.17 (m, 1H), 1.99-1.91 (m, 1H), 1.86-1.81 (m, 1H), 1.63-1.63 (m, 2H). |

| No. | Name | Salt two equivalents unless stated |
|---|---|---|
| 1 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate | Formate |
| 2 | (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate | Formate |
| 3 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-methoxybenzoyl)-4-phenylpiperidine-4-carboxylate | TFA |
| 4 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-chlorobenzoyl)-4-phenylpiperidine-4-carboxylate | Formate |
| 5 | (R)-Quinuclidin-3-yl 1-(3,5-dichloro-4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate | TFA |

| | | |
|---|---|---|
| 6 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-(thiophen-3-yl)benzoyl)-4-phenylpiperidine-4-carboxylate | TFA |
| 7 | (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)phenyl)propanoyl)-4-phenylpiperidine-4-carboxylate | Formate |
| 8 | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate | Formate |
| 9 | (R)-Quinuclidin-3-yl 1-(3-fluoro-4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate | TFA |
| 10 | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-methylbenzoyl)-4-phenylpiperidine-4-carboxylate | Formate |
| 11 | (R)-Quinuclidin-3-yl 1-(2-(3-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate | TFA |
| 12 | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)-3-methylphenyl)acetyl)-4-phenylpiperidine-4-carboxylate | TFA |
| 13 | (R)-Quinuclidin-3-yl 1-(2-(3-fluoro-4-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate | TFA |
| 14 | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)-3-(thiophen-3-yl)phenyl)acetyl)-4-phenylpiperidine-4-carboxylate | TFA |
| 15 | (R)-Quinuclidin-3-yl 1-(2-(6-((5-(((R)-2-hydroxy-2-(8-hydroxy-2-oxo-1,2-dihydroquinolin-5-yl)ethyl)amino)pentyl)oxy)-[1,1'-biphenyl]-3-yl)acetyl)-4-phenylpiperidine-4-carboxylate | TFA |
| 16 | (R)-Quinuclidin-3-yl 1-(3-(6-((5-(((R)-2-hydroxy-2-(8-hydroxy-2-oxo-1,2-dihydroquinolin-5-yl)ethyl)amino)pentyl)oxy)-[1,1'-biphenyl]-3-yl)propanoyl)-4-phenylpiperidine-4-carboxylate | TFA |
| 17 | (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)-3-methylphenyl)propanoyl)-4-phenylpiperidine-4-carboxylate | TFA |
| 18 | (R)-Quinuclidin-3-yl 1-((E)-3-(4-((5-(((R)-2-hydroxy-2-(8-hydroxy-2-oxo-1,2-dihydroquinolin-5-yl)ethyl)amino)pentyl)oxy)-3-methylphenyl)acryloyl)-4-phenylpiperidine-4-carboxylate | None |
| 19 | (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-4-phenylpiperidine-4-carboxylate | Formate |

| | | |
|---|---|---|
| 20 | (R)-Quinuclidin-3-yl 1-(4-(2-(((R)-2-hydroxy-2-(8-hydroxy-2-oxo-1,2-dihydroquinolin-5-yl)ethyl)amino)ethyl)benzoyl)-4-phenylpiperidine-4-carboxylate | TFA |
| 21 | (R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-4-phenylpiperidine-4-carboxylate | TFA |
| 22 | (R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-4-phenylpiperidine-4-carboxylate | TFA |
| 23 | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-4-phenylpiperidine-4-carboxylate | TFA |
| 24 | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-4-phenylpiperidine-4-carboxylate | Formate |
| 25 | (R)-Quinuclidin-3-yl 1-(4-(ethyl(3-(((R)-2-hydroxy-2-(8-hydroxy-2-oxo-1,2-dihydroquinolin-5-yl)ethyl)amino)propyl)carbamoyl)benzoyl)-4-phenylpiperidine-4-carboxylate | TFA |
| 26 | (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)oxy)benzoyl)-4-phenylpiperidine-4-carboxylate | TFA |
| 27 | (R)-Quinuclidin-3-yl 1-(5-((3-(((R)-2-hydroxy-2-(8-hydroxy-2-oxo-1,2-dihydroquinolin-5-yl)ethyl)amino)propyl)(methyl)carbamoyl)thiophene-2-carbonyl)-4-phenylpiperidine-4-carboxylate | Formate |
| 28 | (R)-Quinuclidin-3-yl 1-(5-(benzyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate | TFA |
| 29 | (R)-Quinuclidin-3-yl 1-(5-(ethyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate | TFA |
| 30 | (R)-Quinuclidin-3-yl 1-(2-(4-(4-(((R)-2-hydroxy-2-(8-hydroxy-2-oxo-1,2-dihydroquinolin-5-yl)ethyl)amino)butoxy)phenyl)acetyl)-4-phenylpiperidine-4-carboxylate | Formate |
| 31 | (R)-Quinuclidin-3-yl 1-(3-(4-((((R)-2-hydroxy-2-(8-hydroxy-2-oxo-1,2-dihydroquinolin-5-yl)ethyl)amino)methyl)benzamido)propanoyl)-4-phenylpiperidine-4-carboxylate | TFA |
| 32 | (R)-Quinuclidin-3-yl 1-(3-(4-(4-(((R)-2-hydroxy-2-(8-hydroxy-2-oxo-1,2-dihydroquinolin-5-yl)ethyl)amino)butoxy)phenyl)propanoyl)-4-phenylpiperidine-4-carboxylate | TFA |
| 33 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(4-methylbenzyl)amino)-2-oxoethyl)phenyl)acetyl)-4-phenylpiperidine-4-carboxylate | TFA |

| | | -continued |
|---|---|---|
| 34 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(2-methylbenzyl)amino)-2-oxoethyl)phenyl)acetyl)-4-phenylpiperidine-4-carboxylate | None |
| 35 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-methylbenzyl)amino)-2-oxoethyl)phenyl)acetyl)-4-phenylpiperidine-4-carboxylate | TFA |
| 36 | (R)-Quinuclidin-3-yl 1-(2-(4-(2-(benzyl(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | TFA |
| 37 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-(trifluoromethyl)benzyl)amino)-2-oxoethyl)phenyl)acetyl)-4-phenylpiperidine-4-carboxylate | None |
| 38 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-methoxybenzyl)amino)-2-oxoethyl)phenyl)acetyl)-4-phenylpiperidine-4-carboxylate | None |
| 39 | (R)-Quinuclidin-3-yl 1-(2-(4-(2-((3-cyanobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | TFA |
| 40 | (R)-Quinuclidin-3-yl 1-(2-(4-(2-((3-(3,4-dichlorophenoxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | None |
| 41 | (R)-Quinuclidin-3-yl 1-(2-(4-(2-((3-(benzyloxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | None |
| 42 | (R)-Quinuclidin-3-yl 1-(2-(4-(2-((3-fluorobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | None |
| 43 | (R)-Quinuclidin-3-yl 1-(2-(4-(2-((2-(benzyloxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | TFA |
| 44 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(2-morpholinobenzyl)amino)-2-oxoethyl)phenyl)acetyl)-4-phenylpiperidine-4-carboxylate | TFA |
| 45 | (R)-Quinuclidin-3-yl 1-(2-(4-(2-((2-fluorobenzyl)(3-(((R)-2-hydroxy-2-(8-hydroxy-2-oxo-1,2-dihydroquinolin-5- | TFA |

-continued

| | | |
|---|---|---|
| | yl)ethyl)amino)propyl)amino)-2-oxoethyl)phenyl)acetyl)-4-phenylpiperidine-4-carboxylate | |
| 46 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate | TFA |
| 47 | (R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(methyl)amino)-2-oxoethyl)phenyl)acetyl)-4-phenylpiperidine-4-carboxylate | TFA |
| 48 | (R)-Quinuclidin-3-yl 4-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate | Formate |
| 49 | (R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-4-phenylpiperidine-4-carboxylate | TFA |
| 50 | (R)-Quinuclidin-3-yl 4-(4-bromophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate | TFA |
| 51 | (R)-Quinuclidin-3-yl 4-(4-chlorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate | TFA |
| 52 | (R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate | Formate |
| 53 | (R)-Quinuclidin-3-yl 1-(3-(4-((3-(((R)-2-hydroxy-2-(8-hydroxy-2-oxo-1,2-dihydroquinolin-5-yl)ethyl)amino)propyl)(methyl)carbamoyl)phenyl)propanoyl)-4-phenylpiperidine-4-carboxylate | Formate |
| 54 | (R)-Quinuclidin-3-yl 1-(3-(4-(benzyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate | TFA |
| 55 | (R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-4-phenylpiperidine-4-carboxylate | TFA |
| 56 | (R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-4-phenylpiperidine-4-carboxylate | TFA |
| 57 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)acetamido)methyl)benzoyl)-4-phenylpiperidine-4-carboxylate | None |

| | | -continued |
|---|---|---|
| 58 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)methylsulfonamido)methyl)benzoyl)-4-phenylpiperidine-4-carboxylate | TFA |
| 59 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)benzamido)methyl)benzoyl)-4-phenylpiperidine-4-carboxylate | TFA |
| 60 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)cyclopropanecarboxamido)methyl)benzoyl)-4-phenylpiperidine-4-carboxylate | TFA |
| 61 | (R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)phenylsulfonamido)methyl)benzoyl)-4-phenylpiperidine-4-carboxylate | TFA |
| 62 | (R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)(methoxycarbonyl)amino)methyl)benzoyl)-4-phenylpiperidine-4-carboxylate | TFA |
| 63 | (R)-Quinuclidin-3-yl 1-(4-((1-(4-((((R)-2-hydroxy-2-(8-hydroxy-2-oxo-1,2-dihydroquinolin-5-yl)ethyl)amino)methyl)benzyl)-3-methylureido)methyl)benzoyl)-4-phenylpiperidine-4-carboxylate | TFA |
| 64 | (R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)oxy)methyl)benzoyl)-4-phenylpiperidine-4-carboxylate | TFA |
| 1A | (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate | TFA |
| 2A | (R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-3-phenylazetidine-3-carboxylate | Formate |
| 3A | (R)-Quinuclidin-3-yl 3-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)azetidine-3-carboxylate | TFA |
| 4A | (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate | TFA |
| 5A | (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)phenyl)propanoyl)-3-phenylazetidine-3-carboxylate | TFA |
| 6A | (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)phenyl)acetyl)-3-phenylazetidine-3-carboxylate | TFA |
| 7A | (R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl-3-phenylazetidine-3-carboxylate | TFA |

-continued

| | | |
|---|---|---|
| 8A | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl-3-phenylazetidine-3-carboxylate | |
| 9A | (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-3-phenylazetidine-3-carboxylate | TFA |
| 10A | (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-3-phenylazetidine-3-carboxylate | TFA |
| 11A | (R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-3-phenylazetidine-3-carboxylate | TFA |
| 12A | (R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-3-phenylazetidine-3-carboxylate | TFA |
| 13A | (R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-3-phenylazetidine-3-carboxylate | TFA |
| 14A | (R)-Quinuclidin-3-yl 1-(2-(4-(2-(benzyl(3-(((R)-2-hydroxy-2-(8-hydroxy-2-oxo-1,2-dihydroquinolin-5-yl)ethyl)amino)propyl)amino)-2-oxoethyl)phenyl)acetyl)-3-phenylazetidine-3-carboxylate | TFA |
| 15A | (R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-3-phenylazetidine-3-carboxylate | TFA |
| 16A | (R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)carbamoyl)benzoyl)-3-phenylazetidine-3-carboxylate | TFA |
| 17A | (R)-Quinuclidin-3-yl 1-(4-((4-((((R)-2-hydroxy-2-(8-hydroxy-2-oxo-1,2-dihydroquinolin-5-yl)ethyl)amino)methyl)benzamido)methyl)benzoyl)-3-phenylazetidine-3-carboxylate | TFA |
| 18A | (R)-Quinuclidin-3-yl 1-(4-(4-(((R)-2-hydroxy-2-(8-hydroxy-2-oxo-1,2-dihydroquinolin-5-yl)ethyl)amino)butoxy)benzoyl)-3-phenylazetidine-3-carboxylate | TFA |
| 19A | (R)-Quinuclidin-3-yl 1-(4-((4-((3-(((R)-2-hydroxy-2-(8-hydroxy-2-oxo-1,2-dihydroquinolin-5-yl)ethyl)amino)propyl)carbamoyl)benzyl)oxy)benzoyl)-3-phenylazetidine-3-carboxylate | TFA |
| 20A | (R)-Quinuclidin-3-yl 1-(4-((4-((((R)-2-hydroxy-2-(8-hydroxy-2-oxo-1,2-dihydroquinolin-5-yl)ethyl)amino)methyl)-3-methoxybenzyl)carbamoyl)benzoyl)-3-phenylazetidine-3-carboxylate | TFA |

Biological Characterization

M3 Receptor Radioligand Binding Assay

Human M3 receptor membranes (15 ug/well) from Perkin Elmer were incubated with 0.52 nM Scopolamine Methyl Chloride, (N-methyl-3H) with or without test compounds, or a saturating concentration of Atropine (5 µM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 h at room temperature on an orbital shaker (slow speed). Membranes were harvested onto 96-well unifilter GF/C filter plates pre-treated with 0.5% polyethyleneimine (v/v), using a filter manifold, washed four times with 200 ul of assay buffer. The plates were dried before addition of 50 µl of microscint-0, sealed then read in a Trilux Microbeta scintillation counter. 1050 values are determined from competition curves using a non-linear curve fitting program. Ki values were calculated from 1050 values by the Cheng and Prusoff equation.

The Ki values of the compounds according to the invention are less than 50 nM, most of them even less than 10 nM.

β2 Adrenoceptor Radioligand Binding Assay

Human $\beta_2$ adrenoceptor membranes (7.5 ug/well) from Perkin Elmer were incubated with 0.3 nM 125-I Cyanopindolol with or without test compounds, or a saturating concentration of s-propranolol (2 µM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 h at room temperature on an orbital shaker (slow speed). Membranes were harvested onto 96-well unifilter GF/C filter plates pre-treated with 0.5% polyethyleneimine (v/v), using a filter manifold, washed six times with 200 ul of wash buffer containing 10 mM HEPES and 500 mM NaCl. The plates were dried before addition of 50 µl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the compounds according to the invention are less than 50 nM, most of them even less than 10 nM.

In the following table the compounds tested are classified in terms of binding affinity according to the following ranges:

| Compound Number | M3 | B2 |
| --- | --- | --- |
| 1 | +++ | +++ |
| 2 | ++ | +++ |
| 3 | ++ | +++ |
| 4 | ++ | +++ |
| 5 | ++ | ++ |
| 6 | + | +++ |
| 7 | +++ | +++ |
| 8 | +++ | +++ |
| 9 | ++ | + |
| 10 | ++ | +++ |
| 11 | ++ | +++ |
| 12 | ++ | + |
| 13 | +++ | + |
| 14 | ++ | +++ |
| 15 | + | +++ |
| 16 | ++ | +++ |
| 17 | +++ | +++ |
| 18 | +++ | +++ |
| 19 | ++ | +++ |
| 20 | + | +++ |
| 21 | ++ | +++ |
| 22 | ++ | +++ |
| 23 | +++ | ++ |
| 24 | +++ | +++ |
| 25 | ++ | ++ |
| 26 | +++ | +++ |
| 27 | ++ | +++ |
| 28 | ++ | +++ |
| 29 | ++ | +++ |
| 30 | ++ | +++ |
| 31 | ++ | +++ |
| 32 | +++ | +++ |
| 33 | +++ | ++ |
| 34 | +++ | +++ |
| 35 | +++ | +++ |
| 36 | +++ | +++ |
| 37 | +++ | ++ |
| 38 | +++ | +++ |
| 39 | +++ | +++ |
| 40 | +++ | ++ |
| 41 | +++ | ++ |
| 42 | +++ | +++ |
| 43 | +++ | ++ |
| 44 | +++ | ++ |
| 45 | +++ | +++ |
| 46 | + | + |
| 47 | ++ | ++ |
| 48 | ++ | +++ |
| 49 | +++ | +++ |
| 50 | + | +++ |
| 51 | ++ | +++ |
| 52 | ++ | +++ |
| 53 | ++ | ++ |
| 54 | ++ | ++ |
| 55 | +++ | +++ |
| 56 | ++ | +++ |
| 57 | +++ | ++ |
| 58 | ++ | ++ |
| 59 | +++ | + |
| 60 | +++ | ++ |
| 61 | +++ | + |
| 62 | +++ | ++ |
| 63 | +++ | ++ |
| 64 | +++ | ++ |
| 1A | ++ | +++ |
| 2A | +++ | +++ |
| 3A | ++ | +++ |
| 4A | ++ | +++ |
| 5A | ++ | +++ |
| 6A | ++ | +++ |
| 7A | ++ | +++ |
| 8A | +++ | +++ |
| 9A | +++ | ++ |
| 10A | ++ | +++ |
| 11A | ++ | +++ |
| 12A | ++ | ++ |
| 13A | ++ | ++ |
| 14A | +++ | +++ |
| 15A | +++ | +++ |
| 16A | +++ | +++ |
| 17A | +++ | +++ |
| 18A | ++ | +++ |
| 19A | +++ | +++ |
| 20A | +++ | +++ |

+++: Ki < 1 nM
++: Ki in the range 1-10 nM
+: Ki > 10 nM

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula I:

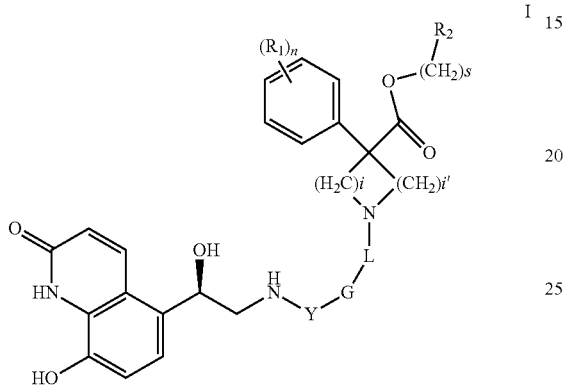

wherein
Y is Y2 or Y1 which are divalent groups of formula

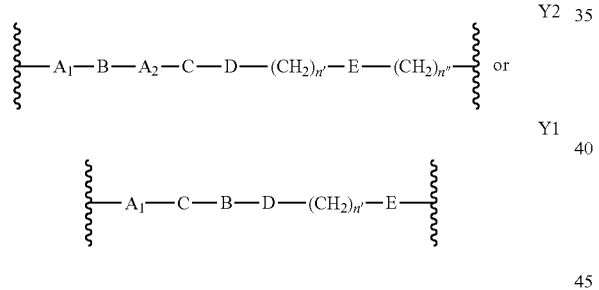

wherein
A1 and A2 are each independently absent or $(C_1-C_{12})$alkylene, $(C_3-C_8)$cycloalkylene or $(C_3-C_8)$heterocycloalkylene optionally substituted by one or more substituents selected from the group consisting of $(C_1-C_6)$alkyl, aryl$(C_1-C_6)$alkyl, and heteroaryl$(C_1-C_6)$alkyl;

B is absent or $(C_3-C_8)$cycloalkylene, $(C_3-C_8)$heterocycloalkylene, arylene, or heteroarylene optionally substituted by one or more groups selected from a halogen, nitrile, $(C_1-C_6)$alkyl, $(C_1-C_6)$alkoxy, and aryl$(C_1-C_6)$alkyl;

C is absent or —O—, —C(O)—, —OC(O)—, —(O)CO—, —S—, —S(O)—, —S(O)$_2$— and —N(R$_7$)—, or is one of the following groups C1-C4

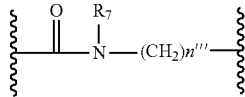

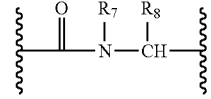

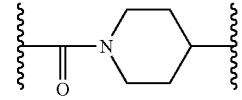

wherein
R$_7$ is at each occurrence independently H, linear or branched $(C_1-C_8)$alkyl, $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl, $(C_1-C_8)$alkylcarbonyl, $(C_3-C_8)$cycloalkylcarbonyl, arylcarbonyl, $(C_1-C_8)$alkoxycarbonyl, $(C_1-C_8)$alkylaminocarbonyl, $(C_1-C_{10})$alkylsulfanyl, $(C_1-C_{10})$alkylsulfinyl, $(C_1-C_{10})$alkylsulfonyl, arylsulfanyl, arylsulfinyl, or arylsulfonyl; wherein R$_7$ may optionally be further substituted by one or more groups selected from the group consisting of halogen, —CN, $(C_1-C_8)$alkyl, halo$(C_1-C_8)$alkyl, aryl, aryl$(C_1-C_6)$alkyl, $(C_1-C_8)$alkoxy, aryl$(C_1-C_8)$alkoxy, $(C_3-C_8)$cycloalkyl, $(C_3-C_8)$heterocycloalkyl, and substituted or unsubstituted aryloxy;

R$_8$ is at each occurrence independently H, linear or branched $(C_1-C_8)$alkyl, $(C_3-C_8)$cycloalkyl, $(C_3-C_8)$heterocycloalkyl, aryl, heteroaryl, aryl$(C_1-C_6)$alkyl, $(C_3-C_8)$cycloalkyl$(C_1-C_6)$alkyl, or heteroaryl$(C_1-C_6)$alkyl;

D is absent or $(C_1-C_{12})$alkylene, arylene, $(C_2-C_{12})$alkenylene, heteroarylene, $(C_3-C_8)$heterocycloalkylene, or $(C_2-C_6)$alkynylene;

n, n', n" and n'" are at each occurrence independently 0 or an integer from 1 to 3;

E is absent or —O—, —NR$_7$—, —NR$_7$—C(O)—, —C(O)—NR$_7$—, —OC(O)—, or —S—;

G is absent or arylene or heteroarylene, optionally substituted by one or more substituents selected from the group consisting of a halogen atom, —OH, oxo (═O), —SH, —NO$_2$, —CN, —CON(R$_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl and $(C_1-C_{10})$alkoxy;

L is absent or a divalent group selected from the group consisting of —C(O)—, —OC(O)—, —S(O)$_2$—, $(C_1-C_8)$alkyl-ene, $(C_1-C_8)$alkylcarbonyl-ene, and $(C_2-C_8)$alkenylcarbonylene; or is one of the following groups L1-L3

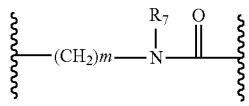

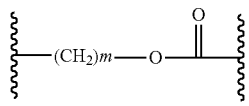

-continued

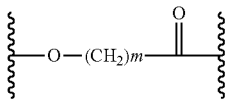
L3 wherein m is 0 or an integer from 1 to 3;
i is 1 or 2;
i' is 1 or 2;
R₁ is at each occurrence independently hydrogen, halogen, (C₁-C₈)alkyl, or (C₁-C₁₀)alkoxy;
s is 0 or an integer from 1 to 3;
R₂ is a nitrogen containing group which is:
  a group (a) which is —NR₃R₄ wherein R₃ and R₄ are independently hydrogen, (C₁-C₄) alkyl, or benzyl; or
  a group (b) of formula J1, J2, J3, J4 or J5

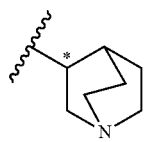
J1

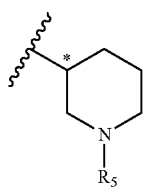
J2

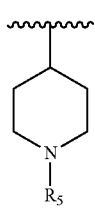
J3

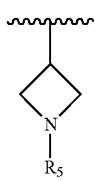
J4

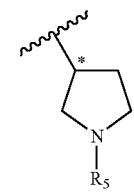
J5

R₅ is a group of formula K

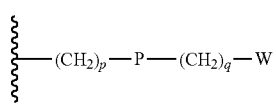
K wherein
p is 0 or an integer from 1 to 4;
q is 0 or an integer from 1 to 4;
P is absent or is a divalent group selected from the group consisting of O, S, SO, SO₂, CO, NR₆CH=CH, N(R₆)SO₂, N(R₆)COO, N(R₆)C(O), SO₂N(R₆), OC(O)N(R₆), and C(O)N(R₆);
W is H, (C₁-C₆)alkyl, (C₃-C₈)cycloalkyl, aryl, heteroaryl, optionally substituted by one or more substituents selected independently from the group consisting of a halogen atom, —OH, oxo (=O), —SH, —NO₂, —CN, —CON(R₆)₂, —NH₂, —NHCOR₆, —CO₂R₆, (C₁-C₁₀)alkylsulfanyl, (C₁-C₁₀)alkylsulfinyl, (C₁-C₁₀)alkylsulfonyl, (C₁-C₁₀)alkyl, (C₁-C₁₀)alkoxy, and aryl;
R₆ is at each occurrence independently H or selected from the group consisting of (C₁-C₁₀)alkyl, (C₁-C₆)haloalkyl, (C₂-C₆)alkynyl, (C₂-C₆)alkenyl, (C₃-C₈)cycloalkyl, (C₃-C₈)cycloalkyl(C₁-C₆)alkyl, heteroaryl, and aryl optionally substituted by one or more substituents selected from the group consisting of a halogen atom, —OH, oxo (=O), —SH, —NO₂, —CN, —CONH₂, —COOH, (C₁-C₁₀)alkoxycarbonyl, (C₁-C₁₀)alkylsulfanyl, (C₁-C₁₀)alkylsulfinyl, (C₁-C₁₀)alkylsulfonyl, (C₁-C₁₀)alkyl and (C₁-C₁₀)alkoxy;
or a pharmaceutically acceptable salt thereof.

2. A compound or pharmaceutically acceptable salt according to claim 1, wherein each of i and i' is 2 of formula IA:

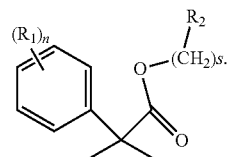
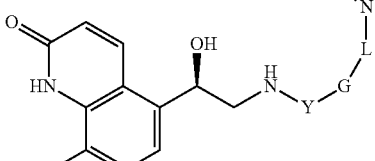
IA

3. A compound or pharmaceutically acceptable salt according to claim 1 wherein each of i and i' is 1 of formula IB:

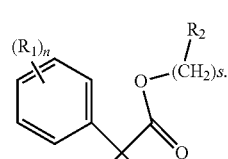
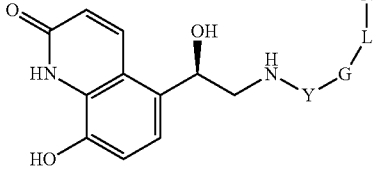
IB

4. A compound or pharmaceutically acceptable salt according to claim 2, wherein Y is $Y_2$ wherein $A_1$ is $(C_1-C_{12})$ alkylene, B is optionally substituted arylene, $A_2$ is alkylene, C is absent, D is absent, n' and n'' are 0, E is —O—, G is optionally substituted arylene or heteroarylene.

5. A compound or pharmaceutically acceptable salt according to claim 4, wherein $A_1$ is $CH_2$ or —$CH_2$—$CH_2$—, B is phenylene, $A_2$ is $CH_2$, G is phenylene, L is —CO— or —$CH_2CO$—, $R_1$ is H, $R_2$ is J1, and s is 0.

6. A compound or pharmaceutically acceptable salt according to claim 2, wherein Y is $Y_1$ wherein $A_1$ is alkylene, C is $C_1$, B is absent or arylene, D is absent, n' is 1, E is —O— or absent, G is arylene or heteroarylene both of them optionally substituted.

7. A compound or pharmaceutically acceptable salt according to claim 6, wherein $A_1$ is $CH_2$, C is $C_1$ wherein n''' is 2 and $R_7$ is a benzyl group, said benzyl being optionally substituted by halogen, $(C_1-C_8)$ alkoxy, —CN or $C_1-C_8$ alkyl, L is —CO— or —$CH_2CO$—, $R_1$ is H, $R_2$ is J1, and s is 0.

8. A compound or pharmaceutically acceptable salt according to claim 2, wherein
  A1 is methylene, ethylene, propylene, butylene, pentylene or hexylene and A2 is absent or methylene;
  B is absent or piperidinylene or phenylene optionally substituted by one methoxy;
  C is absent or is —O—, —C(O)—; or —N($R_7$)— wherein $R_7$ is methylcarbonyl, methylaminocarbonyl, methoxycarbonyl, benzylcarbonyl, cyclopropanecarbonyl, methylsulfonyl or phenylsulfonyl; or C is $C_1$ with $R_7$ being hydrogen, fluoro, methyl, ethyl, benzyl optionally substituted by one groups selected from the group consisting of methyl, methoxy, tri-fluoromethyl, cyanobenzyl, dichlorophenoxy, benzyloxy and morpholinyl and n''' is 0, 1 or 2; or C2 with $R_7$ being hydrogen and n''' 0 or 1; or C4;
  D is absent or piperidinylene;
  n is 0, or n is 1 and $R_1$ is chloro, fluoro, or bromo, n' is 0 or 1, n'' is 0 or 1;
  E is absent or —O— or —$NR_7$—C(O)— with R7 being hydrogen, methyl, or ethyl;
  G is absent or phenylene which is substituted by one or more substituents selected from the group consisting of methyl, methoxy, F, Cl, phenyl, and thyenyl; or G is thienylene;
  L is absent or a divalent group selected from the group consisting of —C(O)—, —$CH_2CO$—, —$CH_2CH_2CO$— and —CH=CHCO—;
  s is 0 and $R_2$ is J1, or
  s is 1 and $R_2$ is J3 and $R_5$ is methyl or benzyl optionally substituted by hydroxyl.

9. A compound or pharmaceutically acceptable salt according to claim 1, which is a compound selected from the group consisting of:
  (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate;
  (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate;
  (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-methoxybenzoyl)-4-phenylpiperidine-4-carboxylate;
  (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-chlorobenzoyl)-4-phenylpiperidine-4-carboxylate;
  (R)-Quinuclidin-3-yl 1-(3,5-dichloro-4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate;
  (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-(thiophen-3-yl)benzoyl)-4-phenylpiperidine-4-carboxylate;
  (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)phenyl)propanoyl)-4-phenylpiperidine-4-carboxylate;
  (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate;
  (R)-Quinuclidin-3-yl 1-(3-fluoro-4-((5-(((R)-2-hydroxy-2-(8-hydroxy-2-oxo-1,2-dihydroquinolin-5-yl)ethyl)amino)pentyl)oxy)benzoyl)-4-phenylpiperidine-4-carboxylate;
  (R)-Quinuclidin-3-yl 1-(4-((5-(((R)-2-hydroxy-2-(8-hydroxy-2-oxo-1,2-dihydroquinolin-5-yl)ethyl)amino)pentyl)oxy)-3-methylbenzoyl)-4-phenylpiperidine-4-carboxylate;
  (R)-Quinuclidin-3-yl 1-(2-(3-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate;
  (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)-3-methylphenyl)acetyl)-4-phenylpiperidine-4-carboxylate;
  (R)-Quinuclidin-3-yl 1-(2-(3-fluoro-4-((5-(((R)-2-hydroxy-2-(8-hydroxy-2-oxo-1,2-dihydroquinolin-5-yl)ethyl)amino)pentyl)oxy)phenyl)acetyl)-4-phenylpiperidine-4-carboxylate;
  (R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)-3-(thiophen-3-yl)phenyl)acetyl)-4-phenylpiperidine-4-carboxylate;
  (R)-Quinuclidin-3-yl 1-(2-(6-((5-(((R)-2-hydroxy-2-(8-hydroxy-2-oxo-1,2-dihydroquinolin-5-yl)ethyl)amino)pentyl)oxy)-[1,1'-biphenyl]-3-yl)acetyl)-4-phenylpiperidine-4-carboxylate;
  (R)-Quinuclidin-3-yl 1-(3-(6-((5-(((R)-2-hydroxy-2-(8-hydroxy-2-oxo-1,2-dihydroquinolin-5-yl)ethyl)amino)pentyl)oxy)-[1,1'-biphenyl]-3-yl)propanoyl)-4-phenylpiperidine-4-carboxylate;
  (R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)-3-methylphenyl)propanoyl)-4-phenylpiperidine-4-carboxylate;
  (R)-Quinuclidin-3-yl 1-((E)-3-(4-((5-(((R)-2-hydroxy-2-(8-hydroxy-2-oxo-1,2-dihydroquinolin-5-yl)ethyl)amino)pentyl)oxy)-3-methylphenyl)acryloyl)-4-phenylpiperidine-4-carboxylate;
  (R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-4-phenylpiperidine-4-carboxylate;
  (R)-Quinuclidin-3-yl 1-(4-(2-(((R)-2-hydroxy-2-(8-hydroxy-2-oxo-1,2-dihydroquinolin-5-yl)ethyl)amino)ethyl)benzoyl)-4-phenylpiperidine-4-carboxylate (R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-4-phenylpiperidine-4-carboxylate;

(R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-4-phenylpiperidine-4-carboxylate;

(R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-4-phenylpiperidine-4-carboxylate;

(R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-4-phenylpiperidine-4-carboxylate;

(R)-Quinuclidin-3-yl 1-(4-(ethyl(3-(((R)-2-hydroxy-2-(8-hydroxy-2-oxo-1,2-dihydroquinolin-5-yl)ethyl)amino)propyl)carbamoyl)benzoyl)-4-phenylpiperidine-4-carboxylate;

(R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)oxy)benzoyl)-4-phenylpiperidine-4-carboxylate;

(R)-Quinuclidin-3-yl 1-(5-((3-(((R)-2-hydroxy-2-(8-hydroxy-2-oxo-1,2-dihydroquinolin-5-yl)ethyl)amino)propyl)(methyl)carbamoyl)thiophene-2-carbonyl)-4-phenylpiperidine-4-carboxylate;

(R)-Quinuclidin-3-yl 1-(5-(benzyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate;

(R)-Quinuclidin-3-yl 1-(5-(ethyl(3-(((R)-2-hydroxy-2-(8-hydroxy-2-oxo-1,2-dihydroquinolin-5-yl)ethyl)amino)propyl)carbamoyl)thiophene-2-carbonyl)-4-phenylpiperidine-4-carboxylate;

(R)-Quinuclidin-3-yl 1-(2-(4-(4-(((R)-2-hydroxy-2-(8-hydroxy-2-oxo-1,2-dihydroquinolin-5-yl)ethyl)amino)butoxy)phenyl)acetyl)-4-phenylpiperidine-4-carboxylate;

(R)-Quinuclidin-3-yl 1-(3-(4-((((R)-2-hydroxy-2-(8-hydroxy-2-oxo-1,2-dihydroquinolin-5-yl)ethyl)amino)methyl)benzamido)propanoyl)-4-phenylpiperidine-4-carboxylate;

(R)-Quinuclidin-3-yl 1-(3-(4-(4-(((R)-2-hydroxy-2-(8-hydroxy-2-oxo-1,2-dihydroquinolin-5-yl)ethyl)amino)butoxy)phenyl)propanoyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(4-methylbenzyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(2-methylbenzyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-methylbenzyl)amino)-2-oxoethyl)phenyl)acetyl)-4-phenylpiperidine-4-carboxylate;

(R)-Quinuclidin-3-yl 1-(2-(4-(2-(benzyl(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-(trifluoromethyl)benzyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(3-methoxybenzyl)amino)-2-oxoethyl)phenyl)acetyl)-4-phenylpiperidine-4-carboxylate;

(R)-Quinuclidin-3-yl 1-(2-(4-(2-((3-cyanobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-(3,4-dichlorophenoxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-(benzyloxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-fluorobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((2-(benzyloxy)benzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(2-morpholinobenzyl)amino)-2-oxoethyl)phenyl)acetyl)-4-phenylpiperidine-4-carboxylate;

(R)-Quinuclidin-3-yl 1-(2-(4-(2-((2-fluorobenzyl)(3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)amino)-2-oxoethyl)phenyl)acetyl)-4-phenylpiperidine-4-carboxylate;

(R)-Quinuclidin-3-yl 1-(2-(4-(2-((3-(((R)-2-hydroxy-2-(8-hydroxy-2-oxo-1,2-dihydroquinolin-5-yl)ethyl)amino)propyl)(methyl)amino)-2-oxoethyl)phenyl)acetyl)-4-phenylpiperidine-4-carboxylate;

(R)-Quinuclidin-3-yl 4-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate;

(R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-4-phenylpiperidine-4-carboxylate;

(R)-Quinuclidin-3-yl 4-(4-bromophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate;

(R)-Quinuclidin-3-yl 4-(4-chlorophenyl)-1-(4-((6-(((R)-2-hydroxy-2-(8-hydroxy-2-oxo-1,2-dihydroquinolin-5-yl)ethyl)amino)hexyl)oxy)benzoyl)piperidine-4-carboxylate;

(R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate;

(R)-Quinuclidin-3-yl 1-(3-(4-((3-(((R)-2-hydroxy-2-(8-hydroxy-2-oxo-1,2-dihydroquinolin-5-yl)ethyl)amino)

propyl)(methyl)carbamoyl)phenyl)propanoyl)-4-phenylpiperidine-4-carboxylate;
(R)-Quinuclidin-3-yl 1-(3-(4-(benzyl(3-(((R)-2-hydroxy-2-(8-hydroxy-2-oxo-1,2-dihydroquinolin-5-yl)ethyl)amino)propyl)carbamoyl)phenyl)propanoyl)-4-phenylpiperidine-4-carboxylate;
(R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-4-phenylpiperidine-4-carboxylate;
(R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-4-phenylpiperidine-4-carboxylate;
(R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)acetamido)methyl)benzoyl)-4-phenylpiperidine-4-carboxylate;
(R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)methylsulfonamido)methyl)benzoyl)-4-phenylpiperidine-4-carboxylate;
(R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)benzamido)methyl)benzoyl)-4-phenylpiperidine-4-carboxylate;
(R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)cyclopropanecarboxamido)methyl)benzoyl)-4-phenylpiperidine-4-carboxylate;
(R)-Quinuclidin-3-yl 1-(4-((N-(4-((((R)-2-hydroxy-2-(8-hydroxy-2-oxo-1,2-dihydroquinolin-5-yl)ethyl)amino)methyl)benzyl)phenylsulfonamido)methyl) benzoyl)-4-phenylpiperidine-4-carboxylate;
(R)-Quinuclidin-3-yl 1-(4-(((4-((((R)-2-hydroxy-2-(8-hydroxy-2-oxo-1,2-dihydroquinolin-5-yl)ethyl)amino)methyl)benzyl)(methoxycarbonyl)amino)methyl) benzoyl)-4-phenylpiperidine-4-carboxylate;
(R)-Quinuclidin-3-yl 1-(4-((1-(4-((((R)-2-hydroxy-2-(8-hydroxy-2-oxo-1,2-dihydroquinolin-5-yl)ethyl)amino)methyl)benzyl)-3-methylureido)methyl)benzoyl)-4-phenylpiperidine-4-carboxylate;
(R)-Quinuclidin-3-yl 1-(4-(((4-(((((R)-2-hydroxy-2-(8-hydroxy-2-oxo-1,2-dihydroquinolin-5-yl)ethyl)amino)methyl)benzyl)oxy)methyl)benzoyl)-4-phenylpiperidine-4-carboxylate;
(R)-Quinuclidin-3-yl 1-(4-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate;
(R)-Quinuclidin-3-yl 1-(4-((6-(((R)-2-hydroxy-2-(8-hydroxy-2-oxo-1,2-dihydroquinolin-5-yl)ethyl)amino)hexyl)oxy)benzoyl)-3-phenylazetidine-3-carboxylate;
(R)-Quinuclidin-3-yl 3-(4-fluorophenyl)-1-(4-((6-(((R)-2-hydroxy-2-(8-hydroxy-2-oxo-1,2-dihydroquinolin-5-yl)ethyl)amino)hexyl)oxy)benzoyl)azetidine-3-carboxylate;
(R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzoyl)-3-phenylazetidine-3-carboxylate;
(R)-Quinuclidin-3-yl 1-(3-(4-((5-(((R)-2-hydroxy-2-(8-hydroxy-2-oxo-1,2-dihydroquinolin-5-yl)ethyl)amino)pentyl)oxy)phenyl)propanoyl)-3-phenylazetidine-3-carboxylate;
(R)-Quinuclidin-3-yl 1-(2-(4-((5-(((R)-2-hydroxy-2-(8-hydroxy-2-oxo-1,2-dihydroquinolin-5-yl)ethyl)amino)pentyl)oxy)phenyl)acetyl)-3-phenylazetidine-3-carboxylate;
(R)-Quinuclidin-3-yl 1-(4-((3-(4-(((R)-2-hydroxy-2-(8-hydroxy-2-oxo-1,2-dihydroquinolin-5-yl)ethyl)amino)butoxy)benzyl)oxy)benzoyl)-3-phenylazetidine-3-carboxylate;
(R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzoyl)-3-phenylazetidine-3-carboxylate;
(R)-Quinuclidin-3-yl 1-(4-((4-((((R)-2-hydroxy-2-(8-hydroxy-2-oxo-1,2-dihydroquinolin-5-yl)ethyl)amino)methyl)benzyl)carbamoyl)benzoyl)-3-phenylazetidine-3-carboxylate;
(R)-Quinuclidin-3-yl 1-(4-((4-(((R)-2-hydroxy-2-(8-hydroxy-2-oxo-1,2-dihydroquinolin-5-yl)ethyl)amino)butyl)carbamoyl)benzoyl)-3-phenylazetidine-3-carboxylate;
(R)-Quinuclidin-3-yl 1-(5-((4-(((R)-2-hydroxy-2-(8-hydroxy-2-oxo-1,2-dihydroquinolin-5-yl)ethyl)amino)butyl)carbamoyl)thiophene-2-carbonyl)-3-phenylazetidine-3-carboxylate;
(R)-Quinuclidin-3-yl 1-(3-(4-(ethyl(3-(((R)-2-hydroxy-2-(8-hydroxy-2-oxo-1,2-dihydroquinolin-5-yl)ethyl)amino)propyl)carbamoyl)phenyl)propanoyl)-3-phenylazetidine-3-carboxylate;
(R)-Quinuclidin-3-yl 1-(3-(4-((4-((((R)-2-hydroxy-2-(8-hydroxy-2-oxo-1,2-dihydroquinolin-5-yl)ethyl)amino)methyl)benzyl)oxy)phenyl)propanoyl)-3-phenylazetidine-3-carboxylate;
(R)-Quinuclidin-3-yl 1-(2-(4-(2-(benzyl(3-(((R)-2-hydroxy-2-(8-hydroxy-2-oxo-1,2-dihydroquinolin-5-yl)ethyl)amino)propyl)amino)-2-oxoethyl)phenyl)acetyl)-3-phenylazetidine-3-carboxylate;
(R)-Quinuclidin-3-yl 1-(2-(4-((4-((((R)-2-hydroxy-2-(8-hydroxy-2-oxo-1,2-dihydroquinolin-5-yl)ethyl)amino)methyl)benzyl)oxy)phenyl)acetyl)-3-phenylazetidine-3-carboxylate;
(R)-Quinuclidin-3-yl 1-(4-((4-(2-(((R)-2-hydroxy-2-(8-hydroxy-2-oxo-1,2-dihydroquinolin-5-yl)ethyl)amino)ethyl)benzyl)carbamoyl)benzoyl)-3-phenylazetidine-3-carboxylate;
(R)-Quinuclidin-3-yl 1-(4-((4-((((R)-2-hydroxy-2-(8-hydroxy-2-oxo-1,2-dihydroquinolin-5-yl)ethyl)amino)methyl)benzamido)methyl)benzoyl)-3-phenylazetidine-3-carboxylate;
(R)-Quinuclidin-3-yl 1-(4-(4-(((R)-2-hydroxy-2-(8-hydroxy-2-oxo-1,2-dihydroquinolin-5-yl)ethyl)amino)butoxy)benzoyl)-3-phenylazetidine-3-carboxylate;
(R)-Quinuclidin-3-yl 1-(4-((3-(((R)-2-hydroxy-2-(8-hydroxy-2-oxo-1,2-dihydroquinolin-5-yl)ethyl)amino)propyl)carbamoyl)benzyl)oxy)benzoyl)-3-phenylazetidine-3-carboxylate; and
(R)-Quinuclidin-3-yl 1-(4-((4-((((R)-2-hydroxy-2-(8-hydroxy-2-oxo-1,2-dihydroquinolin-5-yl)ethyl)amino)methyl)-3-methoxybenzyl)carbamoyl)benzoyl)-3-phenylazetidine-3-carboxylate;
or a pharmaceutically acceptable salt of said compound.

10. A pharmaceutical composition, comprising a compound or pharmaceutically acceptable salt according to claim 1 and one or more pharmaceutically acceptable carriers and/or excipients.

11. A method for the treatment of a disease selected from the group consisting of asthma and COPD, comprising administering to a subject in need thereof an effective amount of a compound or pharmaceutically acceptable salt according to claim 1.

12. A method for the treatment of chronic obstructive pulmonary disease (COPD) comprising administering to a subject in need thereof an effective amount of a compound or pharmaceutically acceptable salt according to claim 1.

13. A pharmaceutical composition according to claim 10, further comprising one or more additional active ingredients selected from the group consisting of a corticosteroid, a P38 MAP kinase inhibitor, a IKK2 inhibitor, a FINE inhibitor, a PDE4 inhibitor, a leukotriene modulator, a NSAID, and a mucus regulator.

14. A pharmaceutical composition according to claim 10, which is an inhalable powder, a propellant-containing metering aerosol, or a propellant-free inhalable formulation.

15. A pharmaceutical composition according to claim 10, which is contained in a single- or multi-dose dry powder inhaler, a metered dose inhaler, or a soft mist nebulizer.

16. A method for the treatment of asthma, comprising administering to a subject in need thereof an effective amount of a compound or pharmaceutically acceptable salt according to claim 1.

* * * * *